US012439976B2

(12) United States Patent
Memari et al.

(10) Patent No.: US 12,439,976 B2
(45) Date of Patent: Oct. 14, 2025

(54) E-CIGARETTE PERSONAL VAPORIZER

(71) Applicant: AYR LTD., London (GB)

(72) Inventors: Kaveh Memari, London (GB); Adrian Bennett, London (GB); Ian Murison, London (GB); Stephen Marsh, London (GB)

(73) Assignee: AYR LTD., London (GB)

( * ) Notice: Subject to any disclaimer, the term of this patent is extended or adjusted under 35 U.S.C. 154(b) by 684 days.

(21) Appl. No.: 17/397,238

(22) Filed: Aug. 9, 2021

(65) Prior Publication Data

US 2021/0360981 A1 Nov. 25, 2021

Related U.S. Application Data

(63) Continuation of application No. 16/825,106, filed on Mar. 20, 2020, now Pat. No. 11,083,228, which is a
(Continued)

(30) Foreign Application Priority Data

Feb. 28, 2014 (GB) ..................................... 1403566
May 8, 2014 (GB) ..................................... 1408173
(Continued)

(51) Int. Cl.
*A24F 47/00* (2020.01)
*A24F 15/015* (2020.01)
(Continued)

(52) U.S. Cl.
CPC ............ *A24F 40/95* (2020.01); *A24F 15/015* (2020.01); *A24F 40/40* (2020.01); *A24F 40/48* (2020.01);
(Continued)

(58) Field of Classification Search
CPC ....... A24F 40/015; A24F 40/48; A24F 40/485
See application file for complete search history.

(56) References Cited

U.S. PATENT DOCUMENTS 2,491,617 A 12/1949 Lebach
3,612,363 A 10/1971 Carter
(Continued)

FOREIGN PATENT DOCUMENTS

CN 201630238 U 11/2010
CN 202276832 U 6/2012
(Continued)

OTHER PUBLICATIONS

"Hidden Formaldehyde in E-Cigarette Aerosols", N. Engl. J. Med. 372:4, NEJM.org, Jan. 22, 2015, 392-394.

*Primary Examiner* — Eric Yaary
(74) *Attorney, Agent, or Firm* — Saul Ewing LLP

(57) ABSTRACT

An e-cigarette PV that includes an air pressure valve or device so that excess air can escape from an e-liquid reservoir in the PV when that reservoir is being filled under pressure with e-liquid from a parent reservoir. The valve or device is a barrier made of an air-porous material, such as a sintered polymer or metal, coated with or otherwise including a barrier or layer of an air-porous substance that is not porous to e-liquid, such as an oleophobic material or a hydrophobic or super-hydrophobic material. The oleophobic material is one of: sintered phosphor bronze, sintered stainless steel and sintered PU plastic.

19 Claims, 123 Drawing Sheets

Related U.S. Application Data continuation of application No. 16/177,708, filed on Nov. 1, 2018, now Pat. No. 10,624,394, which is a continuation of application No. 14/842,067, filed on Sep. 1, 2015, now Pat. No. 10,149,497, which is a continuation-in-part of application No. 14/633,887, filed on Feb. 27, 2015, now Pat. No. 9,247,773.

(60) Provisional application No. 62/045,701, filed on Sep. 4, 2014, provisional application No. 62/045,669, filed on Sep. 4, 2014, provisional application No. 62/045,692, filed on Sep. 4, 2014, provisional application No. 62/045,651, filed on Sep. 4, 2014, provisional application No. 62/045,696, filed on Sep. 4, 2014, provisional application No. 62/045,666, filed on Sep. 4, 2014, provisional application No. 62/045,657, filed on Sep. 4, 2014, provisional application No. 62/045,690, filed on Sep. 4, 2014, provisional application No. 62/045,680, filed on Sep. 4, 2014, provisional application No. 62/045,674, filed on Sep. 4, 2014.

(30) Foreign Application Priority Data

| | | |
|---|---|---|
| Jul. 23, 2014 | (GB) | 1413018 |
| Jul. 23, 2014 | (GB) | 1413019 |
| Jul. 23, 2014 | (GB) | 1413021 |
| Jul. 23, 2014 | (GB) | 1413025 |
| Jul. 23, 2014 | (GB) | 1413027 |
| Jul. 23, 2014 | (GB) | 1413028 |
| Jul. 23, 2014 | (GB) | 1413030 |
| Jul. 23, 2014 | (GB) | 1413032 |
| Jul. 23, 2014 | (GB) | 1413034 |
| Jul. 23, 2014 | (GB) | 1413036 |
| Jul. 23, 2014 | (GB) | 1413037 |

(51) Int. Cl.

| | |
|---|---|
| ***A24F 40/40*** | (2020.01) |
| ***A24F 40/48*** | (2020.01) |
| ***A24F 40/485*** | (2020.01) |
| ***A24F 40/50*** | (2020.01) |
| ***A24F 40/60*** | (2020.01) |
| ***A24F 40/90*** | (2020.01) |
| ***A24F 40/95*** | (2020.01) |
| ***B65B 3/04*** | (2006.01) |
| ***B65B 37/06*** | (2006.01) |
| ***B65D 25/00*** | (2006.01) |
| ***G01F 23/00*** | (2022.01) |
| ***H02J 7/00*** | (2006.01) |
| ***H02J 7/35*** | (2006.01) |
| ***H02J 50/10*** | (2016.01) |
| *A24F 40/10* | (2020.01) |
| *G09F 23/00* | (2006.01) |

(52) U.S. Cl.

CPC ............ *A24F 40/485* (2020.01); *A24F 40/50* (2020.01); *A24F 40/60* (2020.01); *A24F 40/90* (2020.01); *B65B 3/04* (2013.01); *B65B 37/06* (2013.01); *B65D 25/005* (2013.01); *G01F 23/00* (2013.01); *H02J 7/00* (2013.01); *H02J 7/0042* (2013.01); *H02J 7/0044* (2013.01); *H02J 7/35* (2013.01); *H02J 50/10* (2016.02); *A24F 40/10* (2020.01); *A61M 2209/045* (2013.01); *G09F 2023/0025* (2013.01); *H02J 7/0063* (2013.01)

(56) References Cited

U.S. PATENT DOCUMENTS

| | | | | |
|---|---|---|---|---|
| 4,572,253 | A | 2/1986 | Farmer et al. | |
| 4,702,397 | A | 10/1987 | Gortz et al. | |
| 4,848,606 | A * | 7/1989 | Taguchi | B05C 5/02 118/410 |
| 5,024,347 | A | 6/1991 | Baldwin | |
| 5,121,769 | A | 6/1992 | Mccabe et al. | |
| 5,332,125 | A | 7/1994 | Schmitkons | |
| 5,751,320 | A | 5/1998 | Scheffelin et al. | |
| 6,082,593 | A * | 7/2000 | Borcherds | A47K 5/1207 222/321.9 |
| 6,105,809 | A | 8/2000 | Yamanaka | |
| 6,270,720 | B1 | 8/2001 | Mandish | |
| 6,308,482 | B1 | 10/2001 | Strait | |
| 6,428,154 | B1 | 8/2002 | Kamiyama et al. | |
| 6,637,430 | B1 | 10/2003 | Voges et al. | |
| 6,695,136 | B1 | 2/2004 | Torres | |
| 8,249,936 | B1 | 8/2012 | Francisco et al. | |
| D723,733 | S | 3/2015 | Liu | |
| 8,967,382 | B2 | 3/2015 | Liu | |
| 9,066,543 | B2 | 6/2015 | Cameron | |
| 9,883,697 | B2 | 2/2018 | Memari et al. | |
| 2002/0112723 | A1 | 8/2002 | Schuster et al. | |
| 2003/0225396 | A1 | 12/2003 | Cartledge | |
| 2004/0159368 | A1 | 8/2004 | Eddins et al. | |
| 2005/0016550 | A1 | 1/2005 | Katase et al. | |
| 2005/0118468 | A1 | 6/2005 | Adams et al. | |
| 2005/0139693 | A1 | 6/2005 | Robinson et al. | |
| 2005/0168540 | A1 | 8/2005 | Wilson et al. | |
| 2005/0184096 | A1 * | 8/2005 | Levia | B60S 1/50 222/181.2 |
| 2005/0189275 | A1 | 9/2005 | Stewart et al. | |
| 2005/0219302 | A1 | 10/2005 | Vogeley et al. | |
| 2005/0263160 | A1 | 12/2005 | Utley et al. | |
| 2007/0045288 | A1 | 3/2007 | Nelson et al. | |
| 2007/0095861 | A1 | 5/2007 | Yates et al. | |
| 2008/0011875 | A1 | 1/2008 | Sipinski et al. | |
| 2008/0173705 | A1 * | 7/2008 | Girard | B67D 1/0031 222/64 |
| 2008/0230052 | A1 | 9/2008 | Montaser et al. | |
| 2008/0239040 | A1 | 10/2008 | Umeda et al. | |
| 2009/0095311 | A1 | 4/2009 | Han | |
| 2009/0126722 | A1 | 5/2009 | Sugita et al. | |
| 2009/0159140 | A1 | 6/2009 | Auer | |
| 2009/0250119 | A1 | 10/2009 | Whelan | |
| 2009/0266358 | A1 | 10/2009 | Sacristan Rock et al. | |
| 2009/0272379 | A1 | 11/2009 | Thorens et al. | |
| 2010/0024898 | A1 | 2/2010 | Bansal et al. | |
| 2010/0163063 | A1 | 7/2010 | Fernando et al. | |
| 2010/0225725 | A1 | 9/2010 | Roth | |
| 2010/0242975 | A1 | 9/2010 | Hearn et al. | |
| 2010/0243754 | A1 | 9/2010 | Harris et al. | |
| 2010/0243760 | A1 | 9/2010 | Birrenkott et al. | |
| 2010/0276034 | A1 | 11/2010 | Gonnelli et al. | |
| 2010/0313901 | A1 | 12/2010 | Fernando et al. | |
| 2011/0036346 | A1 | 2/2011 | Cohen et al. | |
| 2011/0097060 | A1 | 4/2011 | Michael | |
| 2011/0120565 | A1 | 5/2011 | Saunders et al. | |
| 2011/0226236 | A1 | 9/2011 | Buchberger et al. | |
| 2011/0265806 | A1 | 11/2011 | Alarcon et al. | |
| 2011/0279605 | A1 | 11/2011 | Borra et al. | |
| 2011/0304468 | A1 | 12/2011 | Linsenmeyer et al. | |
| 2012/0048266 | A1 | 3/2012 | Alelov et al. | |
| 2012/0138162 | A1 | 6/2012 | Beaulieu et al. | |
| 2012/0167906 | A1 | 7/2012 | Gysland et al. | |
| 2012/0168977 | A1 | 7/2012 | Mazyar | |
| 2012/0199663 | A1 | 8/2012 | Qiu et al. | |
| 2012/0240783 | A1 | 9/2012 | Daburger et al. | |
| 2012/0312313 | A1 | 12/2012 | Frija et al. | |
| 2013/0037042 | A1 | 2/2013 | Hearn et al. | |
| 2013/0046463 | A1 | 2/2013 | Bengtson et al. | |
| 2013/0081642 | A1 | 4/2013 | Safari | |
| 2013/0111882 | A1 | 5/2013 | Eriksson | |
| 2013/0139894 | A1 | 6/2013 | Fuhr et al. | |
| 2013/0168880 | A1 | 7/2013 | Duke et al. | |
| 2013/0192615 | A1 | 8/2013 | Tucker et al. | |

(56) References Cited

U.S. PATENT DOCUMENTS

| | | | |
|---|---|---|---|
| 2013/0199528 | A1 | 8/2013 | Goodman et al. |
| 2013/0220315 | A1 | 8/2013 | Conley et al. |
| 2013/0255702 | A1 | 10/2013 | Griffith et al. |
| 2013/0276799 | A1 | 10/2013 | Davidson et al. |
| 2013/0284192 | A1 | 10/2013 | Peleg et al. |
| 2013/0284194 | A1 | 10/2013 | Newton et al. |
| 2013/0298905 | A1 | 11/2013 | Levin et al. |
| 2013/0306064 | A1 | 11/2013 | Thorens et al. |
| 2013/0306084 | A1 | 11/2013 | Flick et al. |
| 2013/0319431 | A1 | 12/2013 | Cyphert et al. |
| 2013/0319438 | A1 | 12/2013 | Liu et al. |
| 2013/0327787 | A1 | 12/2013 | Koltay et al. |
| 2013/0340750 | A1 | 12/2013 | Thorens et al. |
| 2013/0341218 | A1 | 12/2013 | Liu |
| 2013/0342157 | A1 | 12/2013 | Liu et al. |
| 2014/0000638 | A1 | 1/2014 | Sebastian et al. |
| 2014/0008452 | A1 | 1/2014 | Iammatteo et al. |
| 2014/0014126 | A1 | 1/2014 | Peleg et al. |
| 2014/0020697 | A1 | 1/2014 | Liu et al. |
| 2014/0053858 | A1 | 2/2014 | Liu et al. |
| 2014/0060554 | A1 | 3/2014 | Collett et al. |
| 2014/0083443 | A1 | 3/2014 | Liu et al. |
| 2014/0096781 | A1 | 4/2014 | Sears et al. |
| 2014/0096782 | A1 | 4/2014 | Ampolini et al. |
| 2014/0097103 | A1 | 4/2014 | Cameron et al. |
| 2014/0107815 | A1 | 4/2014 | Lamothe et al. |
| 2014/0109905 | A1 | 4/2014 | Yamada et al. |
| 2014/0123989 | A1 | 5/2014 | Lamothe et al. |
| 2014/0123990 | A1 | 5/2014 | Timmermans et al. |
| 2014/0166029 | A1 | 6/2014 | Weigensberg et al. |
| 2014/0174459 | A1 | 6/2014 | Burstyn et al. |
| 2014/0190477 | A1 | 7/2014 | Qiu |
| 2014/0190496 | A1 | 7/2014 | Wensley et al. |
| 2014/0208824 | A1 | 7/2014 | Baechi |
| 2014/0212334 | A1 | 7/2014 | Klein et al. |
| 2014/0216961 | A1 | 8/2014 | Liu et al. |
| 2014/0242213 | A1 | 8/2014 | Mccarty |
| 2014/0246016 | A1 | 9/2014 | Terry et al. |
| 2014/0246035 | A1 | 9/2014 | Minskoff et al. |
| 2014/0251324 | A1 | 9/2014 | Xiang |
| 2014/0253144 | A1 | 9/2014 | Novak et al. |
| 2014/0261487 | A1 | 9/2014 | Chapman et al. |
| 2014/0261491 | A1 | 9/2014 | Hawes et al. |
| 2014/0270727 | A1 | 9/2014 | Ampolini et al. |
| 2014/0283825 | A1 | 9/2014 | Buchberger et al. |
| 2014/0283946 | A1 | 9/2014 | Kribs et al. |
| 2014/0286002 | A1 | 9/2014 | Liu et al. |
| 2014/0299137 | A1 | 10/2014 | Kieckbusch et al. |
| 2014/0299140 | A1 | 10/2014 | Liu et al. |
| 2014/0299141 | A1 | 10/2014 | Flick et al. |
| 2014/0299491 | A1 | 10/2014 | Liu et al. |
| 2014/0299492 | A1 | 10/2014 | Liu et al. |
| 2014/0321837 | A1 | 10/2014 | Flick |
| 2014/0334804 | A1 | 11/2014 | Choi |
| 2014/0338685 | A1 | 11/2014 | Amir |
| 2014/0345606 | A1 | 11/2014 | Talon |
| 2014/0345635 | A1 | 11/2014 | Rabinowitz et al. |
| 2014/0353185 | A1 | 12/2014 | Liu |
| 2014/0366898 | A1 | 12/2014 | Monsees et al. |
| 2015/0007835 | A1 | 1/2015 | Liu |
| 2015/0019258 | A1 | 1/2015 | Duke et al. |
| 2015/0022448 | A1 | 1/2015 | Chang |
| 2015/0027457 | A1 | 1/2015 | Janardhan et al. |
| 2015/0041345 | A1 | 2/2015 | Kerkar |
| 2015/0053217 | A1 | 2/2015 | Steingraber et al. |
| 2015/0097513 | A1 | 4/2015 | Guenther et al. |
| 2015/0101625 | A1 | 4/2015 | Newton et al. |
| 2015/0101940 | A1 | 4/2015 | Ash |
| 2015/0101945 | A1 | 4/2015 | Scatterday |
| 2015/0114409 | A1 | 4/2015 | Brammer et al. |
| 2015/0117842 | A1 | 4/2015 | Brammer et al. |
| 2015/0128966 | A1 | 5/2015 | Lord |
| 2015/0136158 | A1 | 5/2015 | Stevens et al. |
| 2015/0142387 | A1 | 5/2015 | Alarcon et al. |
| 2015/0144145 | A1 | 5/2015 | Chang et al. |
| 2015/0157053 | A1 | 6/2015 | Mayor |
| 2015/0164138 | A1 | 6/2015 | Liu |
| 2015/0181945 | A1 | 7/2015 | Tremblay |
| 2015/0196053 | A1 | 7/2015 | Liu |
| 2015/0196058 | A1 | 7/2015 | Lord |
| 2015/0208726 | A1 | 7/2015 | Liu |
| 2015/0208731 | A1 | 7/2015 | Malamud et al. |
| 2015/0216236 | A1 | 8/2015 | Bless et al. |
| 2015/0230521 | A1 | 8/2015 | Talon |
| 2015/0245654 | A1 | 9/2015 | Memari et al. |
| 2015/0245660 | A1 | 9/2015 | Lord |
| 2015/0258288 | A1 | 9/2015 | Sullivan |
| 2015/0272216 | A1 | 10/2015 | Xu et al. |
| 2015/0272217 | A1 | 10/2015 | Chen |
| 2015/0289565 | A1 | 10/2015 | Cadieux et al. |
| 2015/0305409 | A1 | 10/2015 | Recio et al. |
| 2015/0313284 | A1 | 11/2015 | Liu |
| 2015/0313287 | A1 | 11/2015 | Lu et al. |
| 2015/0327596 | A1 | 11/2015 | Alarcon et al. |
| 2015/0335074 | A1 | 11/2015 | Leung |
| 2015/0359263 | A1 | 12/2015 | Bellinger |
| 2015/0366268 | A1 | 12/2015 | Shabat |
| 2016/0021930 | A1 | 1/2016 | Minskoff et al. |
| 2016/0037826 | A1 | 2/2016 | Hearn et al. |
| 2016/0050976 | A1 | 2/2016 | Righetti |
| 2016/0052700 | A1 | 2/2016 | Hearn et al. |
| 2016/0053988 | A1 | 2/2016 | Quintana |
| 2016/0057811 | A1 | 2/2016 | Alarcon et al. |
| 2016/0073692 | A1 | 3/2016 | Alarcon et al. |
| 2016/0106936 | A1 | 4/2016 | Kimmel |
| 2016/0128384 | A1 | 5/2016 | Luciani et al. |
| 2016/0150824 | A1 | 6/2016 | Memari et al. |
| 2016/0157524 | A1 | 6/2016 | Leon et al. |
| 2016/0198770 | A1 | 7/2016 | Alarcon |
| 2016/0206000 | A1 | 7/2016 | Mullin et al. |
| 2016/0213066 | A1 | 7/2016 | Borkovec et al. |
| 2016/0219933 | A1 | 8/2016 | Henry, Jr. et al. |
| 2016/0255877 | A1 | 9/2016 | Wu |
| 2016/0271347 | A1 | 9/2016 | Raichman et al. |
| 2016/0271959 | A1 | 9/2016 | Campbell-Brown et al. |
| 2016/0278435 | A1 | 9/2016 | Choukroun et al. |
| 2016/0280450 | A1 | 9/2016 | Hearn et al. |
| 2016/0286860 | A1 | 10/2016 | Flayler et al. |
| 2016/0331913 | A1 | 11/2016 | Bourque |
| 2016/0338407 | A1 | 11/2016 | Kerdemelidis |
| 2016/0345621 | A1 | 12/2016 | Smith et al. |
| 2016/0353801 | A1 | 12/2016 | Zinovik et al. |
| 2016/0360789 | A1 | 12/2016 | Bramley et al. |
| 2016/0366939 | A1 | 12/2016 | Alarcon et al. |
| 2017/0013883 | A1 | 1/2017 | Han et al. |
| 2017/0014582 | A1 | 1/2017 | Skoda |
| 2017/0020192 | A1 | 1/2017 | Fregonese et al. |
| 2017/0042244 | A1 | 2/2017 | Batista et al. |
| 2017/0071257 | A1 | 3/2017 | Lin |
| 2017/0105449 | A1 | 4/2017 | Hearn et al. |
| 2017/0135401 | A1 | 5/2017 | Dickens et al. |
| 2017/0156399 | A1 | 6/2017 | Freeman et al. |
| 2017/0188946 | A1 | 7/2017 | Klusmann et al. |
| 2017/0215485 | A1 | 8/2017 | Zitzke |
| 2017/0222468 | A1 | 8/2017 | Schennum et al. |
| 2017/0238613 | A1 | 8/2017 | Suess et al. |
| 2017/0245551 | A1 | 8/2017 | Reevell |
| 2017/0334605 | A1 | 11/2017 | Murphy et al. |
| 2017/0347709 | A1* | 12/2017 | Laakso .................. A24F 40/42 |
| 2017/0360093 | A1 | 12/2017 | Fernando |
| 2018/0042306 | A1 | 2/2018 | Atkins et al. |
| 2018/0104958 | A1 | 4/2018 | Campbell-Brown et al. |
| 2018/0220707 | A1 | 8/2018 | Biel et al. |
| 2019/0046745 | A1 | 2/2019 | Nettenstrom et al. |

FOREIGN PATENT DOCUMENTS

| | | | |
|---|---|---|---|
| CN | 202679020 | U | 1/2013 |
| CN | 103914013 | A | 7/2014 |
| CN | 203873004 | U | 10/2014 |
| CN | 204232301 | U | 4/2015 |
| CN | 204273244 | U | 4/2015 |
| CN | 104783332 | A | 7/2015 |
| CN | 105494479 | A | 4/2016 |

(56) References Cited

FOREIGN PATENT DOCUMENTS

| | | | |
|---|---|---|---|
| DE | 102007011120 | A1 | 9/2008 |
| EP | 1618803 | A1 | 1/2006 |
| EP | 2022349 | A1 | 2/2009 |
| EP | 2047914 | A | 4/2009 |
| EP | 2060397 | A1 | 5/2009 |
| EP | 2201850 | A1 | 6/2010 |
| EP | 2399636 | A1 | 12/2011 |
| EP | 2454956 | A1 | 5/2012 |
| EP | 2468116 | A1 | 6/2012 |
| EP | 2468118 | A1 | 6/2012 |
| EP | 2727619 | A2 | 5/2014 |
| EP | 3020290 | A1 | 5/2016 |
| EP | 3127439 | A1 | 2/2017 |
| GB | 2507102 | A | 4/2014 |
| GB | 2512325 | A | 10/2014 |
| GB | 2512326 | A | 10/2014 |
| GB | 2518598 | A | 4/2015 |
| GB | 2523585 | A | 9/2015 |
| GB | 2525725 | A | 11/2015 |
| GB | 2525727 | A | 11/2015 |
| GB | 2529629 | A | 3/2016 |
| GB | 2529919 | A | 3/2016 |
| GB | 2531830 | A | 5/2016 |
| GB | 2534726 | A | 8/2016 |
| GB | 2535239 | A | 8/2016 |
| JP | H09149781 | A | 6/1997 |
| KR | 20110009056 | U | 9/2011 |
| KR | 1020130091473 | A1 | 8/2013 |
| WO | 2005/025654 | A | 3/2005 |
| WO | 2009001078 | A2 | 12/2008 |
| WO | 2010/073018 | A1 | 7/2010 |
| WO | 2010073122 | A1 | 7/2010 |
| WO | 2011026846 | A1 | 3/2011 |
| WO | 2011/095781 | A1 | 8/2011 |
| WO | 2013020220 | A4 | 3/2013 |
| WO | 2013/060781 | A1 | 5/2013 |
| WO | 2013/098397 | | 7/2013 |
| WO | 2013138384 | A2 | 9/2013 |
| WO | 2014/040988 | A1 | 3/2014 |
| WO | 2014/054035 | A1 | 4/2014 |
| WO | 2014/102091 | A1 | 7/2014 |
| WO | 2014/190079 | A2 | 11/2014 |
| WO | 2015028814 | A1 | 3/2015 |
| WO | 2015035741 | A1 | 3/2015 |
| WO | 2015051538 | A1 | 4/2015 |
| WO | 2015/063126 | A1 | 5/2015 |
| WO | 2015/091258 | A1 | 6/2015 |
| WO | 2015/127429 | A4 | 8/2015 |
| WO | 2015/128667 | A1 | 9/2015 |
| WO | 2015/149242 | A1 | 10/2015 |
| WO | 2015/165059 | A1 | 11/2015 |
| WO | 2015/179002 | A2 | 11/2015 |
| WO | 2015179641 | A1 | 11/2015 |
| WO | 2016/009202 | A1 | 1/2016 |
| WO | 2016/040575 | A1 | 3/2016 |
| WO | 2016/096728 | A1 | 6/2016 |
| WO | 2016/096780 | A1 | 6/2016 |
| WO | 2016/150922 | A2 | 9/2016 |

* cited by examiner

PUMP WITH PISTON ASSY IN “START” POSITION
FLUID CHAMBER CHARGED

PUMP WITH FEED THRO HOLE IN "OPEN" POSITION

PUMP WITH PISTON ASSY IN "DOWN" POSITION

VIEW SHOWING PUMP WITH PISTON ASSEMBLY AT END OF 3mm STROKE – FLUID IN CHAMBER NO LONGER PRESSURISED, PISTON PUSHED BACK OVER FEED THRO HOLE BY BIAS SPRING.

PUMP WITH PISTON ASSY IN "START" POSITION
FLUID CHAMBER CHARGING

INTEGRATED PUMP / RESERVOIR / OVERFLOW VALVE IN "START" POSITION

INTEGRATED PUMP / RESERVOIR / OVERFLOW VALVE IN "OPEN" POSITION

INTEGRATED PUMP / RESERVOIR / OVERFLOW VALVE IN "DOWN" POSITION

INTEGRATED PUMP / RESERVOIR / OVERFLOW VALVE IN “BYPASS” CONDITION

THIS POSITION IS CONDITIONAL ON HYDRAULIC DESIGN LIMIT BEING EXCEEDED

INTEGRATED PUMP / RESERVOIR / OVERFLOW VALVE IN "RETURN" POSITION

VAPING VARIABLE AIR INTAKE
SQUARE INNER & OUTER MATRIX
AIR PATH WITH 5 ROWS OF HOLES LINED UP

EXPLODED VIEW OF HELICAL HELIX OUTER TUBE AND SQUARE MATRIX INNER TUBE

FLUID MOVEMENT

1. CARTRIDGE BODY IS FILLED WITH FLUID & SEALED WITH FOIL CAP
2. SYRINGE CARTRIDGE INSERTED INTO PV BODY & FOIL CAP PENETRATED BY HOLLOW SPIGOT
3. PISTON ADVANCES ALONG CARTRIDGE BODY WHEN SCREW IS TURNED
4. FLUID AHEAD OF PISTON IS TRANSFERRED THROUGH NOZZLE INTO HOLLOW SPIGOT

FLUID MOVEMENT
FIGURE 101 A, B & C
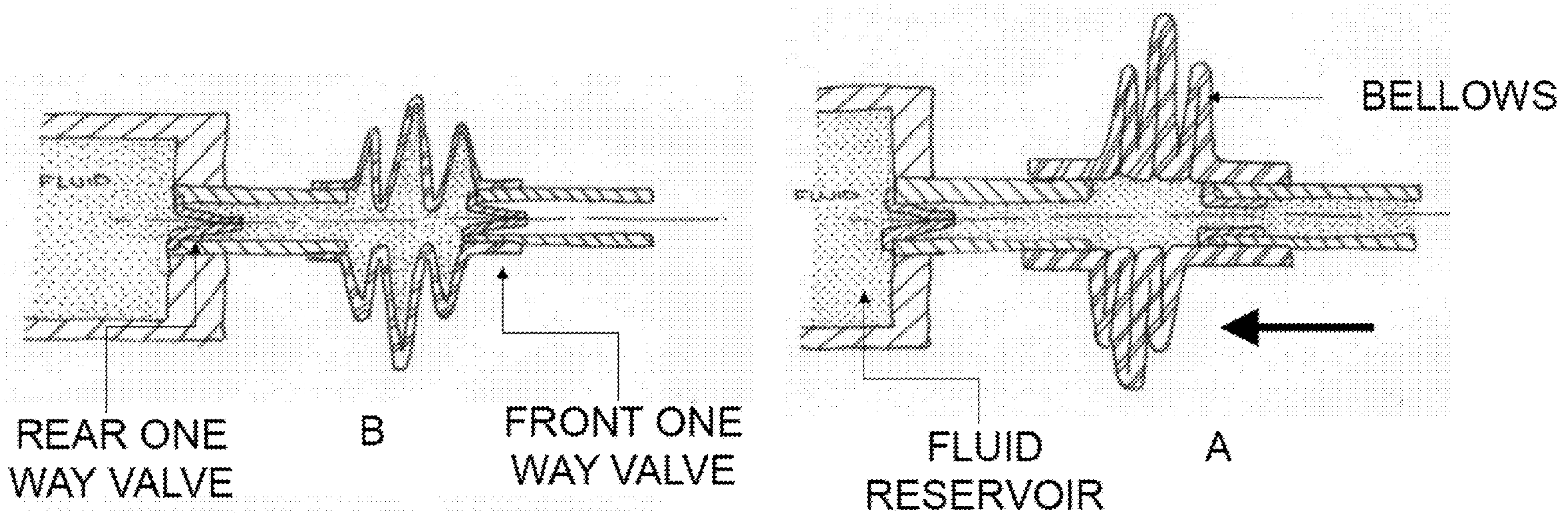
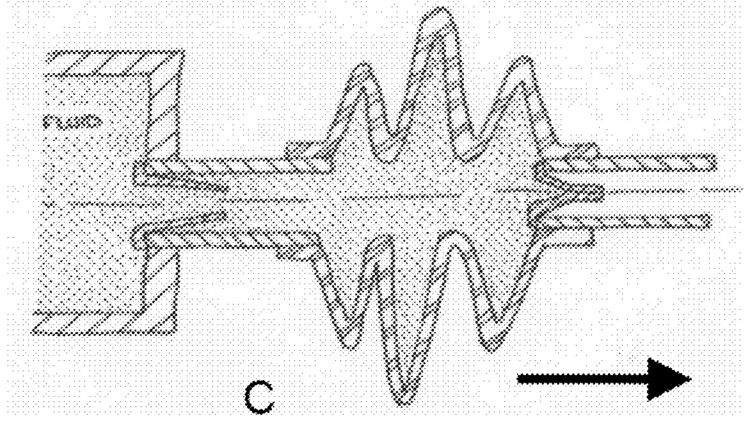
1. BELLOWS FORMS AN INTEGRAL PART OF CARTRIDGE
2. 2 ONE WAY VALVES IN FLUID LINE
3. FIG A – BELLOWS FILLS WITH FLUID WHEN OPENED
4. FIG B – BELLOWS COMPRESSED EXPELLING FLUID THROUGH FRONT ONE WAY VALVE
5. FIG C - BELLOWS REFILLS WITH FLUID WHEN OPENED FLUID MOVEMENT FIGURE 102 A&B
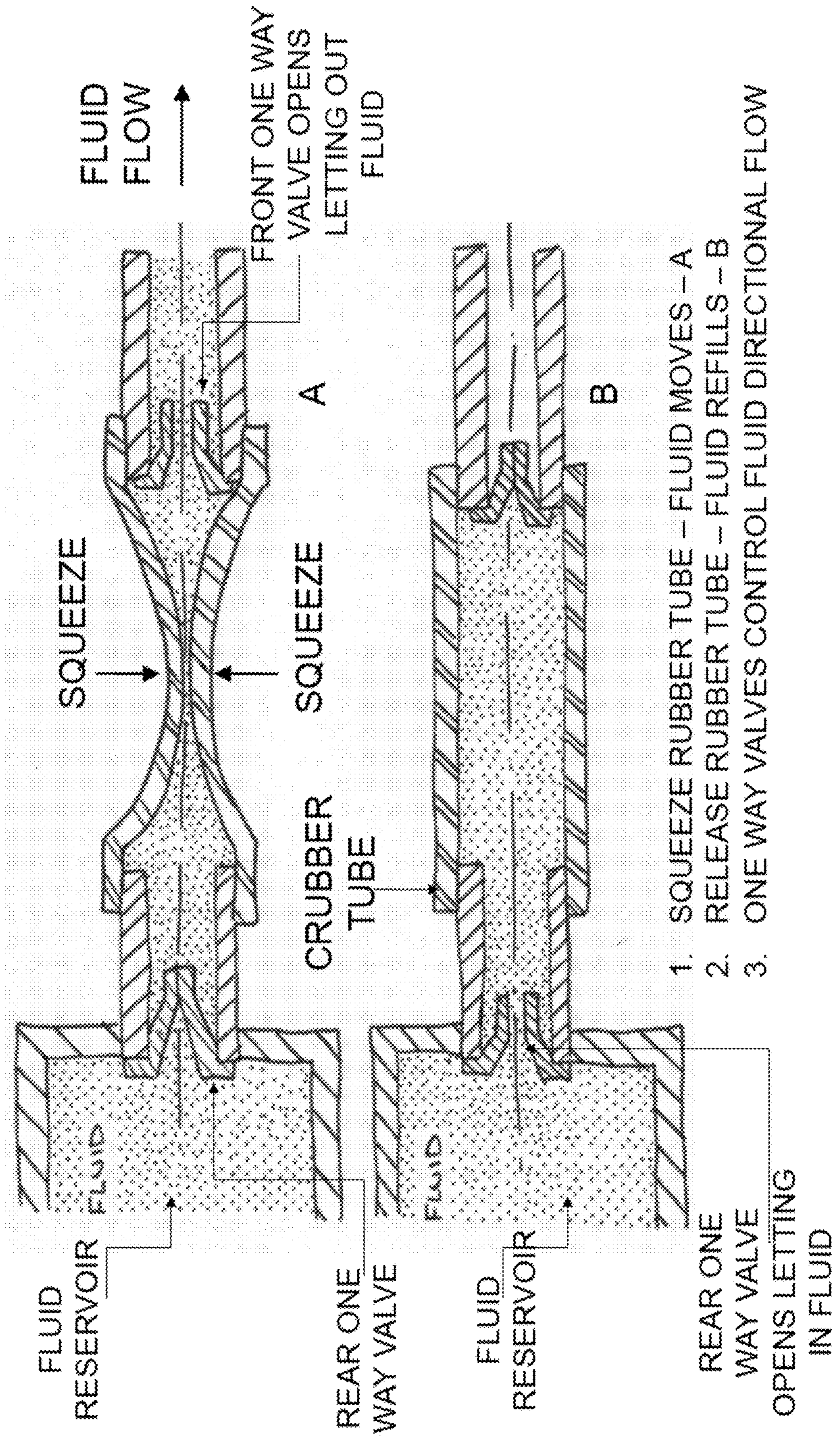

FLUID MOVEMENT

1. PUMP IS ROTATED COMPRESSING TUBE
2. FLUID FLOWS FROM TUBE TO COIL/WICK
3. TUBE DRAWS FLUID FROM CARTRIDGE RESERVOIR

FLUID MOVEMENT

1. SEALED & FLUID FILLED CARTRIDGE INSERTED INTO PV
2. PV HOLLOW FLUID SPIGOT PENETRATES FOIL CAP & SEALS
3. LINEAR MOVEMENT OF OUTER COLLAR MOVES PISTON – SCREW THREAD
4. PISTON MAGNETICALLY COUPLED TO OUTER COLLAR

FLUID MOVEMENT FIGURE 105

1. FILLED CARTRIDGE PUMP INSERTED INTO PV
2. PUMP STEM PUSHED INWARDS TRANSFERRING FLUID FROM CARTRIDGE PARENT RESERVOIR TO PV CHILD RESERVOIR
3. PUMP STEM RETURNS LIFTING ONE WAY VALVE OFF IT'S SEAT & REPLENISHES PUMP CHAMBER
4. WHOLE CARTRIDGE / PUMP FITS INTO PV AND SEALS WITH "O" RINGS

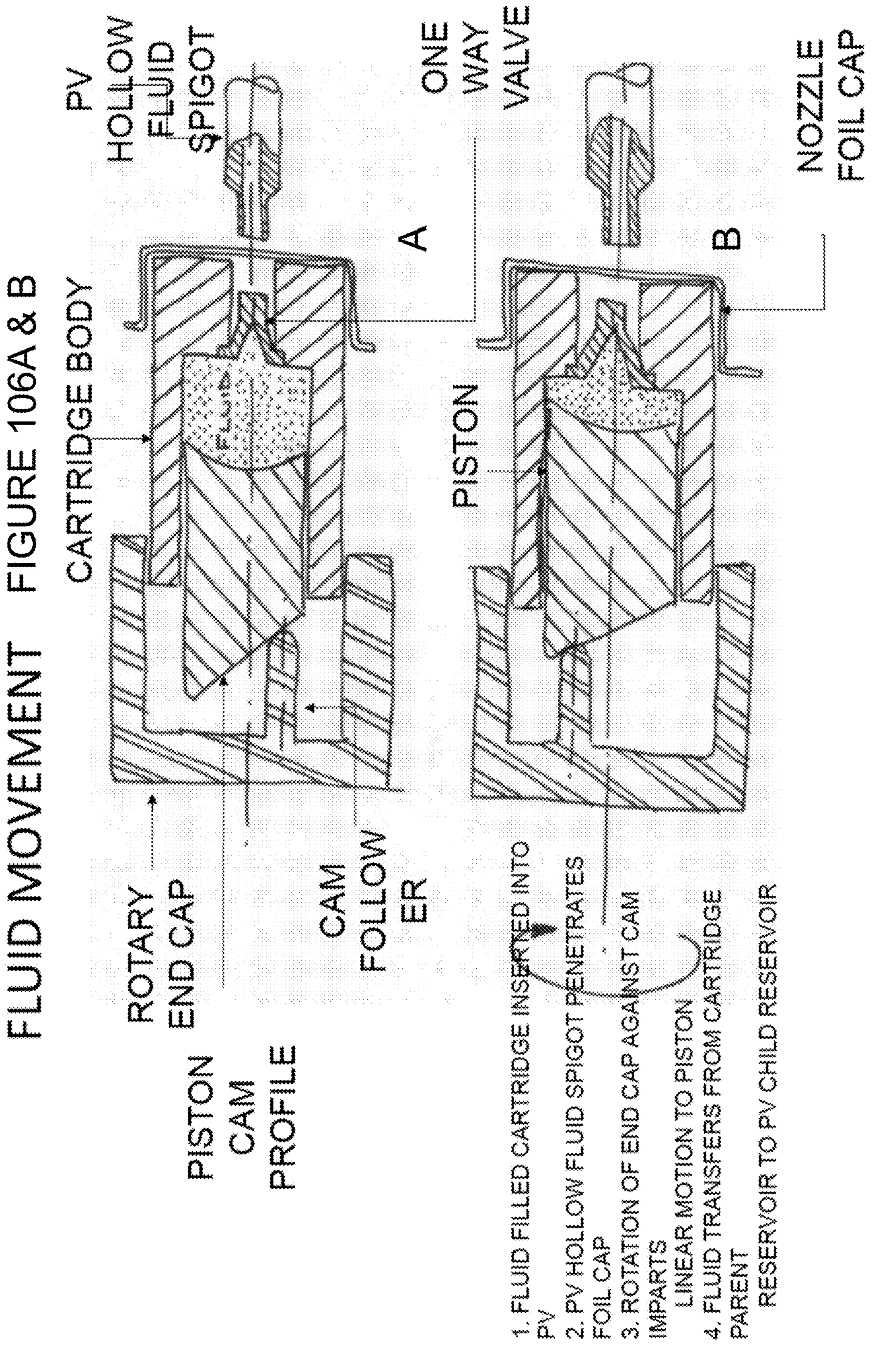
FLUID MOVEMENT FIGURE 106A & B
CARTRIDGE BODY
PV HOLLOW FLUID SPIGOT
ONE WAY VALVE
A
B
NOZZLE FOIL CAP
PISTON
ROTARY END CAP
PISTON CAM PROFILE
CAM FOLLOW ER
1. FLUID FILLED CARTRIDGE INSERTED INTO PV
2. PV HOLLOW FLUID SPIGOT PENETRATES FOIL CAP
3. ROTATION OF END CAP AGAINST CAM IMPARTS
LINEAR MOTION TO PISTON
4. FLUID TRANSFERS FROM CARTRIDGE PARENT
RESERVOIR TO PV CHILD RESERVOIR

FLUID MOVEMENT FIGURE 107

1. FLUID FILLED & SEALED CARTRIDGE INSERTED INTO PV
2. NOZZLE PENETRATES PV
3. ROTATING END CAP CAUSES ARCHIMEDES SCREW TO ROTATE DISPLACING FLUID FROM CARTRIDGE PARENT RESERVOIR TO PV CHILD RESERVOIR

FLUID MOVEMENT FIGURE 108

1. FLUID FILLED CARTRIDGE INSERTED INTO PV
2. PV HOLLOW FLUID SPIGOT PENETRATES FOIL CAP & SEALS
3. ROTATION OF END CAP IMPARTS LINEAR MOTION TO PISTON VIA EXTERNAL THREAD
4. FLUID TRANSFERS FROM CARTRIDGE PARENT RESERVOIR TO PV CHILD RESERVOIR

FLUID MOVEMENT FIGURE 109

1. FLUID FILLED CARTRIDGE INSERTED INTO PV
2. PV HOLLOW FLUID SPIGOT PENETRATES FOIL CAP & SEALS
3. PISTON REMAINS FIXED WITH CARTRIDGE BODY MOVING IN LINEAR DIRECTION MOVING FLUID AHEAD
4. FLUID TRANSFERS FROM CARTRIDGE PARENT RESERVOIR TO PV CHILD RESERVOIR

FLUID MOVEMENT FIGURE 110A

1. FLUID FILLED CARTRIDGE INSERTED INTO PV – FLUID IN CONCENTRIC RING – COULD BE PV FULL LENGTH
2. PV FLUID SPIGOT WITH SEALING “O” RINGS DOCKS WITH CONCENTRIC CARTRIDGE
3. FLUID TRANSFERS FROM CARTRIDGE PARENT RESERVOIR TO PV CHILD RESERVOIR UNDER GRAVITY
4. OLEOPHOBIC WASHER ALLOWS AIR PRESSURE EQUALISATION ALLOWING FREE FLOW OF FLUID

FLUID MOVEMENT FIGURE 110B

FLUID MOVEMENT

1. TAPERED TRIANGULAR GEOMETRY FLUID RESERVOIR FOR INCREASED CAPACITY
2. COULD FIT INSIDE SIMILAR SHAPE PV
3. COULD CONNECT TO BACK OF PV SUCH THAT RESERVOIR BECOMES PART OF THE PRODUCT
4. GRAVITY TRANSFER OF LIQUID FROM PARENT RESRVOIR IN CARTRIDGE TO CHILD RESERVOIR IN PV

1. PYRAMID GEOMETRY FLUID RESERVOIR FOR INCREASED CAPACITY
2. PV RECHARGE FROM PYRAMID BY INSERTING INTO APEX OF PYRAMID
3. COULD CONNECT TO BACK OF PV SUCH THAT RESERVOIR BECOMES PART OF THE PRODUCT

FLUID MOVEMENT FIGURE 116A
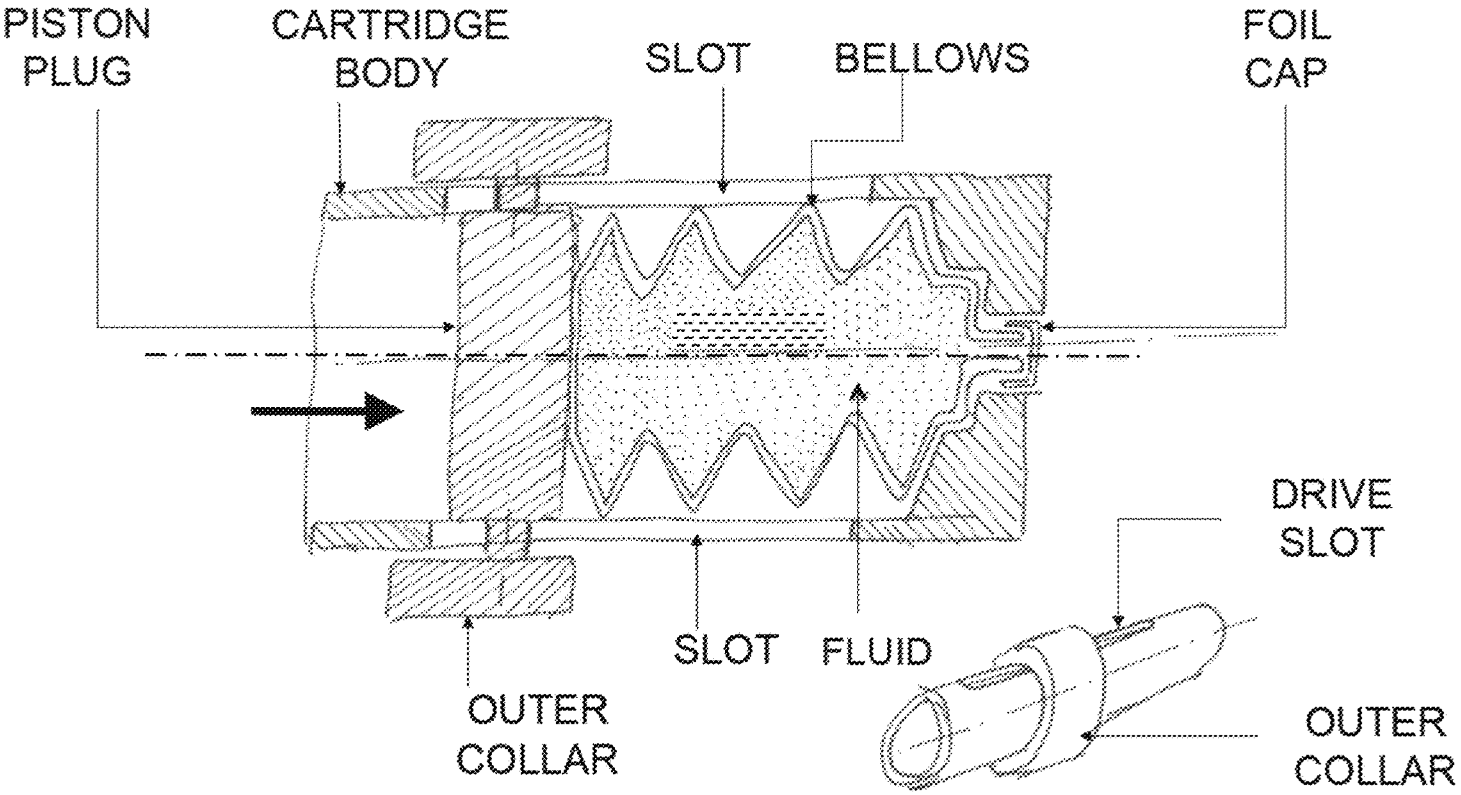
1. FLEXIBLE BELLOWS CARTRIDGE FULL OF FLUID AND SEALED WITH FOIL CAP
2. BELLOWS CARTRIDGE INSERTED INTO PV – FOIL CAP PENETRATED BY HOLLOW FLUID PV SPIGOT
2. OUTER COLLAR SLID IN A LINEAR MOTION COMPRESSING THE BELLOWS DISPLACING FLUID FROM PARENT RESERVOIR TO PV CHILD RESERVOIR FLUID MOVEMENT FIGURE 116B
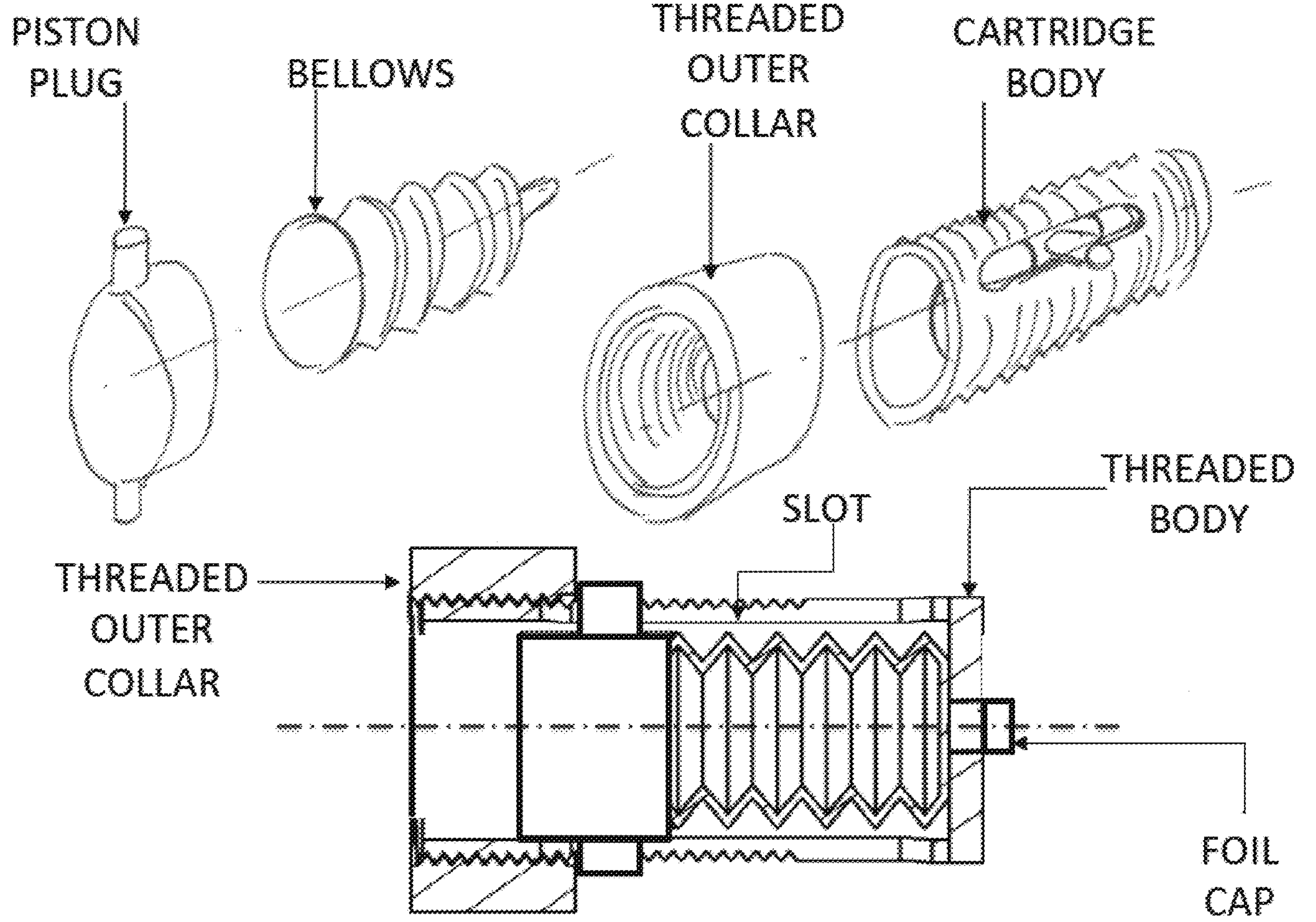
1. FLEXIBLE BELLOWS CARTRIDGE FULL OF FLUID AND SEALED WITH FOIL CAP
2. BELLOWS CARTRIDGE INSERTED INTO PV – FOIL CAP PENETRATED BY HOLLOW FLUID PV SPIGOT
3. PARENT RESERVOIR TO PV CHILD RESERVOIR. OUTER COLLAR MOVED BY SCREW THREAD.

FLUID MOVEMENT FIGURE 116C
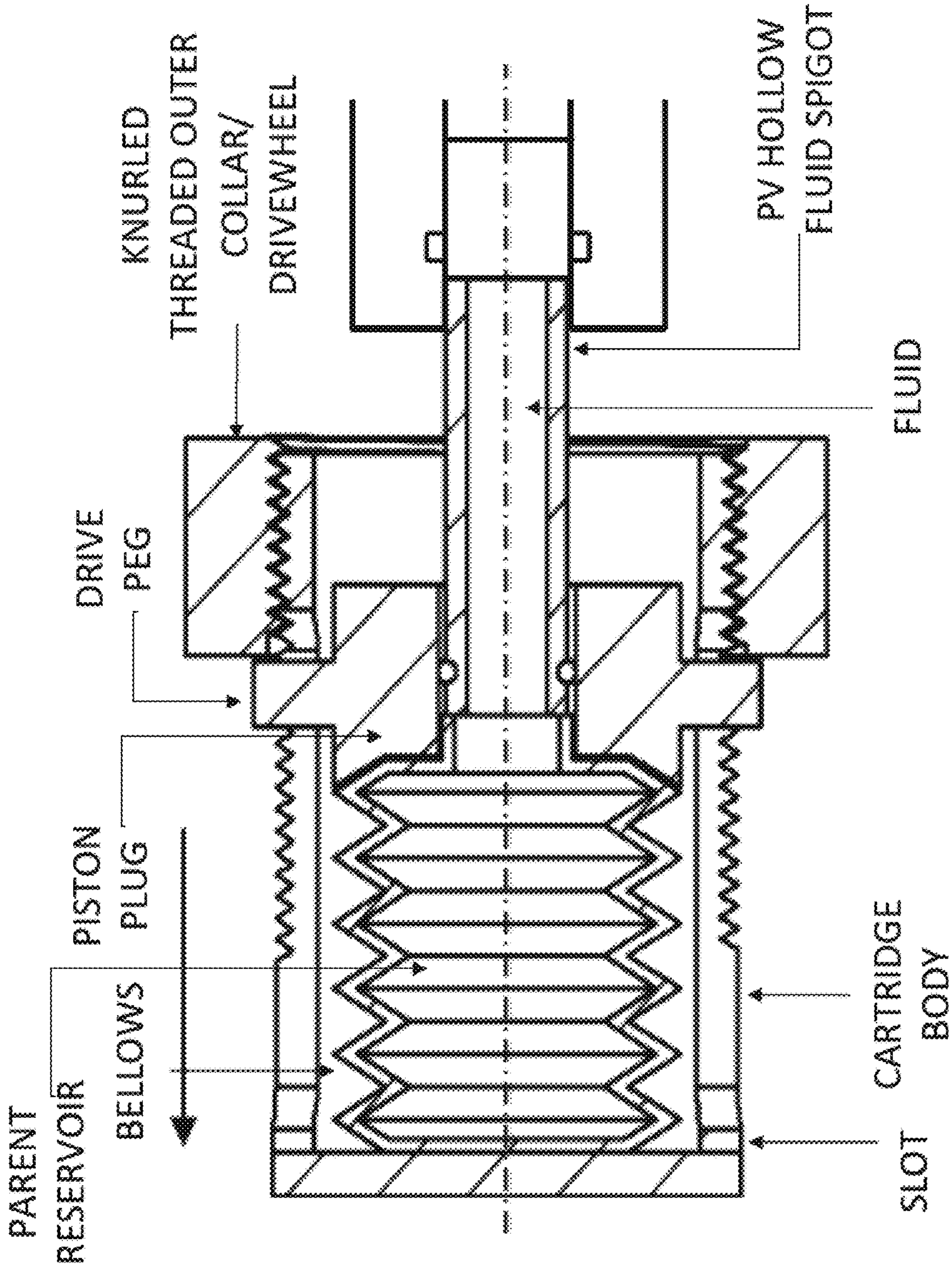
1. FLEXIBLE BELLOWS CARTRIDGE FULL OF FLUID AND SEALED WITH FOIL CAP.
2. BELLOWS CARTRIDGE INSERTED INTO PV & CONNECTS TO PV HOLLOW FLUID SPIGOT
3. OUTER COLLAR SCREWS AGAINST DRIVE PEGS (RUNNING IN DRIVE SLOTS) COMPRESSING BELLOWS & DRIVING FLUID FROM CARTRIDGE PARENT RESERVOIR TO PV CHILD RESERVOIR

FLUID MOVEMENT FIGURE 116E

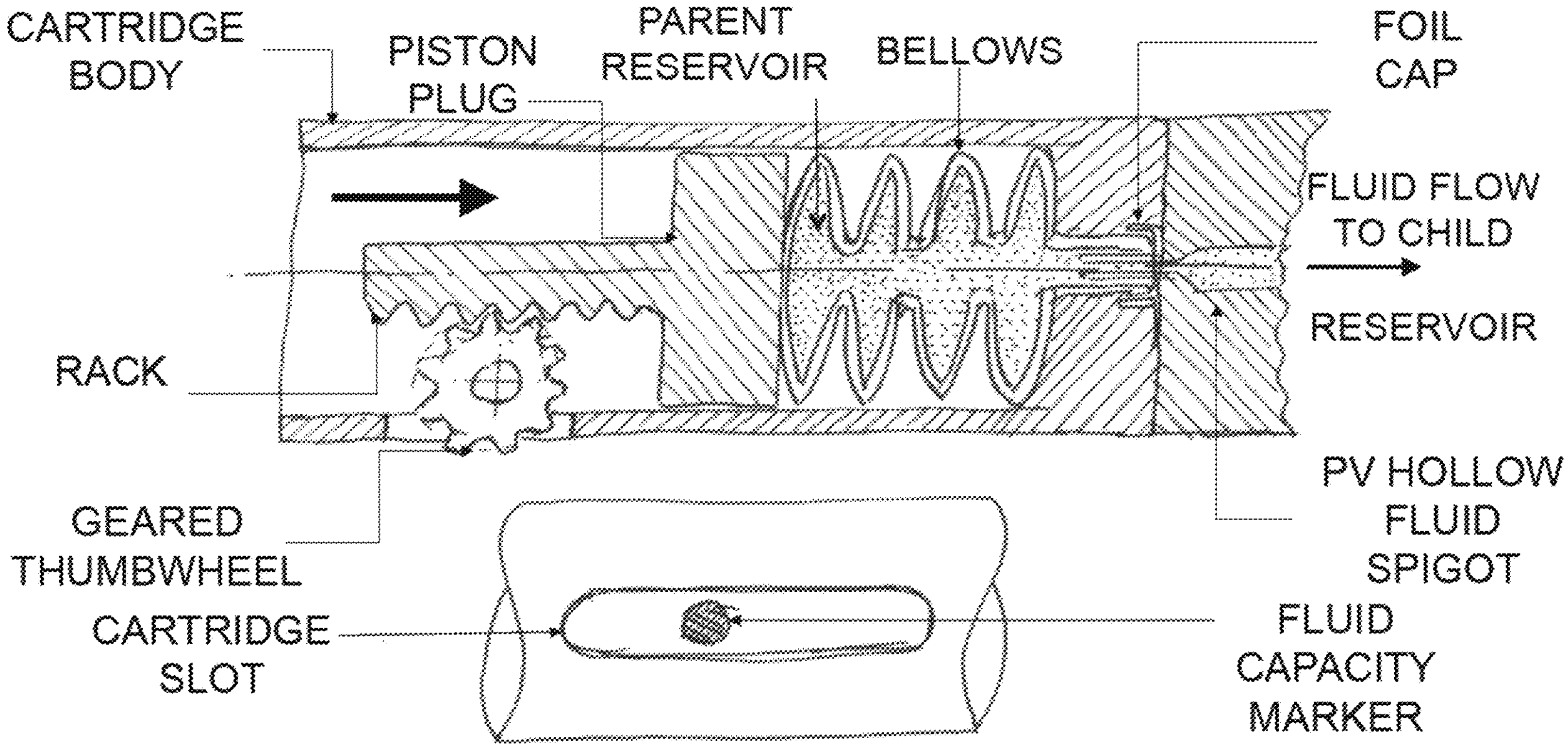

1. FLEXIBLE BELLOWS CARTRIDGE FULL OF FLUID AND SEALED WITH FOIL CAP.
2. BELLOWS CARTRIDGE INSERTED INTO PV.
3. PV HOLLOW FLUID SPIGOT PIERCES FOIL CAP AND CONNECTS TO FLUID PARENT RESERVOIR
3. GEARED THUMBWHEEL ROTATED & IMPARTS LINEAR MOTION TO PISTON PLUG COMPRESSING FLUID FILLED BELLOWS
4. LIQUID TRANSFERS FROM PARENT RESERVOIR IN CARTRIDGE TO CHILD RESERVOIR IN PV
5. GEARED THUMBWHEEL POSITION FIXED, FLUID CAPACITY INDICATED BY MARKER ON PISTON PLUG VISIBLE THROUGH SLOT IN CARTRIDGE

E-CIGARETTE PERSONAL VAPORIZER

CROSS-REFERENCE TO RELATED APPLICATIONS

This application is a continuation of U.S. application Ser. No. 16/825,106, filed on Mar. 20, 2020, which is a continuation of U.S. application Ser. No. 16/177,708, filed Nov. 1, 2018, which is a continuation of U.S. application Ser. No. 14/842,067, filed Sep. 1, 2015, which is a continuation-in-part of U.S. application Ser. No. 14/633,887, filed Feb. 27, 2015, which is based on and claims priority to GB Application No. 1403566.1, filed Feb. 28, 2014; GB Application No. 1408173.1, filed May 8, 2014; GB Application No. 1413018.1, filed Jul. 23, 2014; GB Application No. 1413019.9, filed Jul. 23, 2014; GB Application No. 1413021.5, filed Jul. 23, 2014; GB Application No. 1413025.6, filed Jul. 23, 2014; GB Application No. 1413027.2, filed Jul. 23, 2014; GB Application No. 1413028.0, filed Jul. 23, 2014; GB Application No. 1413030.6, filed Jul. 23, 2014; GB Application No. 1413032.2, filed Jul. 23, 2014; GB Application No. 1413034.8, filed Jul. 23, 2014; GB Application No. 1413036.3, filed Jul. 23, 2014; GB Application No. 1413037.1, filed Jul. 23, 2014; U.S. Provisional Application No. 62/045,651, filed Sep. 4, 2014; U.S. Provisional Application No. 62/045,657, filed Sep. 4, 2014; U.S. Provisional Application No. 62/045,666, filed Sep. 4, 2014; U.S. Provisional Application No. 62/045,669, filed Sep. 4, 2014; U.S. Provisional Application No. 62/045,674, filed Sep. 4, 2014; U.S. Provisional Application No. 62/045,680, filed Sep. 4, 2014; U.S. Provisional Application No. 62/045,688, filed Sep. 4, 2014; U.S. Provisional Application No. 62/045,690, filed Sep. 4, 2014; U.S. Provisional Application No. 62/045,692, filed Sep. 4, 2014; U.S. Provisional Application No. 62/045,696, filed Sep. 4, 2014; and U.S. Provisional Application No. 62/045,701, filed Sep. 4, 2014, the entire contents of each of which being fully incorporated herein by reference.

BACKGROUND OF THE INVENTION

1. Field of the Invention

The field of the invention relates to an electronic cigarette personal vapouriser, also known as an electronic cigarette (e-cig or e-cigarette), vapestick, modding kit, personal vaporizer (PV), advanced personal vaporizer (APVs) or electronic nicotine delivery system (ENDS). In this specification, we will typically use 'PV' or 'e-cigarette' as the generic term. A PV vapourises 'e-liquid' or vaping substance to produce a non-pressurised vapour or mist for inhalation for pleasure or stress-relief, replicating or replacing the experience of smoking a cigarette. An 'E-liquid' or vaping substance is a liquid (or gel or other state) from which vapour or mist for inhalation can be generated and whose primary purpose is to deliver nicotine.

PVs are therefore mass-market consumer products that are equivalent to cigarettes, and are typically used by smokers as part of a cigarette reduction or cessation program. The main ingredients of e-liquids are usually a mix of propylene glycol and glycerine and a variable concentration of tobacco-derived nicotine. E-liquids can include various flavourings and also come with varying strengths of nicotine; users on a nicotine reduction or cessation program can hence choose decreasing concentrations of nicotine, including at the limit zero concentration nicotine e-liquid. The term 'e-liquid' will be used in this specification as the generic term for any kind of vaping substance.

E-cigarette PVs were first conceived in 1963 and for the last 50 years of development have generally been seen as a separate and distinct category compared with conventional medicinal delivery systems. To emphasise the difference over medicinal devices, we will also in this specification use the term 'e-cigarette PV', as opposed to the term 'PV'.

Despite this sector being over 50 years old, there are still many practical problems that have not yet been solved and that are a barrier to e-cigarette PVs achieving mass-market success; they are still a long way from replacing conventional cigarettes. If they were to largely replace cigarettes, then some experts state that large-scale adoption could bring significant public health benefits. Writing in the British Journal of General Practice, DOI: 10.3399/bjgp14X681253, published 1 Sep. 2014, Prof Robert West and Dr Jamie Brown from University College London stated that "For every million smokers who switched to an e-cigarette we could expect a reduction of more than 6000 premature deaths in the UK each year, even in the event that e-cigarette use carries a significant risk of fatal diseases, and users were to continue to use them indefinitely."

2. Technical Background

PVs are typically battery-powered devices which simulate tobacco smoking by producing inhalable vapour (typically propylene glycol and nicotine). They generally use a heating element known as an atomizer, that vaporizes a liquid solution known as e-liquid or 'juice'. E-liquids usually contain a mixture of propylene glycol, vegetable glycerin, nicotine, and flavorings, while others release a flavored vapor without nicotine. Vaporization is an alternative to burning (smoking) that avoids the inhalation of many irritating toxic and carcinogenic by-products. Apart from simulating tobacco smoking, the electronic vapouriser can also be used as a smoking-cessation aid or for nicotine (or other substance) dosage control.

Most electronic cigarettes take an overall cylindrical shape although a wide array of shapes can be found: box, pipe styles etc. First generation electronic cigarettes were usually designed to simulate cigarettes in their use and appearance. They are often called 'cig-a-likes'. Cig-a-likes are usually disposable, low cost items and the user-experience is often quite poor. New generation electronic cigarettes, often called mods, modding-kits or APV's (advanced personal vaporizer) have an increased nicotine-dispersal performance, housing higher capacity batteries and come in various form factors, including metal tubes and boxes. Many electronic cigarettes are composed of standardized replaceable parts that are interchangeable from one brand to the other, while disposable devices combine all components into a single part that is discarded when its liquid is depleted. Common components include a liquid delivery and container system like a cartridge or a tank, an atomizer, and a power source.

Atomizer

An atomizer generally consist of a small heating element responsible for vaporizing e-liquid, as well as a wicking material that draws liquid in. Along with a battery, the atomizer is the central component of every personal vaporizer. Differences between atomizers cause differences in the ingredients and their concentrations delivered to users, even when the same liquid is used.

A small length of resistance wire is coiled around the wicking material and then connected to the positive and negative poles of the device. When activated the resistance wire (or coil) quickly heats up, thus turning the liquid into a vapor, which is then inhaled by the user.

Wicking materials vary greatly from one atomizer to another but silica fibers are the most commonly used in manufactured atomizers. A wide array of atomizers and e-liquid container combinations are available.

Cartomizers

A cartomizer (a portmanteau of cartridge and atomizer) or 'carto' consists of an atomizer surrounded by a liquid-soaked poly-foam that acts as an e-liquid holder. It is usually disposed of once the e-liquid acquires a burnt taste, which is usually due to an activation when the coil is dry or when the cartomizer gets consistently flooded (gurgling) because of sedimentation of the wick. Most cartomizers are refillable even if not advertised as such.

Cartomizers can be used on their own or in conjunction with a tank that allows more e-liquid capacity. In this case the portmanteau word of "carto-tank" has been coined. When used in a tank, the cartomizer is inserted in a plastic, glass or metal tube and holes or slots have to be punched on the sides of the cartomizer to allow liquid to reach the coil.

Clearomizers

Clearomizers or "clearos", not unlike cartotanks, use a clear tank in which an atomizer is inserted. Unlike carto-tanks, however, no poly-foam material can be found in them. There are a lot of different wicking systems employed inside of clearomizers to ensure good moistening of the wick without flooding the coil. Some rely on gravity to bring the e-liquid to the wick and coil assembly (bottom coil clearomizers for example) whereas others rely on capillary action and to some degree the user agitating the e-liquid while handling the clearomizer (top coil clearomizers)

Power

Most portable devices contain a rechargeable battery, which tends to be the largest component of an electronic cigarette. The battery may contain an electronic airflow sensor whereby activation is triggered simply by drawing breath through the device, while other models employ a power button that must be held during operation. An LED to indicate activation may also be employed. Some manufacturers also offer a cigarette pack-shaped portable charging and re-filling case (PCC), which contains a larger battery capable of charging e-cigarettes. Devices aimed at more experienced users may sport additional features, such as variable power output and support of a wide range of internal batteries and atomizer configurations and tend to stray away from the cigarette form factor. Some cheaper recent devices use an electret microphone with a custom IC to detect airflow and indicate battery status on the included blue LED.

Variable Power and Voltage Devices

Variable voltage or power personal vaporizers are devices that contain a built in electronic chip that allows the user to adjust the power that goes through the heating element. They usually incorporate a LED screen to display various information. Variable PV's eliminate the need of having to replace an atomizer with another one of lower or higher electrical resistance to change the intensity of the vapour (the lower the resistance, the higher the vapour intensity). They also feature voltage regulation and some battery protection.

Some of these devices offer additional features through their menu system such as: atomizer resistance checker, remaining battery voltage, puff counter, activation cut-off etc.

E-Liquid

E-liquid, e-juice or simply "juice", refers to a liquid solution that produces a mist or vapour when heated by an atomizer. The main ingredients of e-liquids are usually a mix of propylene glycol (PG), vegetable glycerin (VG), and/or polyethylene glycol 400 (PEG400), sometimes with differing levels of alcohol mixed with concentrated or extracted flavorings; and a variable concentration of tobacco-derived nicotine. There is variability in the purity, kinds and concentrations of chemicals used in liquids, and significant variability between labeled content and concentration and actual content and concentration E-liquid is often sold in bottles or pre-filled disposable cartridges, or as a kit for consumers to make their own. Components are also available individually and consumers may choose to modify or boost their flavor, nicotine strength, or concentration with various offerings. Pre-made e-liquids are manufactured with various tobacco, fruit, and other flavors, as well as variable nicotine concentrations (including nicotine-free versions). The standard notation "mg/ml" is often used in labeling for denoting nicotine concentration, and is sometimes shortened to a simple "mg".

Source acknowledgement for this Technical Background section: Wikipedia entry on e-cigarettes.

3. Discussion of Related Art

The patent literature in this field is quite extensive, with the earliest e-cigarette PV dating from 1963.

Some of the more relevant patent disclosures in this space include the following. We highlight some of the main reasons why each item of prior art lacks relevance.

US 2014/020697 Liu.
- Just a PV charging device
- No e-liquid re-filling capability
- No user-replaceable e-liquid cartridge
- No data processor with communications capability CN 202679020 Chen:
- Just a PV charging device
- No e-liquid re-filling capability
- No user-replaceable e-liquid cartridge
- No data processor with communications capability US 2013/342157 Liu
- Just a PV charging device
- No e-liquid re-filling capability
- No user-replaceable e-liquid cartridge
- No data processor with communications capability CN 201630238 Jian
- Just a PV charging device
- No e-liquid re-filling capability
- No user-replaceable e-liquid cartridge
- No data processor with communications capability WO 2011/095781 Kind
- Not e-liquid, e-cigarette related
- No e-liquid re-filling capability—fills a pressurised gas instead
- No user-replaceable e-liquid cartridge (the gas canister is not described as being user-replaceable and doing so would in fact require the user to take the entire unit to pieces, so it teaches away from user-replaceability)
- No electrical charging capability (device has no battery)
- No data processor with communications capability US 2012/167906 Gysland
- Not a PV charging device
- Just an e-liquid filling device, using a standard e-liquid squeezable bottle; the user unscrews the PV, separating it into an atomiser portion and an e-liquid chamber portion, and then screws the e-liquid chamber portion into one end of this device and screws the squeezable bottle into the other end of this device and then squeezes the bottle to transfer the e-liquid over.
No charging capability
No data processor with communications capability
WO 2011/026846 Wedegree
Not e-liquid PV related—instead, it's a propane powered heat-based device
No e-liquid re-filling, just re-fills a device with liquid propane
Mouthpiece is removed before the device is inserted for gas re-filling
No charging capability
No user-replaceable cartridge
No data processor with communications capability
WO 2009/001078 Kind
Not e-liquid, e-cigarette related
No e-liquid re-filling—fills pressurised gas instead
No user-replaceable cartridge (gas canister in the refill unit is itself re-filled)
No charging capability
No data processor with communications capability For completeness, we mention also another item of non-analogous art, which is firmly in the medical inhalation field and lacks any specific reference to e-cigarettes or nicotine delivery. The field of this invention is rather different from medical inhalation devices, such as asthma inhalers or other metered dose inhalers, since cigarette smoking is vey clearly not a medicinal activity. Specifically, the mind-set of the e-cigarette designer is to replicate as closely as possible the non-medicinal cigarette smoking experience, but without combusting tobacco. Metered dose inhalers on the other hand are typically designed for accurate, rapid, and very occasional (e.g. emergency-only) oral delivery of one or two doses of pressurised medicinal aerosol; the user experience of a PV is quite different, with relatively slow, but frequently repeated inhalations of a mist or vapour from a non-pressurised source; the experience is designed to be similar to, and hence an effective replacement for, the experience of smoking a conventional tobacco cigarette. One example of a metered dose inhaler is shown in U.S. Pat. No. 6,637,430 Ponwell. This lacks relevance for the following reasons:

No explicit relevance to e-cigarettes—primarily, this is a piezo-electric metered dose inhaler system for respiratory medicines—a very different field from e-cigarette PVs
Not suitable for re-filling PVs since it uses a needle in the case to puncture a rubber septum in the metered dose inhaler (a conventional approach used in the medicinal context where maintaining sterility of the medicament is key). But this rubber septum would degrade and tear with more than a few re-insertions; this is not an issue for a metered dose inhaler which is used relatively infrequently and sterility of the medicament is more important than durability of the medicament transfer mechanism.
No user-replaceable liquid cartridge (in fact, teaches re-filling the medicament container, so it is not a user-replaceable cartridge)
Is not a combined carrying and storage case for the metered dose inhaler Emphasising the distance between the field of metered dose inhalers and e-cigarette PV design, one of the many problems facing the designer of an e-cigarette PV is how to minimise any toxins in the vapour produced by the PV.

For example, in the paper in the New England Journal of Medicine, 'Hidden Formaldehyde in E-Cigarette Aerosols' N Engl J Med 2015; 372:392-394, the authors describe how they tested for the presence of formaldehyde-releasing agents (whose safety when inhaled is not fully understood) in the vapour of an e-cigarette PV with a variable voltage power source: 'At low voltage (3.3 V), we did not detect the formation of any formaldehyde-releasing agents (estimated limit of detection, approximately 0.1 μg per 10 puffs). At high voltage (5.0 V), a mean (±SE) of 380±90 μg per sample (10 puffs) of formaldehyde was detected as formaldehyde-releasing agents.' They go on to state 'How formaldehyde-releasing agents behave in the respiratory tract is unknown, but formaldehyde is an International Agency for Research on Cancer group 1 carcinogen.' One solution would appear to be to ensure that e-cigarette PVs run at low voltage (e.g. 3.3V) and not higher voltages, like 5V. But the problem that then arises is that the PV current has to be higher for a good 'vaping' experience, and that in turn means that (a) the PV battery runs down more quickly, and (b) the e-liquid is consumed more rapidly.

This is inconvenient with conventional designs of PV because recharging or replacing a battery takes time and because re-filling with e-liquid takes time; users would for example then need to carry around spare batteries or charging cables and e-liquid bottles. This is very different from the relatively straightforward and simple experience (and, to smokers, deeply attractive ritual) of opening a pack of conventional cigarettes and just lighting up. Because we see replicating the behavioural aspects of the cigarette smoking user experience as key to a successful product, these are major drawbacks for conventional PV designs.

One solution is to use a large 'modding-kit' type PV with a very large capacity battery that can run at the low 3.3V voltage associated with no formaldehyde release and a large e-liquid reservoir. These devices can be the size of several packets of cigarettes, and so the user sacrifices easy portability. But the performance or user experience can be good, since these devices can produce good quantities of vapour, without the need for frequent and inconvenient battery re-charging or replacement and e-liquid re-filling. When e-liquid does need to be replenished however, that is typically done by dis-assembling the unit to expose the reservoir and to then squeeze e-liquid into the reservoir from a small bottle; this can be slow and cumbersome; users often then carry around a replacement bottle or e-liquid, especially if they are using e-cigarettes to quit tobacco smoking, since if they were to run out of e-liquid, then the temptation to buy a packet of cigarettes to smoke could prove hard to resist. And this complex e-liquid re-filling process clearly has none of the simplicity or attractive ritual of opening a packet of cigarettes and lighting up.

An ideal solution would be an e-cigarette PV with the form factor of a conventional cigarette, and with the best aspects of the performance and user experience of a large modding kit type PV. This specification describes such a solution. The solution is designed to replicate many of the key behavioural and experiential aspects that make smoking attractive to smokers (e.g. the tactile satisfaction of holding a cigarette packet and opening the lid and withdrawing a cigarette; the action of holding a slim cigarette; the simplicity of the user's only action being to light up). Replicating these user experience aspects is we believe key to the successful mass-market adoption of e-cigarettes and hence delivering on their considerable public health potential.

SUMMARY OF THE INVENTION

A e-cigarette PV that includes an air pressure valve or device so that excess air can escape from an e-liquid reservoir in the PV when that reservoir is being filled under pressure with e-liquid from a parent reservoir.

Other optional features:

- the reservoir is a child reservoir and is filled by a parent reservoir, being an e-liquid cartridge that is removable from the PV or a case that stores, re-fills with e-liquid and re-charges the PV with power.
- the child reservoir is designed to enable the atomizing unit to draw in controlled amounts of e-liquid for vaping.
- the parent reservoir is a user-removable and replaceable, sealed or closed e-liquid capsule or cartridge, of capacity 10 mL or less, and is slotted into or otherwise used by the PV or a portable re-fill/re-charge case for the PV, and a fluid transfer mechanism operates to transfer e-liquid from the capsule or cartridge into the child reservoir in the PV, of capacity 3 mL or less.
- the child reservoir is connected to one or more small channels that lead into a second child reservoir which surrounds the atomising unit and from which e-liquid is drawn (e.g. by a wick or other porous member) into the atomising chamber (e.g. a heating coil inside an air chamber).
- the valve or device permits air to enter into the child reservoir in the PV as e-liquid is consumed in normal use.
- the valve or device permits air to enter into the child reservoir if the ambient air pressure changes, for example in an aircraft.
- the valve or device is a barrier made of an air-porous material, such as a sintered polymer or metal, coated with or otherwise including a barrier or layer of an air-porous substance that is not porous to e-liquid.
- the barrier or layer of the air-porous substance that is not porous to e-liquid as an oleophobic material or a hydrophobic or super-hydrophobic material.
- the valve or device in which the oleophobic material is one of: sintered phosphor bronze, sintered stainless steel and sintered PU plastic.

BRIEF DESCRIPTION OF THE FIGURES

Examples of the invention will now be described with reference to the accompanying diagrams, in which.

All of the remaining figures depict elements of an e-cigarette PV or PV case that solve problems with the prior art.

Figure 2:
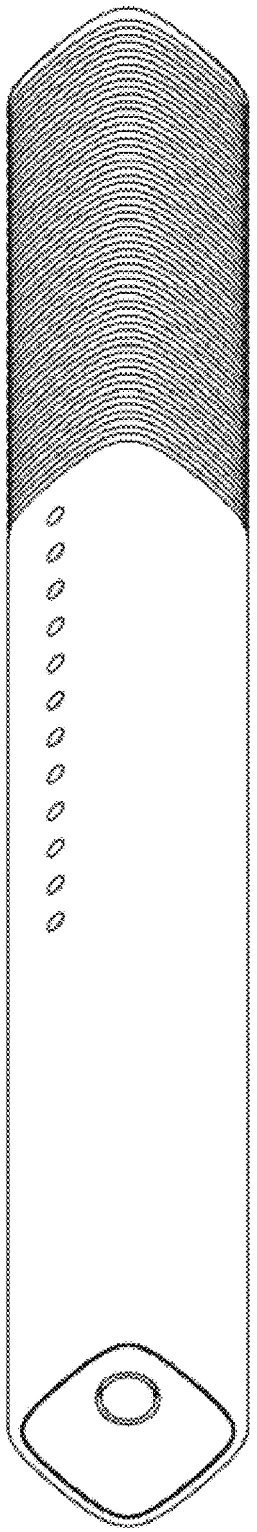
Figure 3:
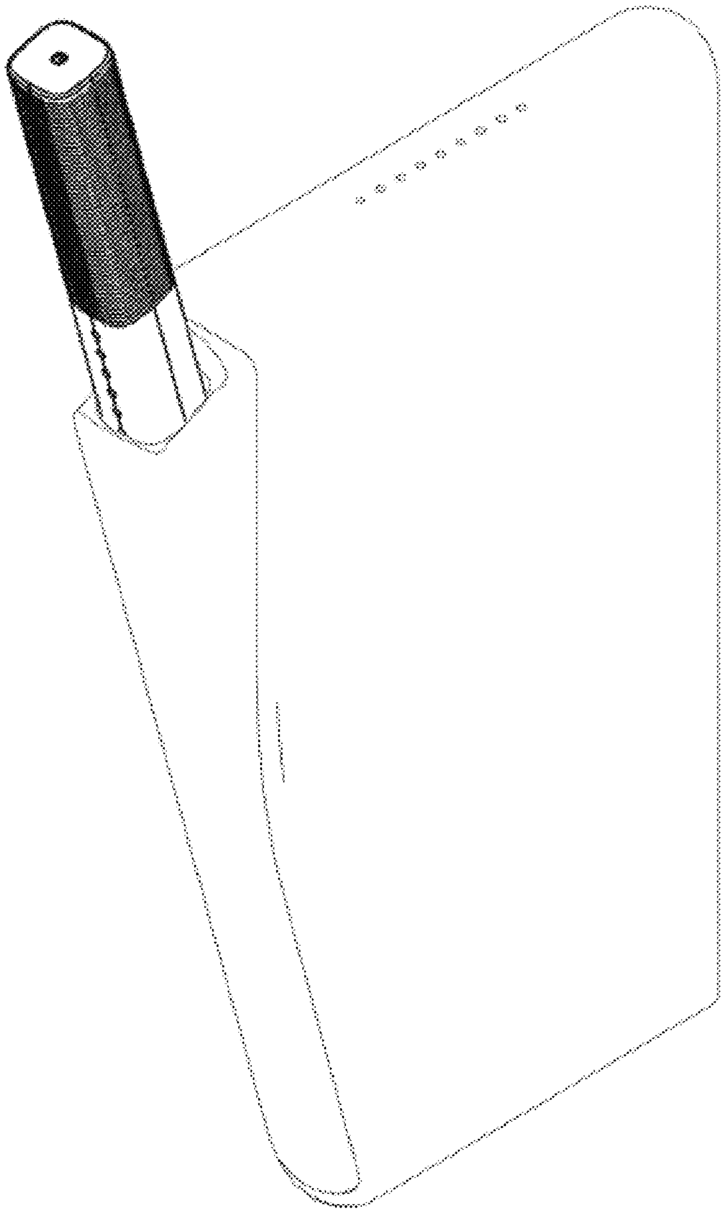
Figure 4:
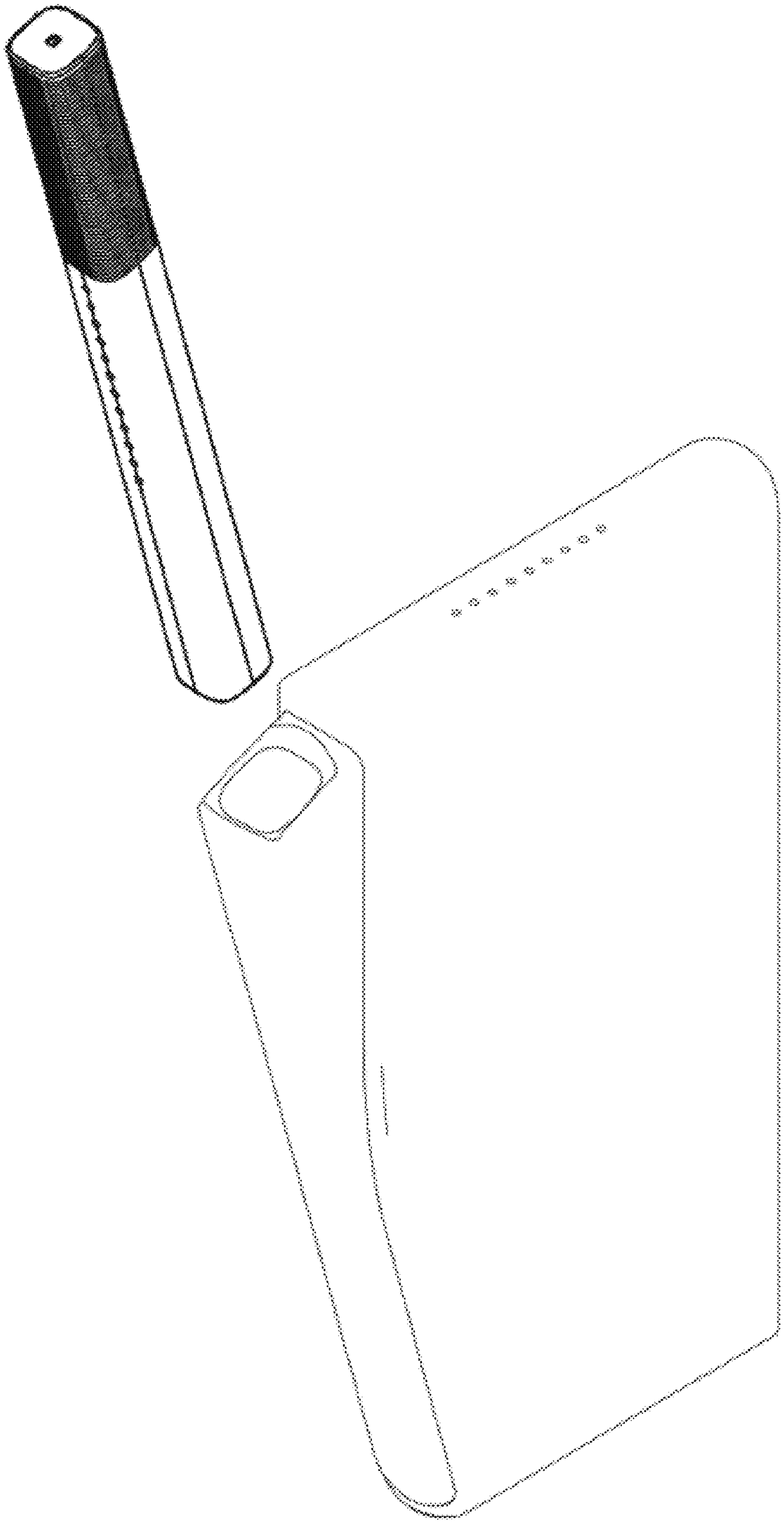
Figure 5:
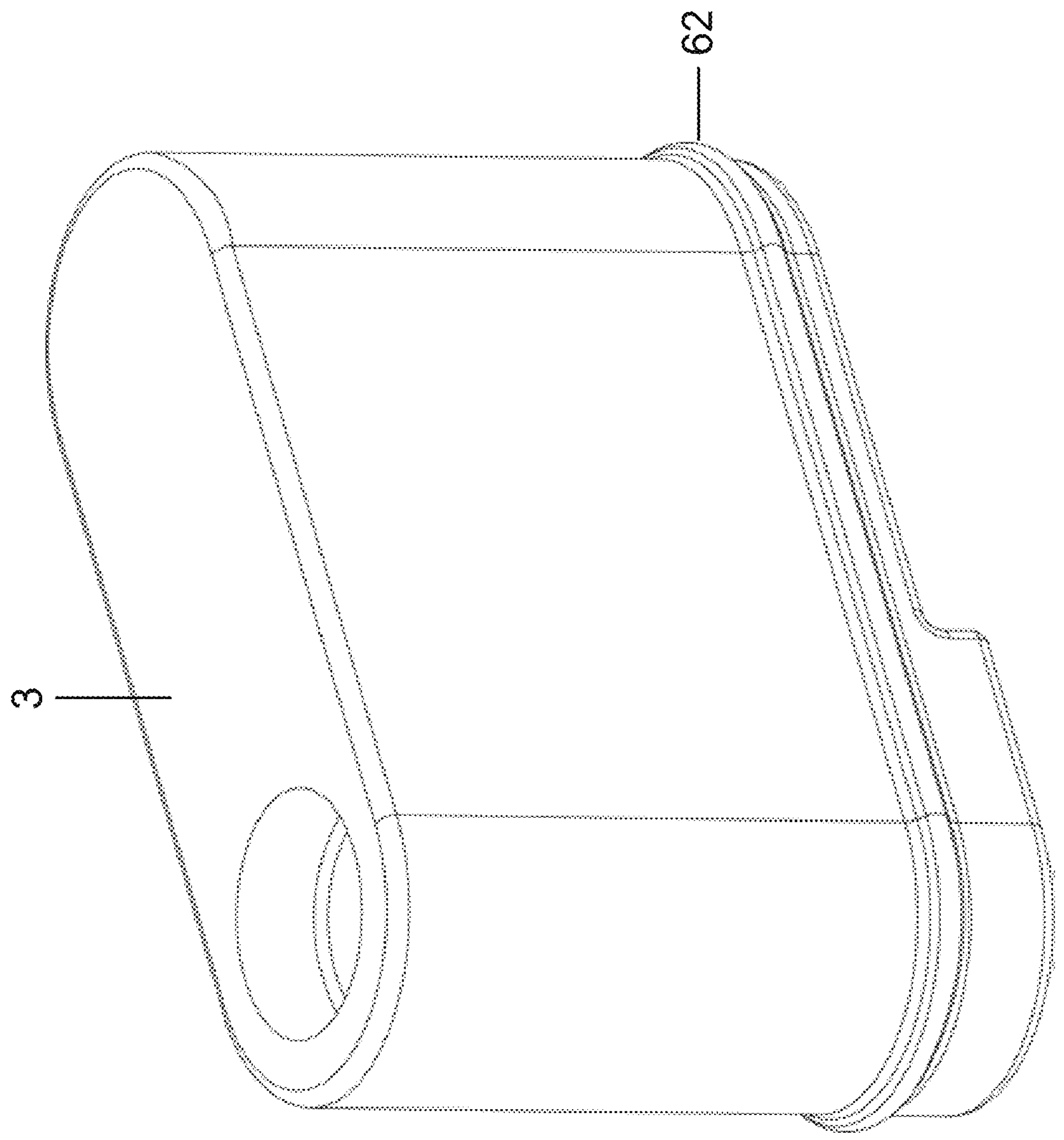
Figure 6B:
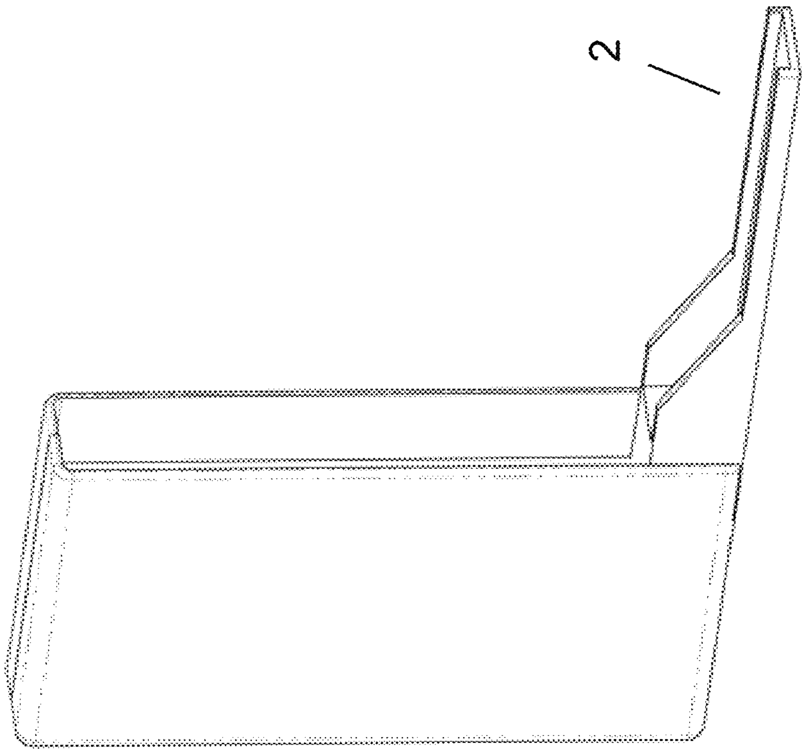
Figure 6A:
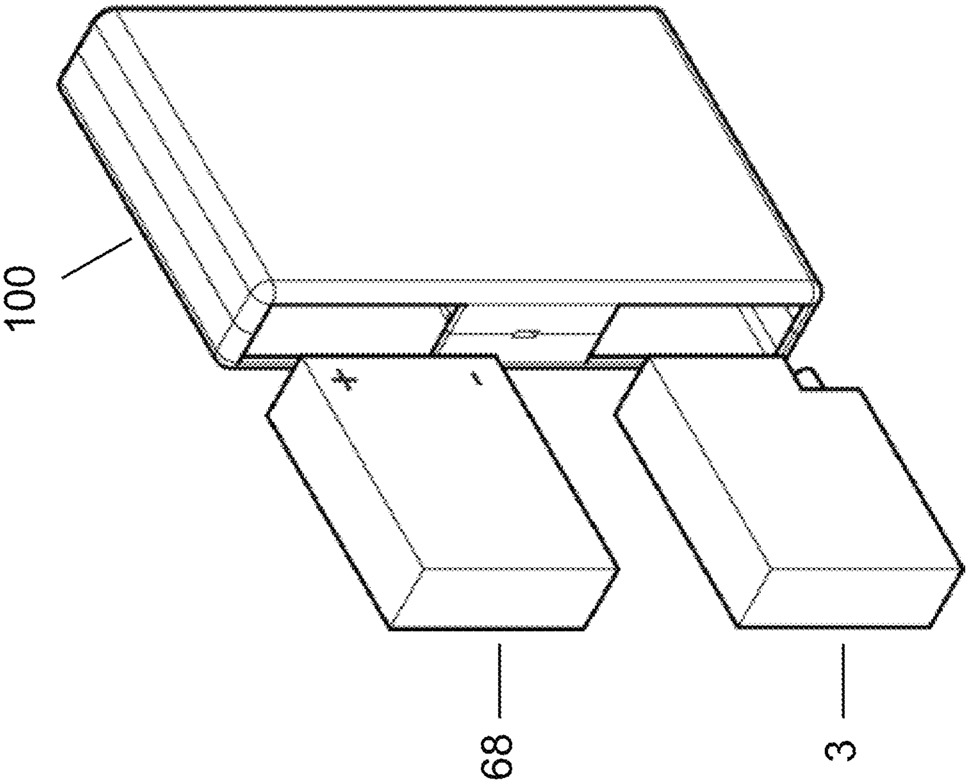
Figure 7:
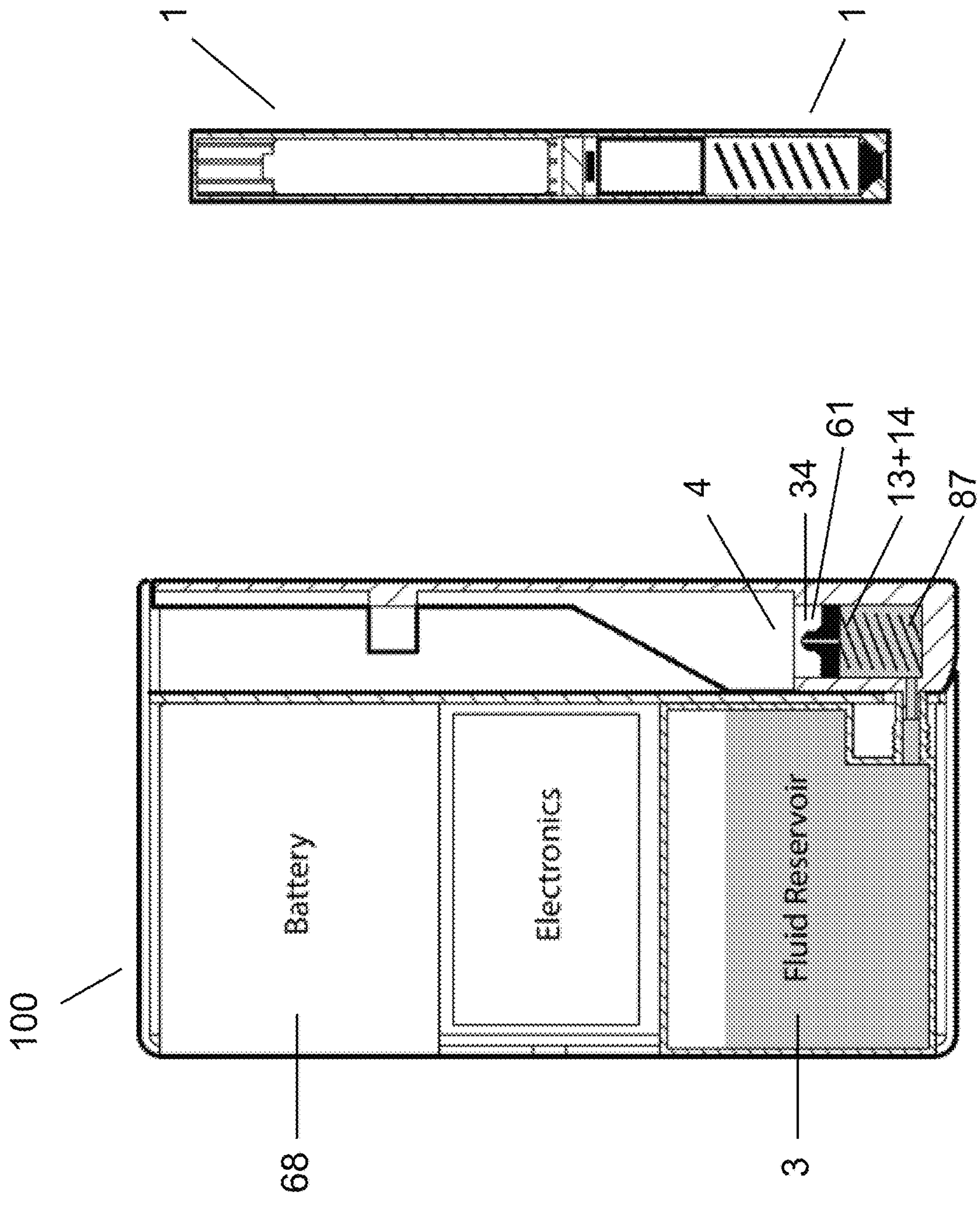
Figure 8:
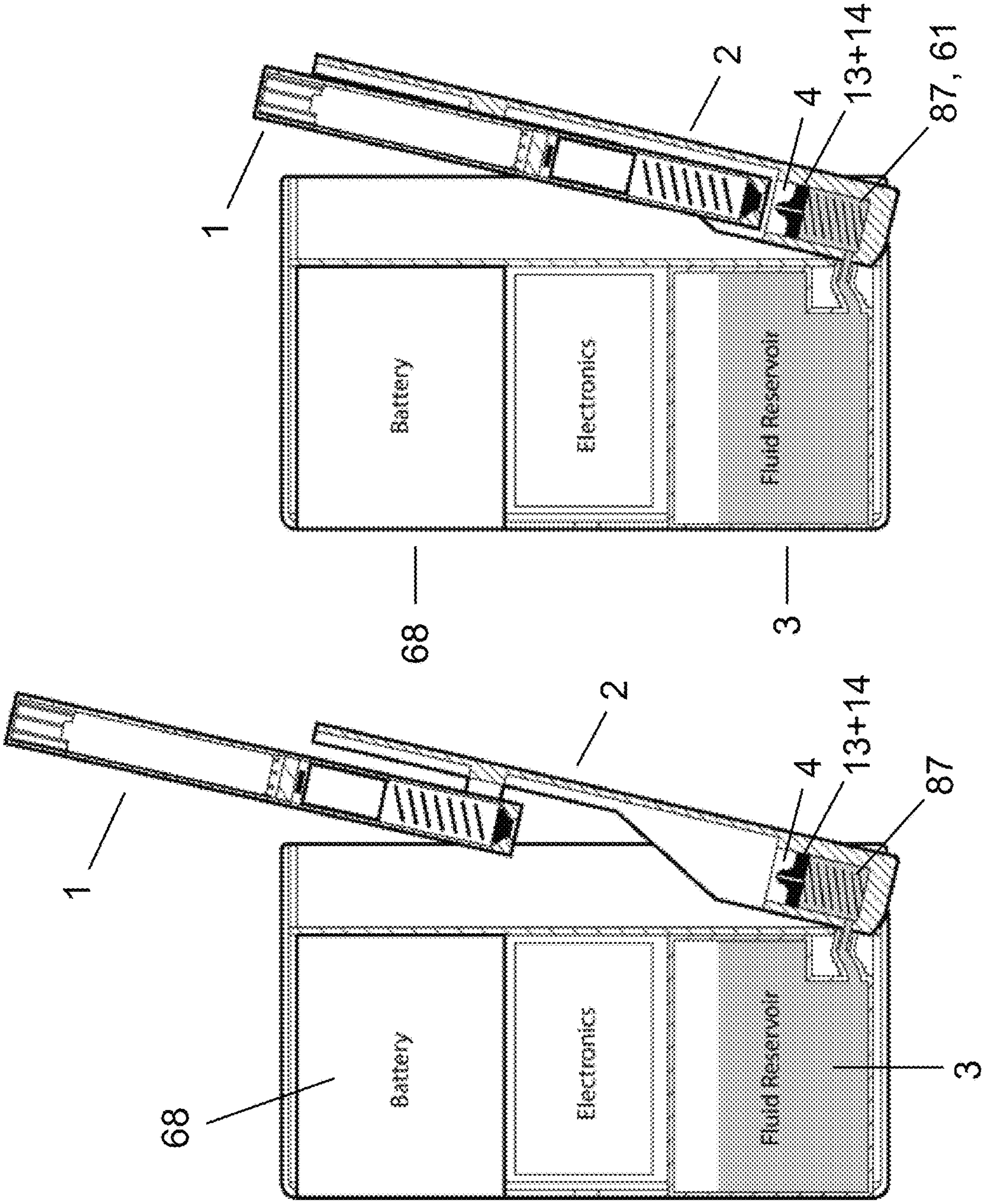
Figure 9:
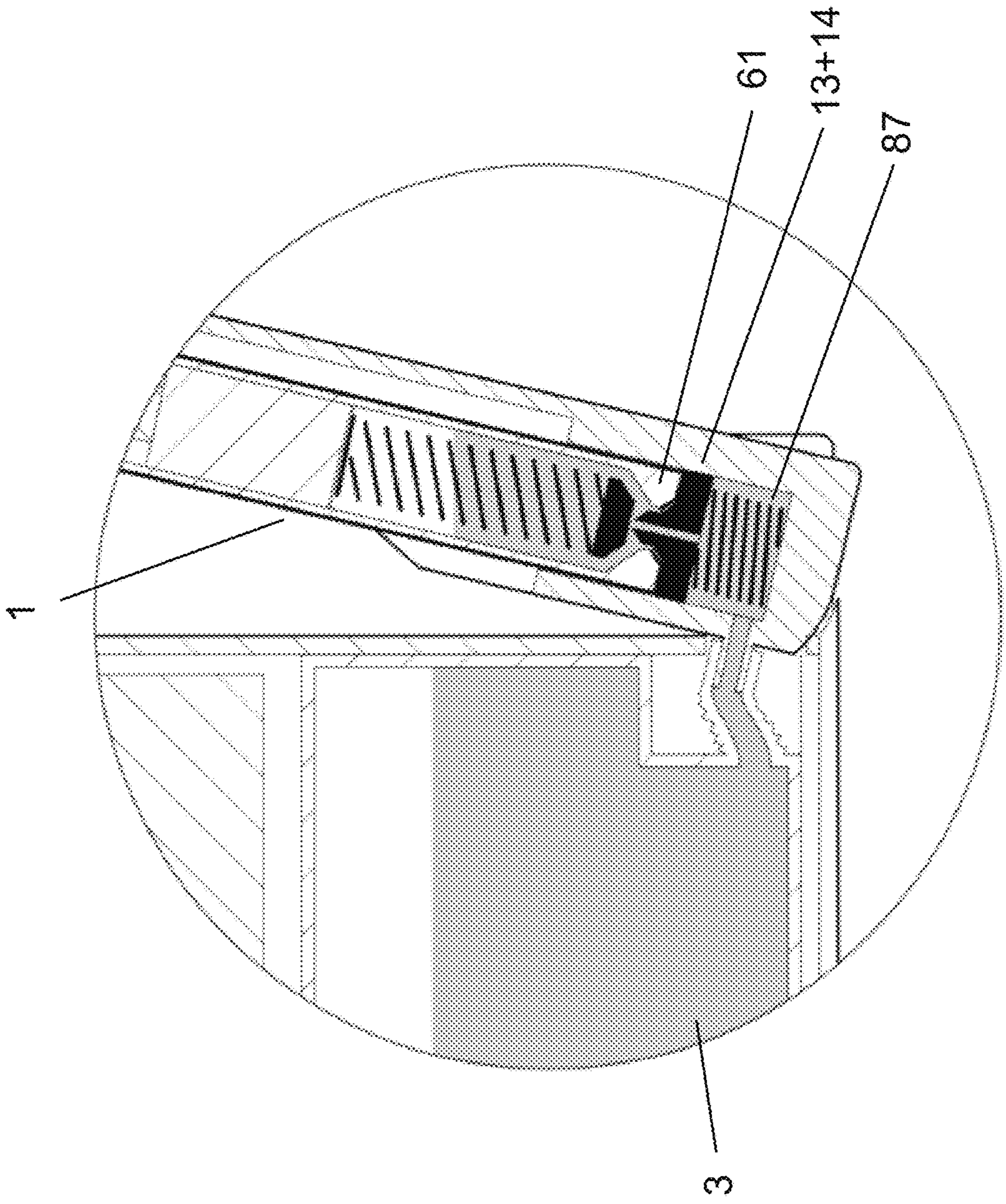
Figure 10:
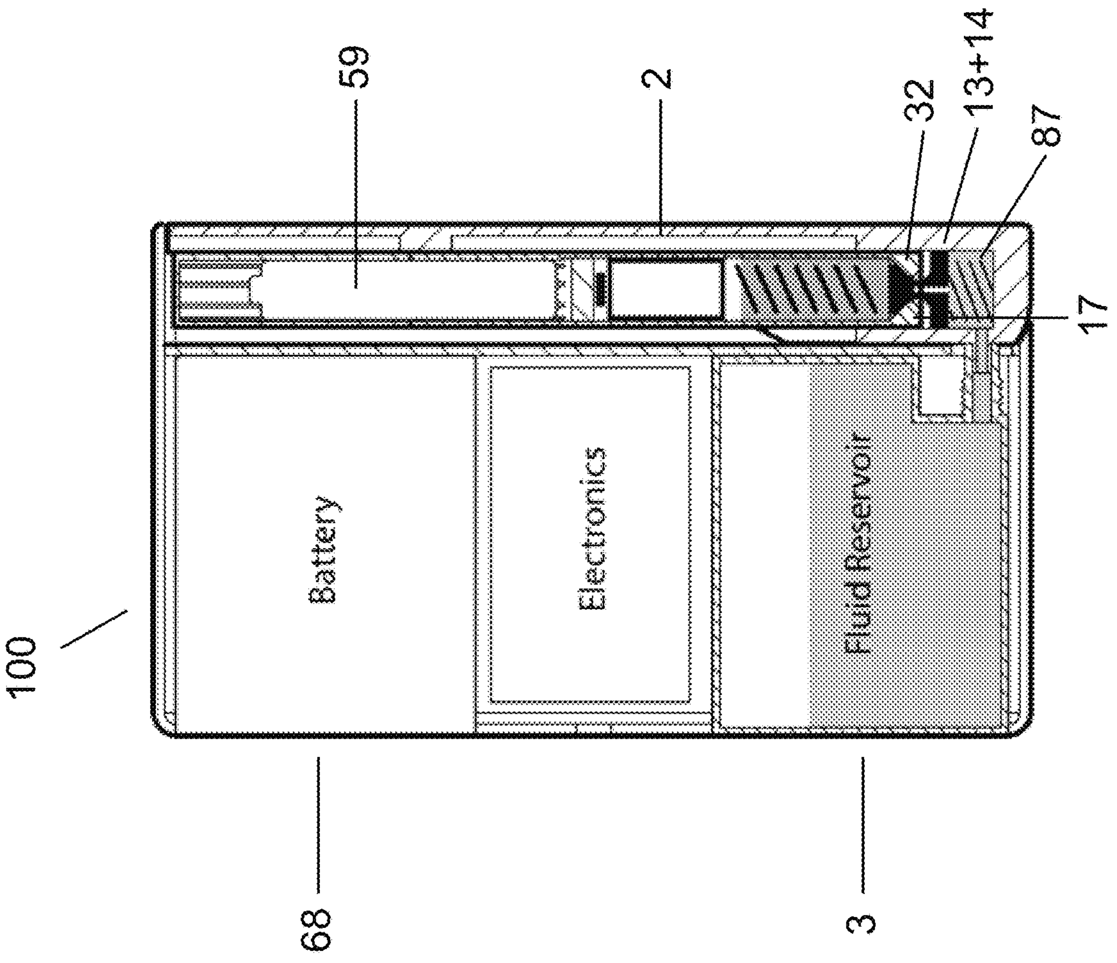
Figure 11:
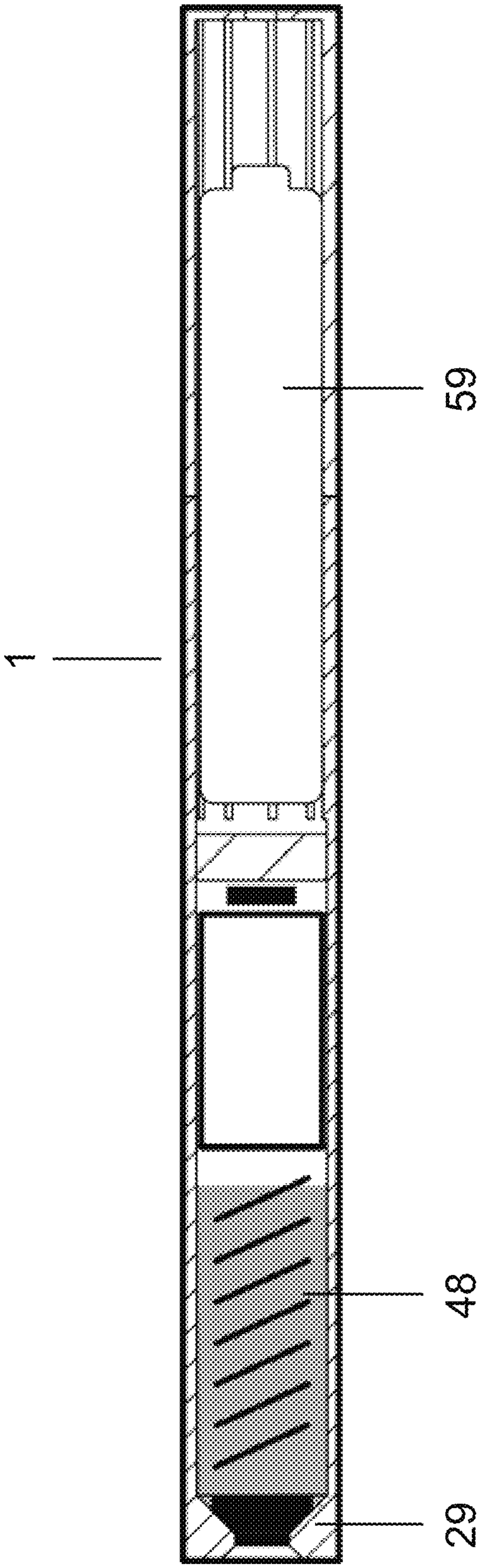
Figure 12:
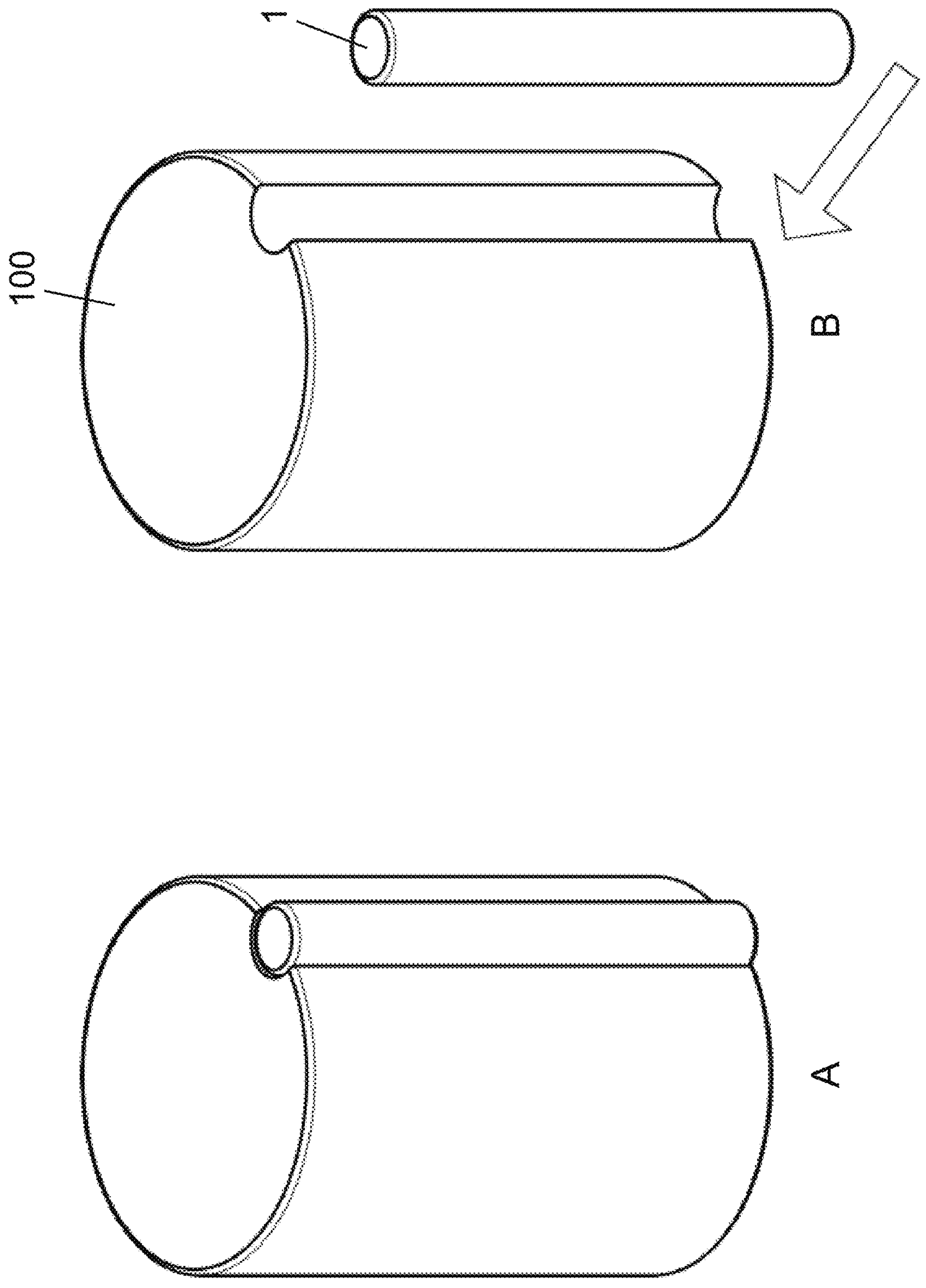
Figure 13:
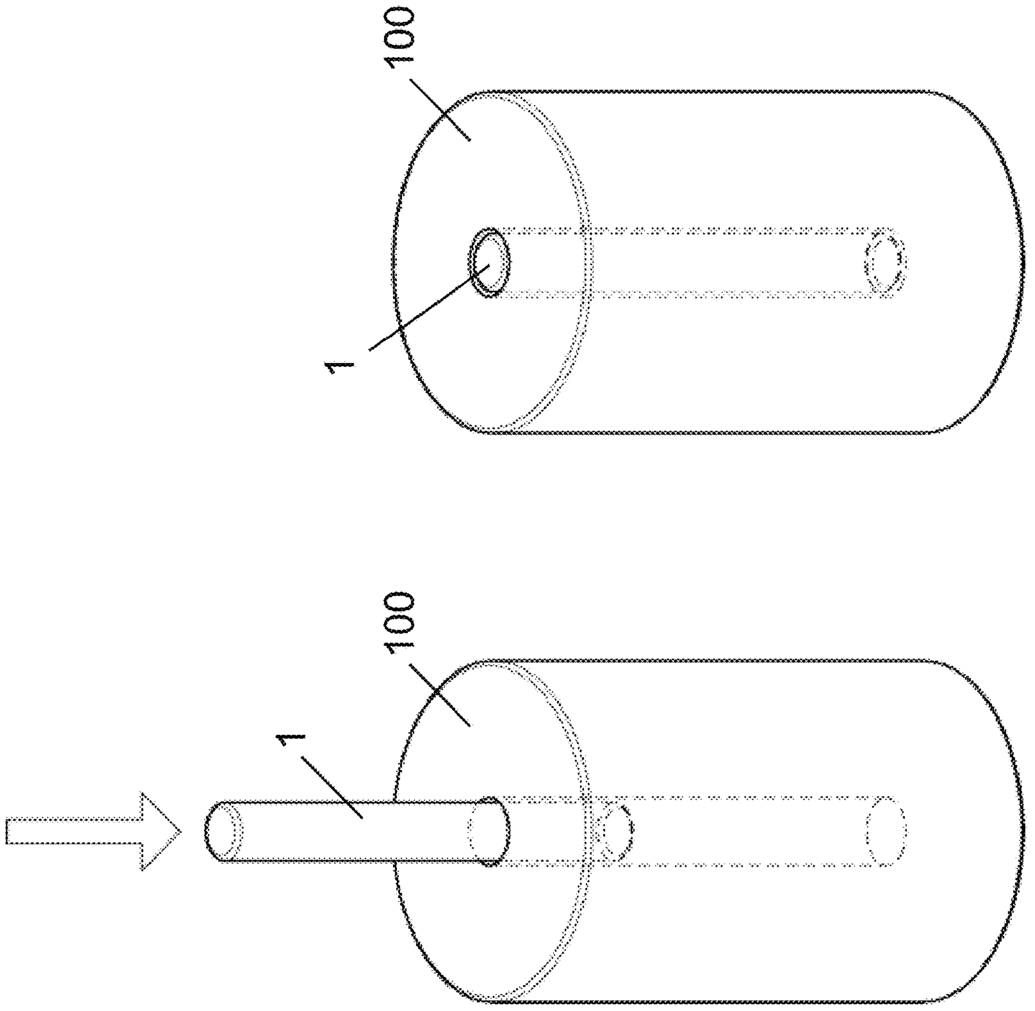
Figure 14:
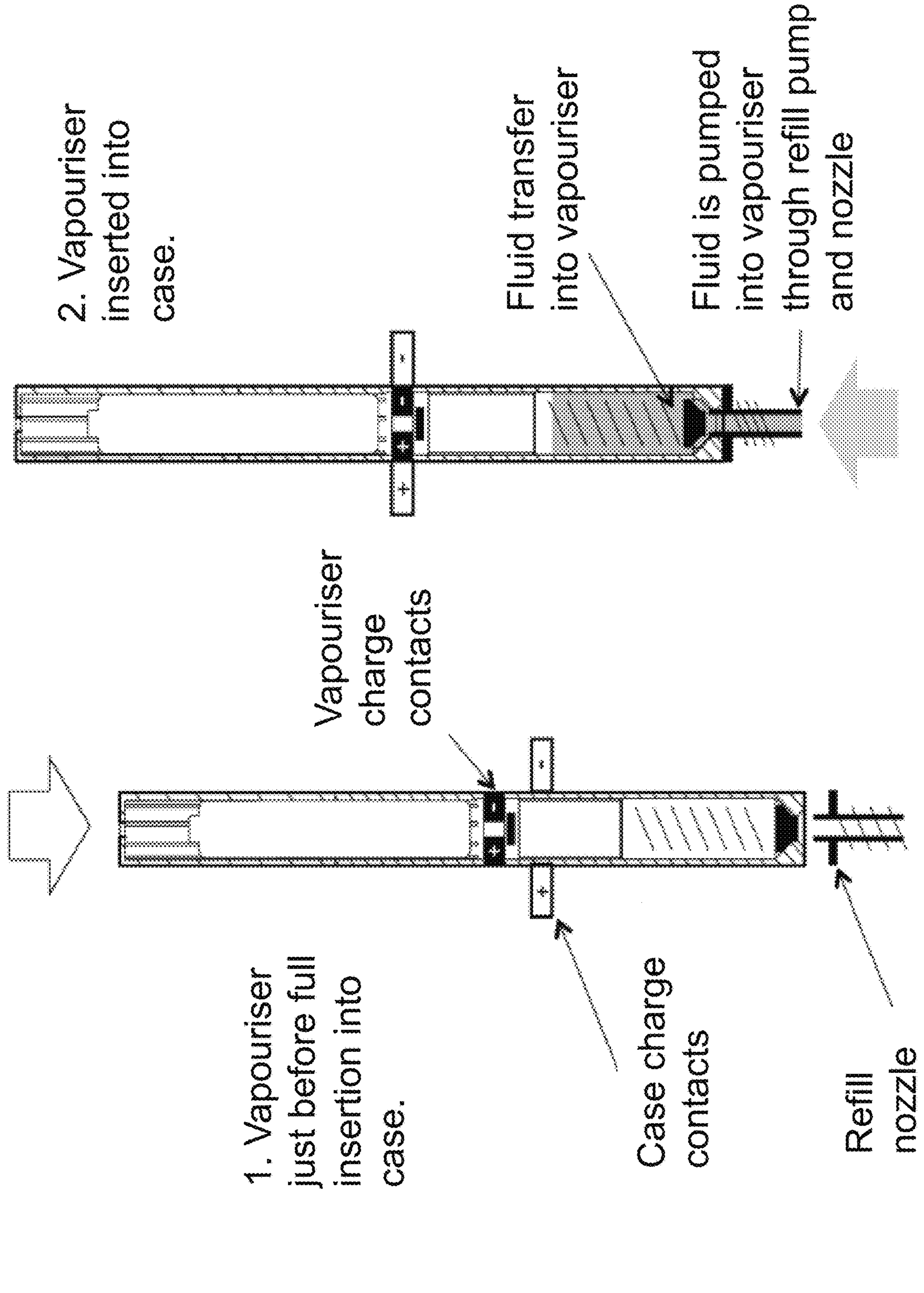
Figure 15:
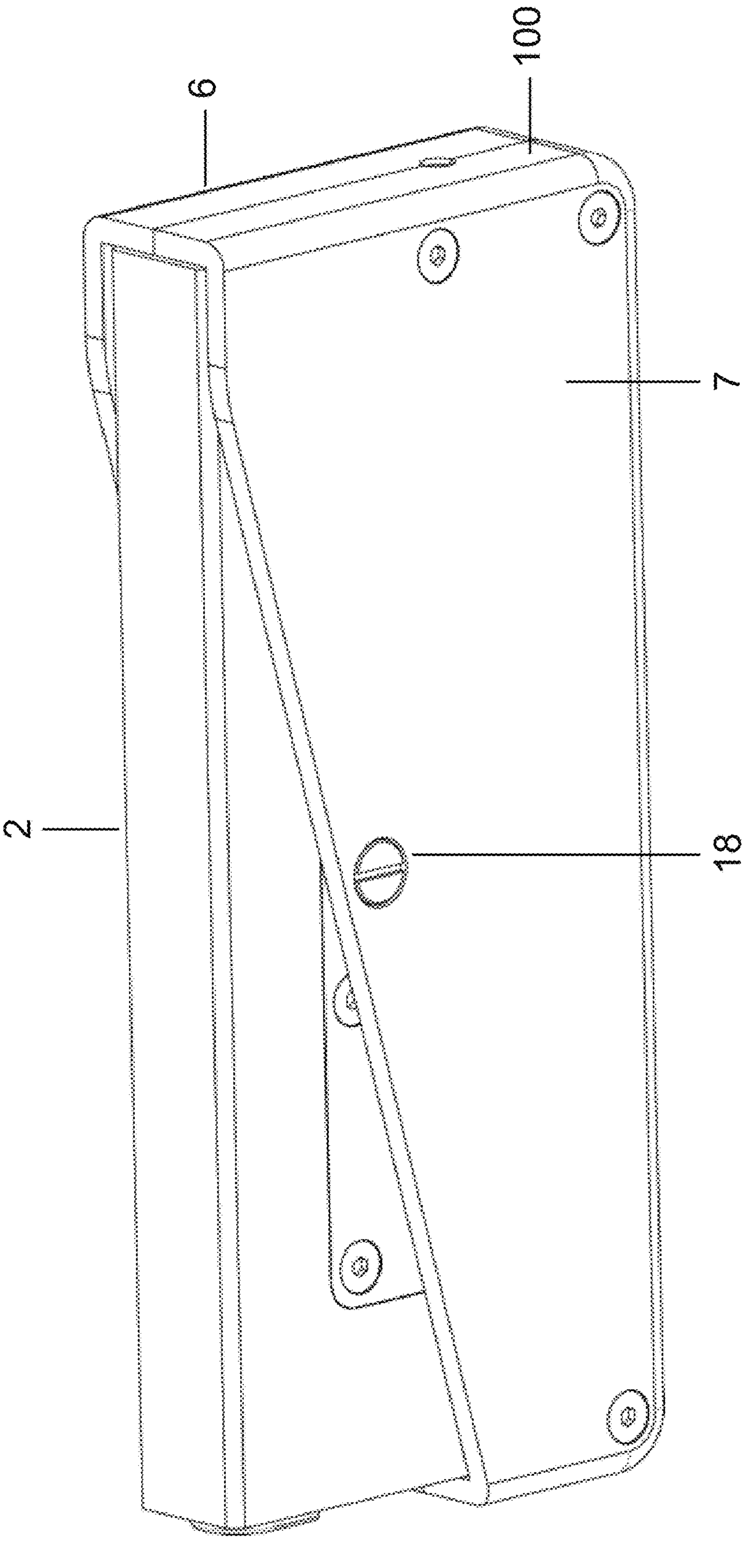
Figure 16:
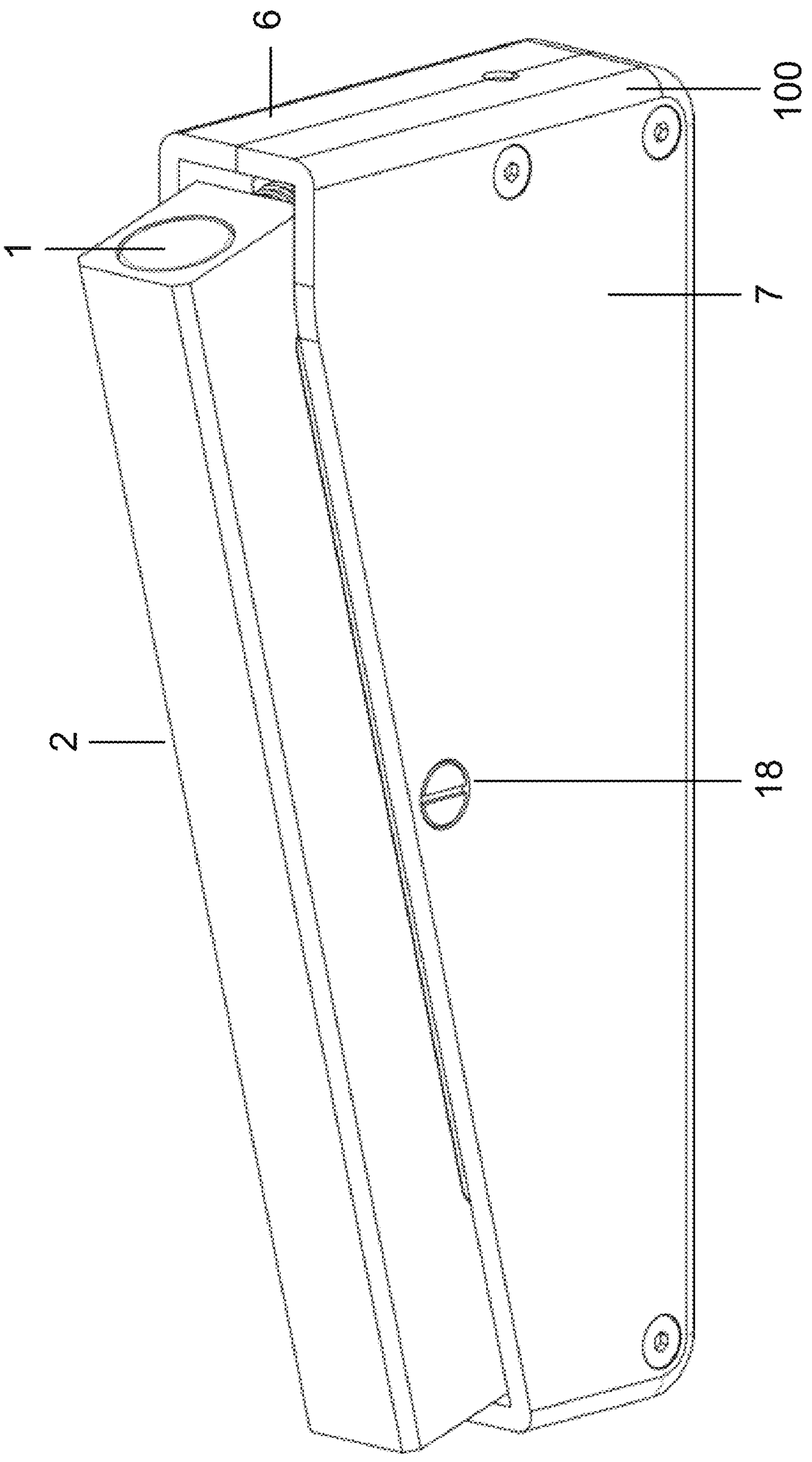
Figure 17:
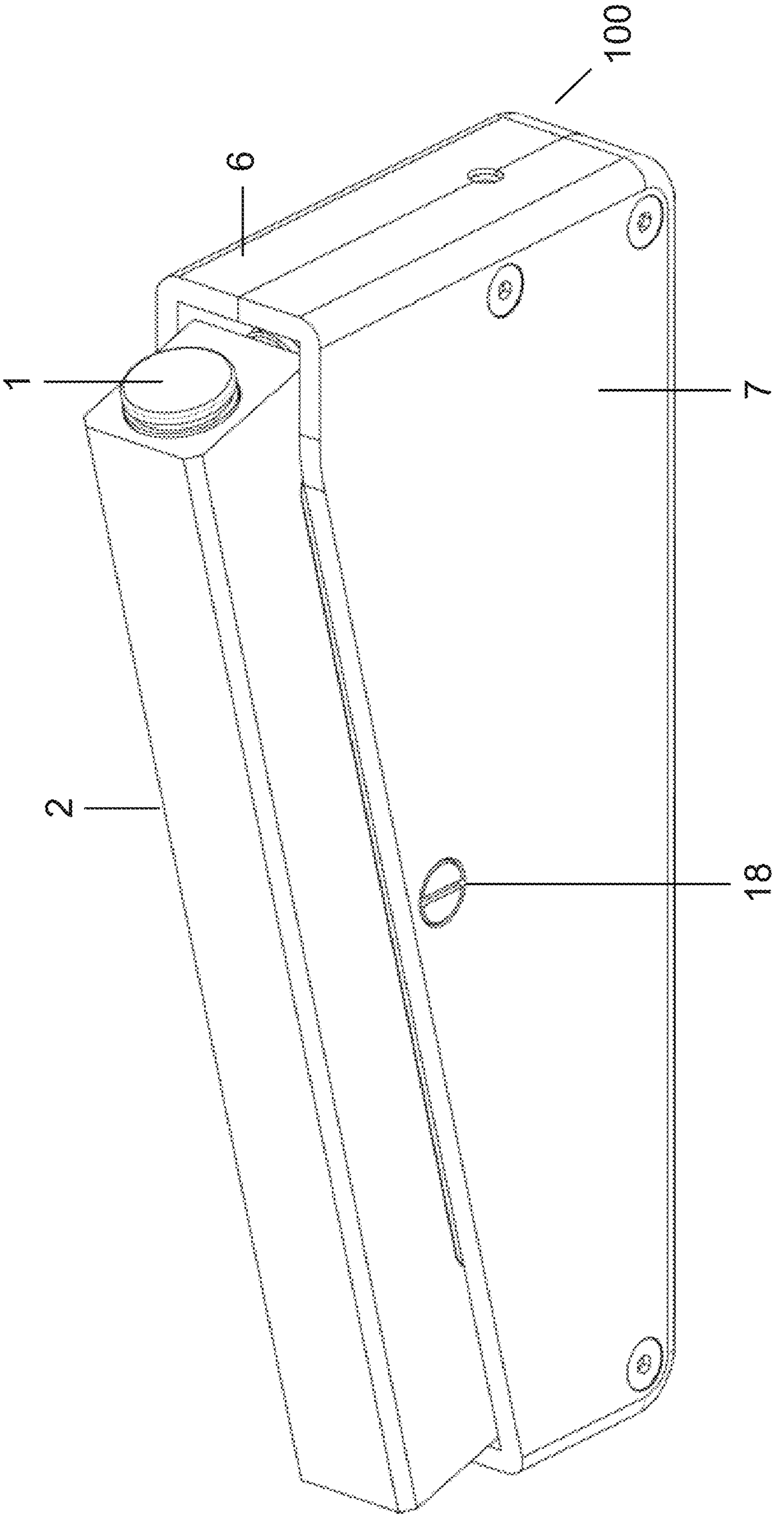
Figure 18:
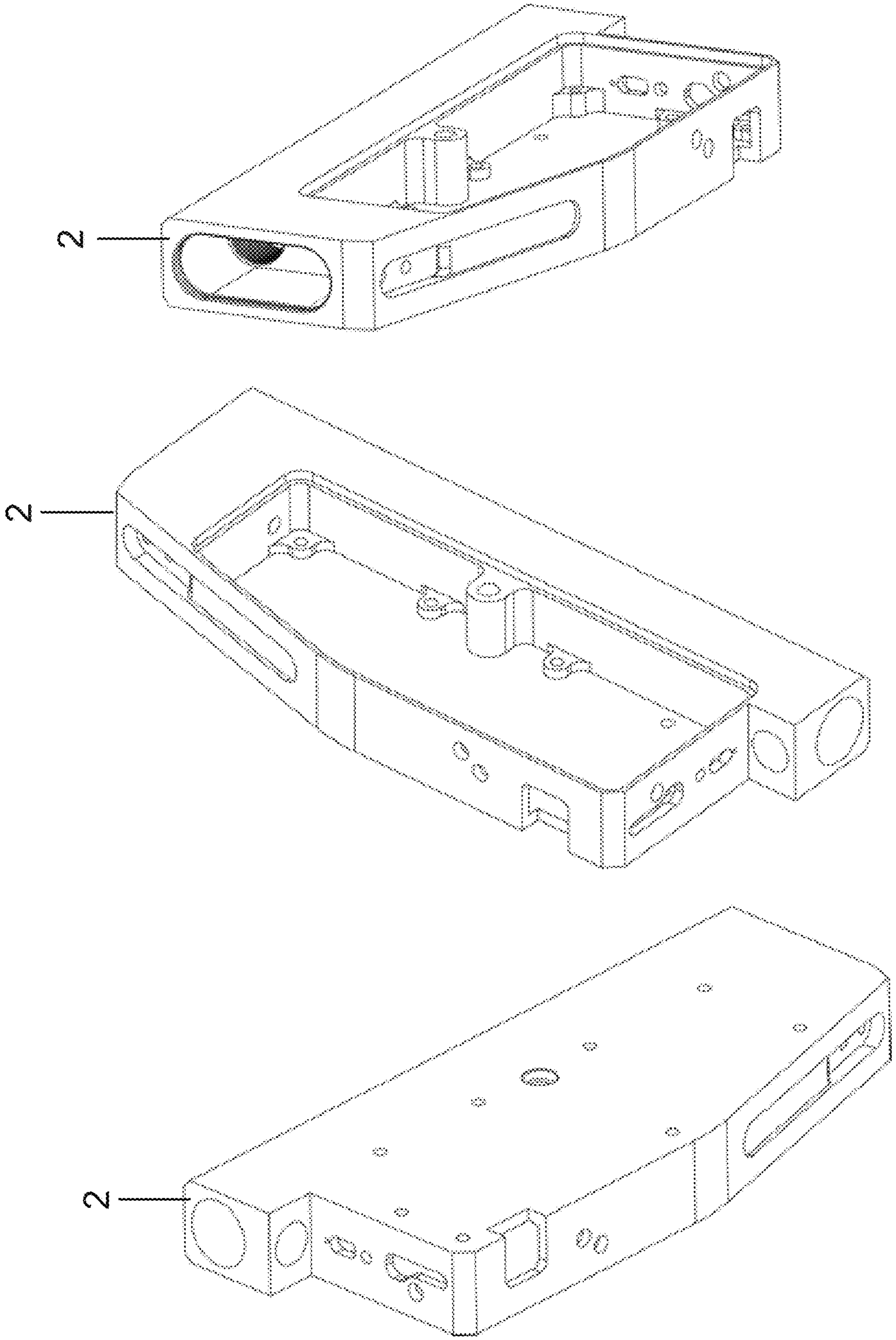
Figure 19:
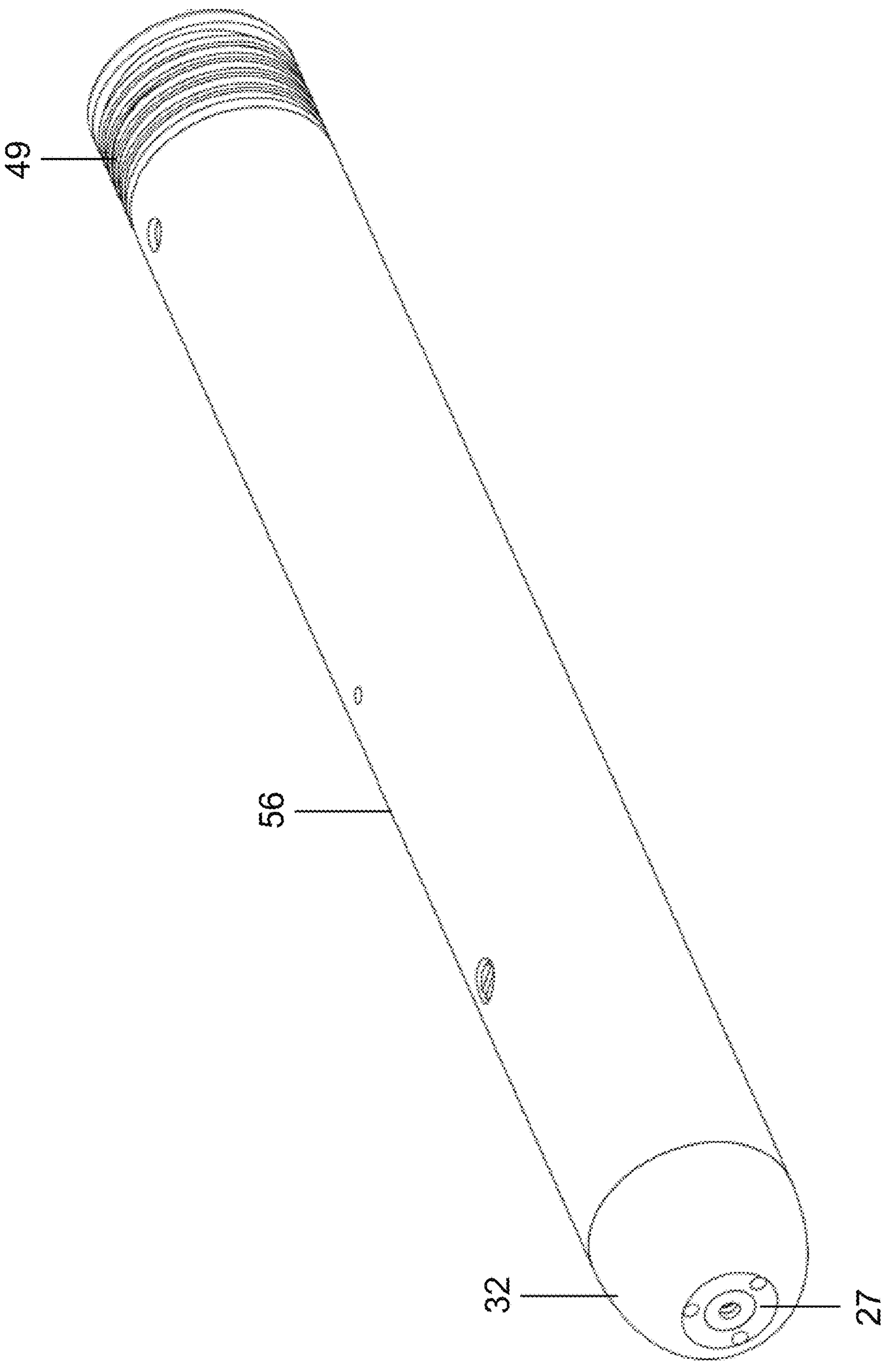
Figure 20:
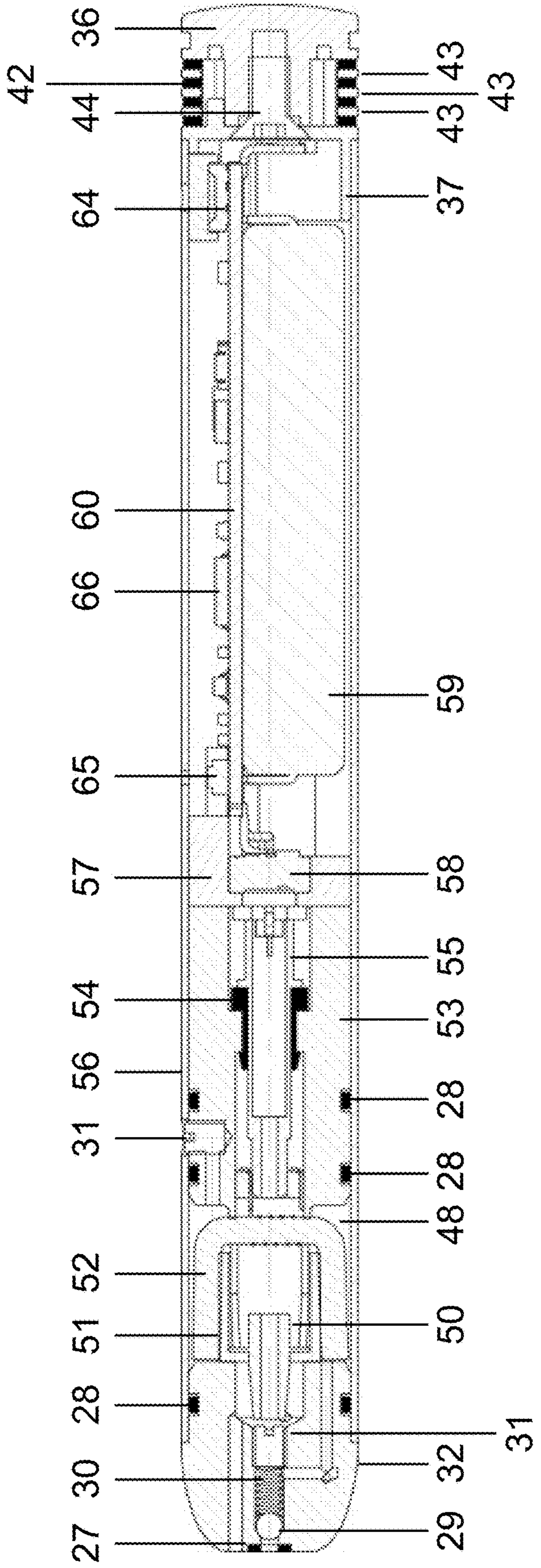
Figure 21:
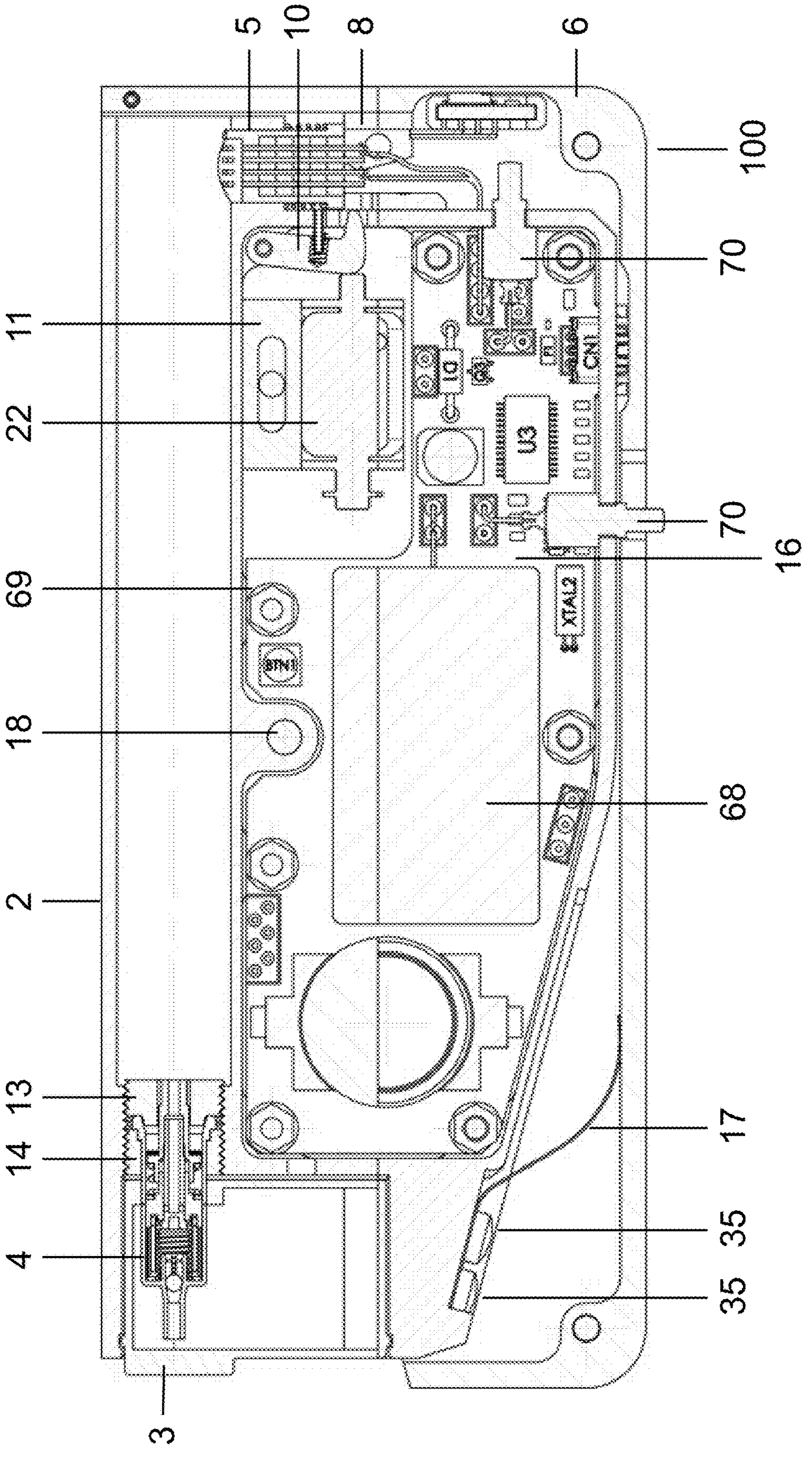
Figure 22:
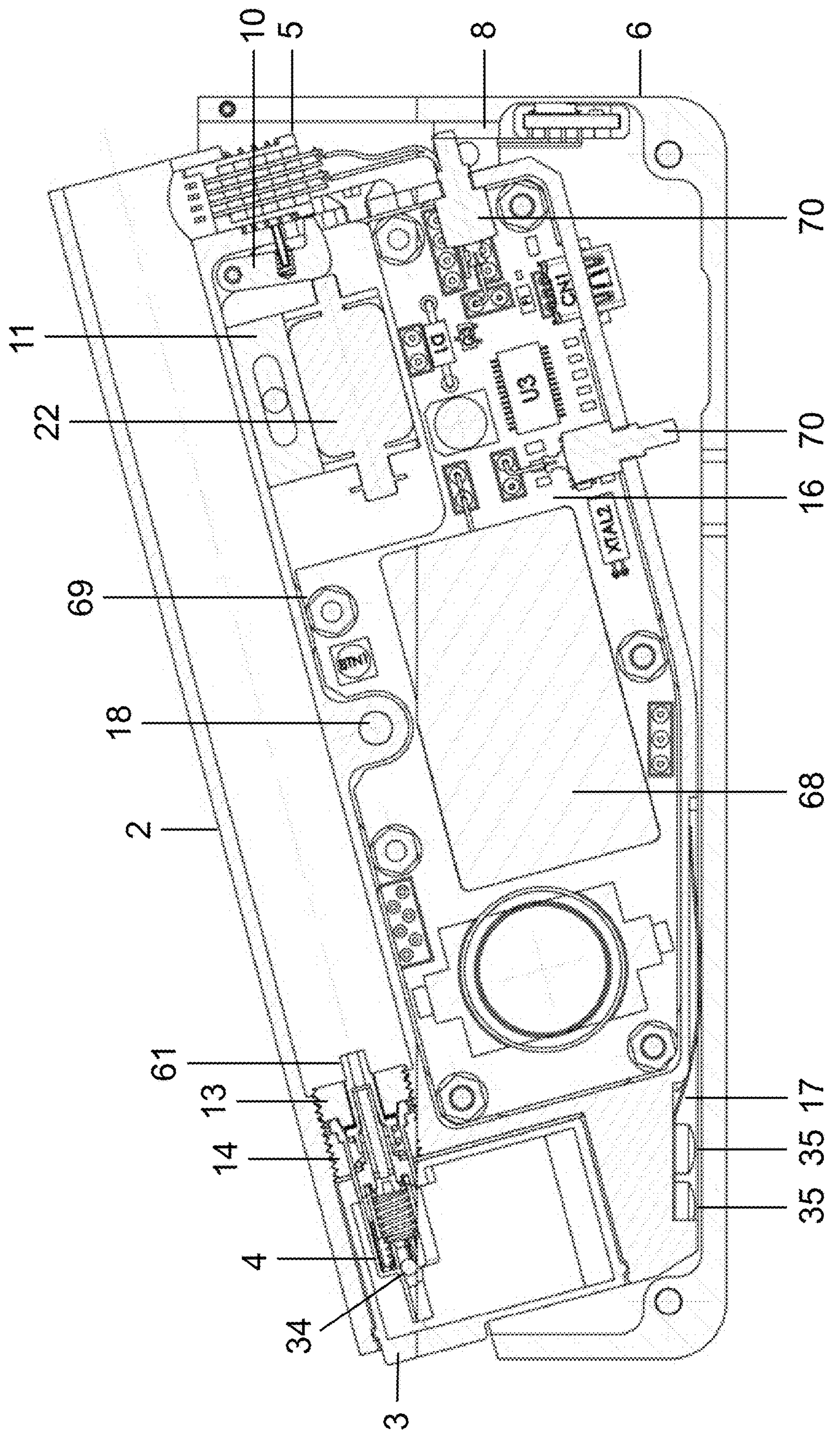
Figure 23:
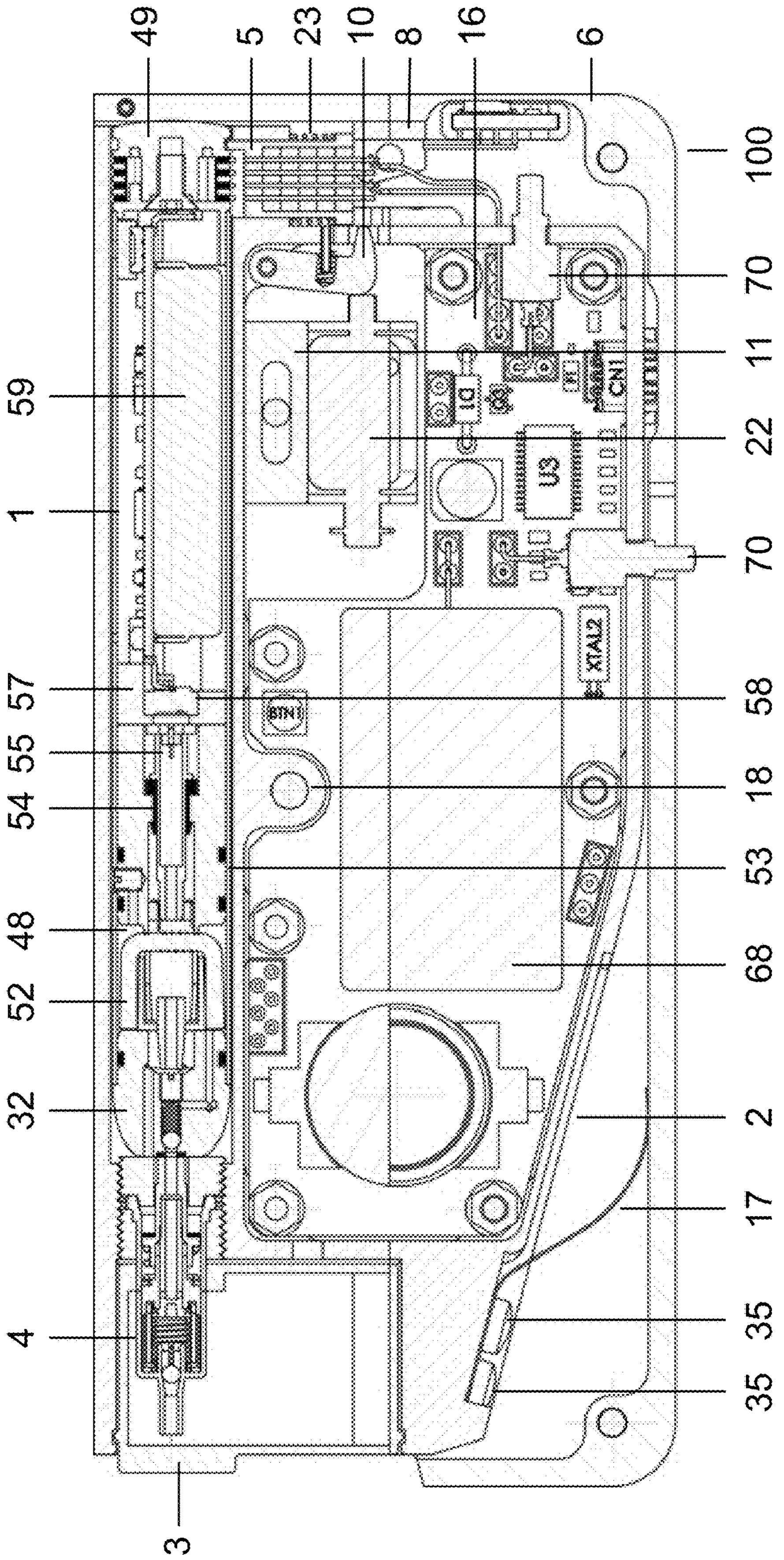
Figure 24:
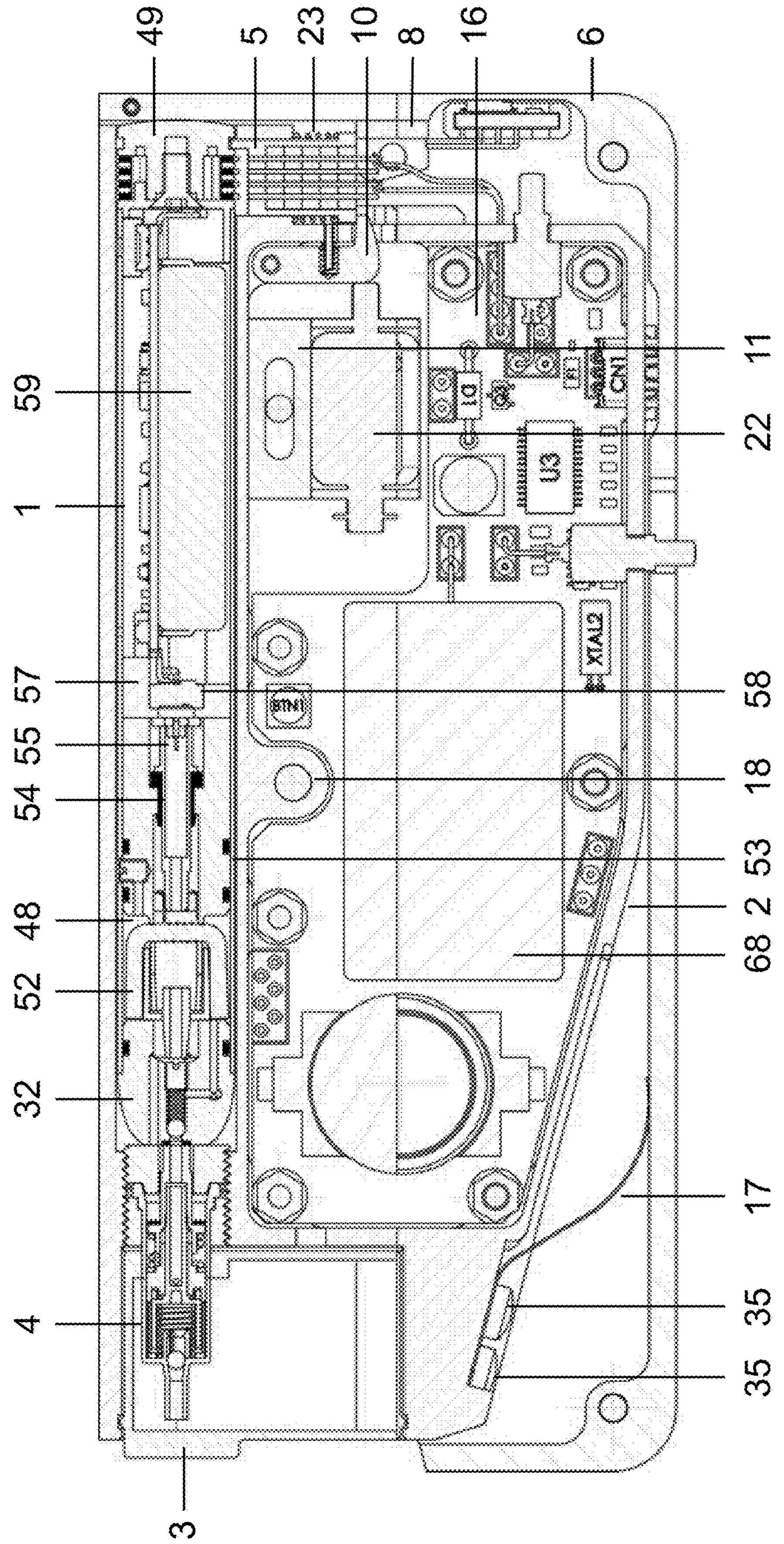
Figure 25:
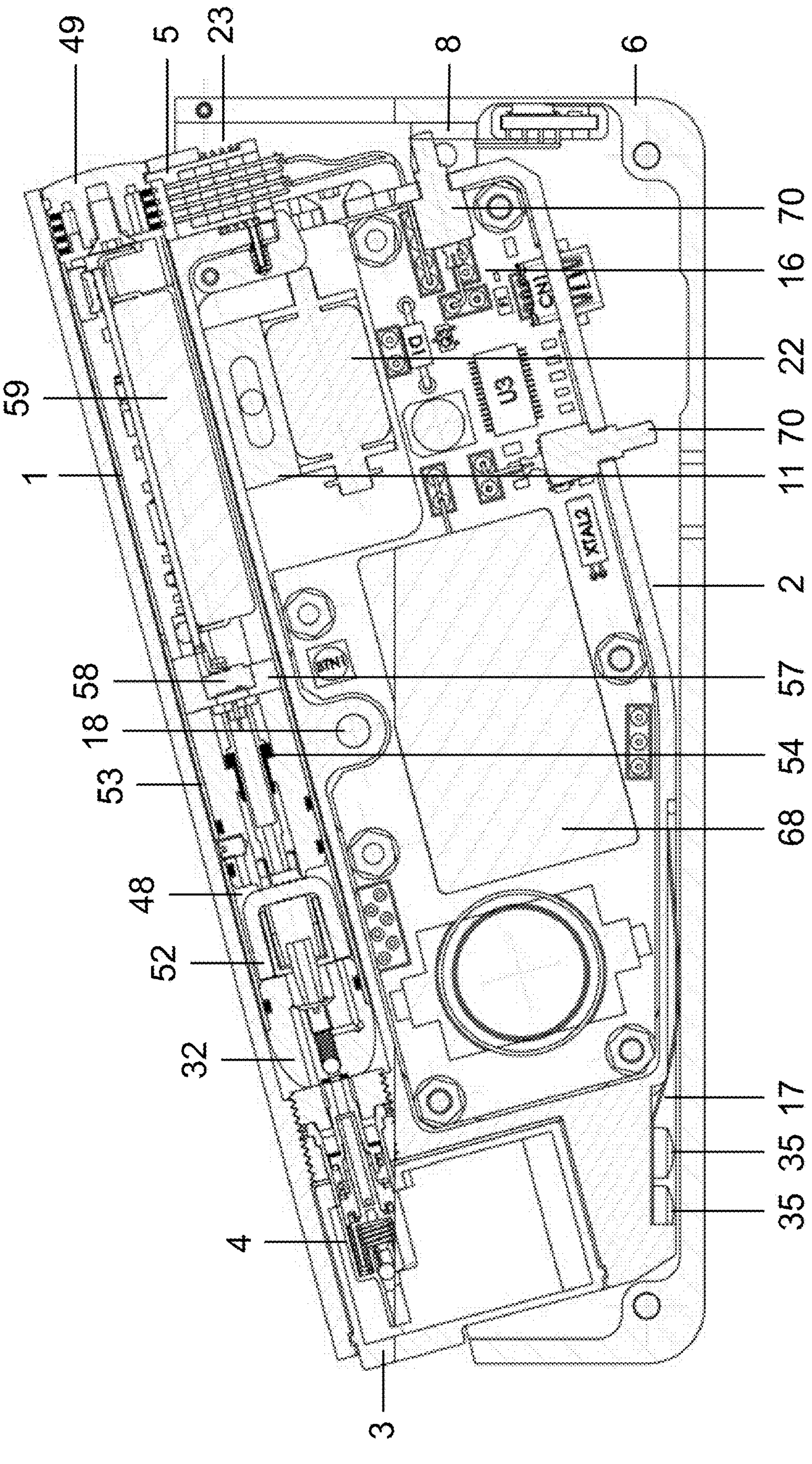
Figure 26:
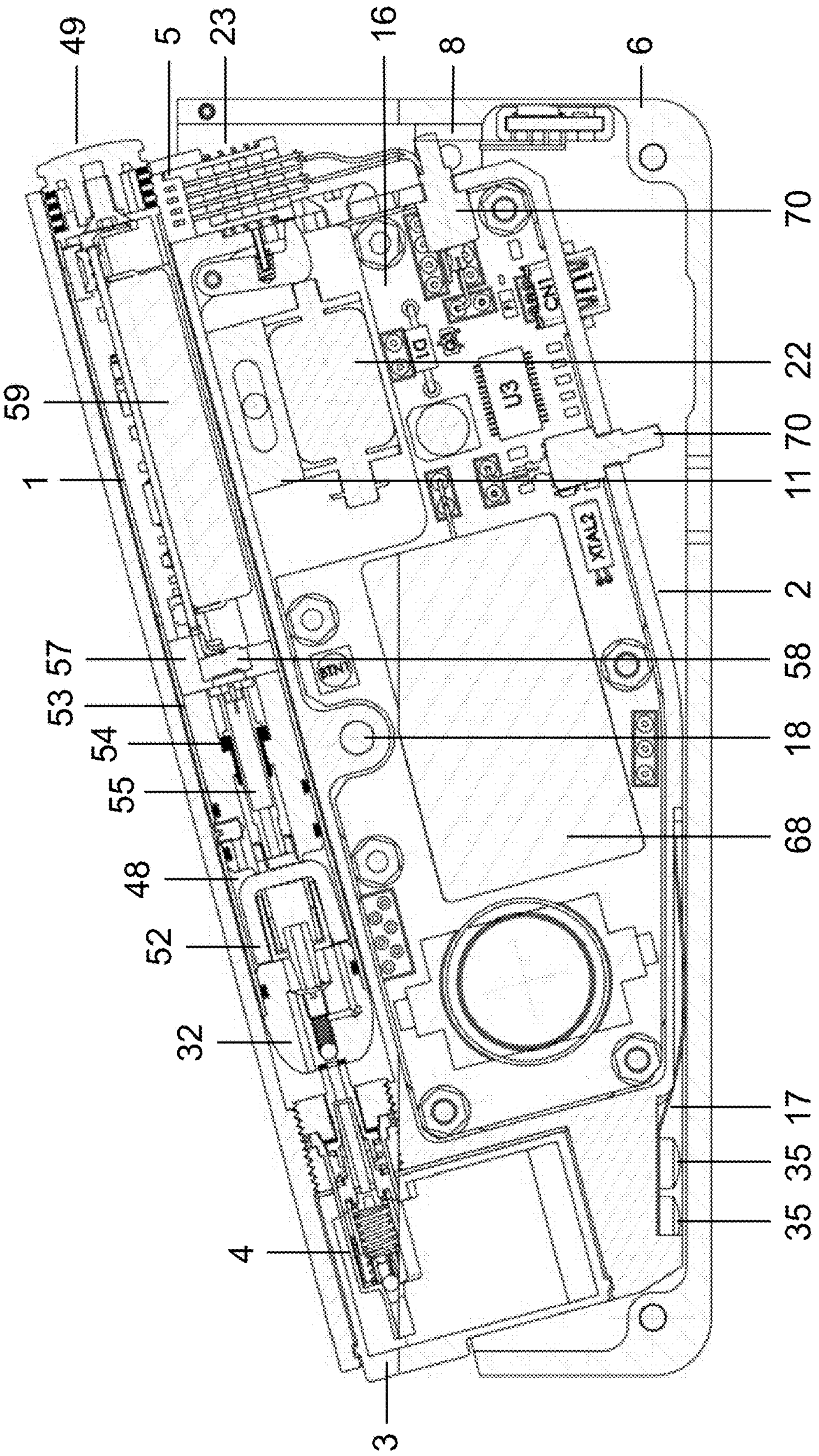
Figure 31:
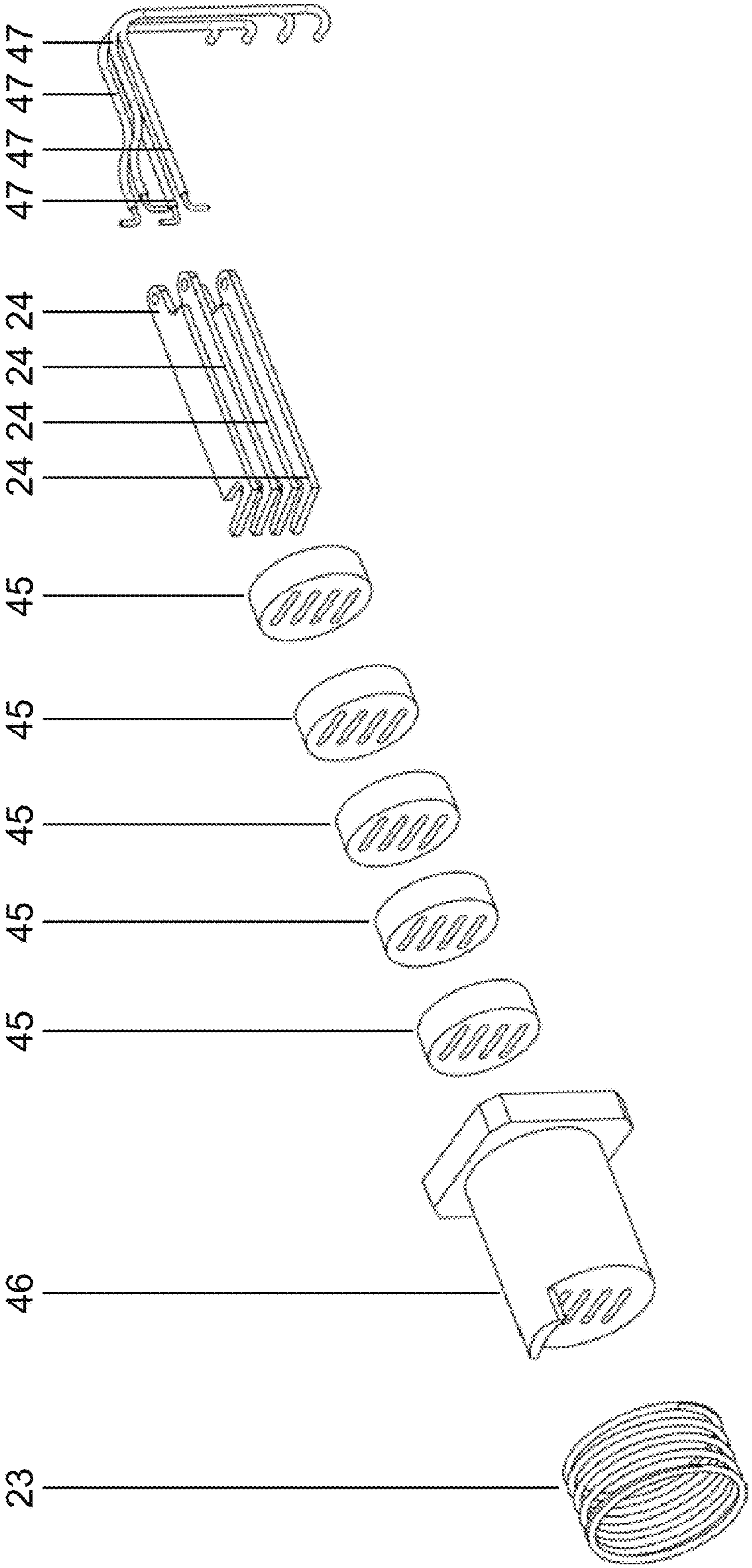
Figure 32A:
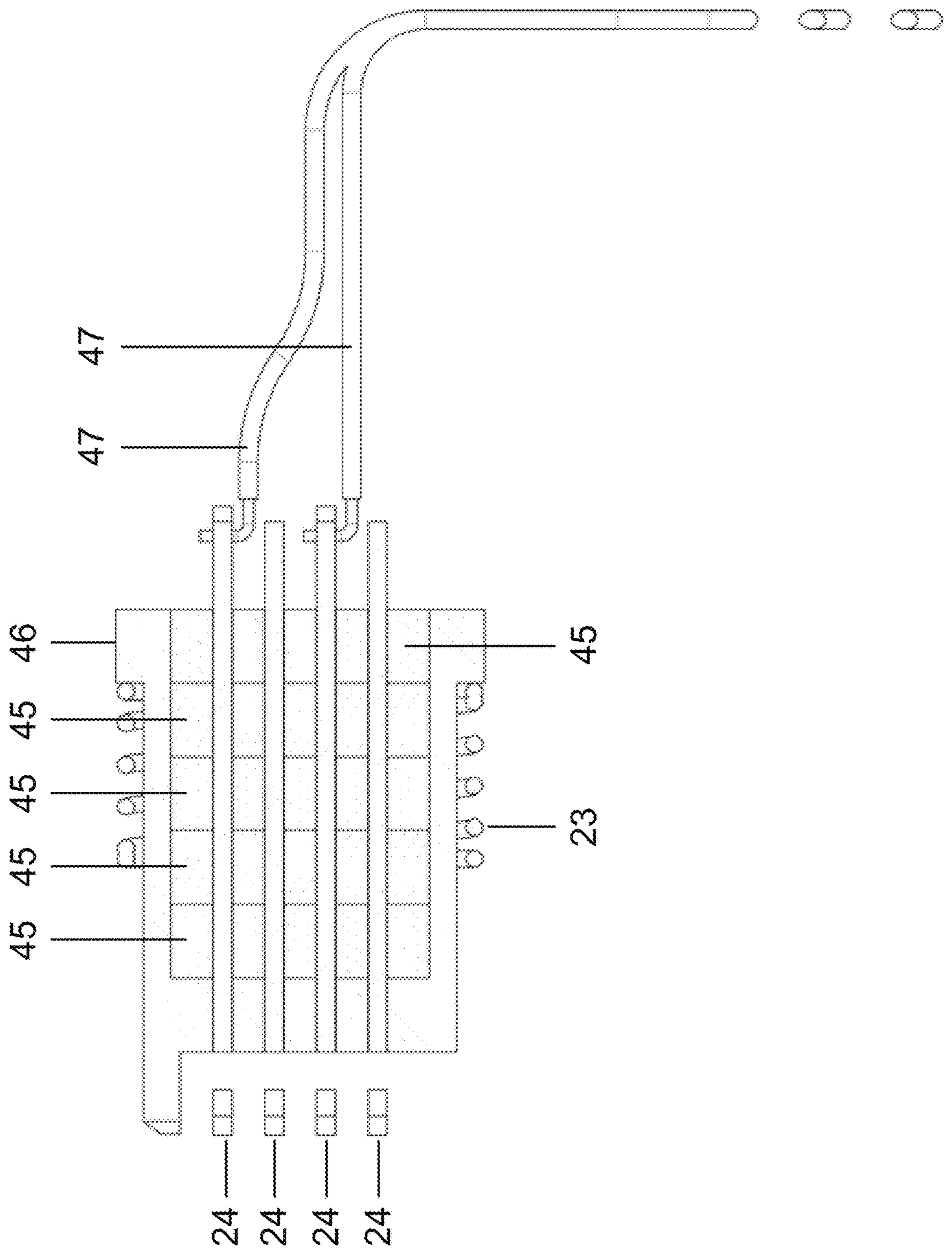
Figure 32B:
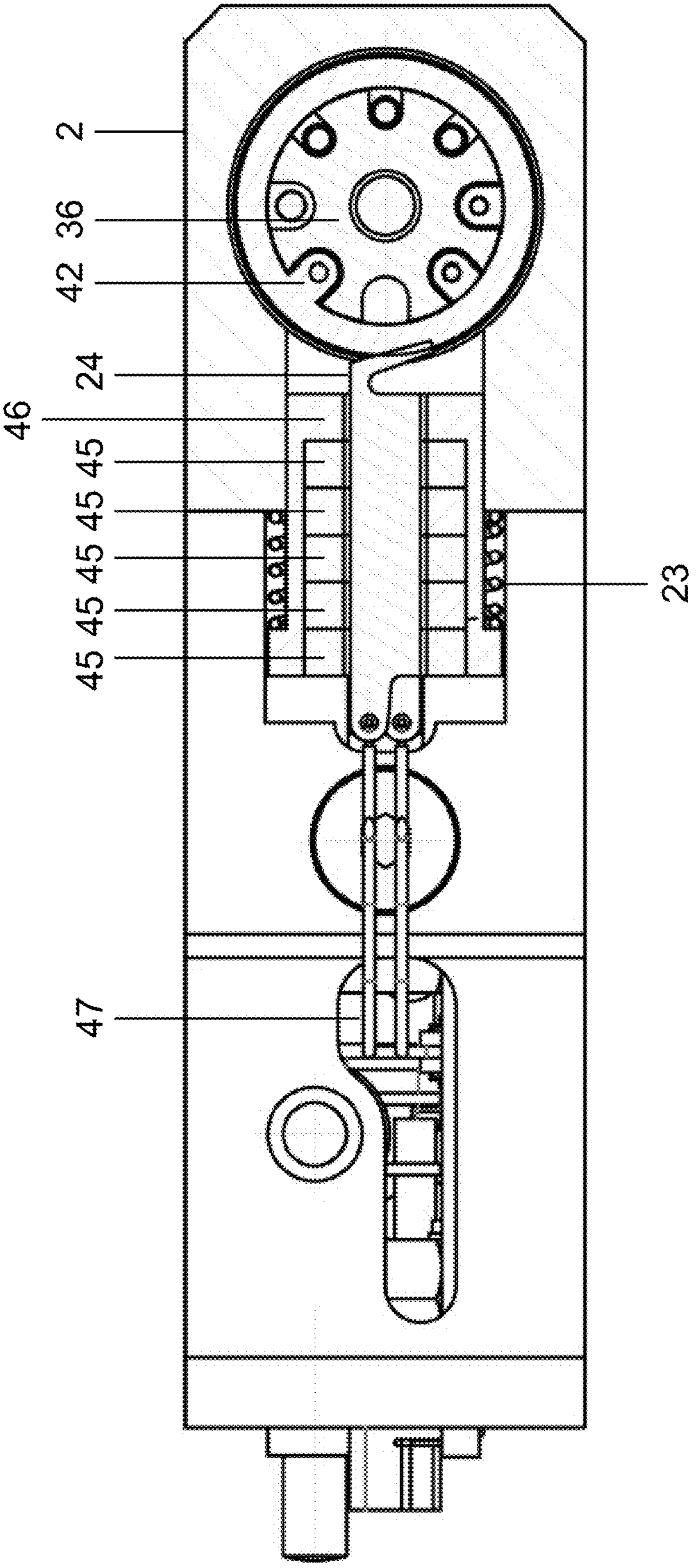
Figure 33:
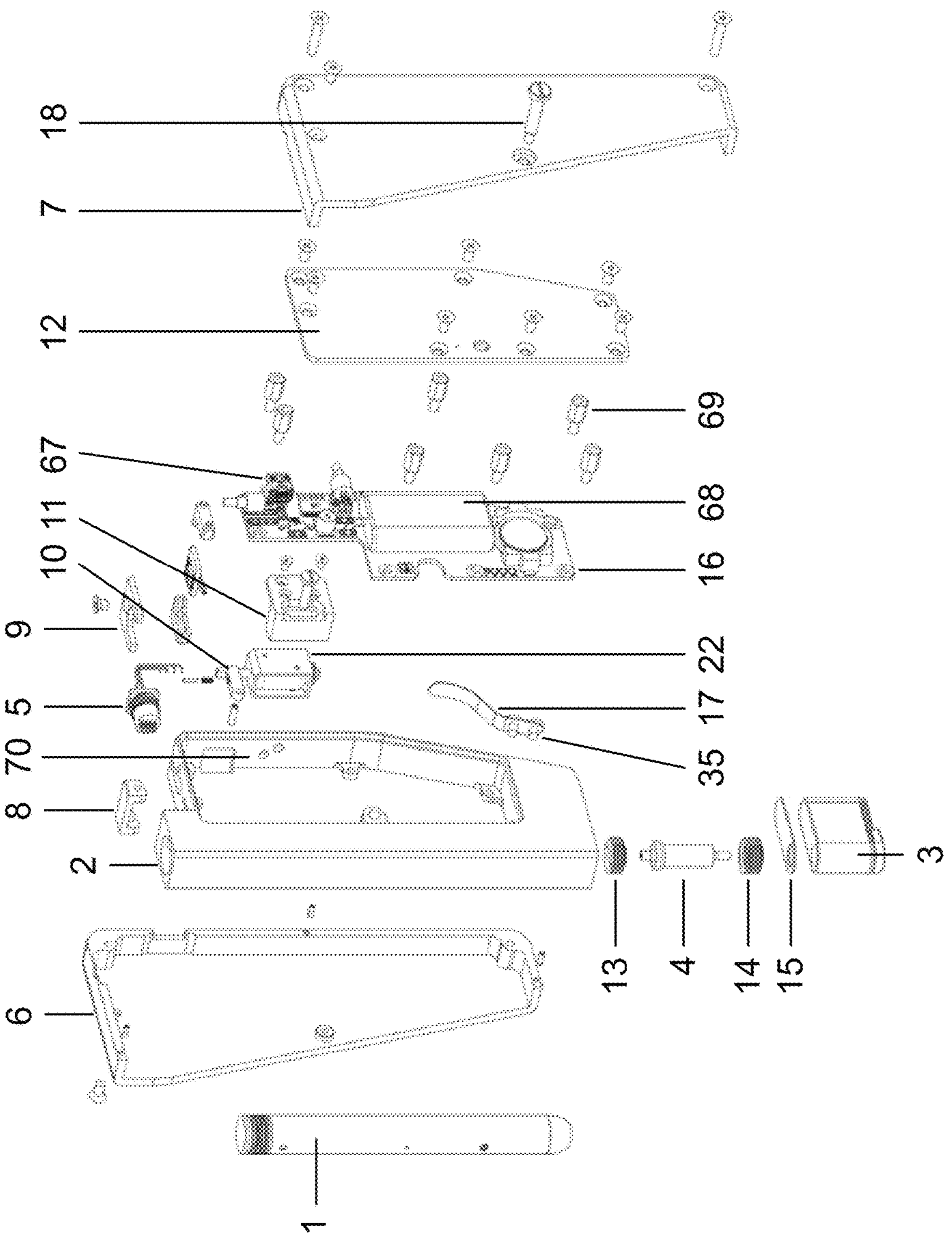
Figure 34:
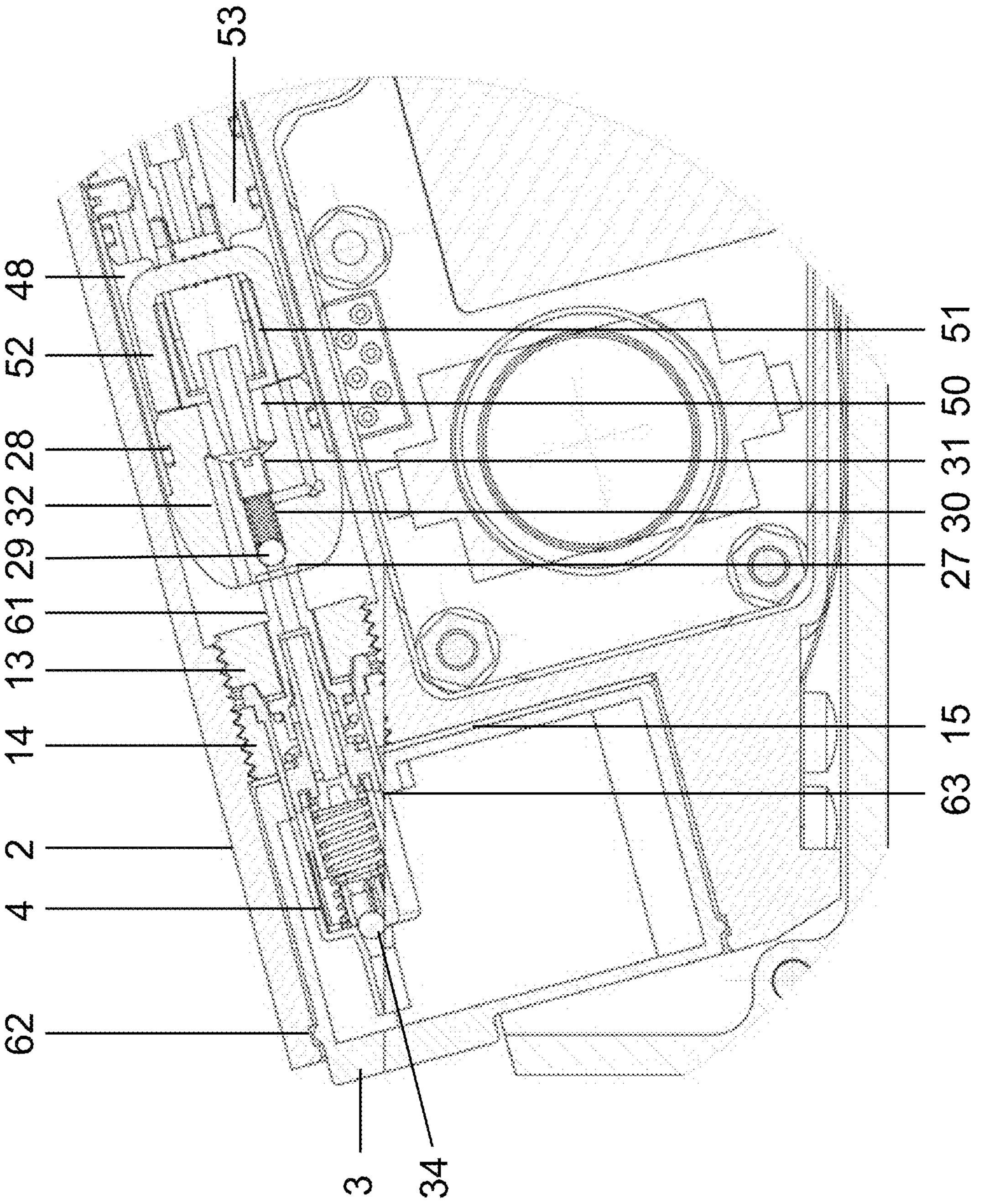
Figure 35:
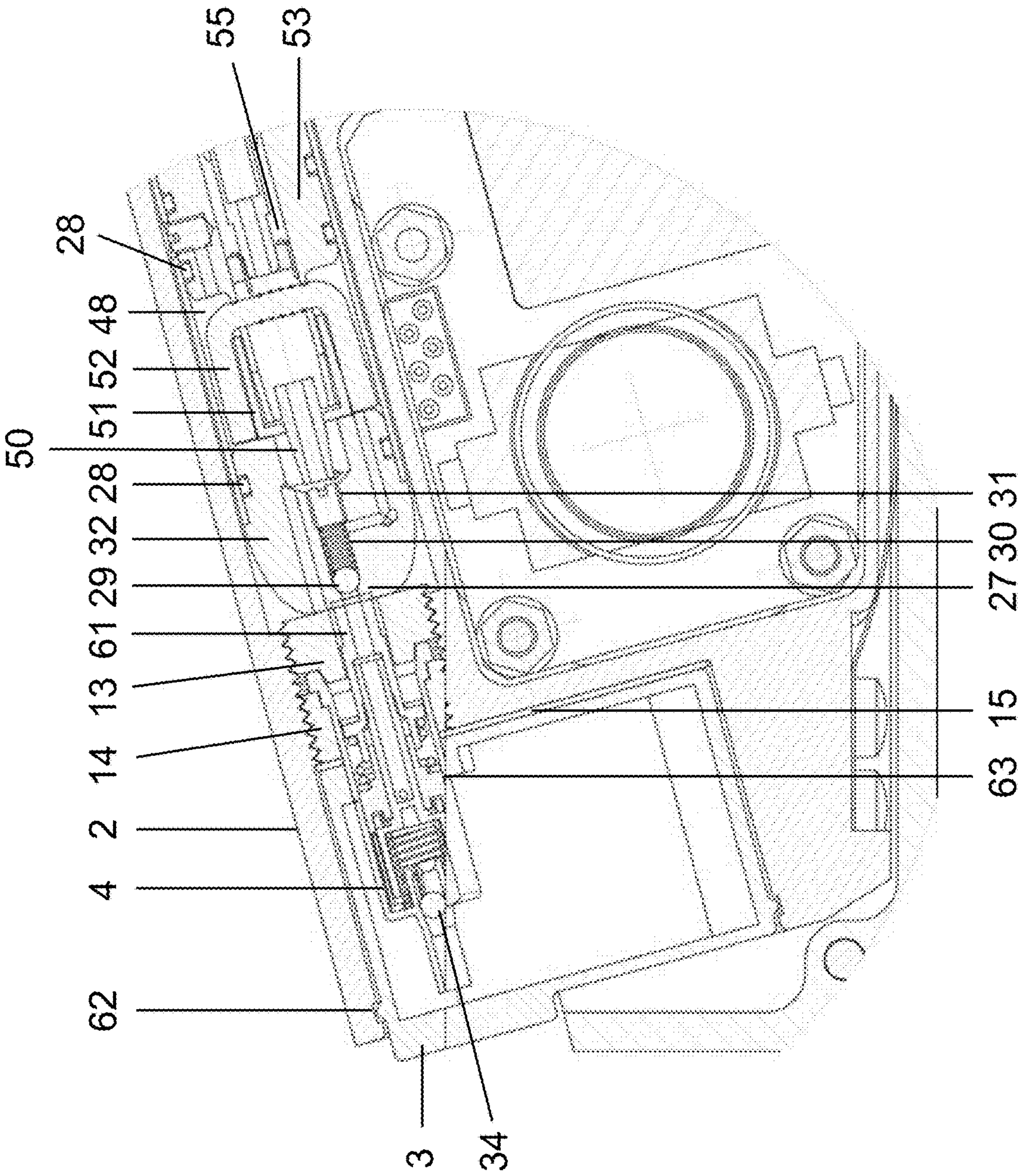
Figure 36:
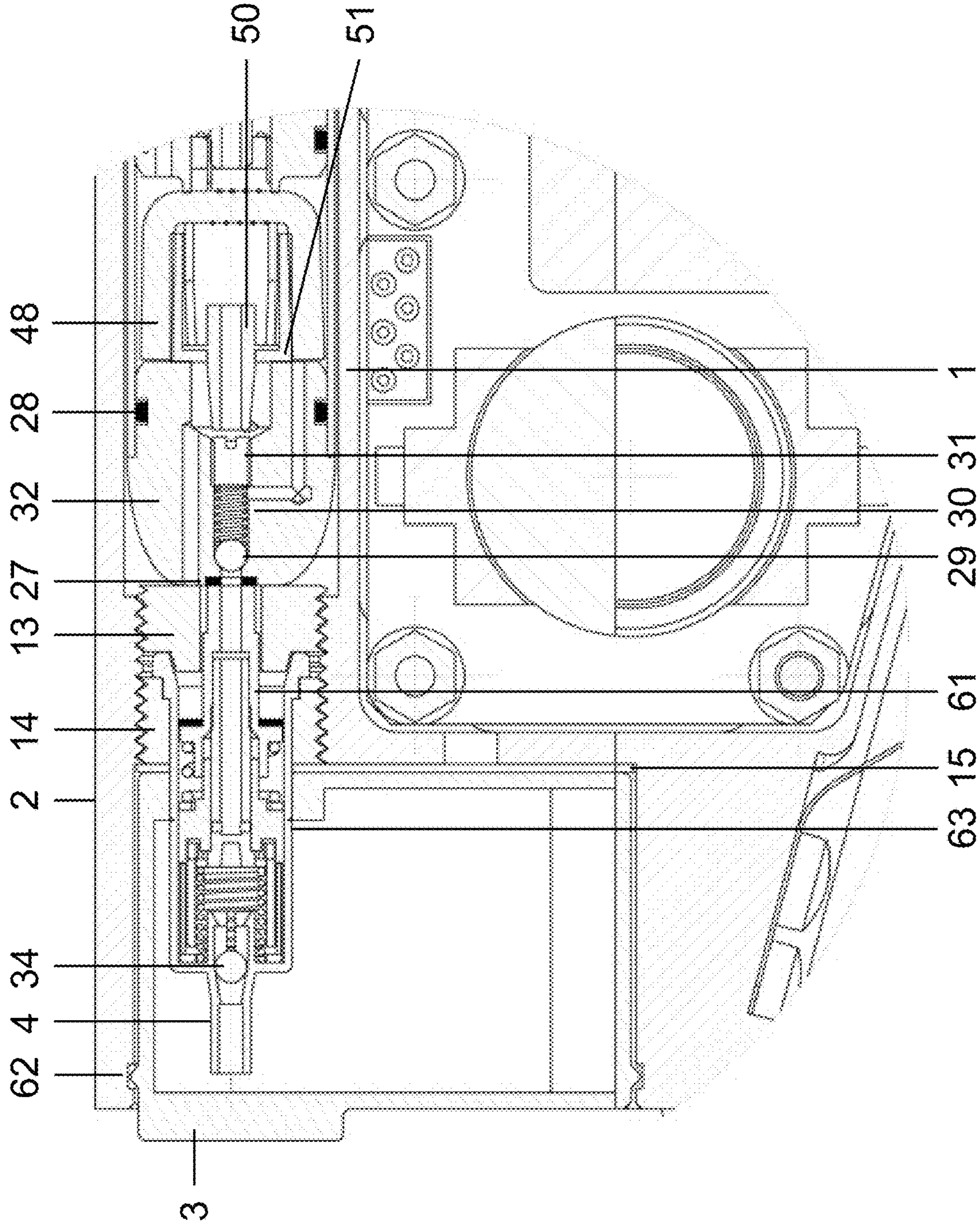
Figure 46:
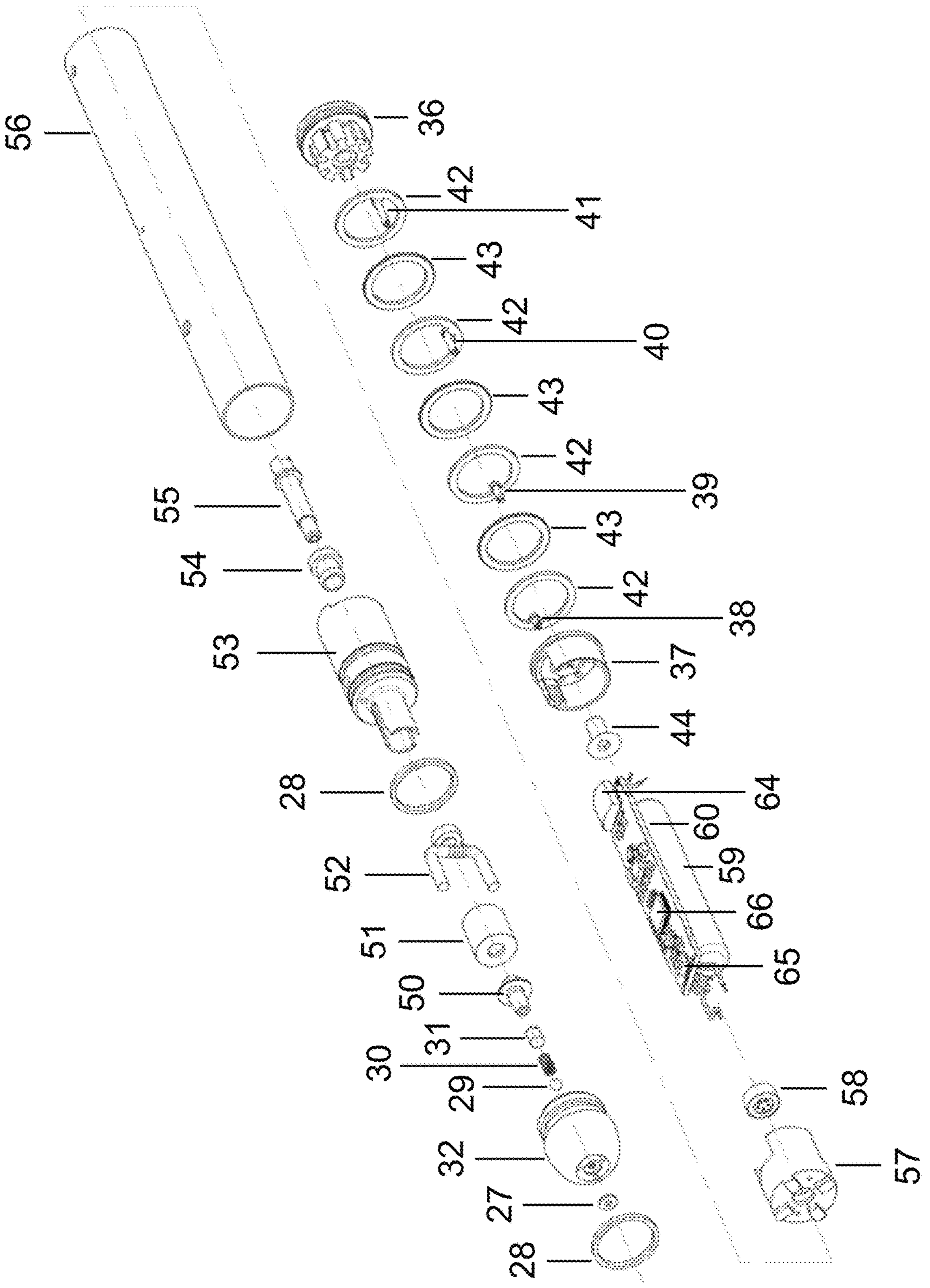
Figure 47:
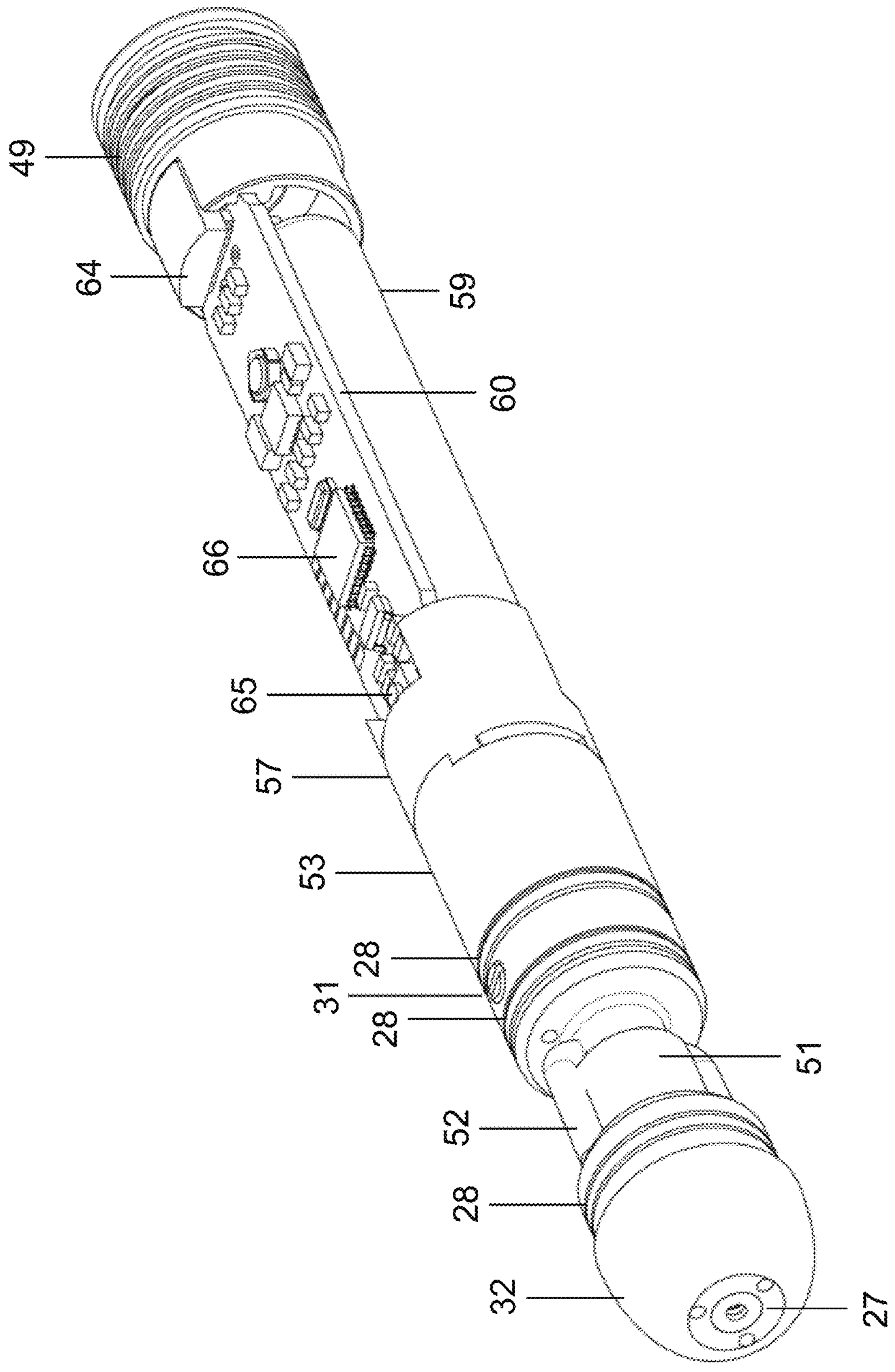
Figure 48:
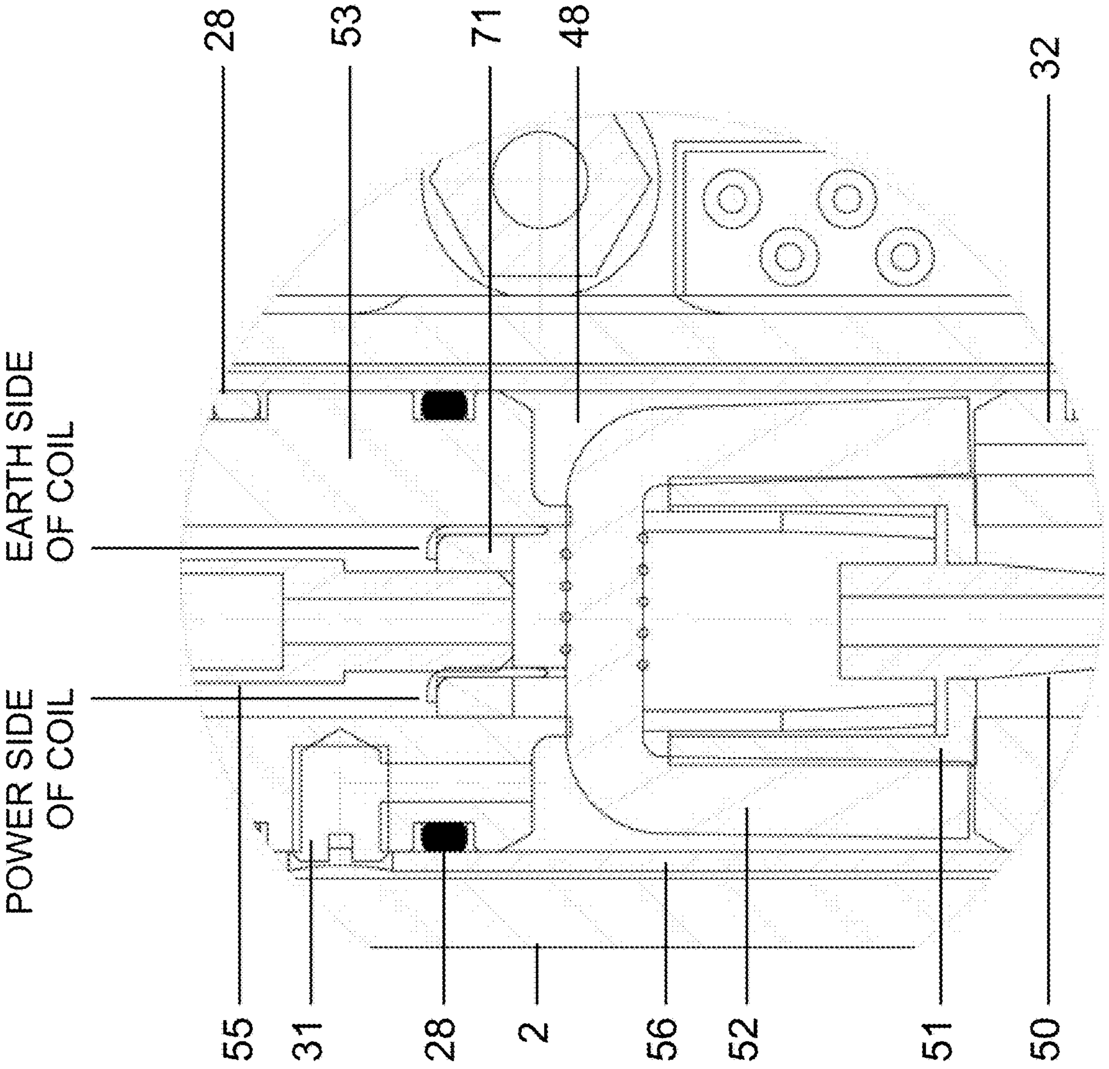
Figure 49:
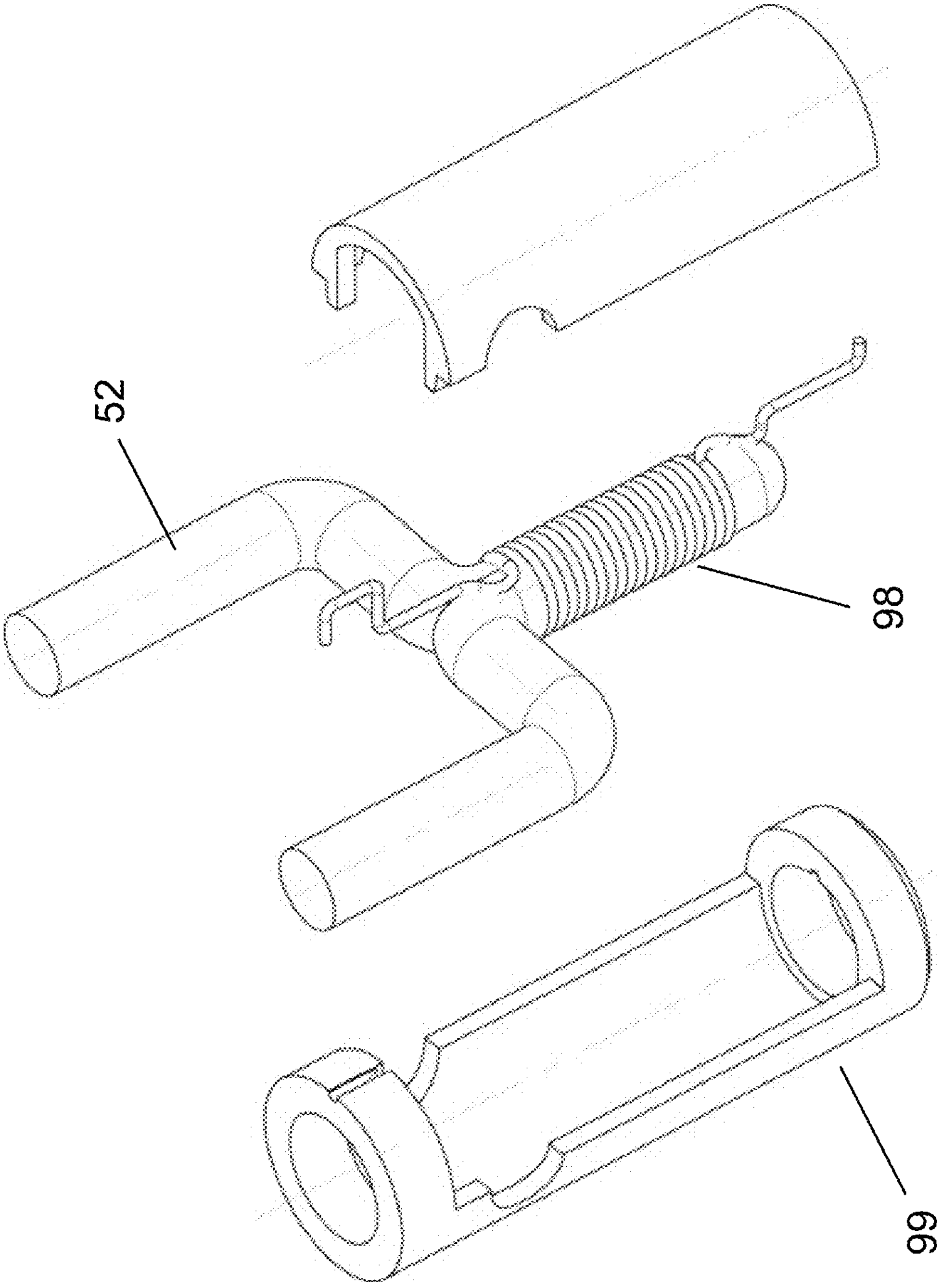
Figure 50:
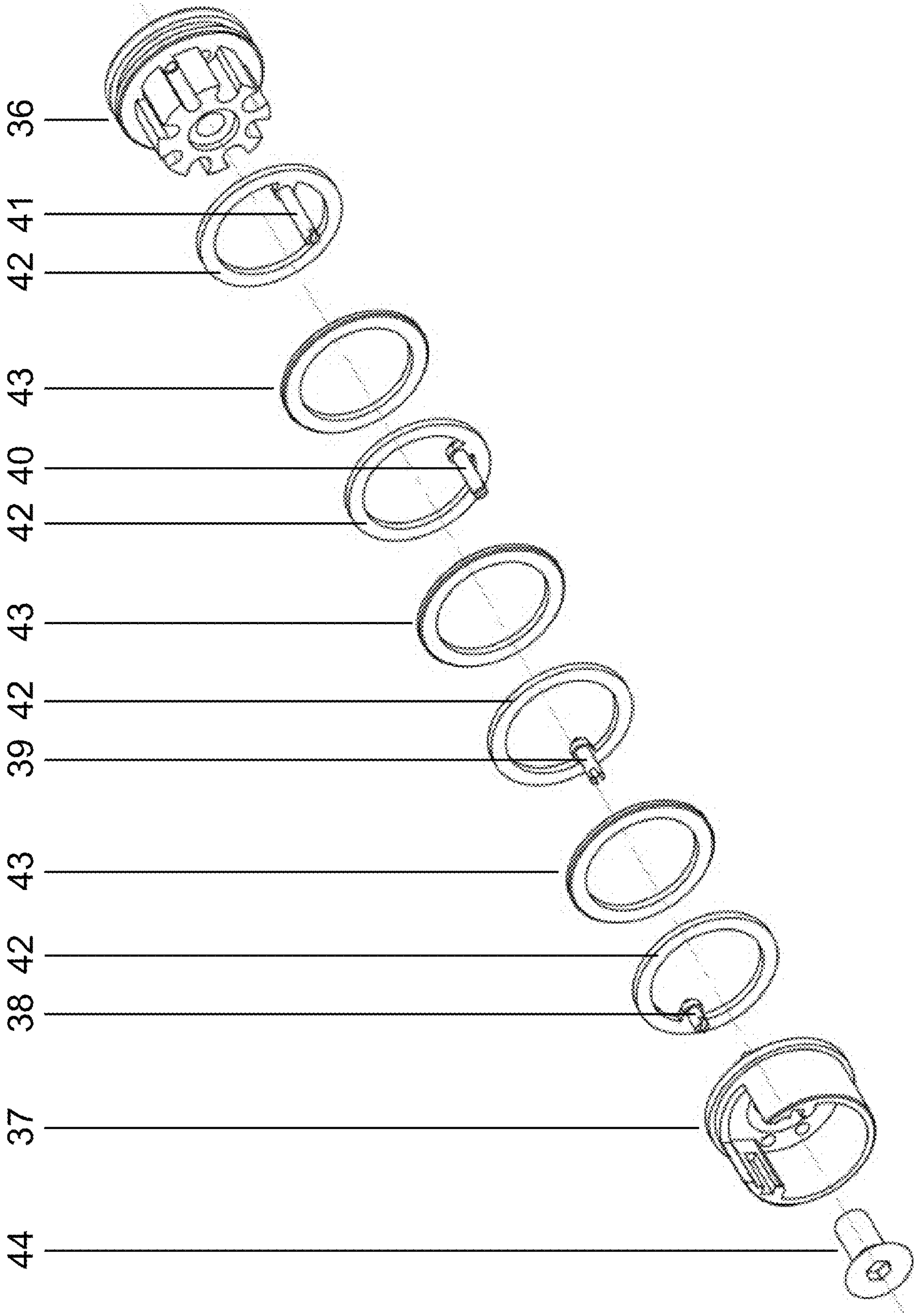
Figure 51:
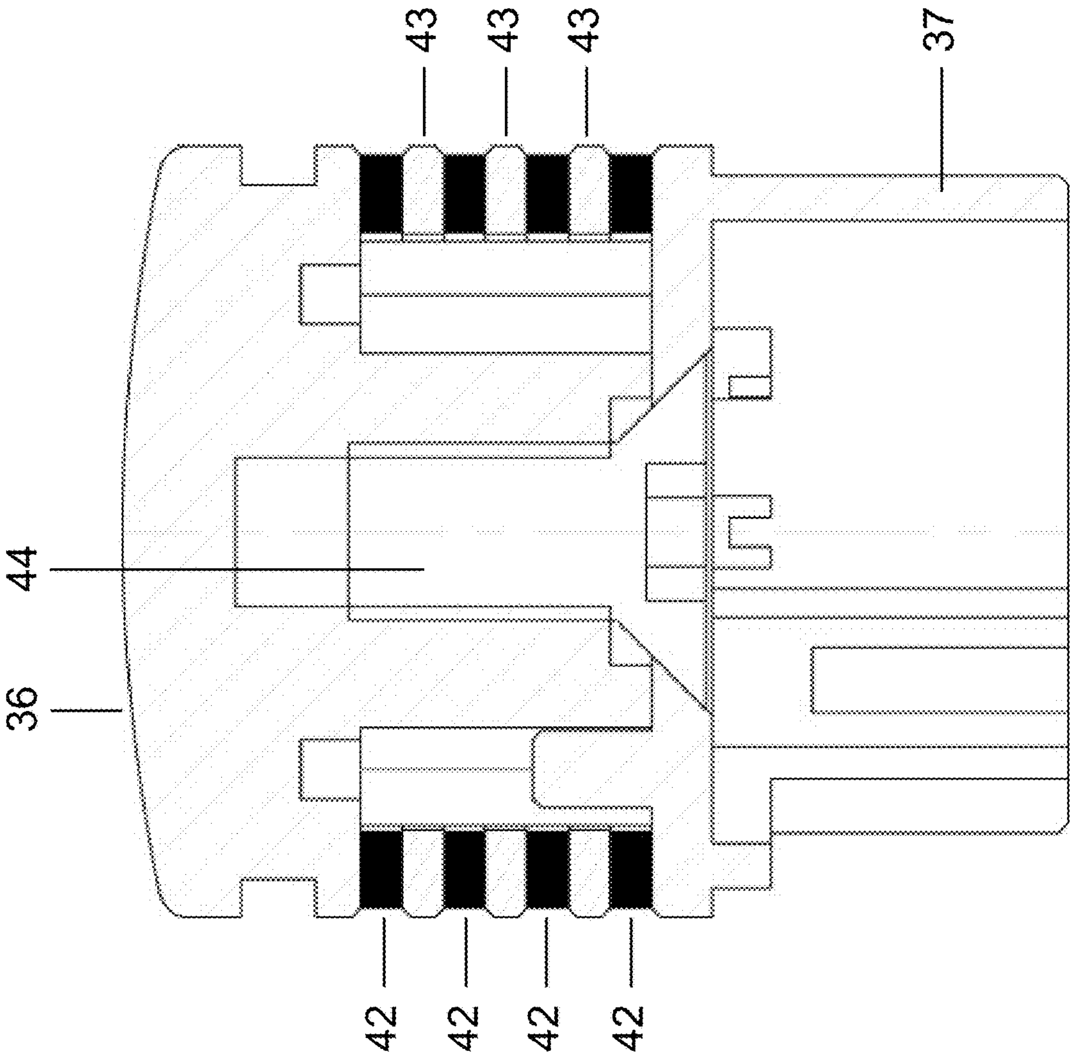
Figure 52:
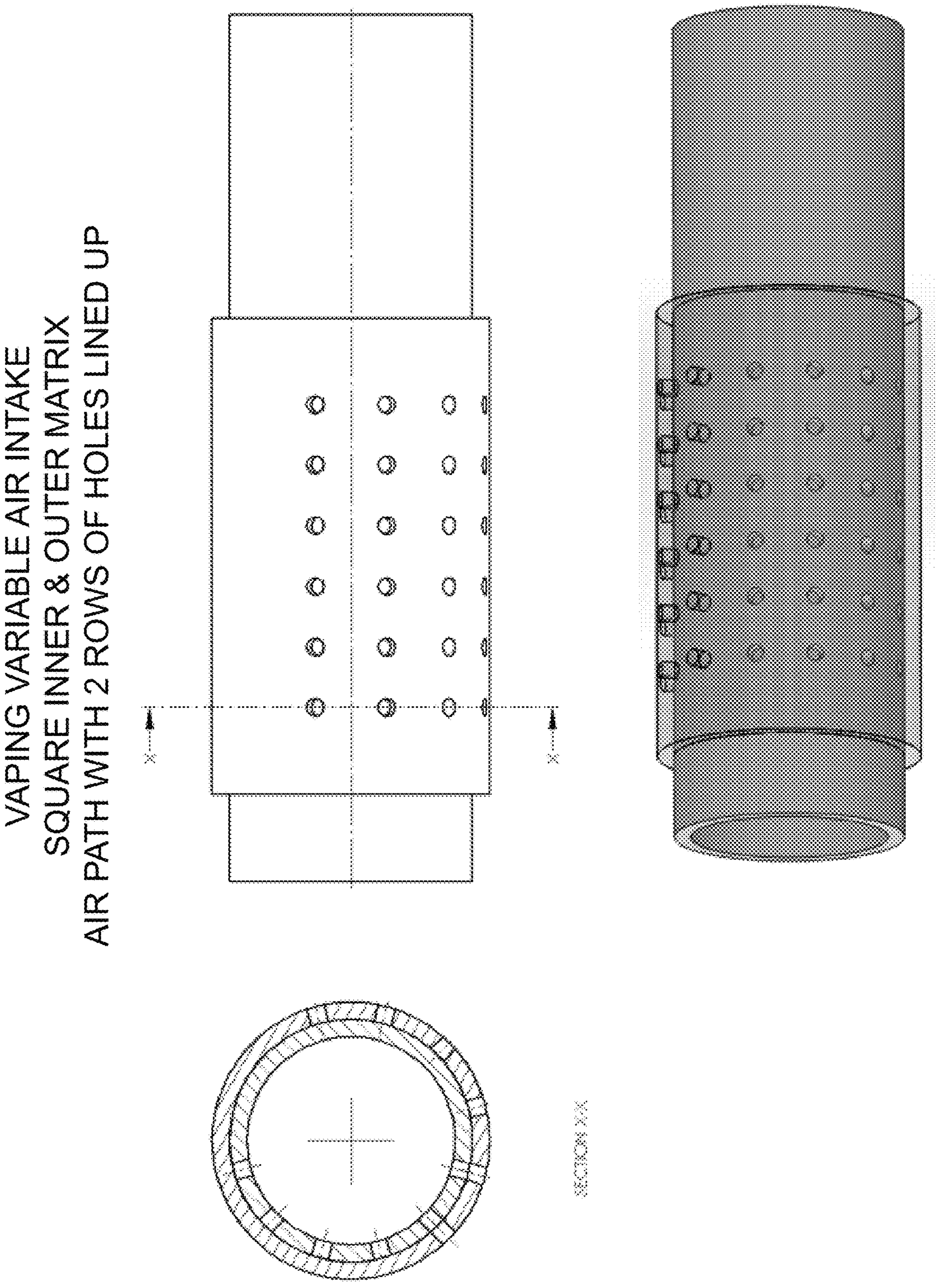
Figure 53:
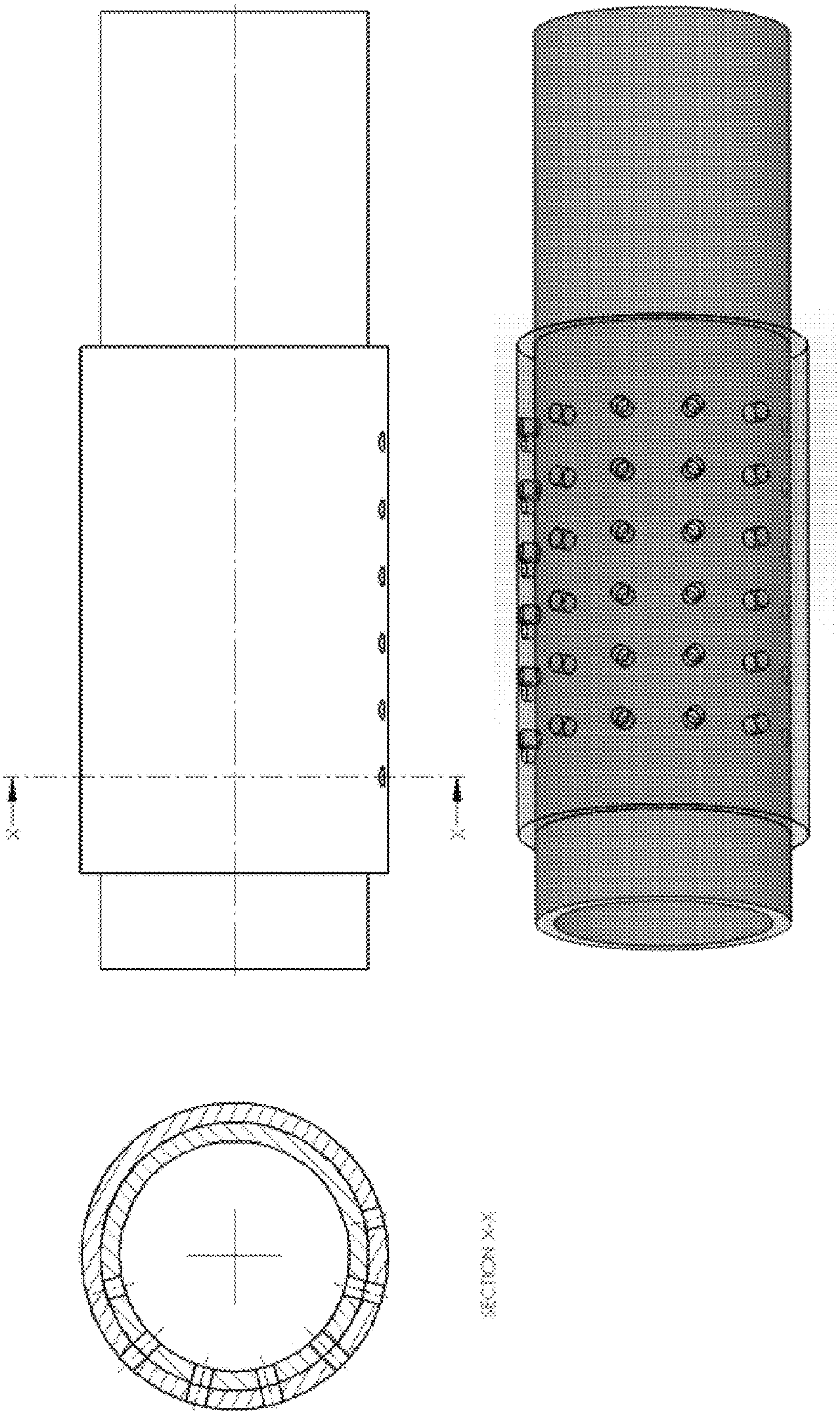
Figure 54:
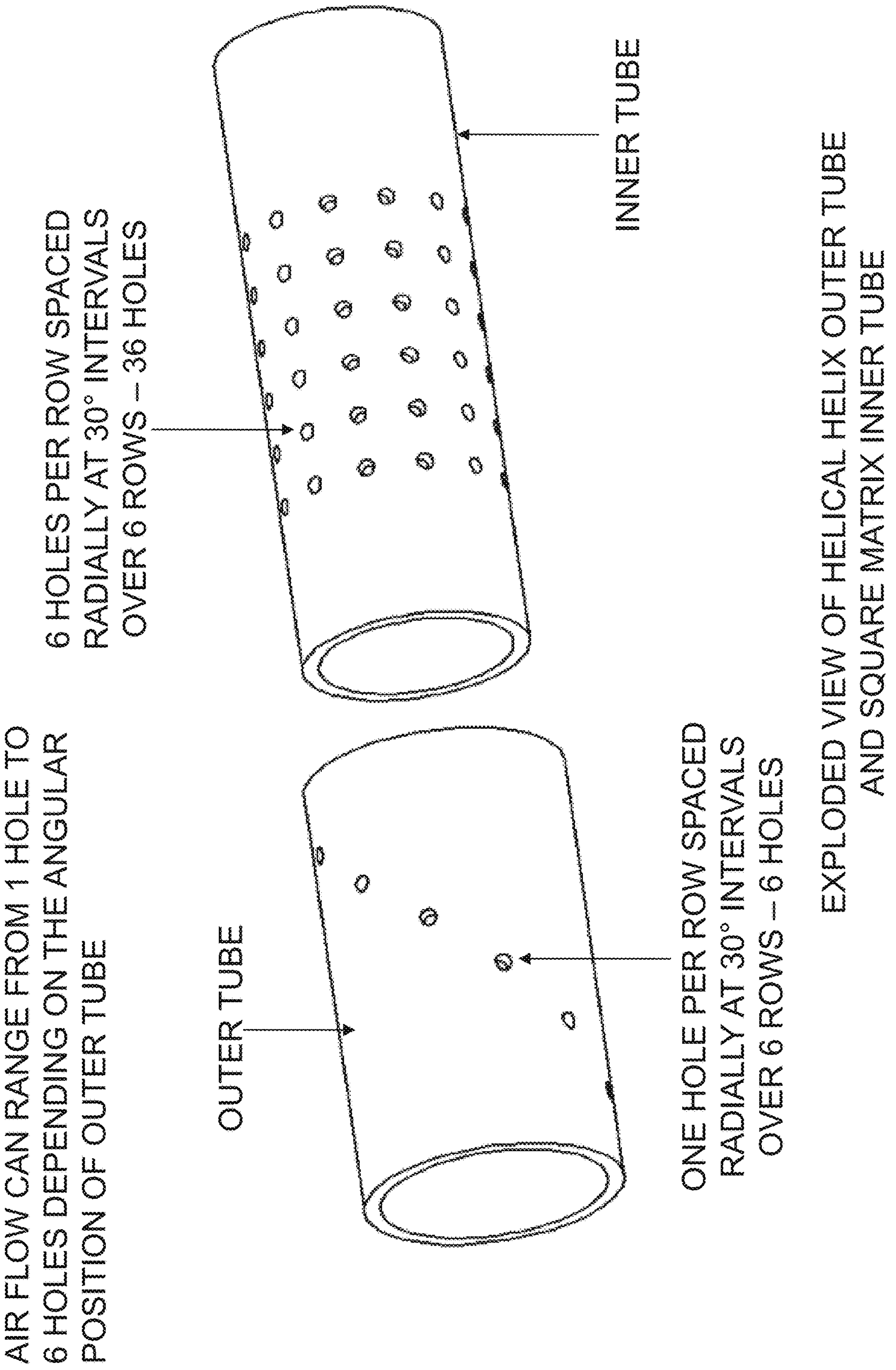
Figure 55:
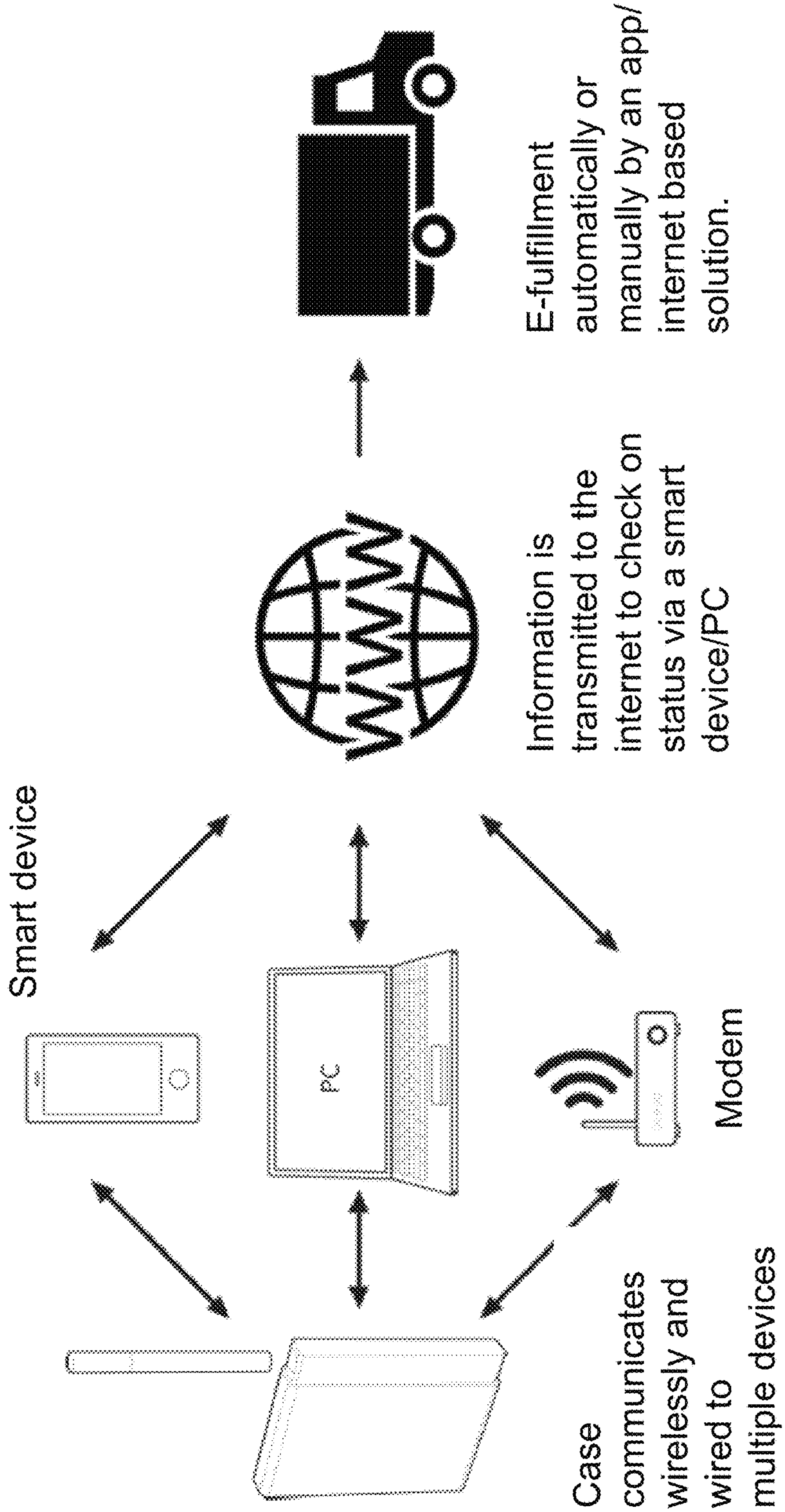
Figure 56:
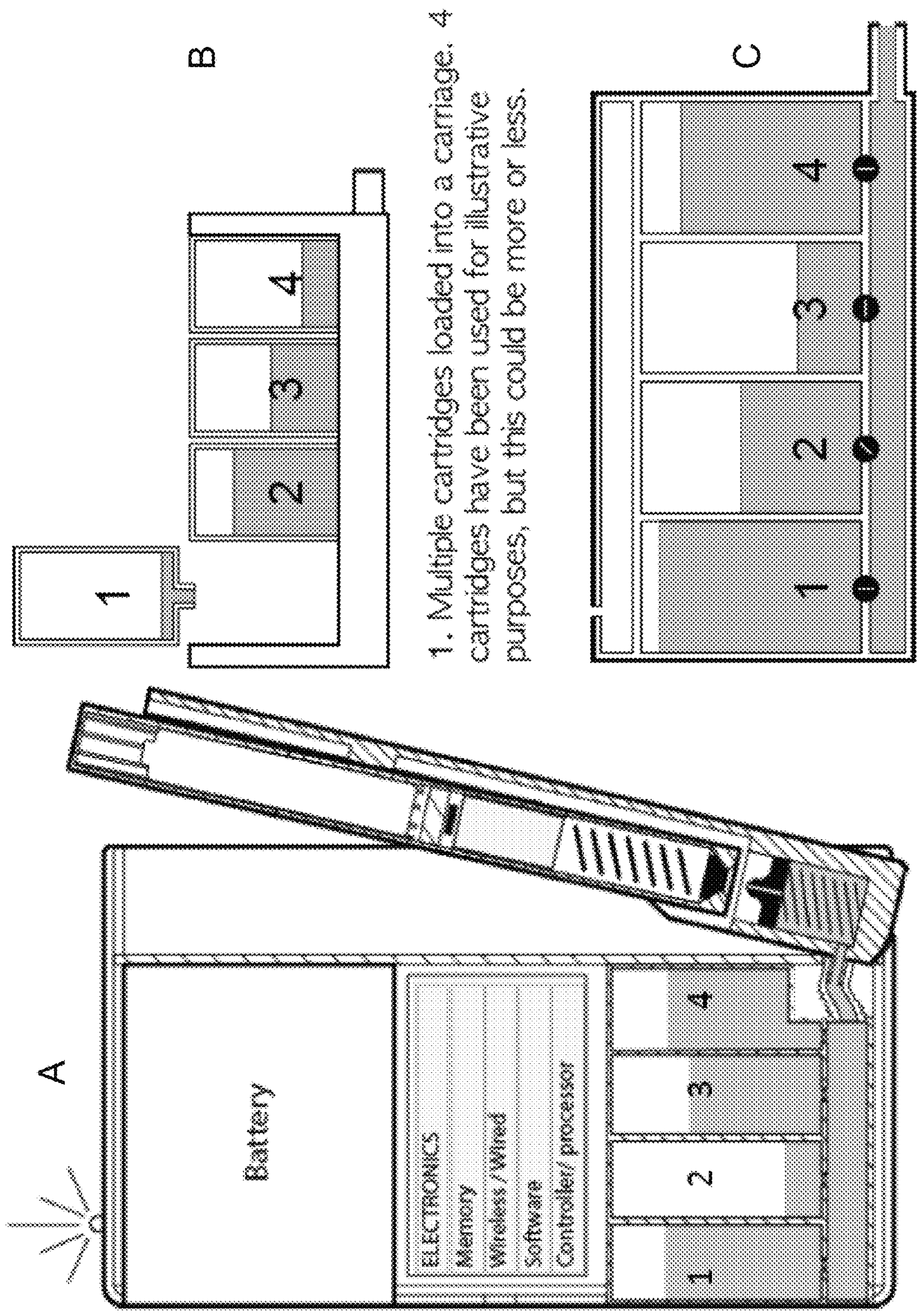
Figure 57:
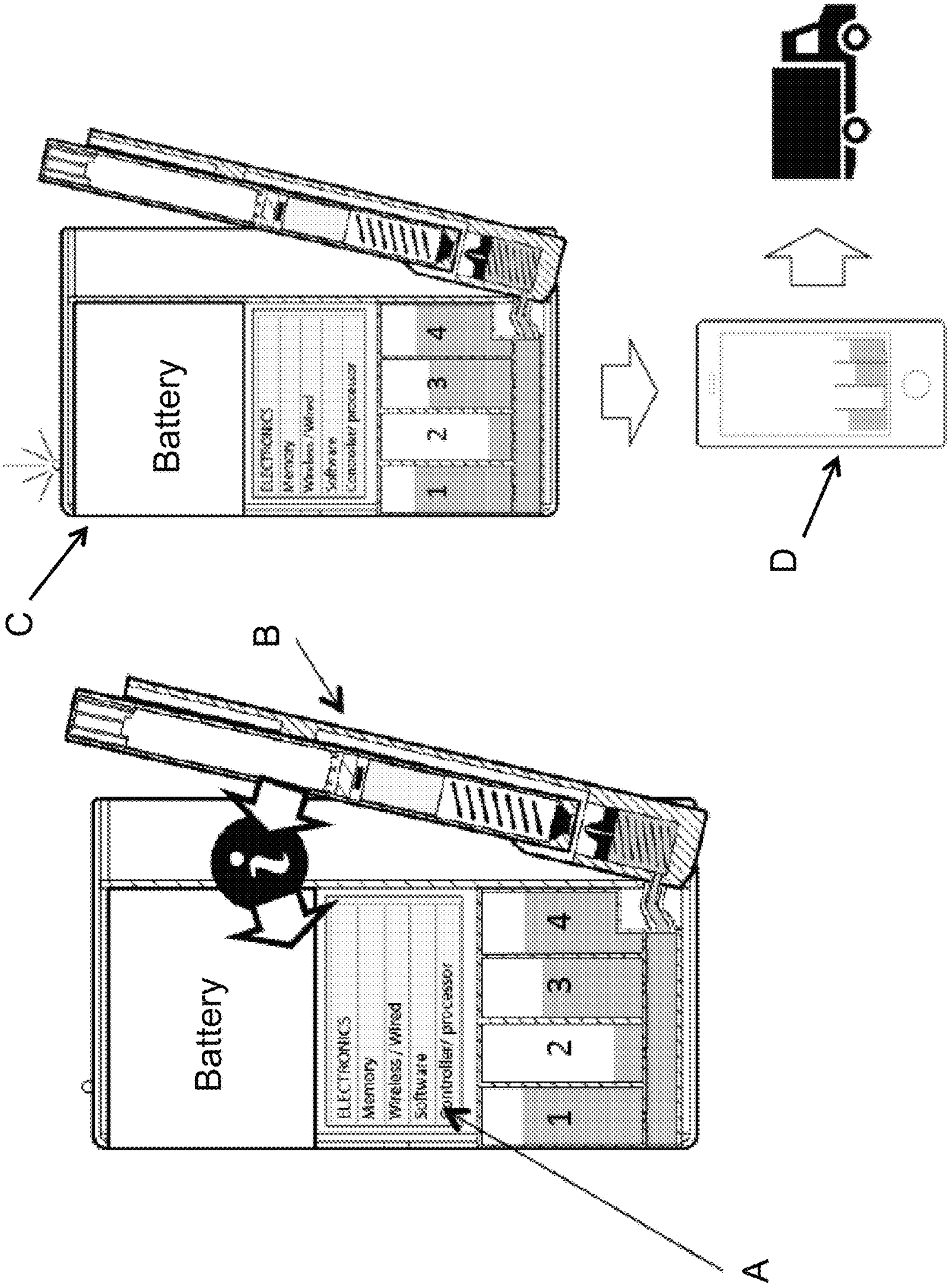
Figure 58:
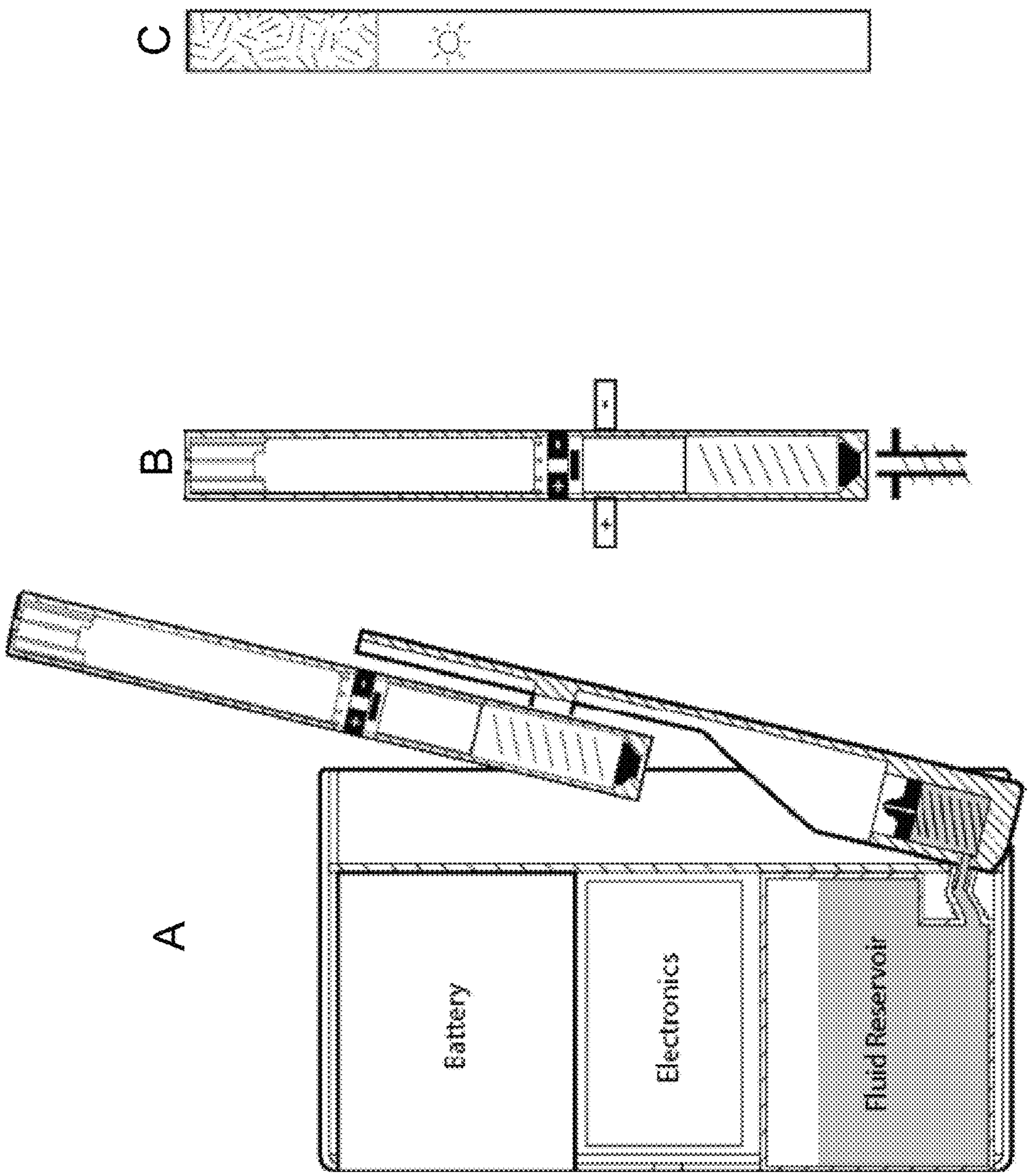
Figure 59:
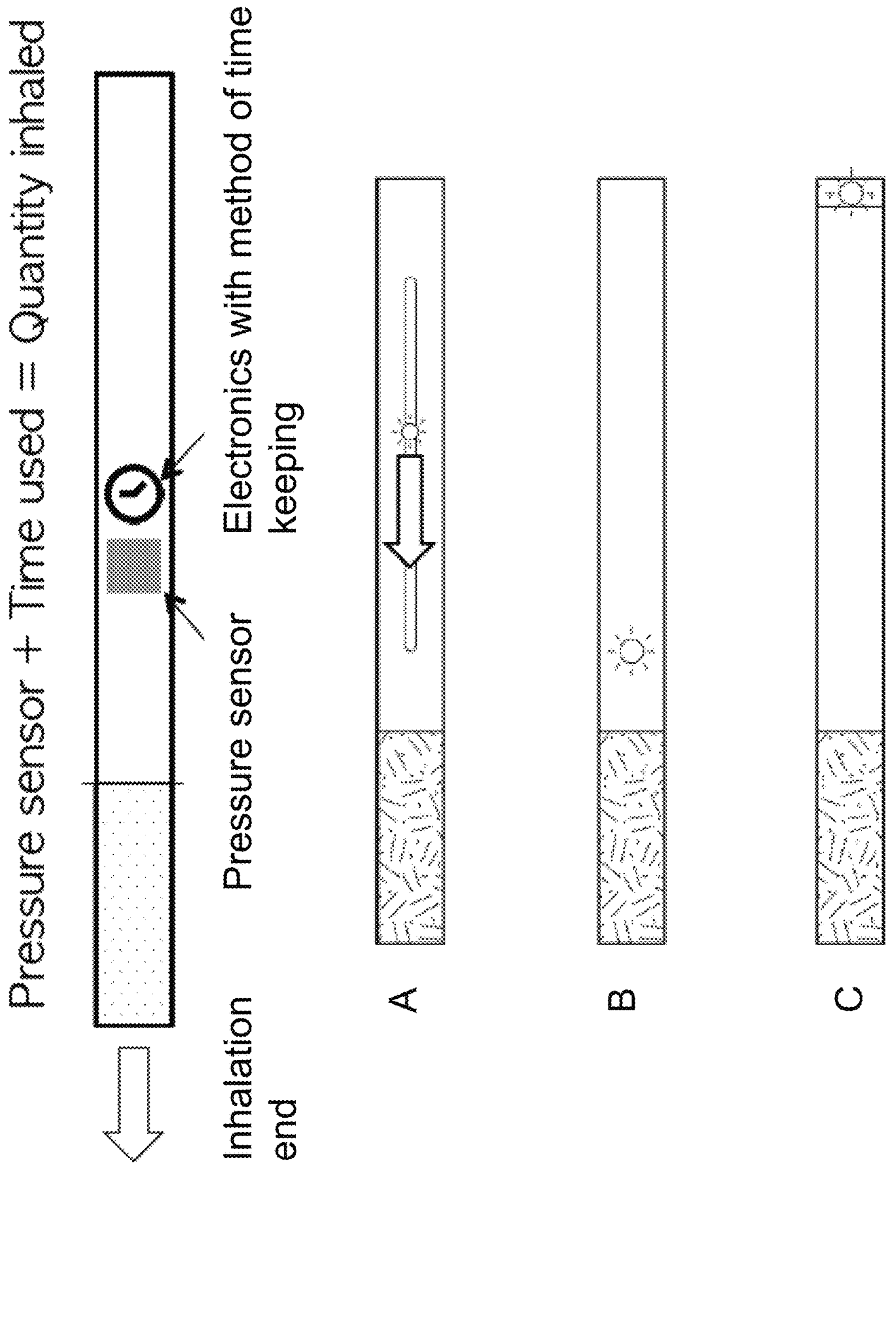
Figure 60:
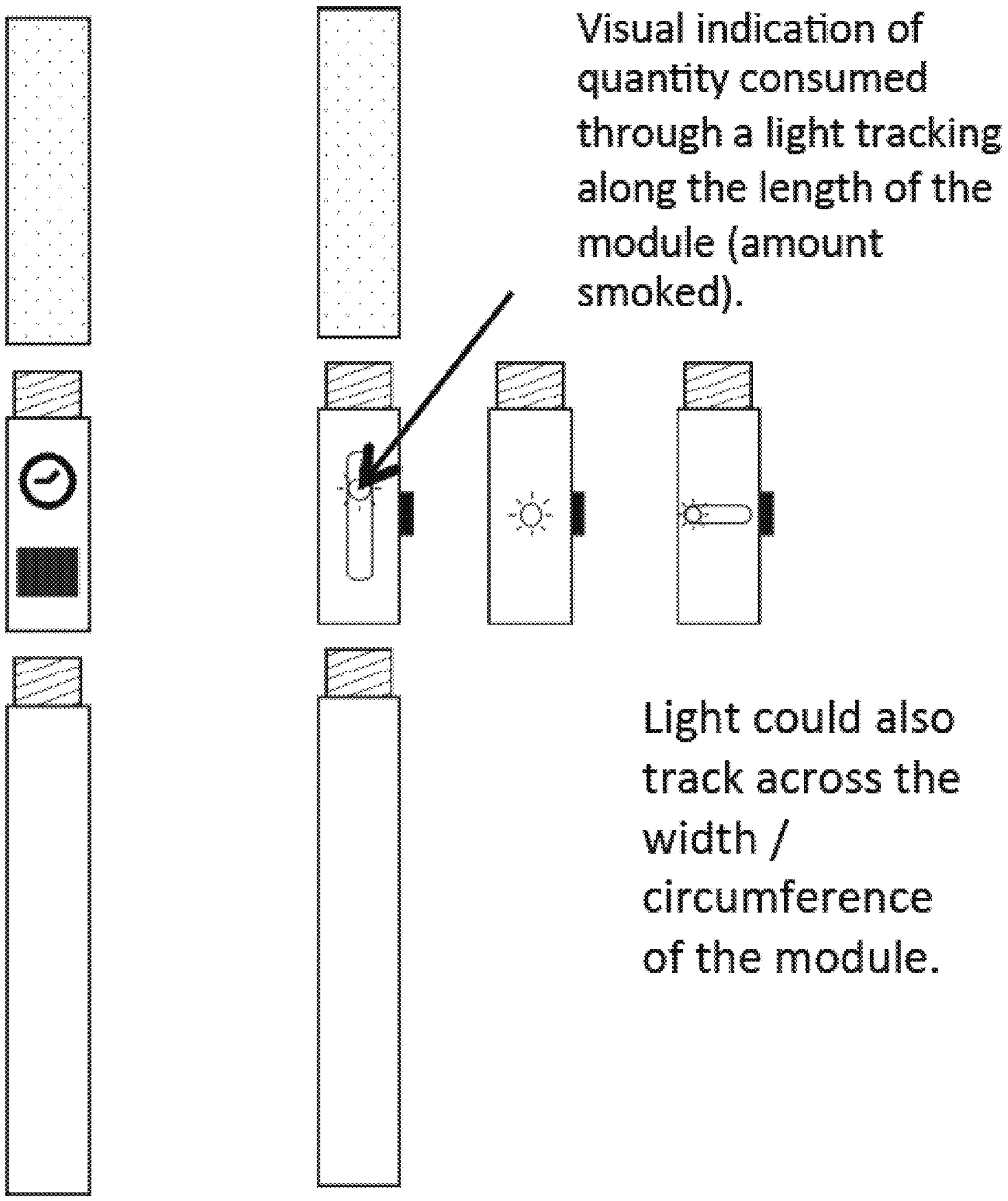
Figure 61:
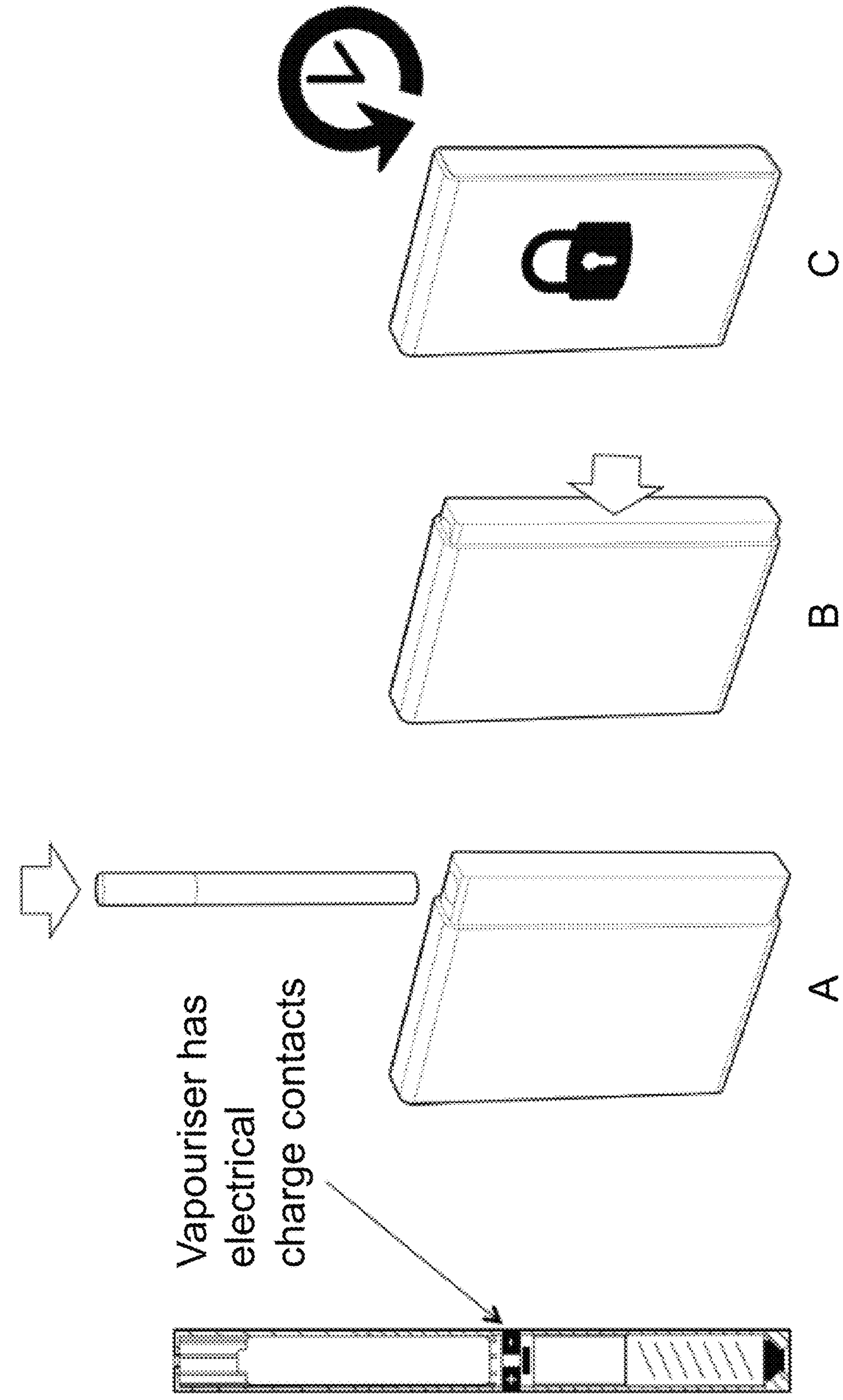
Figure 62:
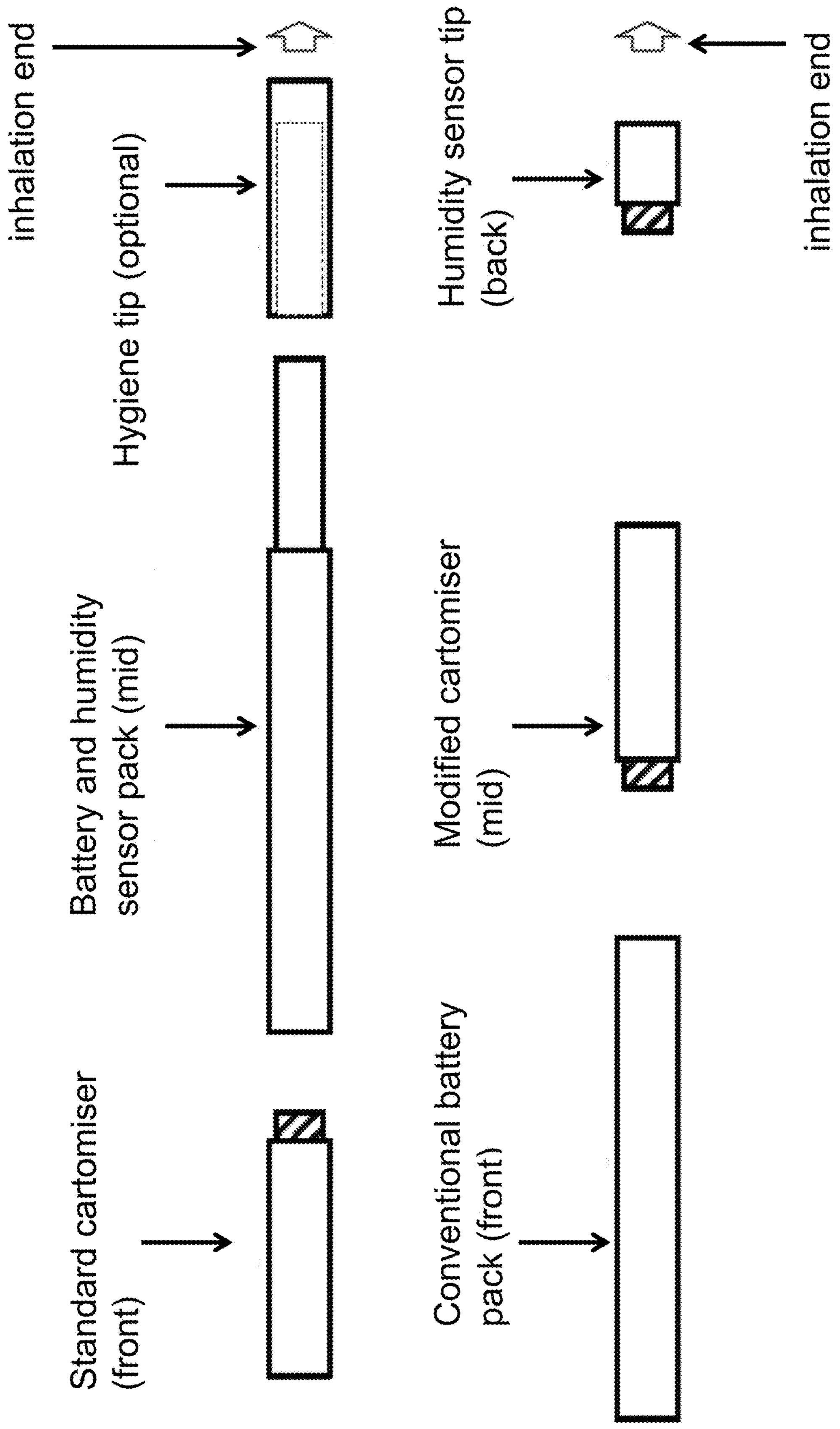
Figure 63:
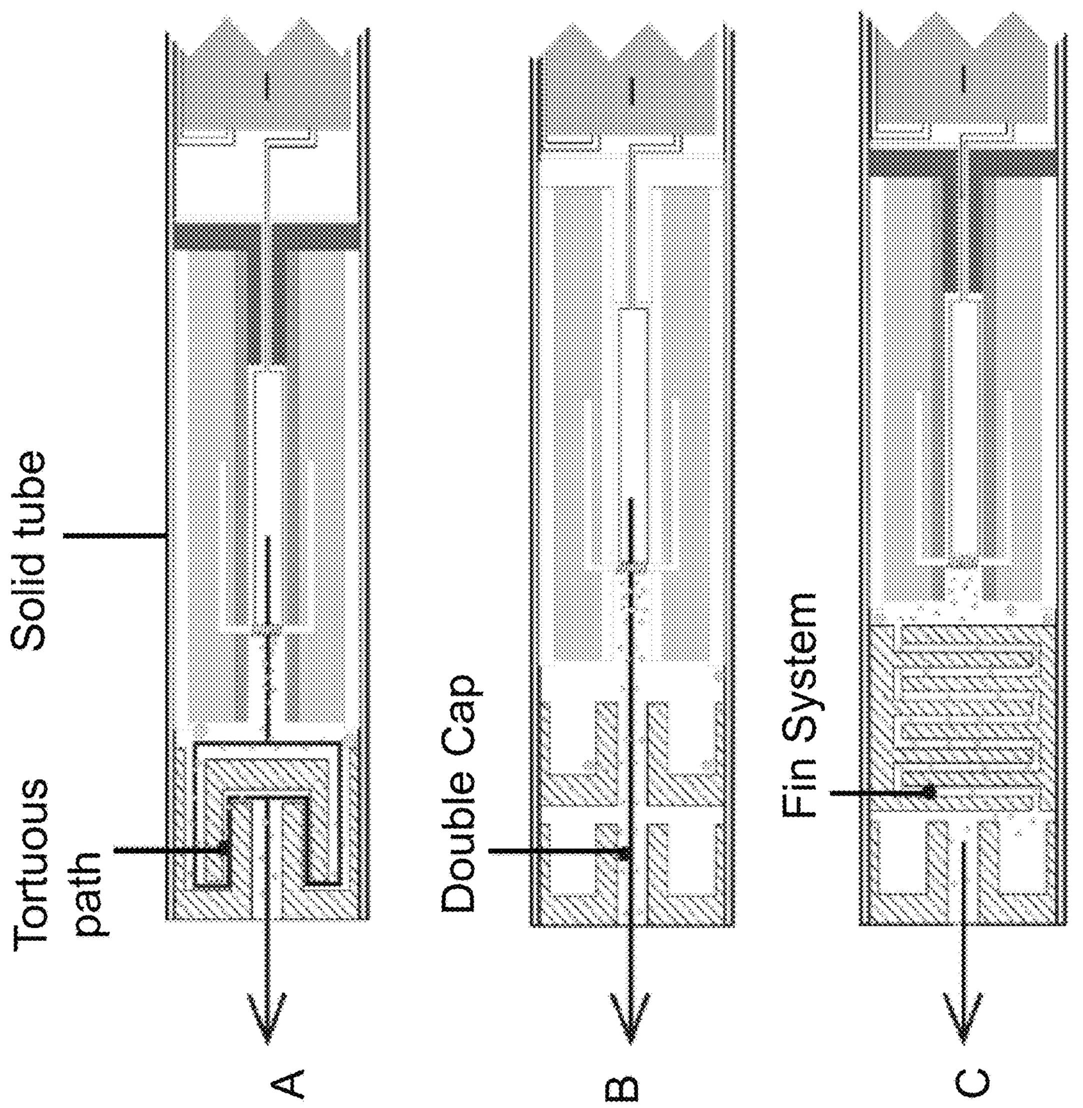
Figure 68:
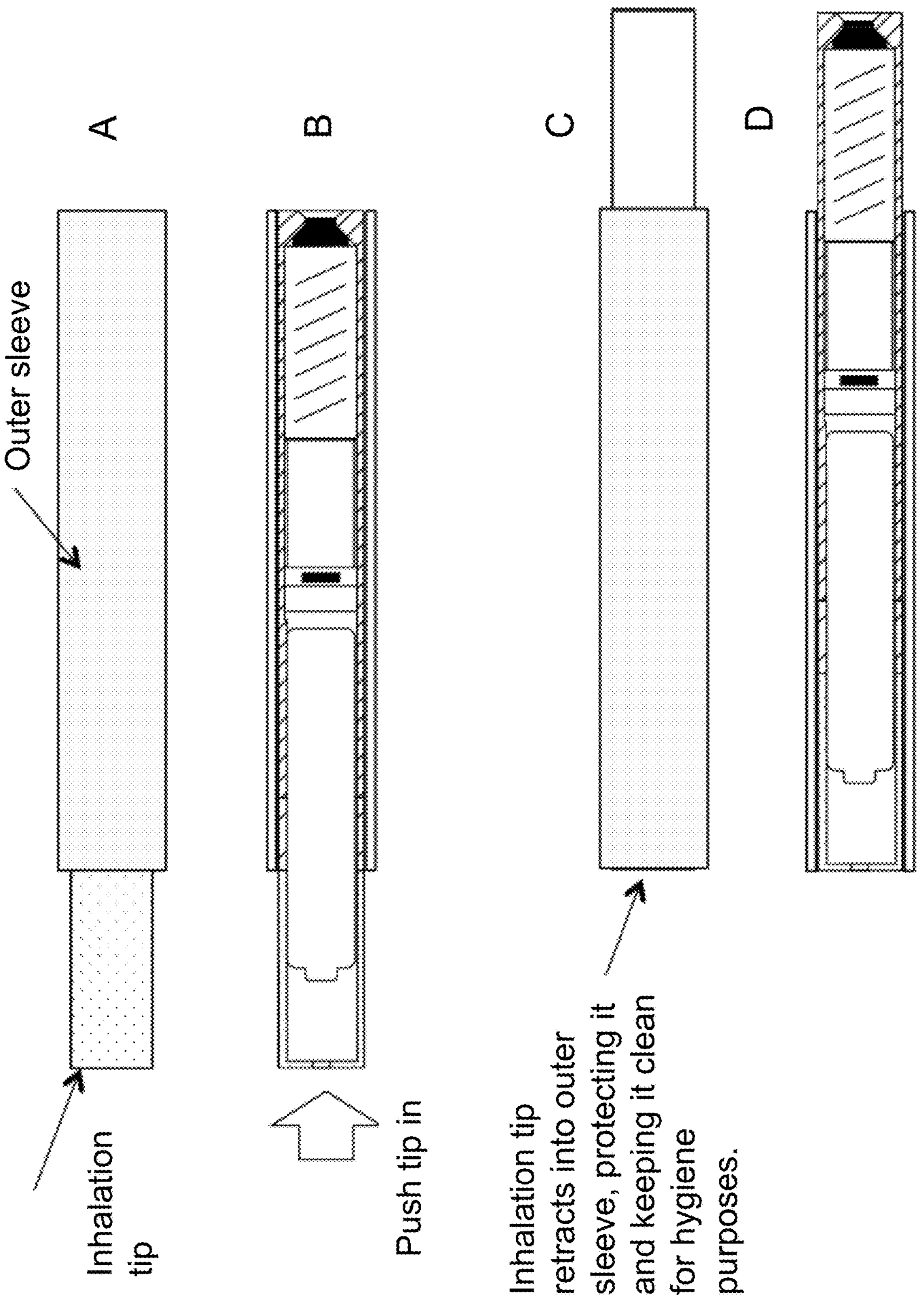
Figure 69:
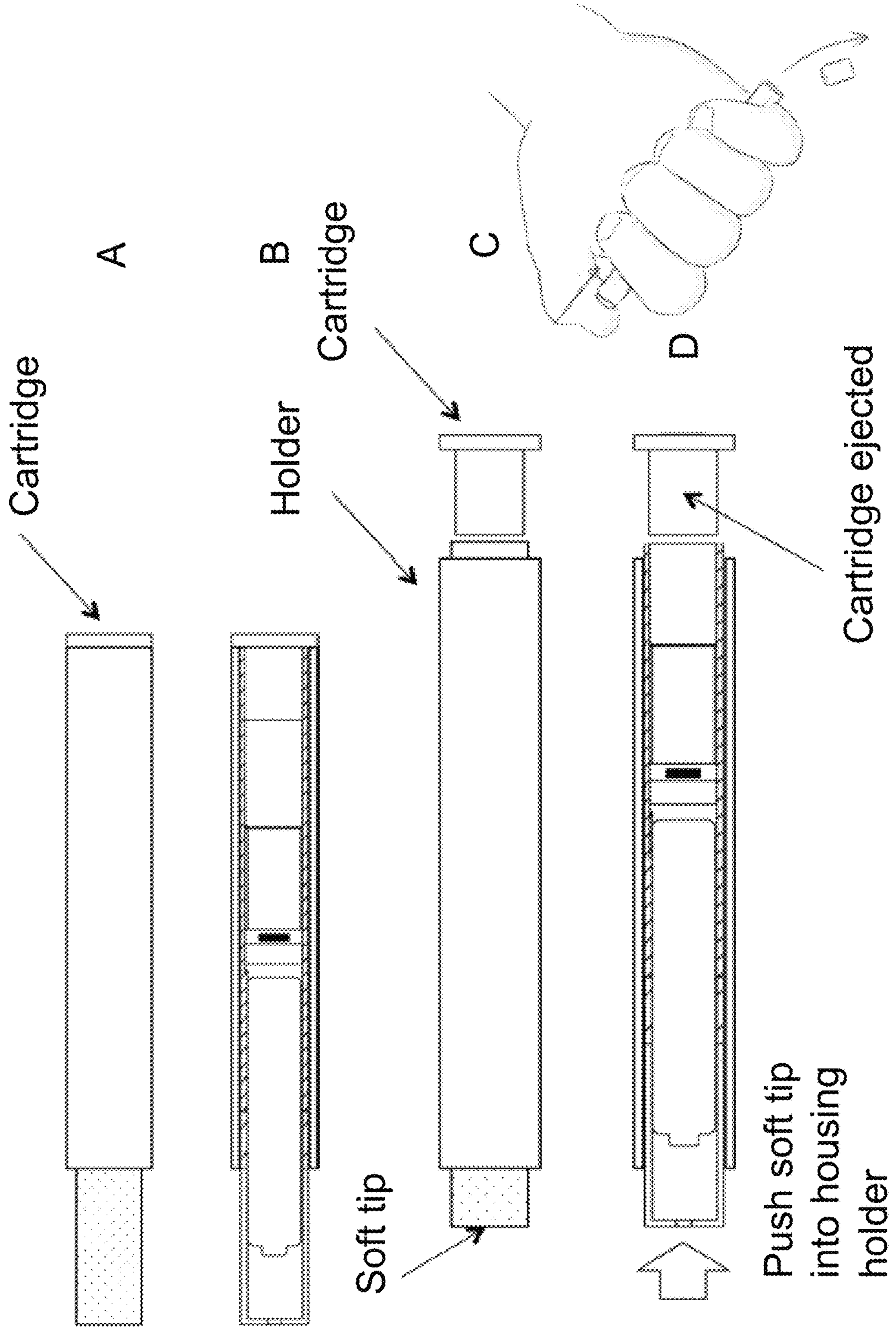
Figure 70:
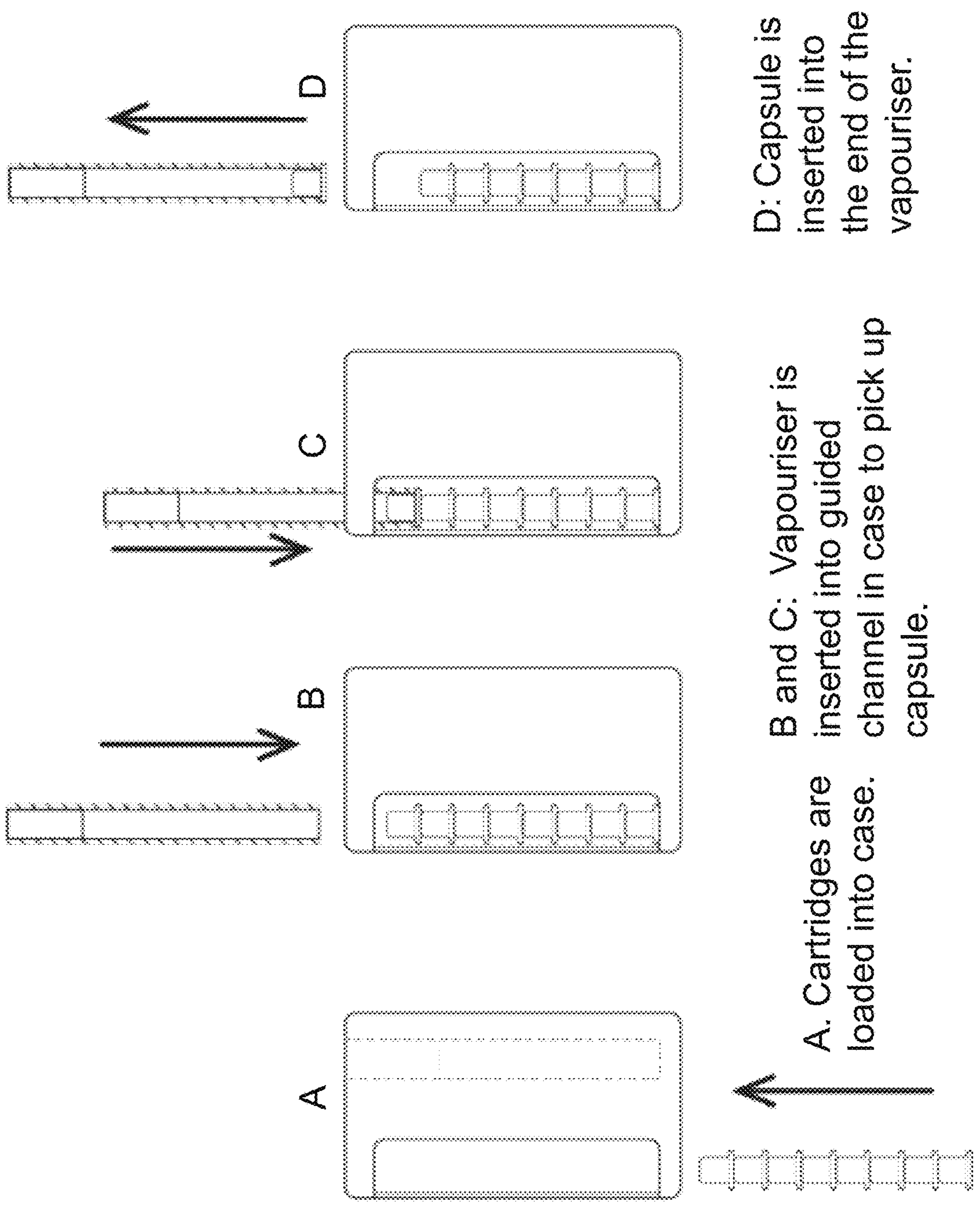
Figure 77:
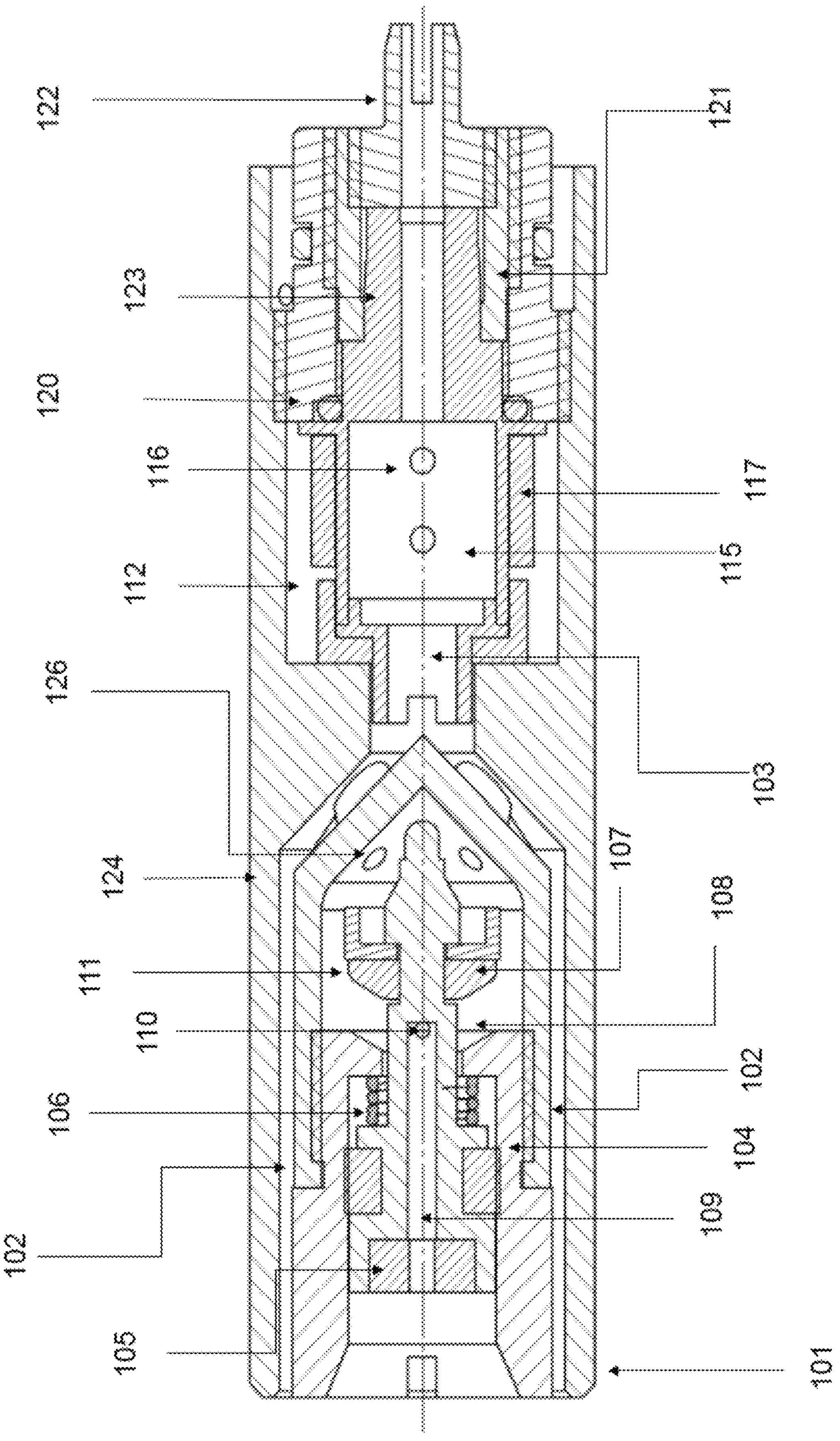
Figure 78:
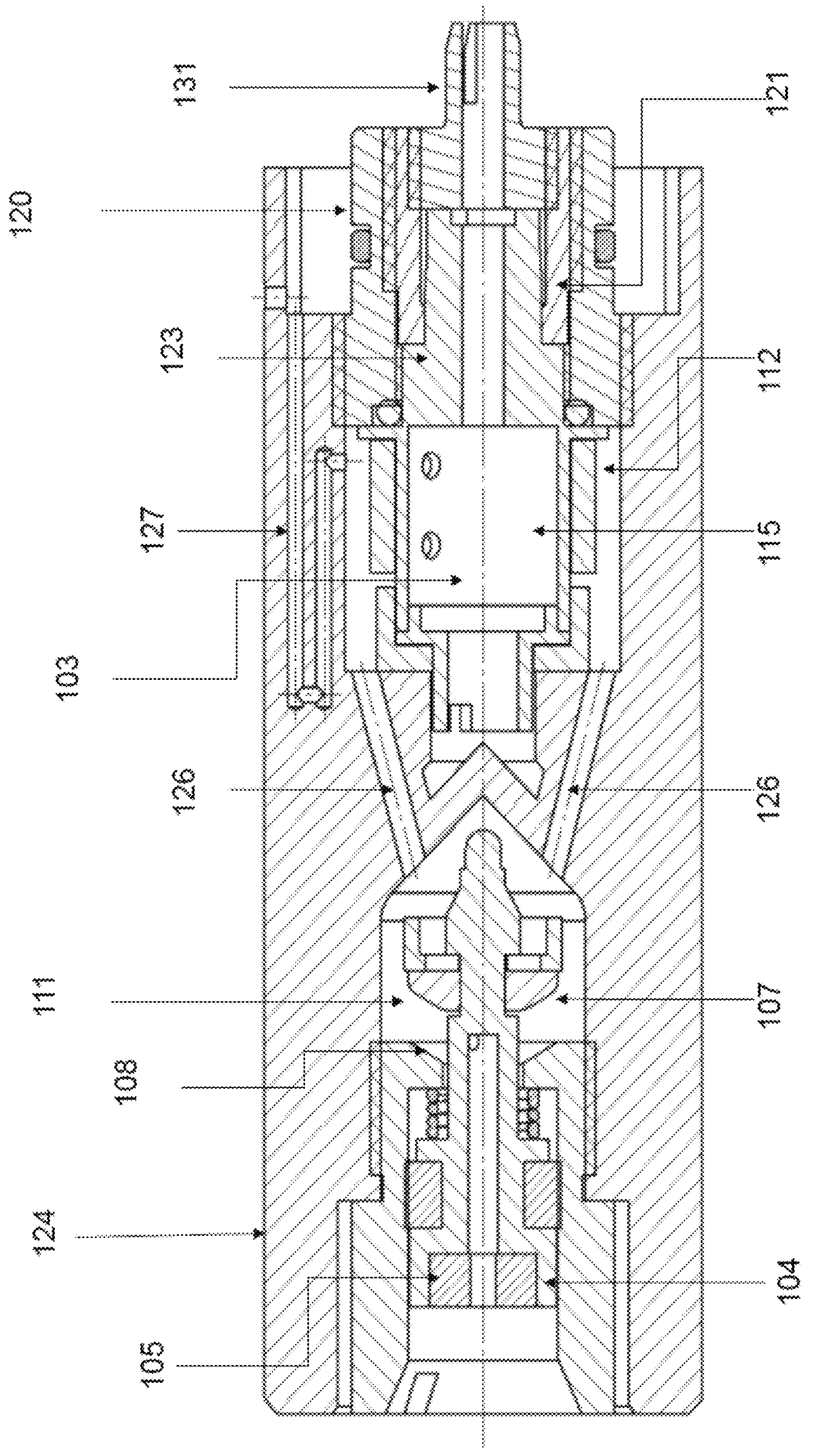
Figure 79A:
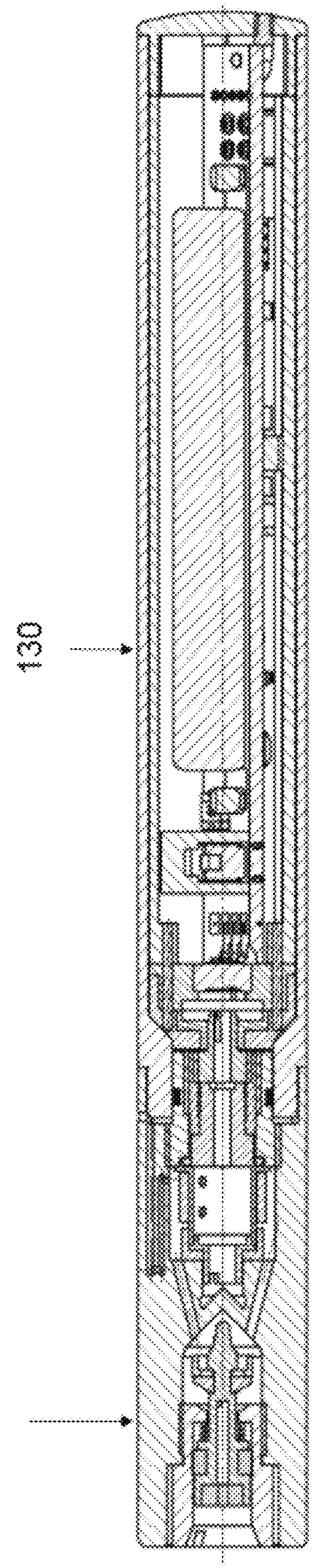
Figure 79B:
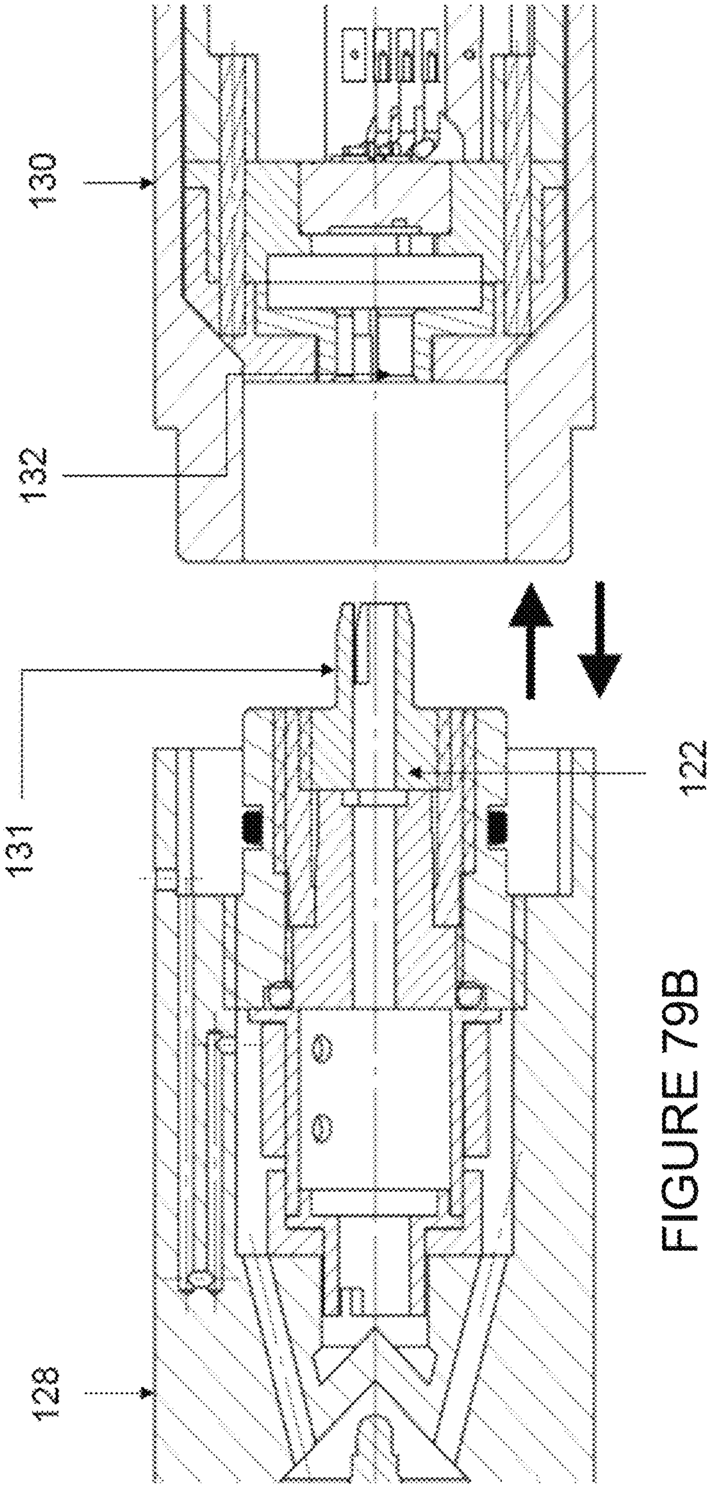
Figures 80A, 80B:
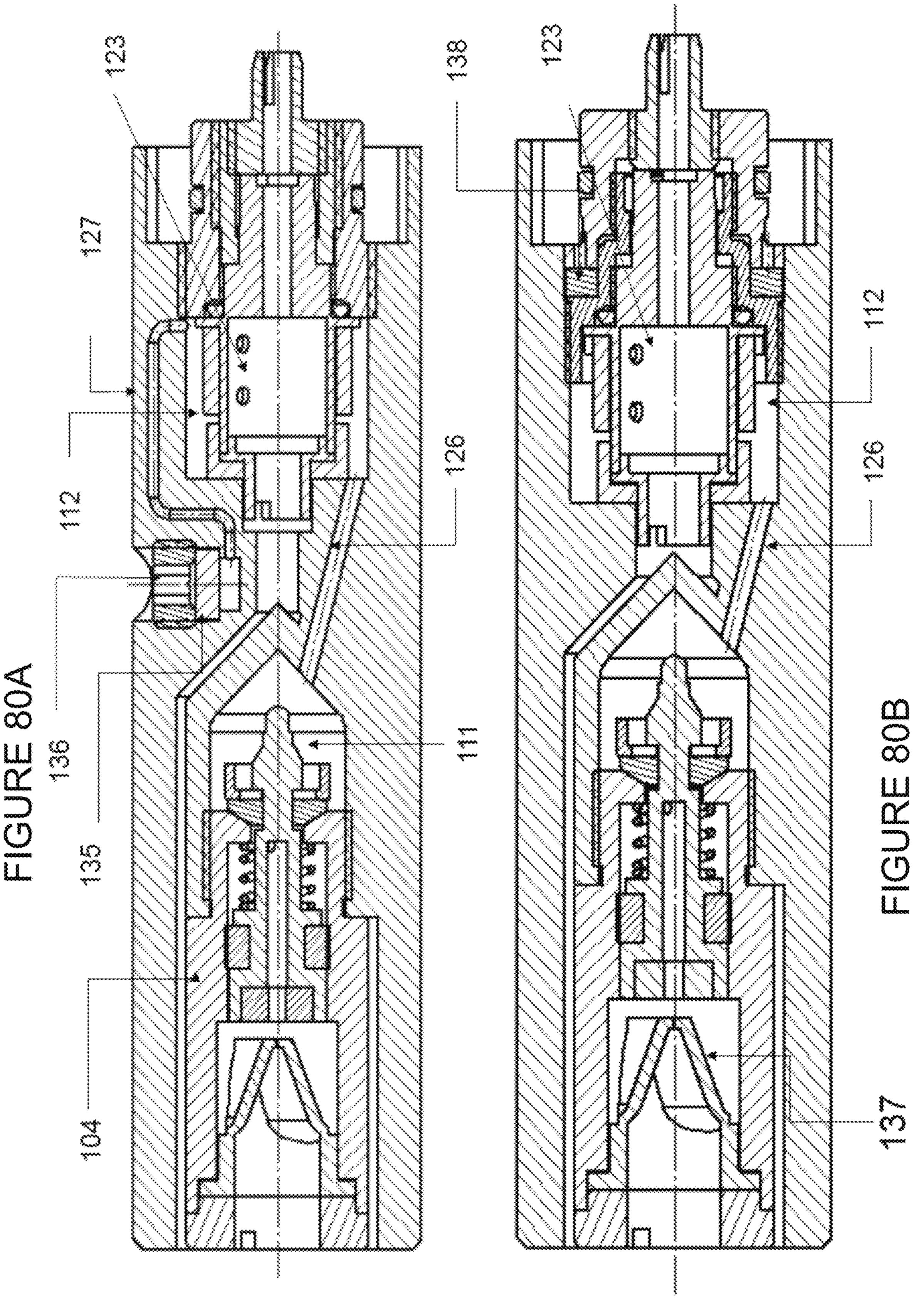
Figure 81:
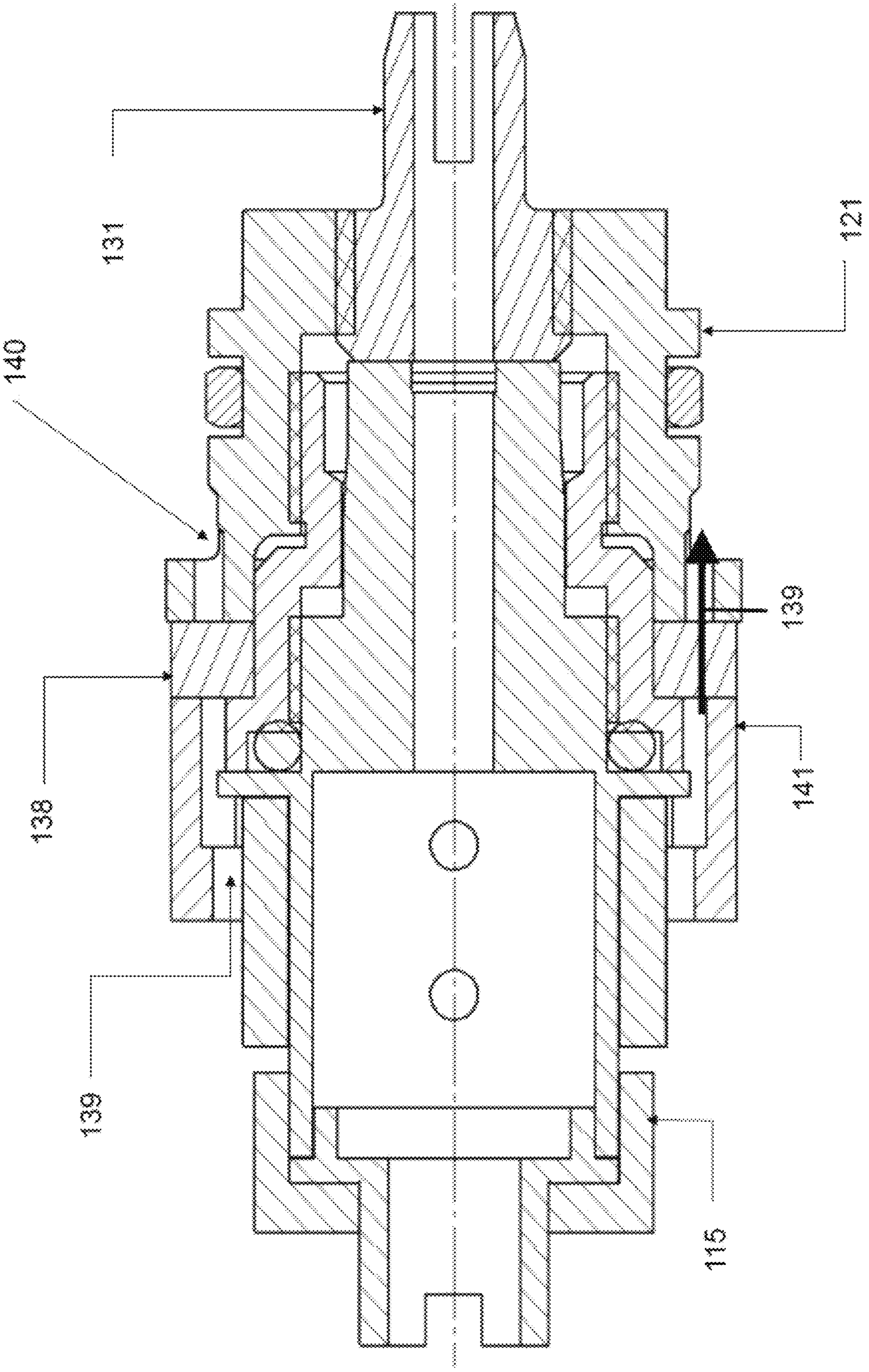
Figure 82:
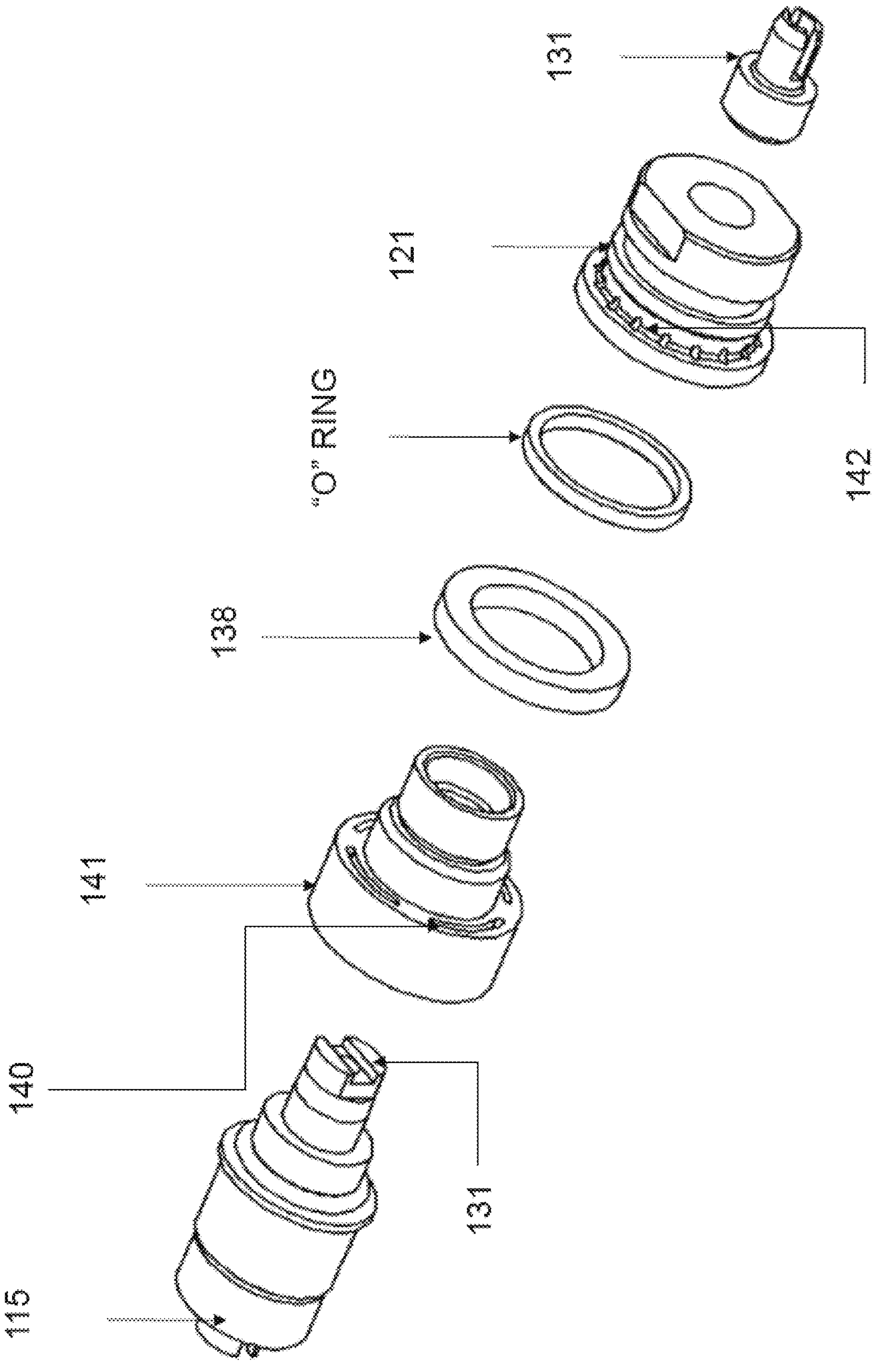
Figure 83:
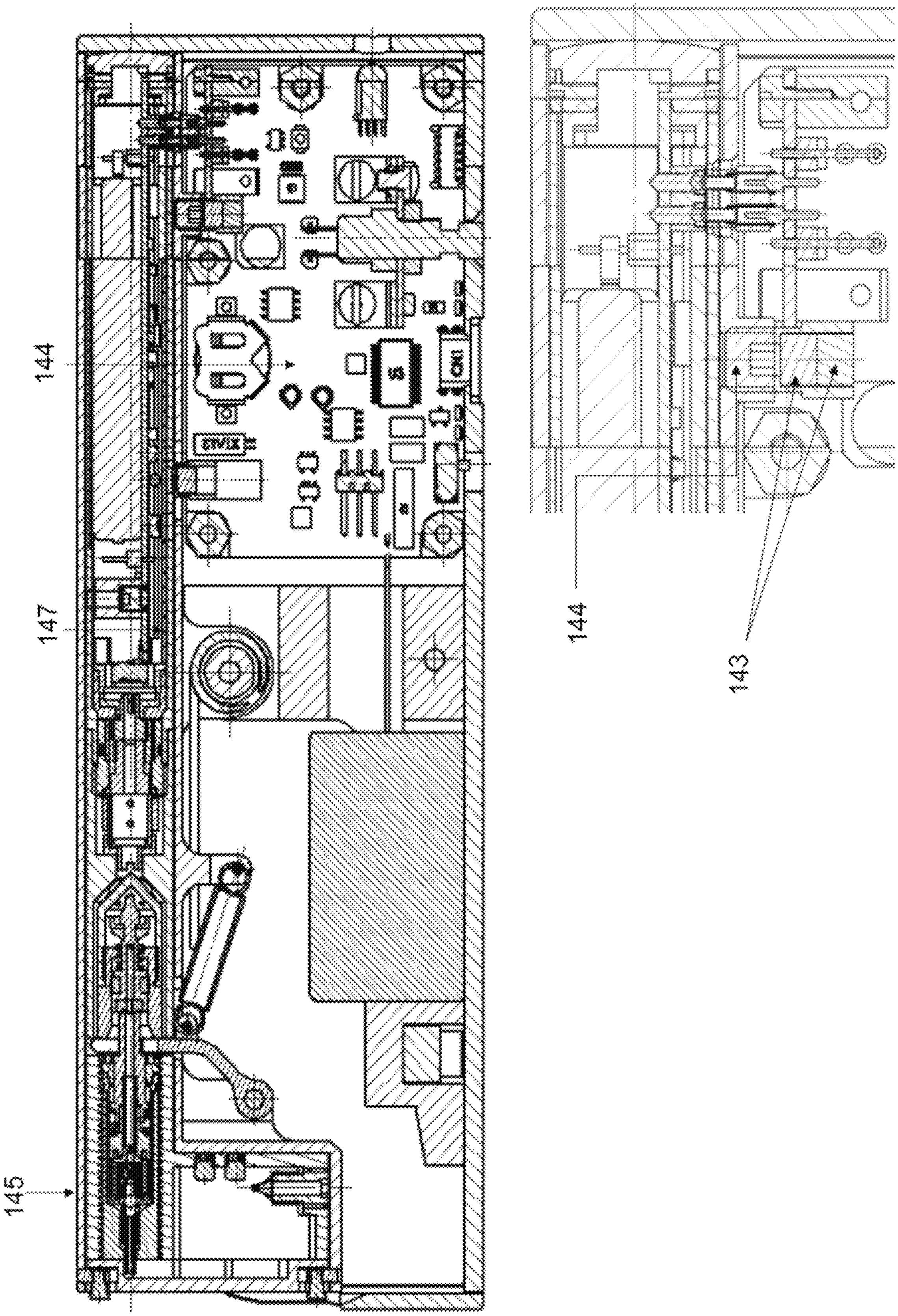
Figure 84:
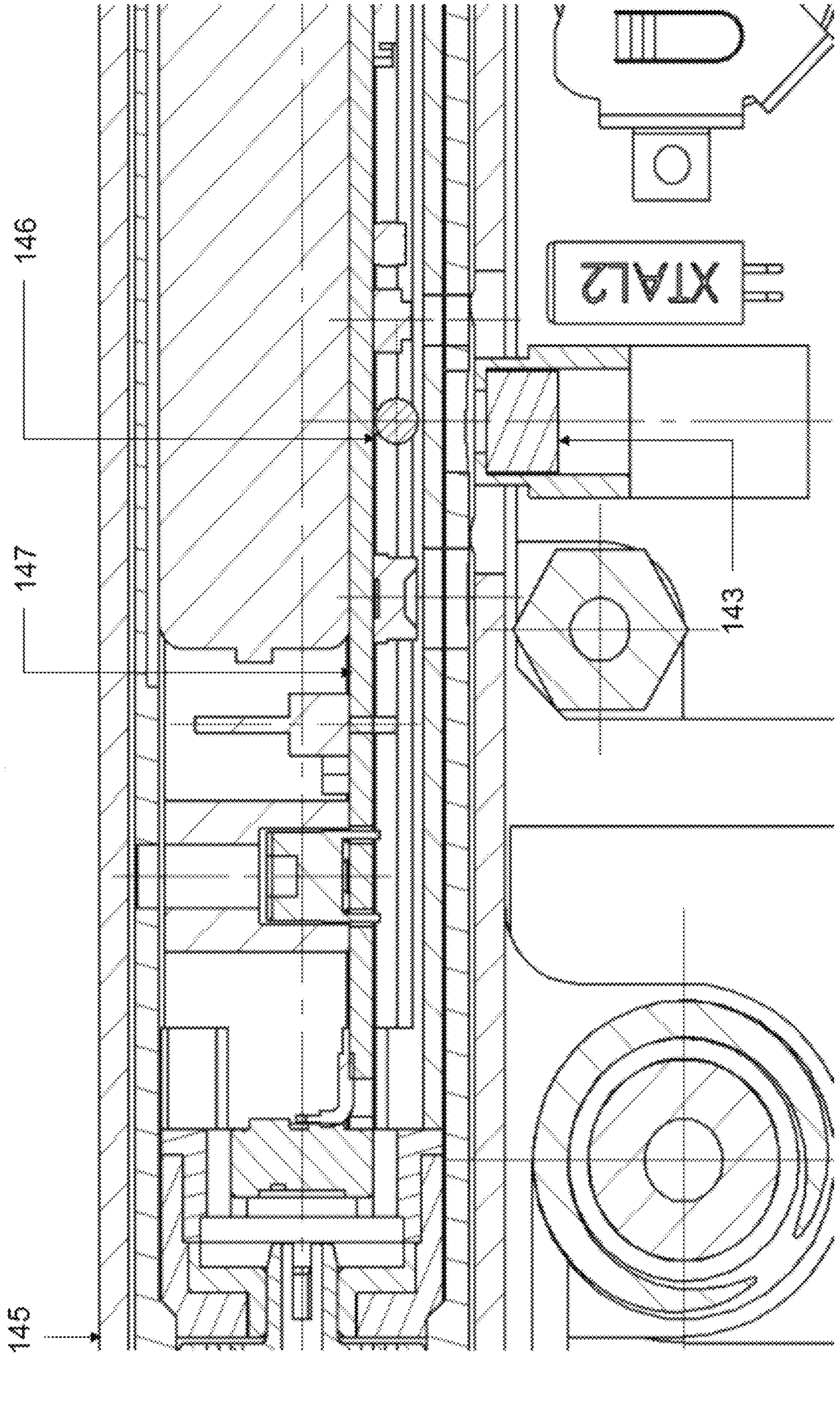
Figure 85A:
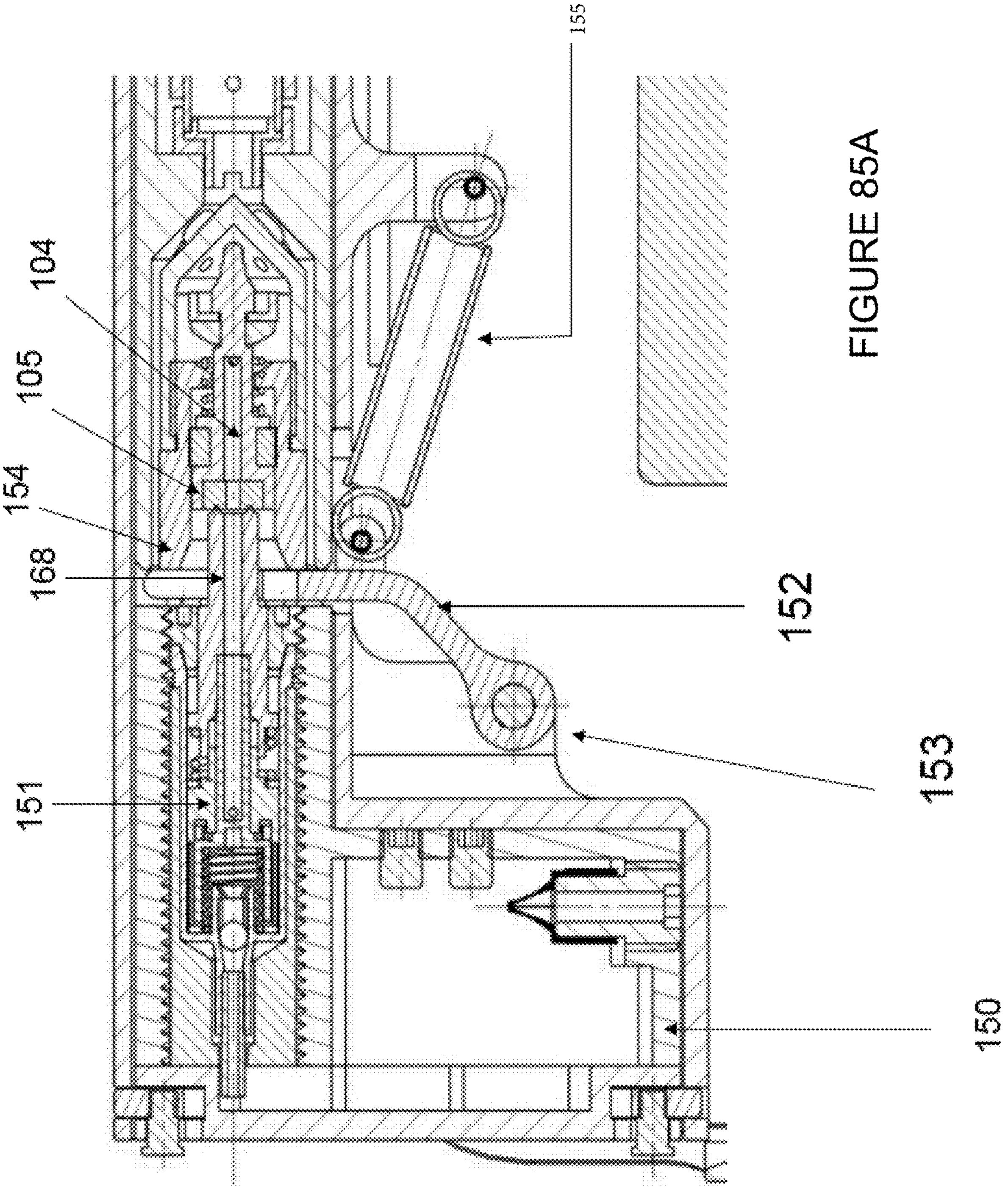
Figure 85B:
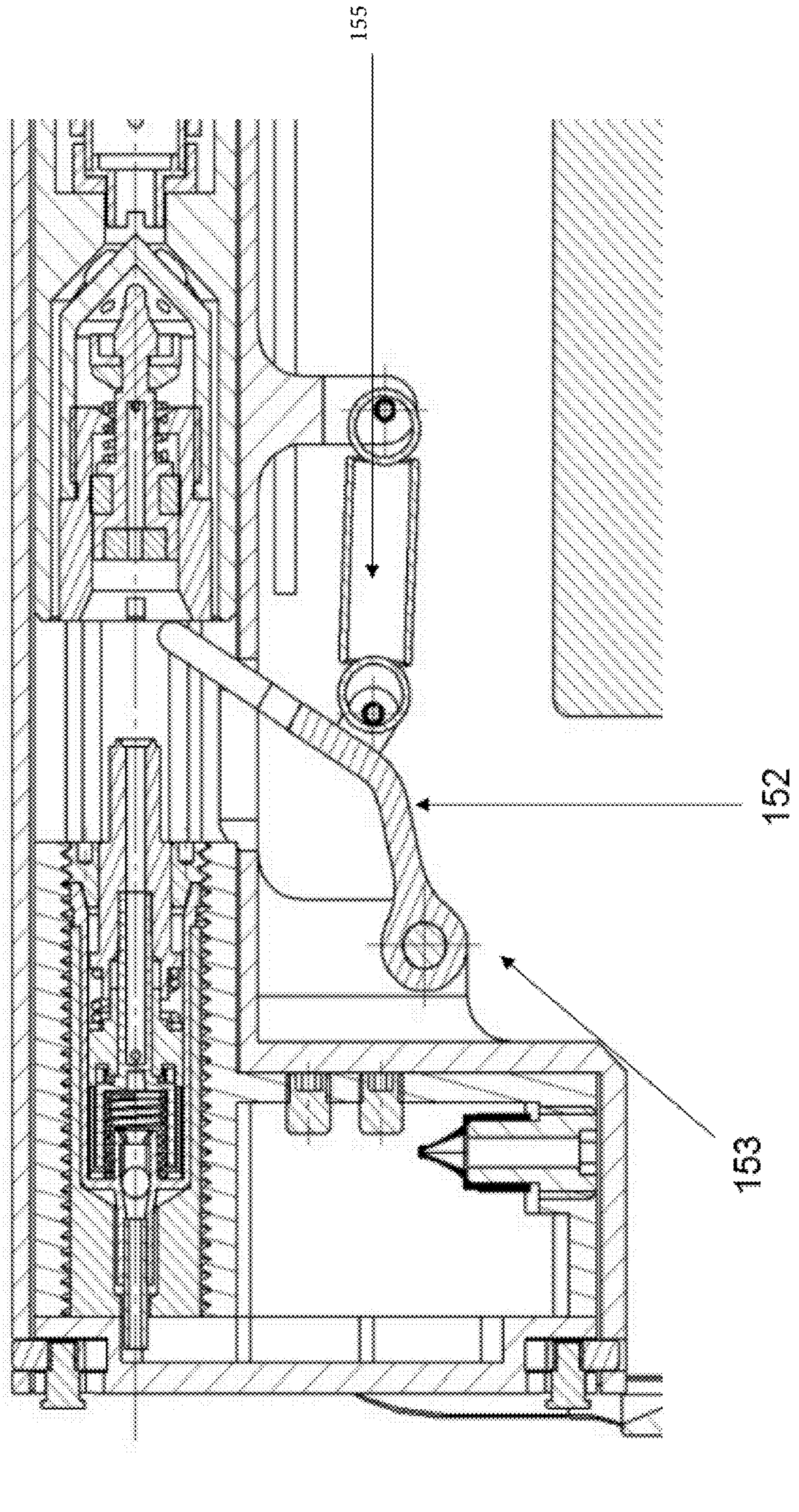
Figure 86:
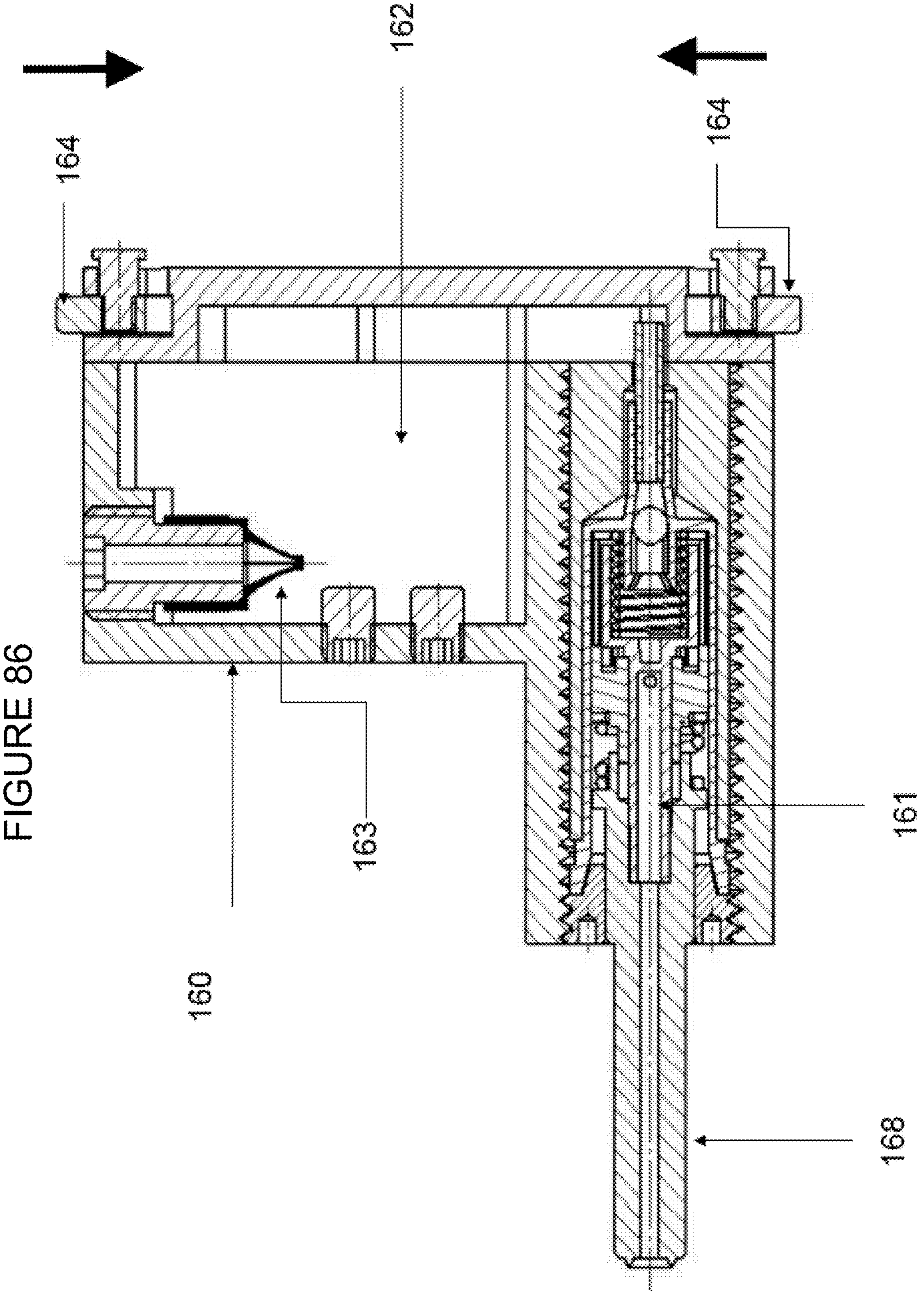
Figure 87:
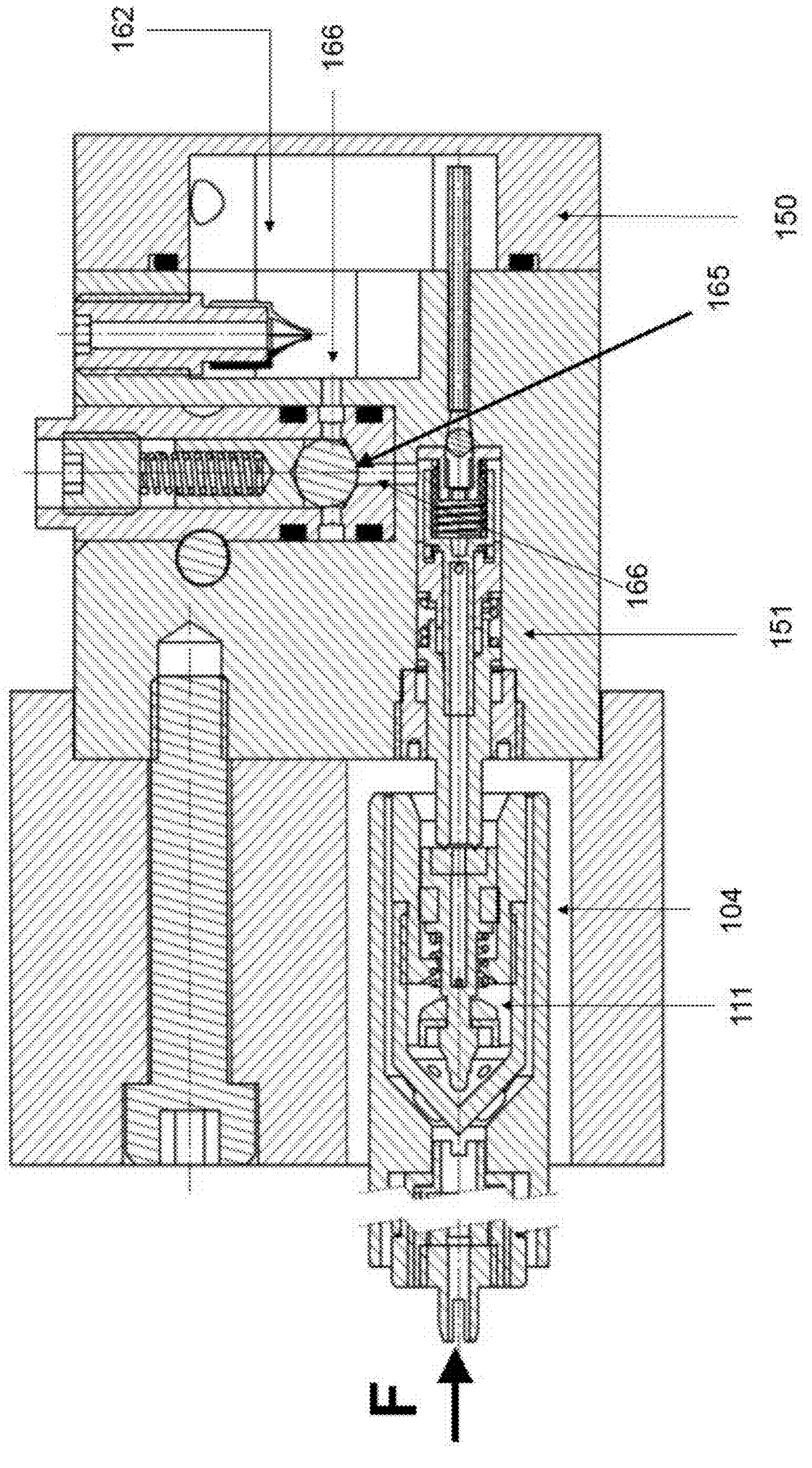
Figure 88:
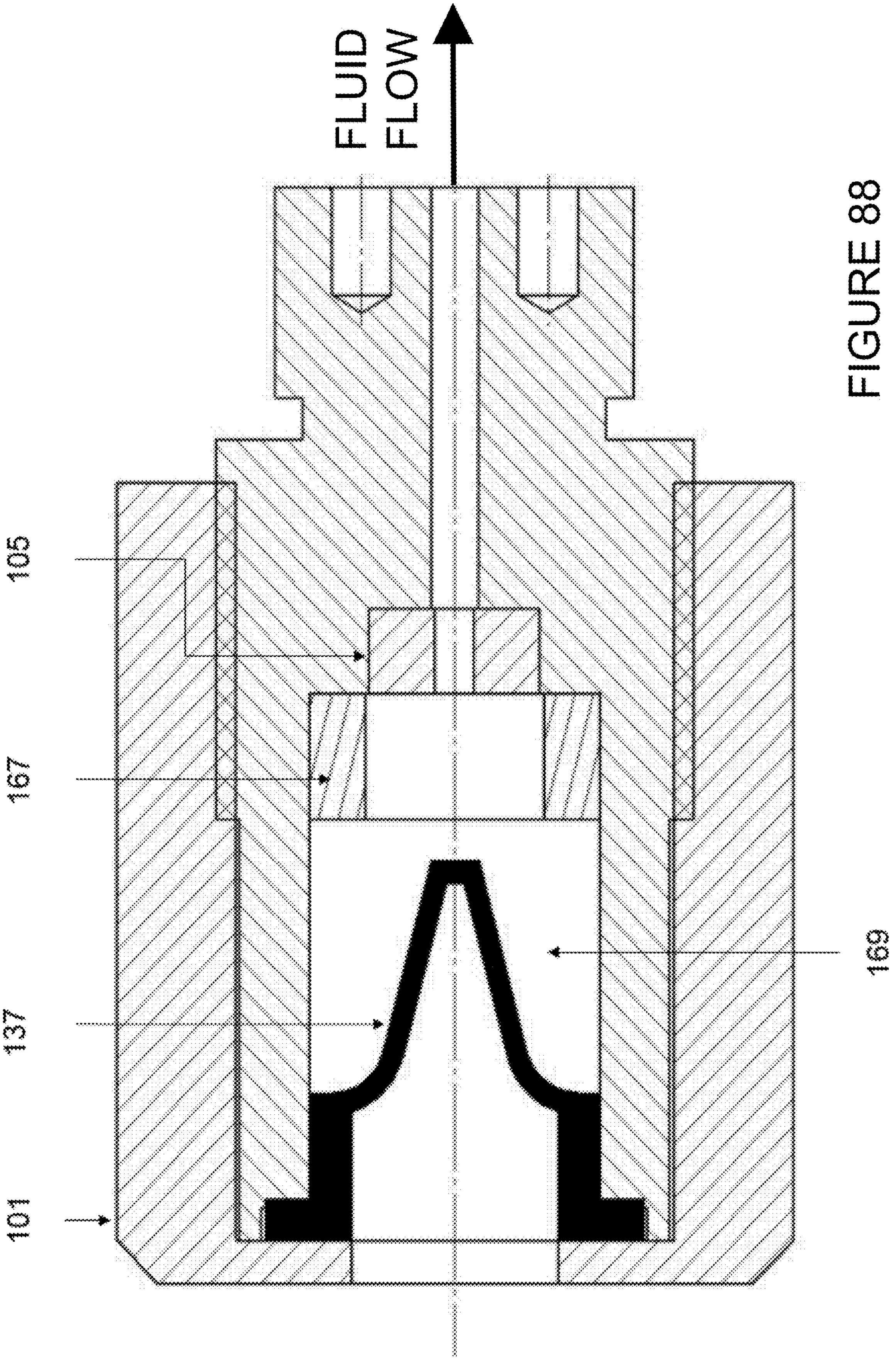
Figure 89:
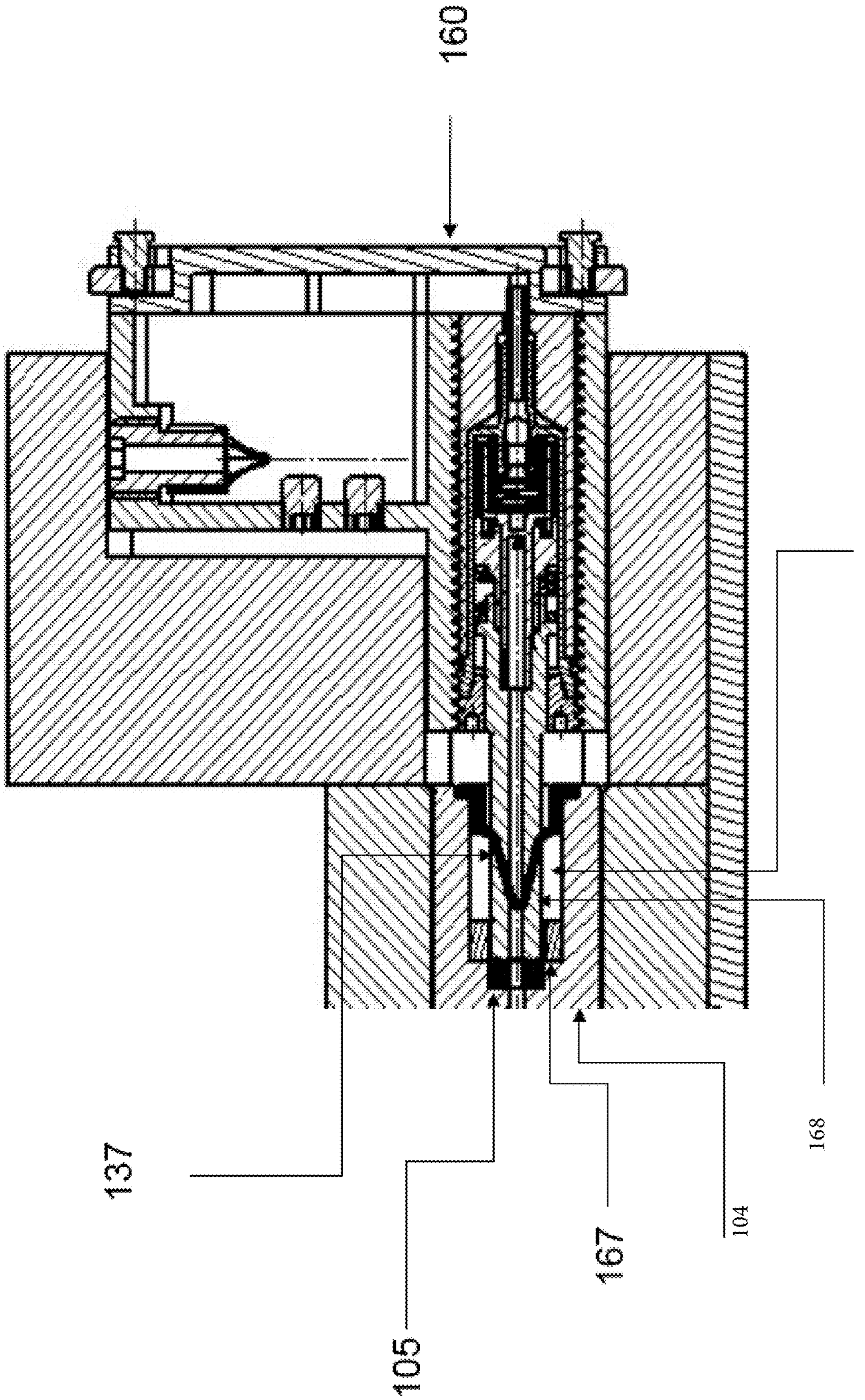
Figure 90:
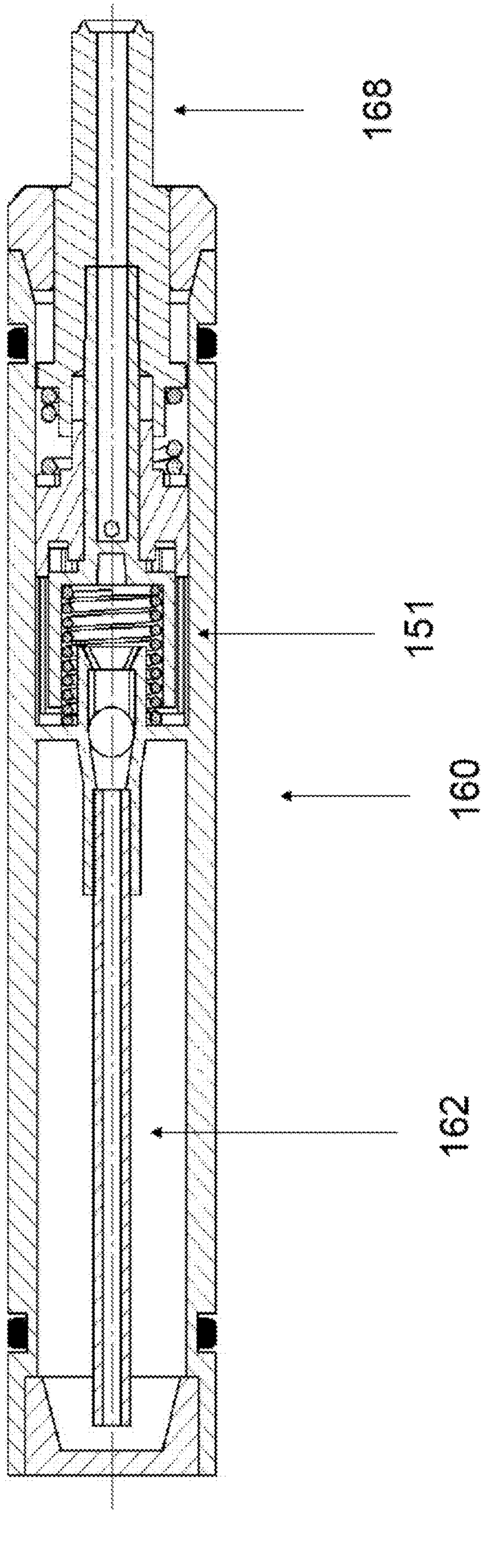

FIG. 2 is an isometric view of an e-cigarette PV;

FIGS. 3 and 4 show that e-cigarette partly withdrawn from its portable, personal storage and carrying case;

FIG. 5 shows a user-replaceable e-liquid cartridge adapted to be inserted into or attached to a portable, personal storage and carrying case for a PV;

FIG. 6A is view of a simplified version of the case showing the user replaceable e-liquid cartridge and the battery withdrawn from the portable re-filling and re-charging and re-filling case and FIG. 6B sows the case with the PV holder hinged downwards, ready to accept a PV;

FIG. 7 is a cross sectional view of the portable case of FIG. 6, together with an e-cigarette PV;

FIG. 8 shows the PV being inserted into the portable case of FIG. 6 for re-filling with e-liquid;

FIG. 9 is a detailed view of the e-liquid-filling mechanism in the portable case of FIG. 6;

FIG. 10 is a cross sectional view of the PV when stored in the portable case of FIG. 6;

FIG. 11 is a cross-sectional view of the PV of FIG. 6;

FIG. 12 is an example of a portable case with side-loading of the PV;

FIG. 13 is an example of a portable case with top-loading of the PV;

FIG. 14 is a cross-sectional view of the PV as it re-fills with e-liquid when pushed down onto the re-fill mechanism;

FIG. 15 shows an isometric view of a working prototype of the case, with the PV holder or chassis shown closed;

FIG. 16 shows an isometric view of the working prototype of the case, with the PV holder or chassis shown opened, and the PV fully inserted into the holder;

FIG. 17 shows an isometric view of the working prototype of the case, with the PV holder or chassis shown opened, and the PV raised upwards, ready for withdrawal by the user;

FIG. 18 are isometric views of the holder or chassis;

FIG. 19 is an isometric view of the PV used in the working prototype;

FIG. 20 is a cross-section view of the PV;

FIG. 21 is a cross-section view of the case, with chassis closed and no PV present;

FIG. 22 is a cross-section view of the case, with chassis open and no PV present;

FIG. 23 is a cross-section view of the case, with chassis closed and PV present; the inter-lock is not engaged with the sliding contact block;

FIG. 24 is a cross-section view of the case, with chassis closed and PV present; the inter-lock is engaged with the sliding contact block;

FIG. 25 is a cross-section view of the case, with chassis open and PV present; the inter-lock is engaged with the sliding contact block and the PV is being heated;

FIG. 26 is a cross-section view of the case, with chassis open and PV present; the inter-lock is no longer engaged with the sliding contact block and the PV is shown popped up from the chassis, ready for the user to extract;

FIG. 27-30 is a close up of the sliding contact block assembly and PV in each of the four FIGS. 23-26;

FIG. 31 is an exploded view of the sliding contact block assembly;

FIG. 32A is a side view of the sliding contact block assembly;

FIG. 32B is a top view of the sliding contact block assembly;

FIG. 33 is an exploded view of the key components, including PV, chassis, cartridge, and the sides of the case;

FIG. 34 is a close up showing the PV resting against the pump in the case; chassis is open;

FIG. 35 is a close up showing the PV pushed down against the pump; chassis is open;

FIG. 36 is a close up showing the PV pushed down against the pump; chassis is closed;

FIGS. 37-40 show the pump at its various positions;

FIGS. 41-45 shows the user-replaceable e-liquid cartridge, with integrated pump and overflow valve, in its various positions;

FIG. 46 is an exploded isometric view of the PV;

FIG. 47 is an isometric view of the PV;

FIG. 48 is a close-up view of the wick and coil assembly; the coil runs perpendicular across the long axis of the PV;

FIG. 49 is a close-up view of a different design of wick and coil assembly; the coil runs parallel to the long axis of the PV;

FIG. 50 is an exploded view of the ring connector that provides power and data contacts on the PV;

FIG. 51 is a cross-sectional view of the ring connector;

FIGS. 52-54 show the variable air intakes of the PV;

FIG. 55 is a high-level schematic showing a portable re-filling case able to communicate wirelessly and also through a wired connection to a smartphone, a laptop and a modem;

FIG. 56 shows schematically that the portable re-filling unit includes electronics componentry, such as a memory, wireless/wired connectivity, software, and a controller/processor; there are four e-liquid cartridges, each with a different flavor and/or strength of nicotine;

FIG. 57 shows how the user's smartphone can display the current levels of e-liquid in each separate cartridge;

FIG. 58 shows a PV being withdrawn from its case; this automatically initiates heating of the e-liquid using the battery in the PV. A 'ready' light on the PV illuminates when the device is ready to use;

FIG. 59 shows an example of a PV including an indication of how much substance has been vapourised;

FIG. 60 shows a conventional two-part PV, with an e-liquid cartridge above the atomizer and the atomiser above the battery, plus a third module in the middle that indicates the amount of e-liquid consumed;

FIG. 61 shows a time-locked case for a PV;

FIG. 62 shows a humidity sensor for a PV;

FIGS. 63-67 show various approaches to eliminating or reducing leakage of e-liquid from the PV;

FIG. 68 shows a PV with a hygienic mouthpiece;

FIG. 69 shows a PV with a hygienic mouthpiece and that uses a single-dose e-liquid capsule at the end of the PV furthest from the mouthpiece;

FIG. 70 shows a PV and a dispenser for single-dose e-liquid capsules;

FIGS. 71-76 show cross-sectional views of a PV with various atomization improvements;

FIG. 77 shows a cross section through the front portion of a PV, showing the integrated manifold, tip and coil assembly;

FIG. 78 is another cross section through the front portion of a PV, showing the integrated manifold, tip and coil assembly; it also shows how the e-liquid moves from the child reservoir to the secondary child reservoir that sits around and directly feeds the coil unit;

FIG. 79A shows a cross-section of the complete PV, so that the portion shown in FIGS. 77 and 78, the tip/manifold/coil assembly 128 can be understood in context;

FIG. 79B shows the tip/manifold/coil assembly 128 joined to the electronics module assembly 130, which includes all electronics and the battery;

FIG. 80A shows another cross section through the tip/manifold/coil assembly 128, with the valve back on its seat and preventing leakage of e-liquid out from the tip;

FIG. 80B shows how the region that contains e-liquid is separated from the portion of the PV containing the electronics and battery using another oleophobic barrier;

FIG. 81 shows the air path through the oleophobic barrier;

FIG. 82 shows an exploded view of the components that include the oleophobic barrier;

FIG. 83 shows a cross section view of the re-fill and re-charge case with a PV securely held within it;

FIG. 84 is a close-up cross-sectional view of a portion of the re-fill and re-charge case with a PV securely held within it;

FIGS. 85A and 85B show a cross-sectional view of a portion of the re-fill and re-charge case with a PV securely held within it, this time showing the automatic PV lifting mechanism;

FIG. 86 shows a cross-sectional view through the user-replaceable, e-liquid cartridge;

FIG. 87 shows a cross-sectional view through a different design of user-replaceable, e-liquid cartridge 150;

FIG. 88 shows a cross-sectional view of the PV front tip showing the one-way duckbill valve;

FIG. 89 shows how the duckbill valve operates in practice;

FIG. 90 shows a variant for a user-replaceable e-liquid cartridge that can be inserted directly into a PV and not a re-fill/re-charge case.

Figure 91:
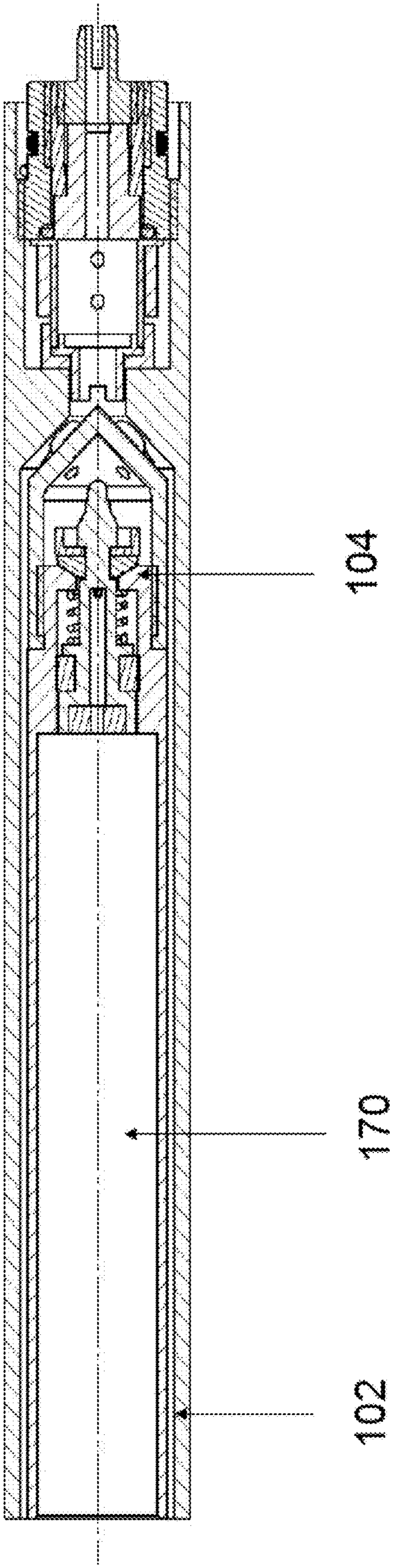
Figure 92:
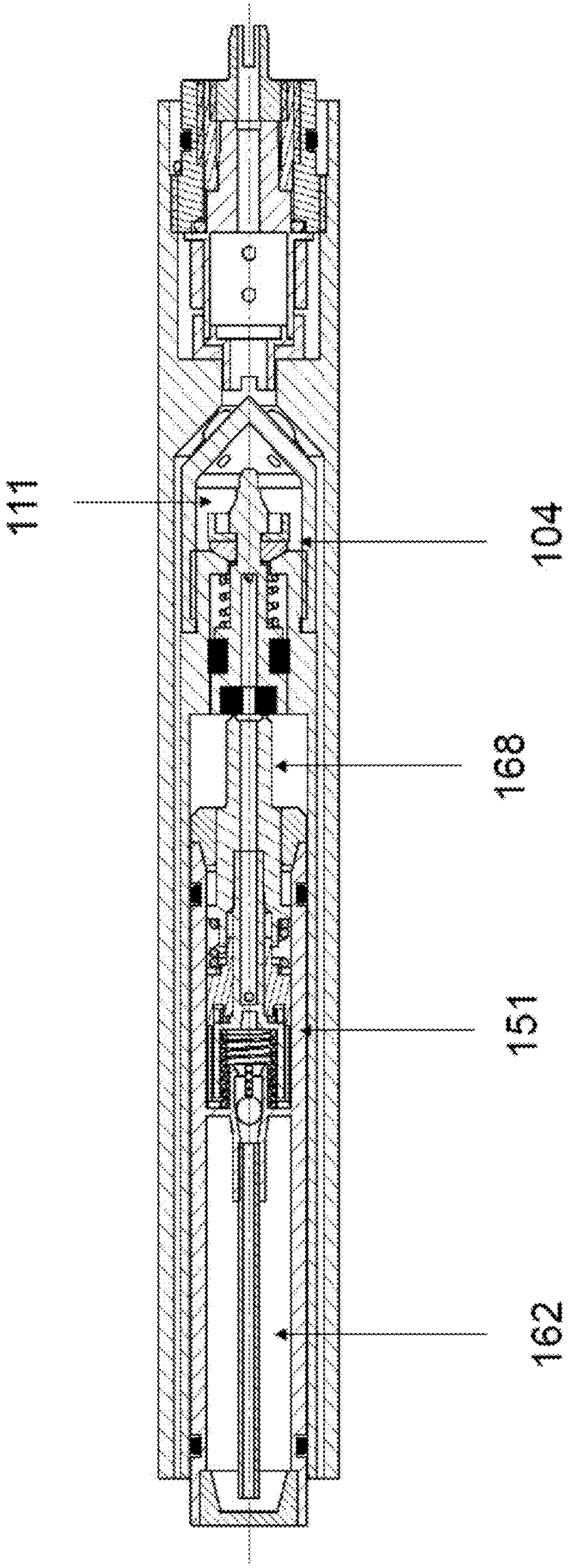
Figure 93:
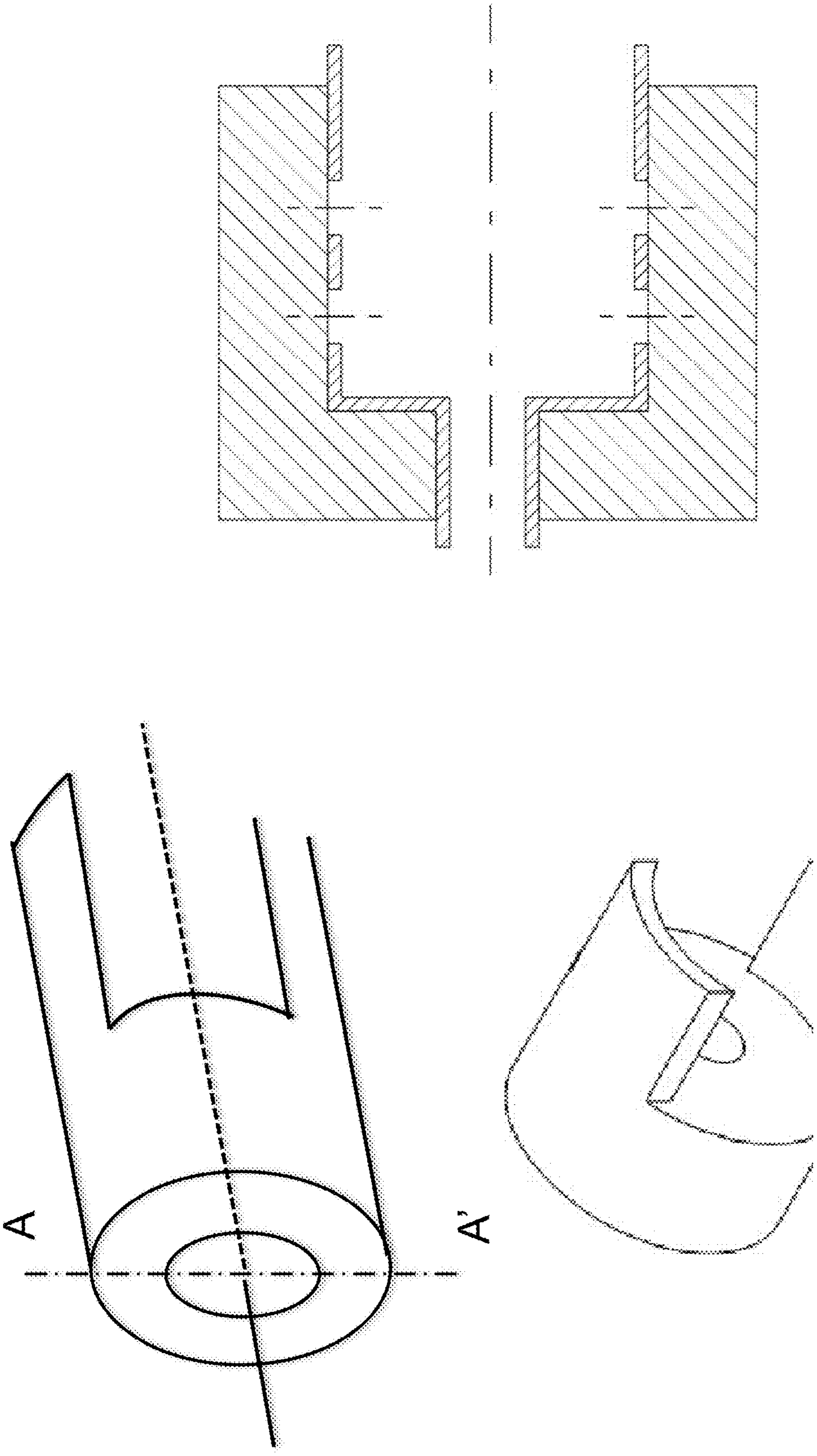

FIG. 91 shows the front portion of the PV that includes the mechanical fluid transfer valve, the coil assembly and the annular inhalation orifice or channel;

FIG. 92 shows the cartridge of FIG. 90 positioned in the cavity of the PV shown in FIG. 91;

FIGS. 93-99 are sketches showing various approaches to preventing high pressure e-liquid from entering the coil unit;

FIG. 93 shows a perspective view of the coil unit and a sectional view of the unit along the line A-A'.

Figure 94:
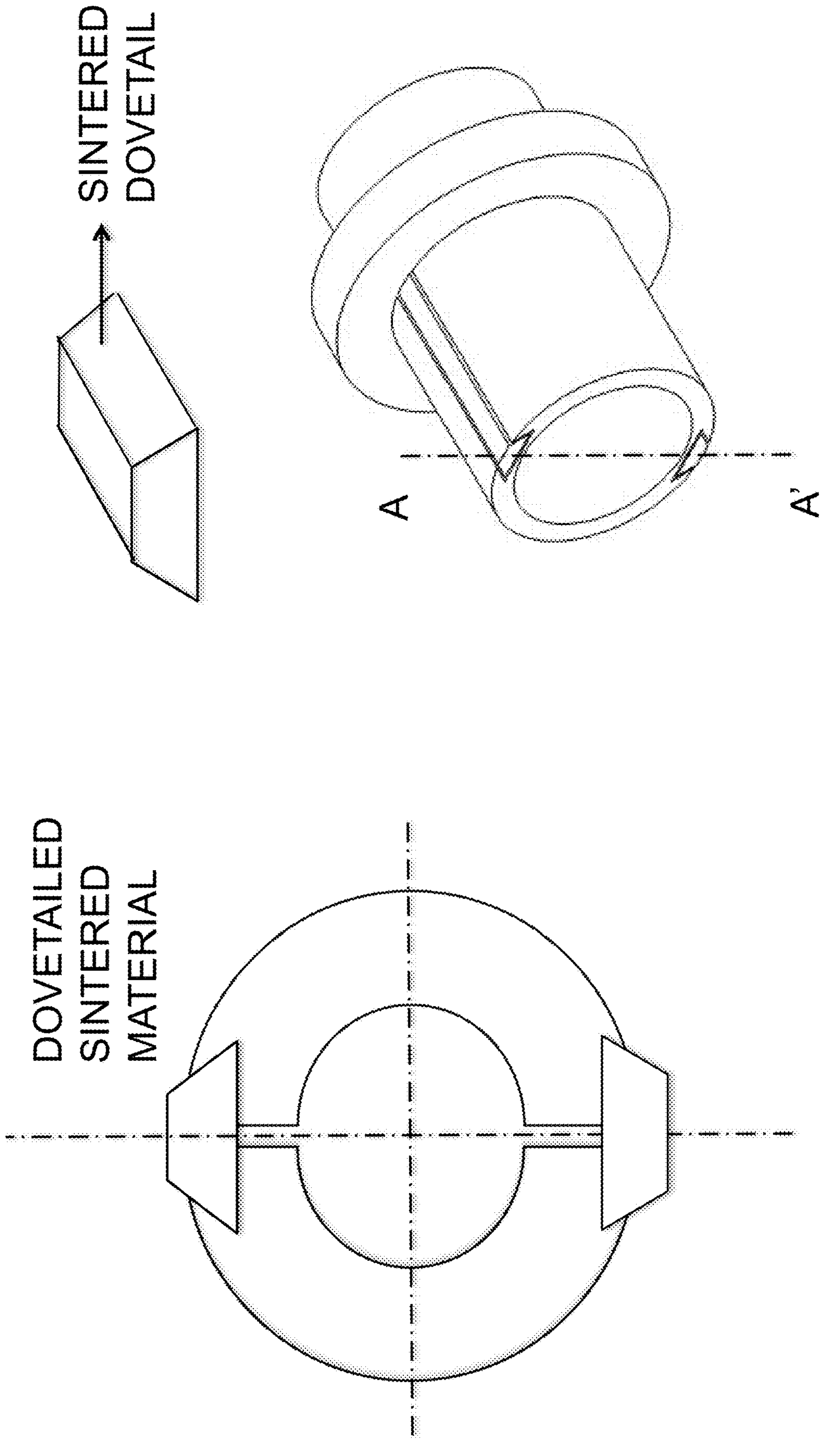

FIG. 94 shows a perspective view of the coil unit and the sintered dovetail, and a sectional view of the coil unit along the line A-A'.

Figure 95:
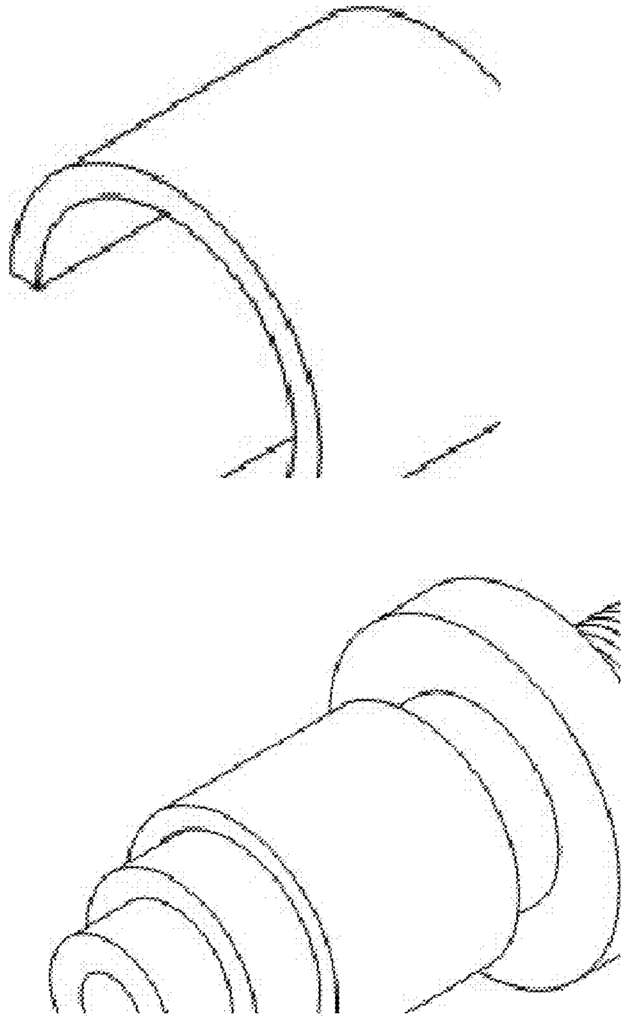

FIG. 95 shows a perspective view of the coil unit and the cover.

Figure 96:
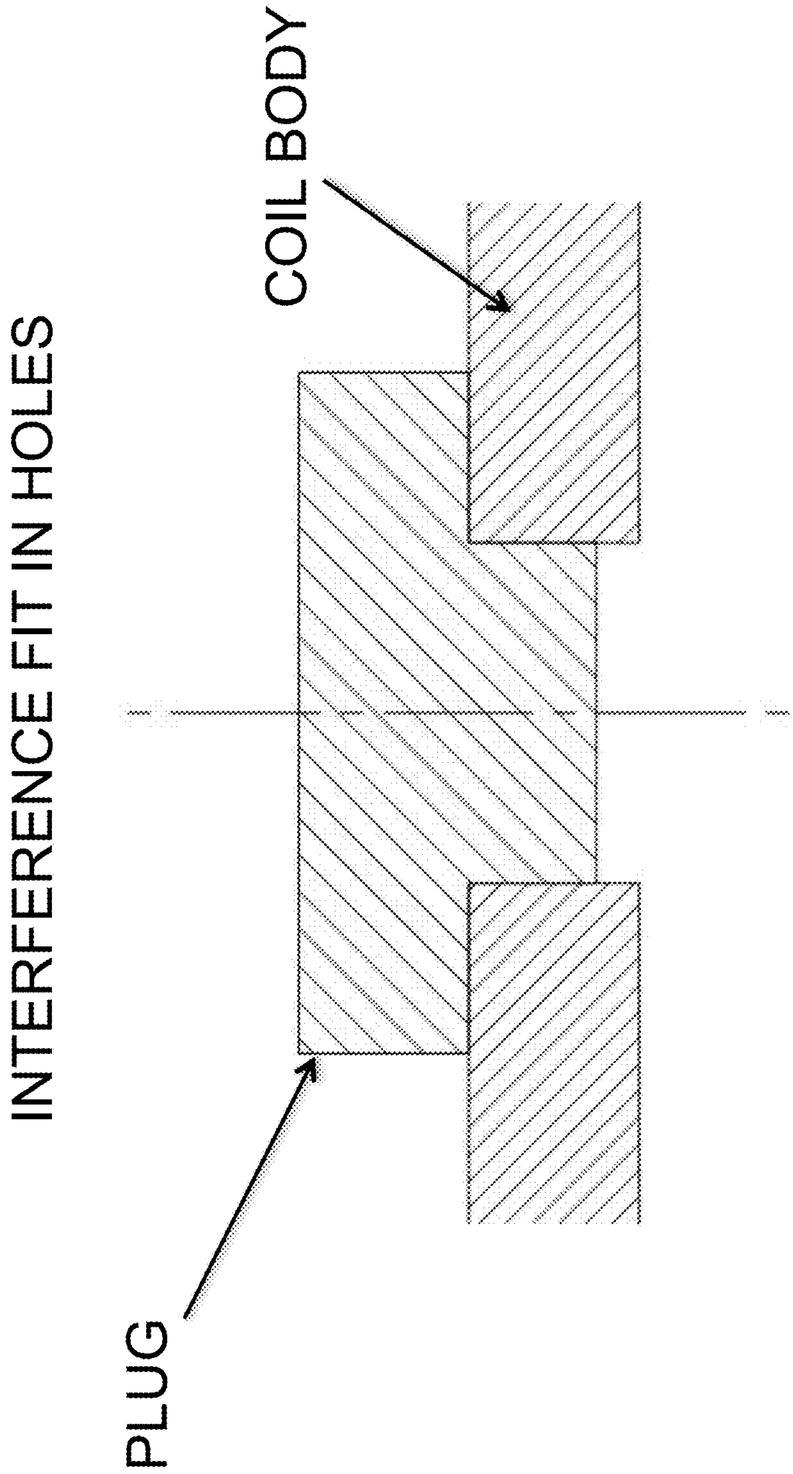

FIG. 96 shows a sectional view of interference fitting in holes in the coil unit.

Figure 97:
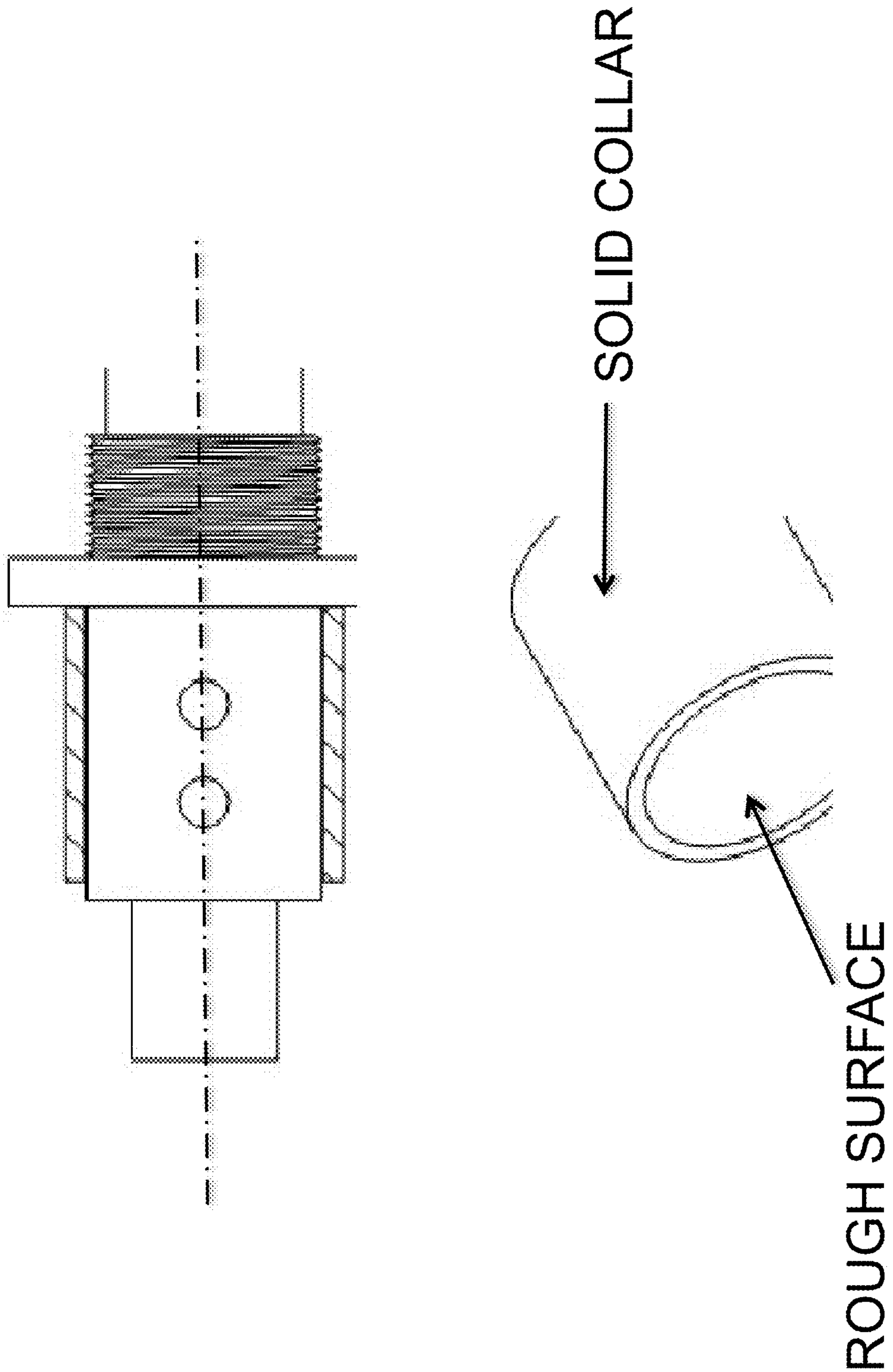

FIG. 97 shows a sectional view of the coil unit and a perspective view of outer coil body.

Figure 98:
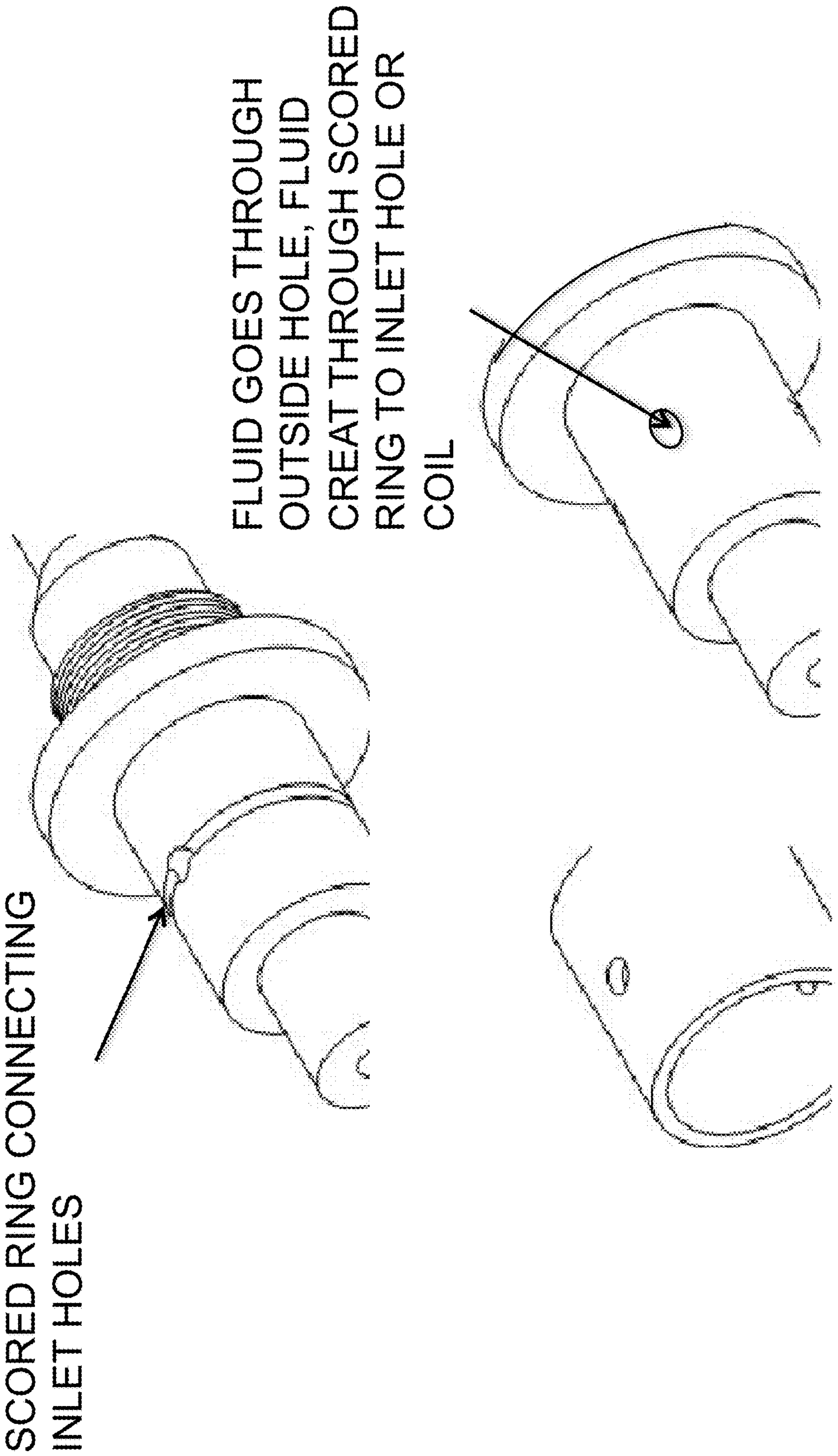

FIG. 98 shows a perspective view of the coil unit and a view of the coil unit disassembled.

Figure 99:
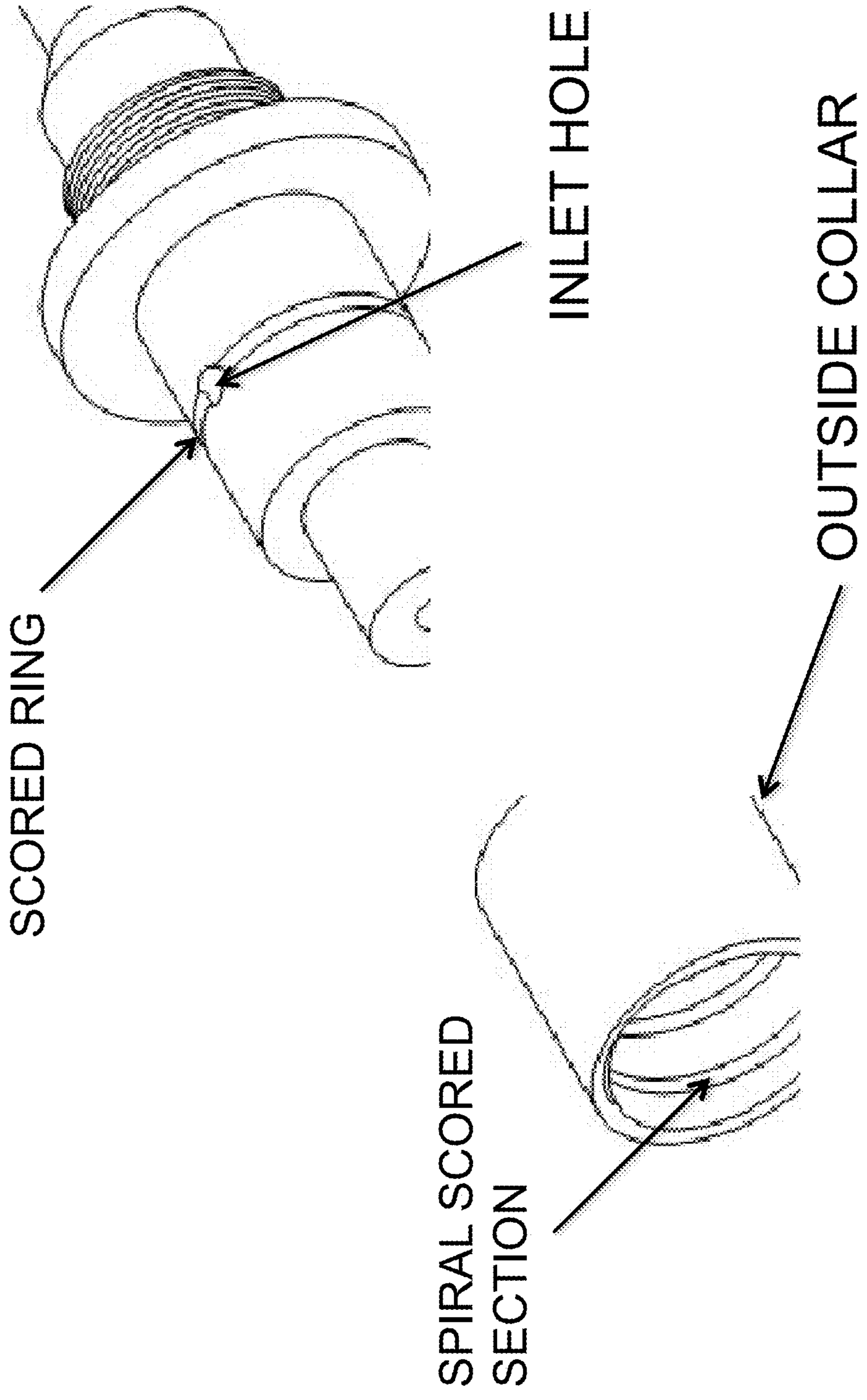

FIG. 99 shows an exploded view of the coil unit.

Figure 100:
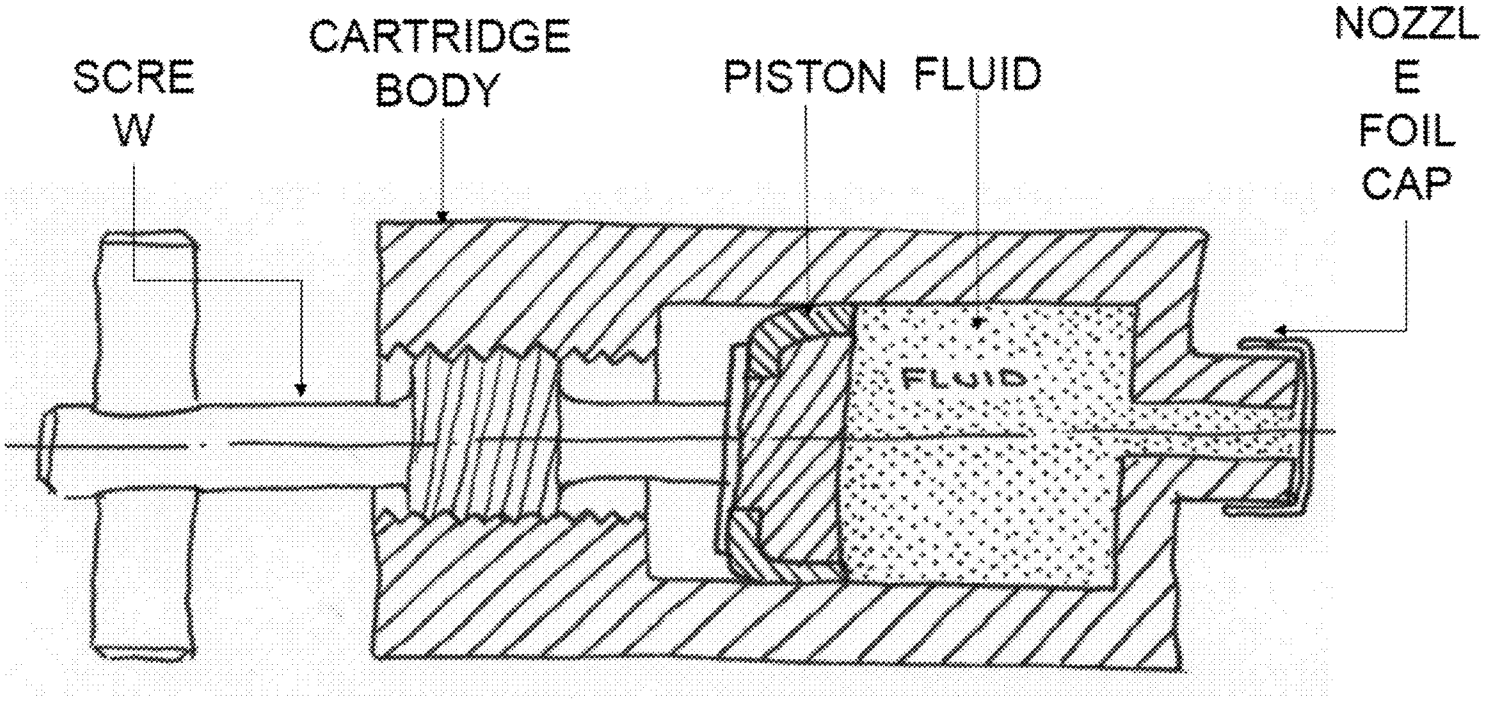

FIG. 100 is a sketch showing an approach for fluid transfer.

FIGS. 101A, 101B and 101C show an example of how the bellows fills and refills via one way valves.

FIGS. 102A and 102B show an example of fluid transfer when squeezing and releasing the rubber.

Figure 103:
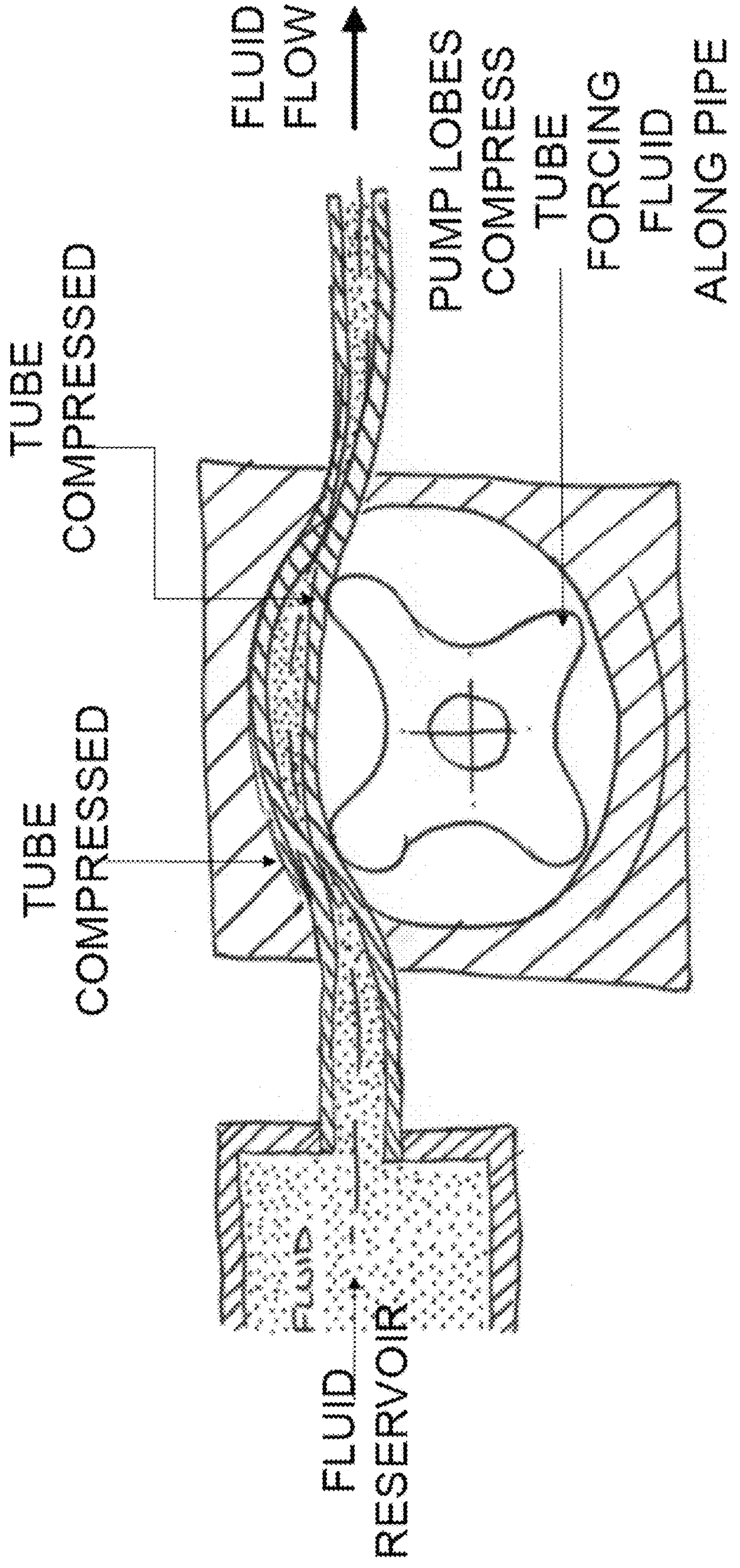
Figure 104:
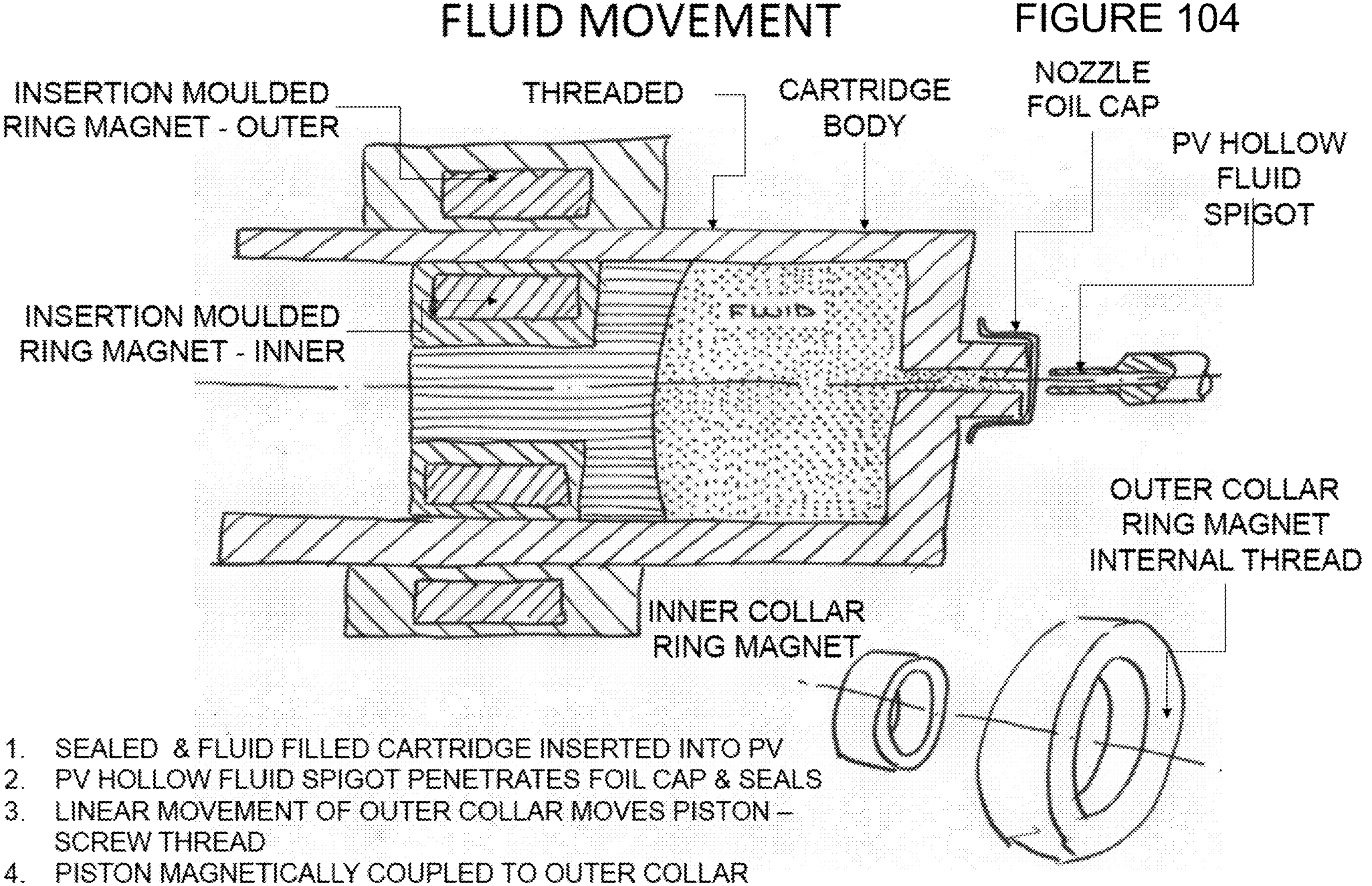
Figure 105:
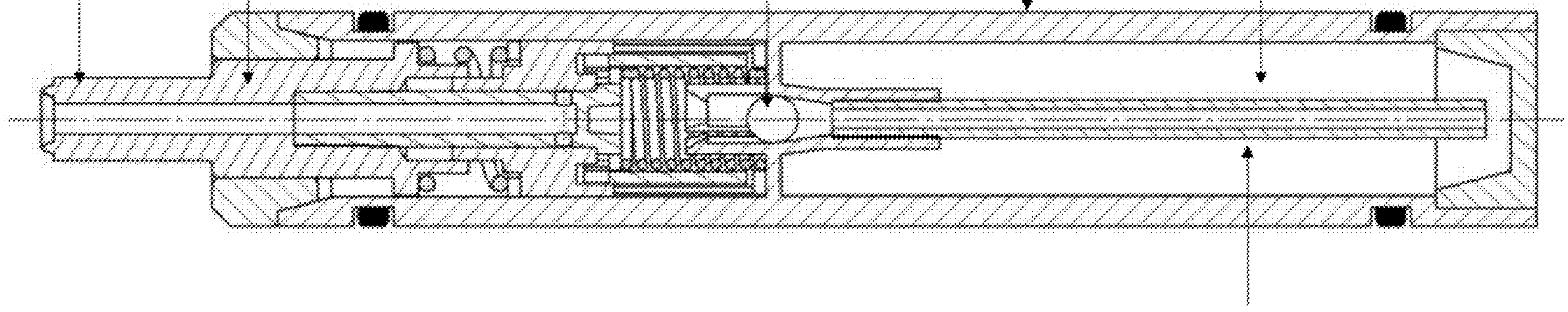

FIGS. 103-105 are sketches showing various approaches for fluid transfer.

Figure 106:
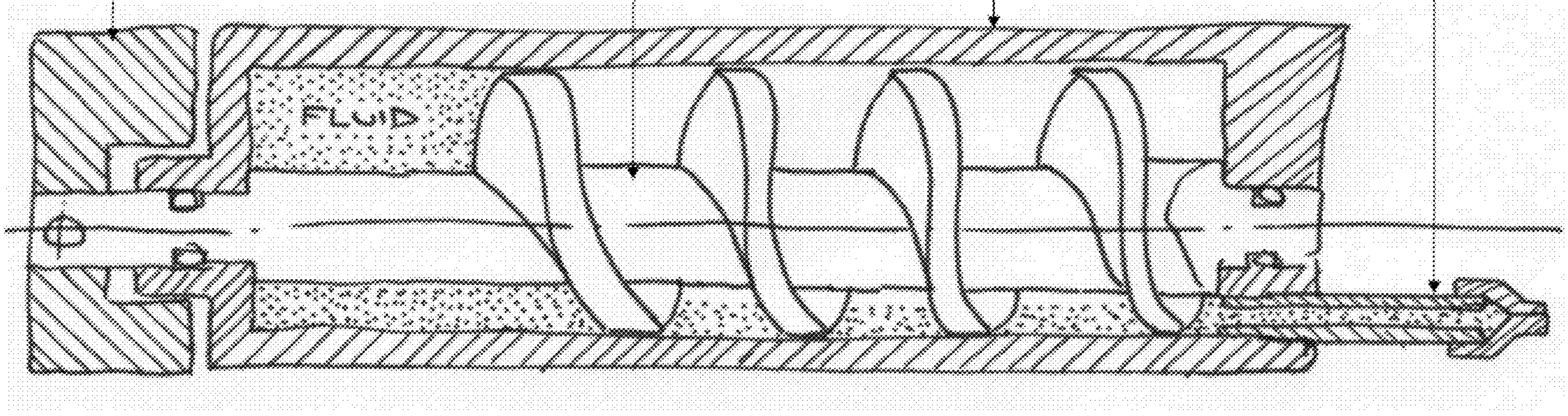
Figure 107:
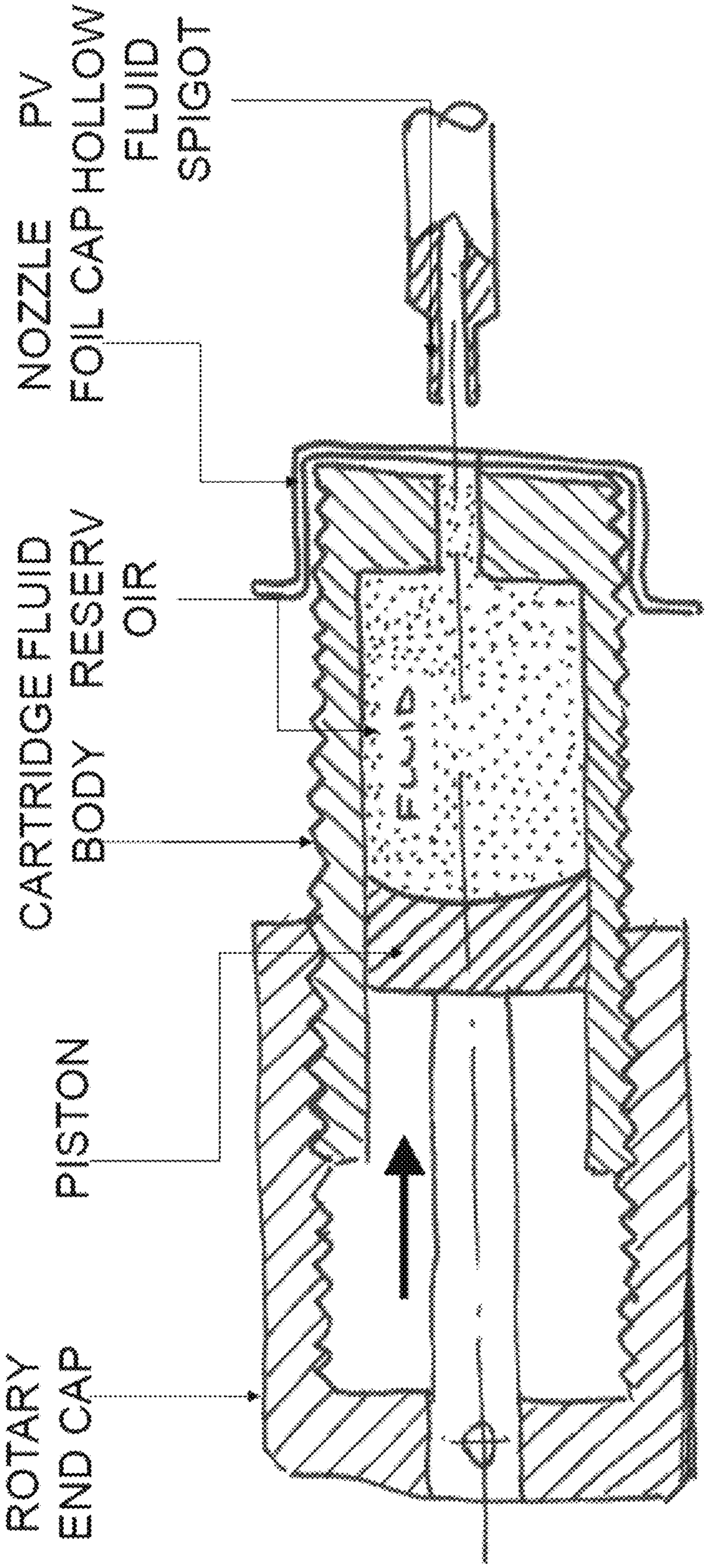
Figure 108:
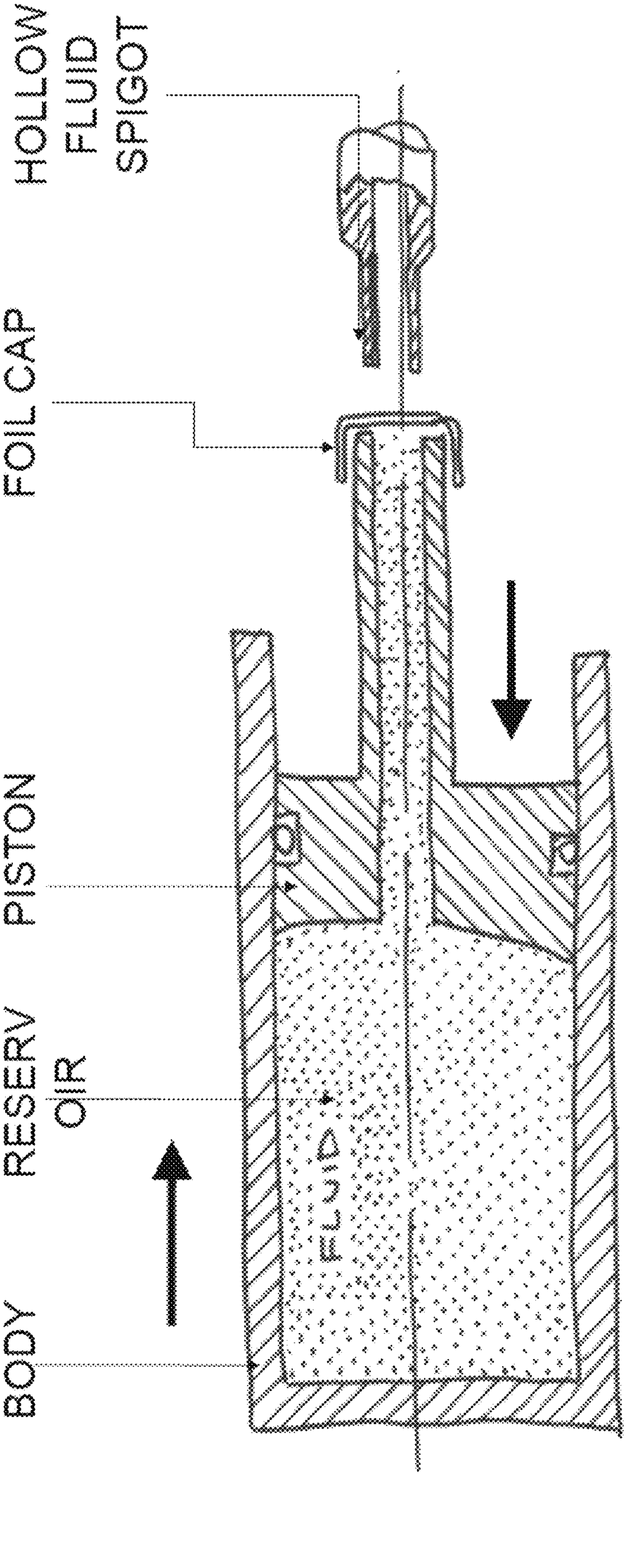
Figure 109:
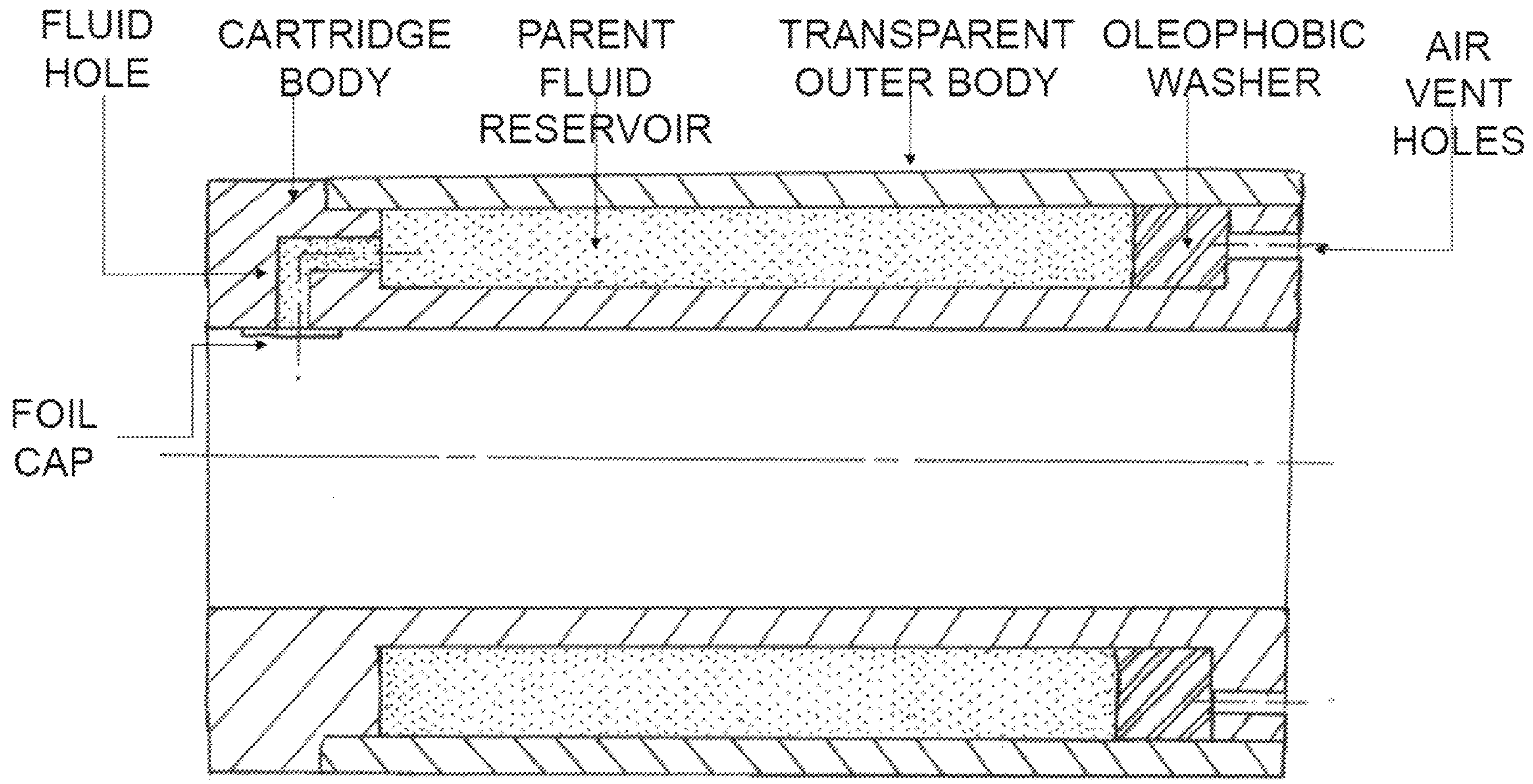
Figure 110:
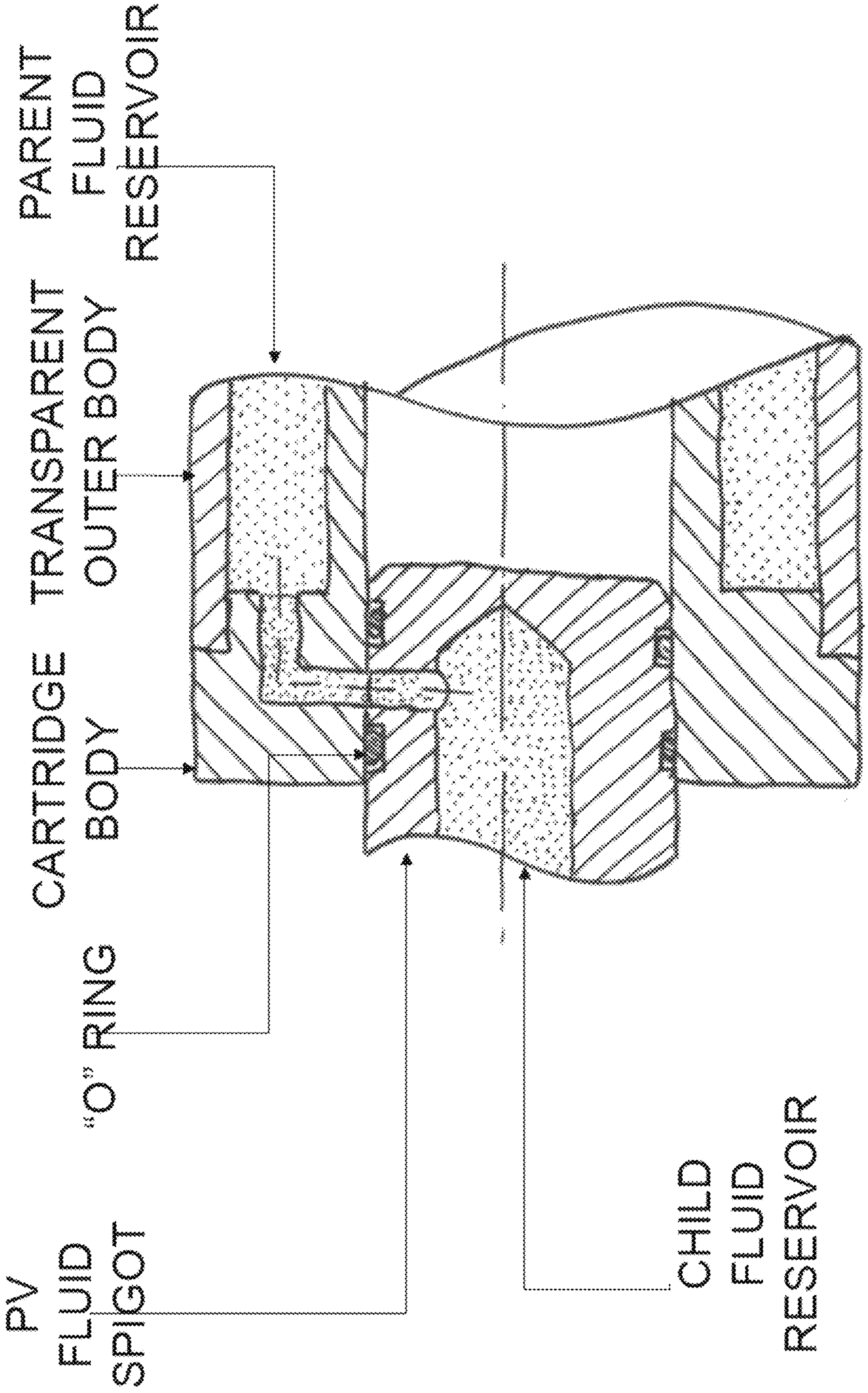

FIGS. 106A and 106B show an example of fluid transfer from cartridge parent reservoir to PV child reservoir.

FIGS. 107-110B are sketches showing various approaches for fluid transfer.

Figure 111:
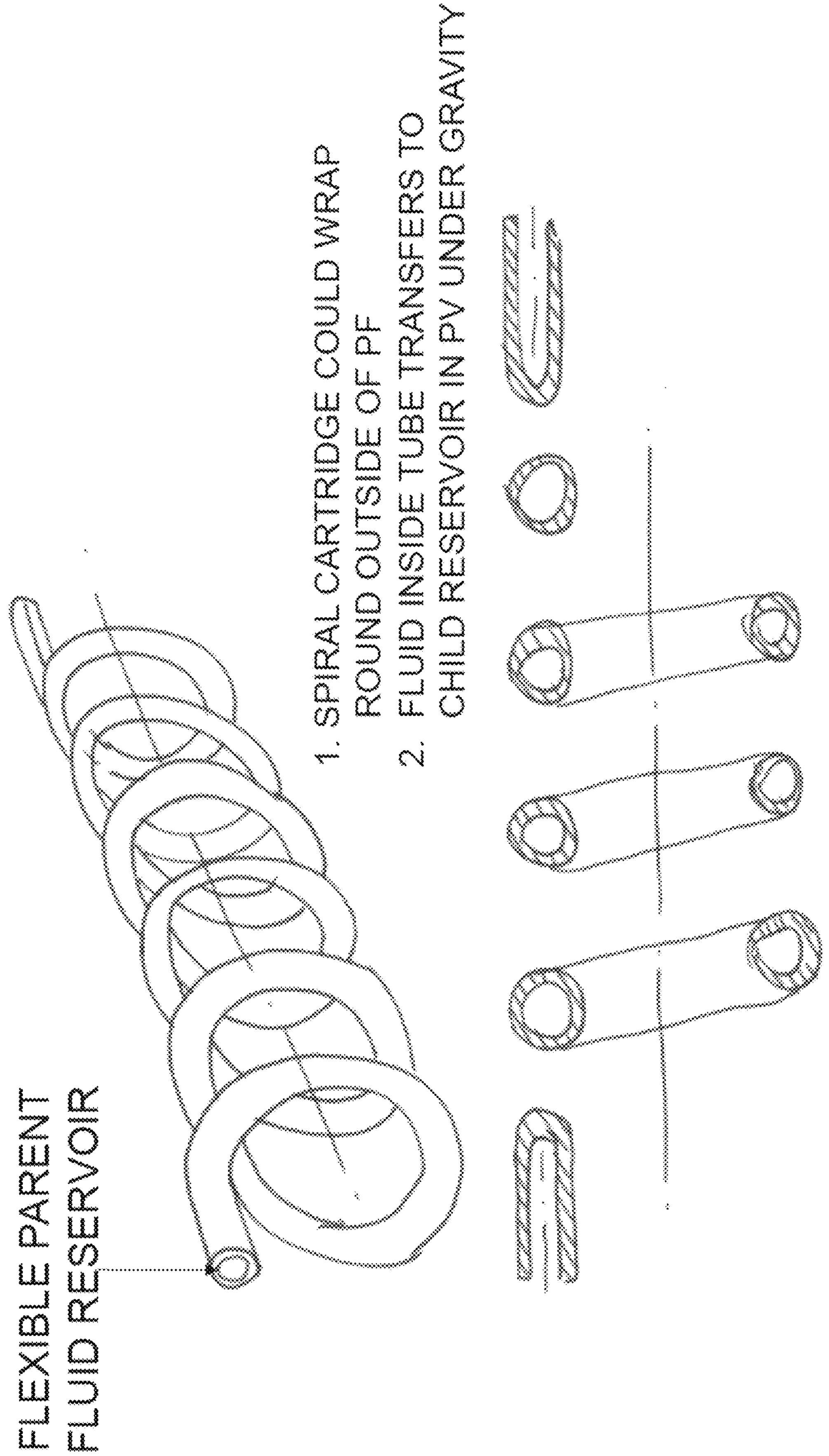
Figure 112:
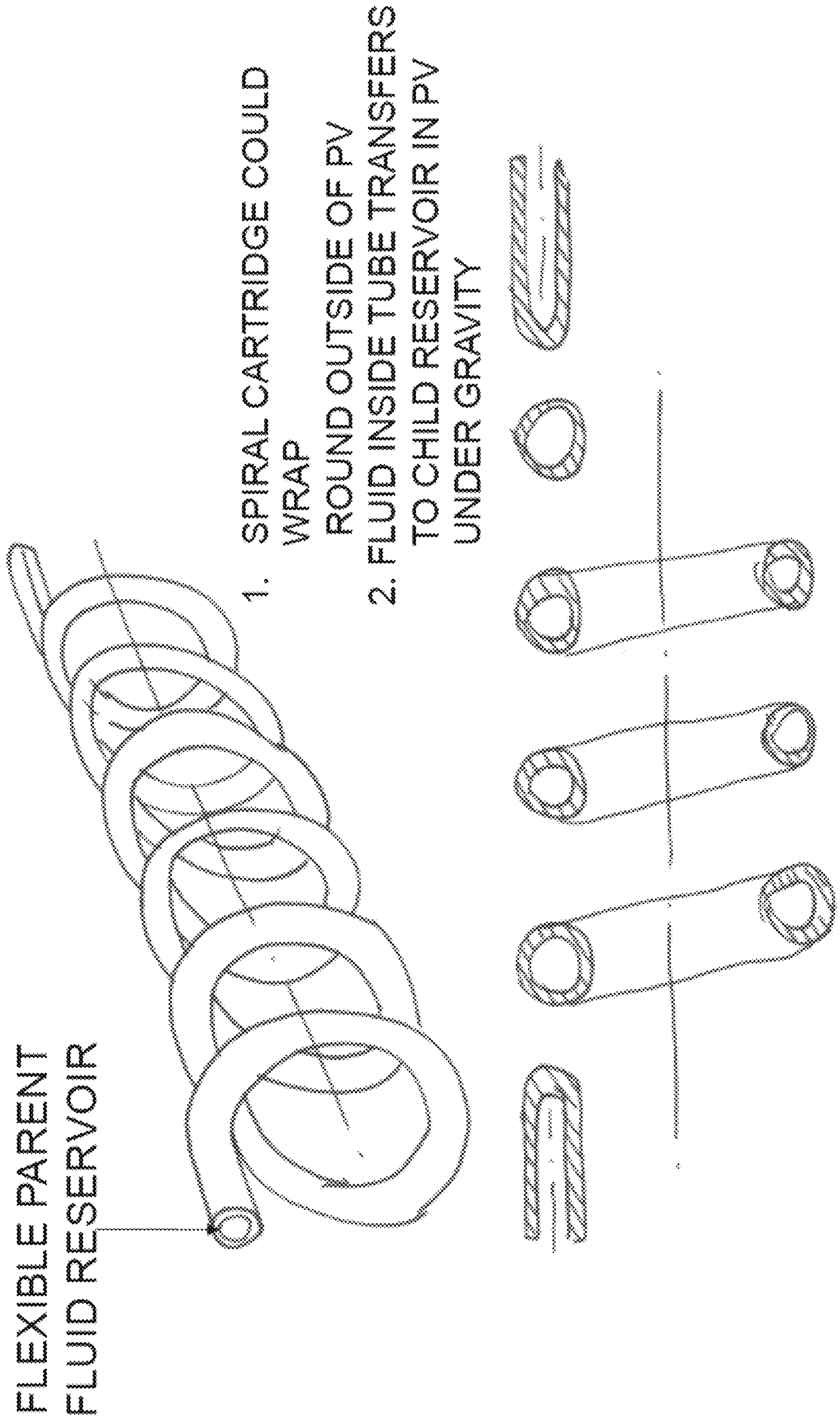

FIGS. 111 and 112 show a perspective view of a spiral cartridge parent reservoir and a cross sectional view of the parent reservoir.

Figure 113:
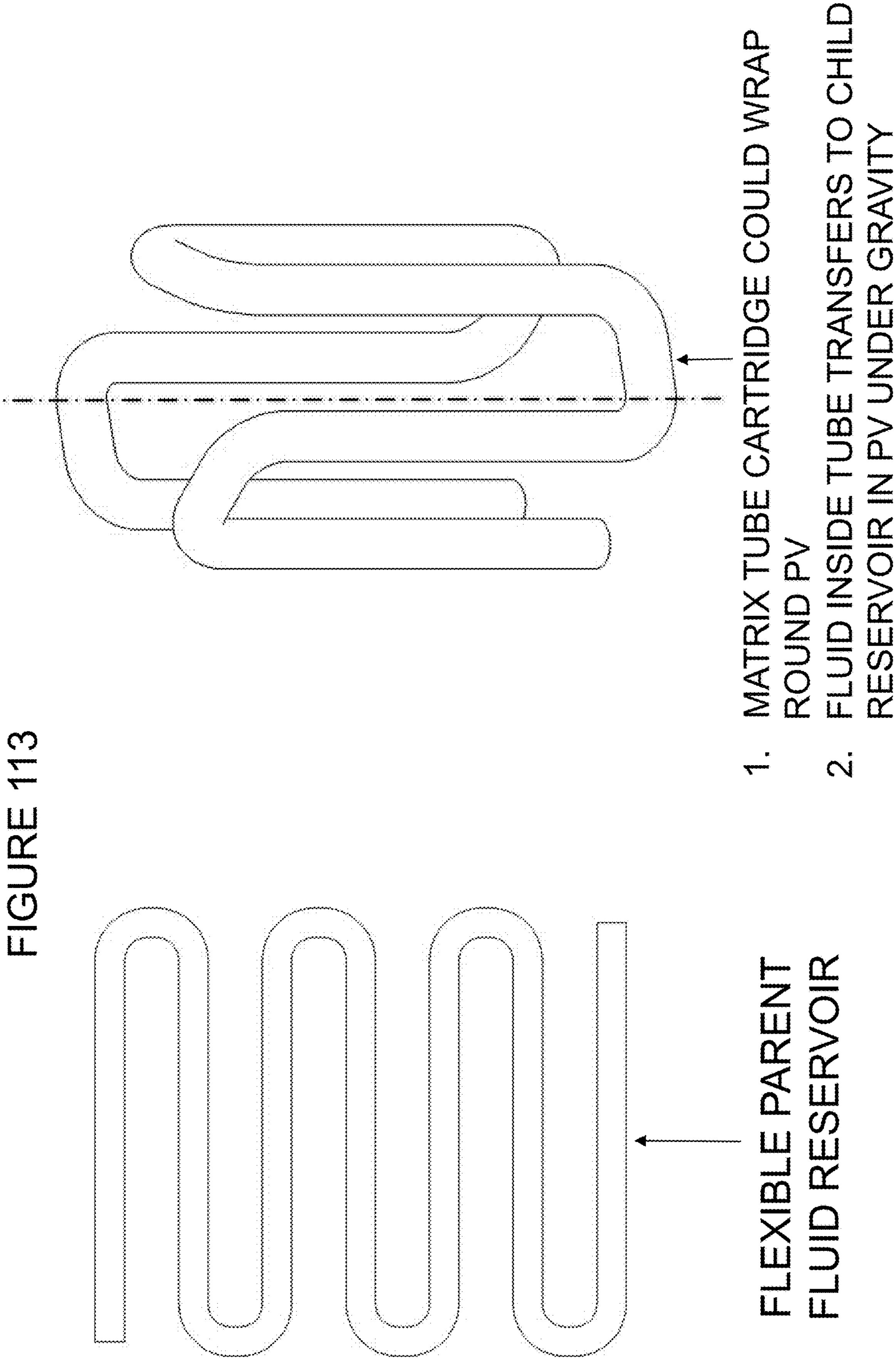

FIG. 113 shows an example of vertical and horizontal views of the flexible parent reservoir.

Figure 114:
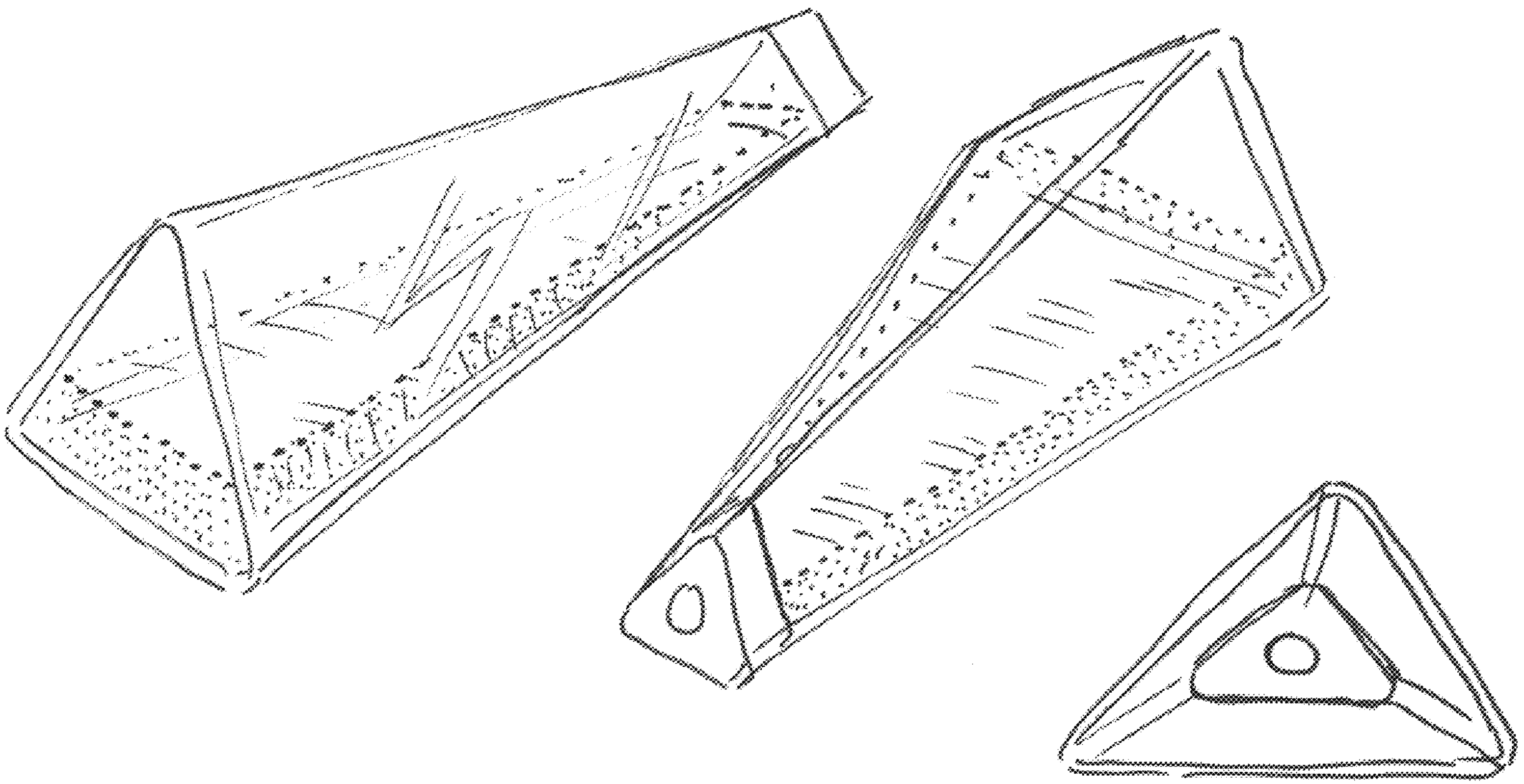

FIG. 114 shows an example of front and back views of the triangular geometry reservoir.

Figure 115:
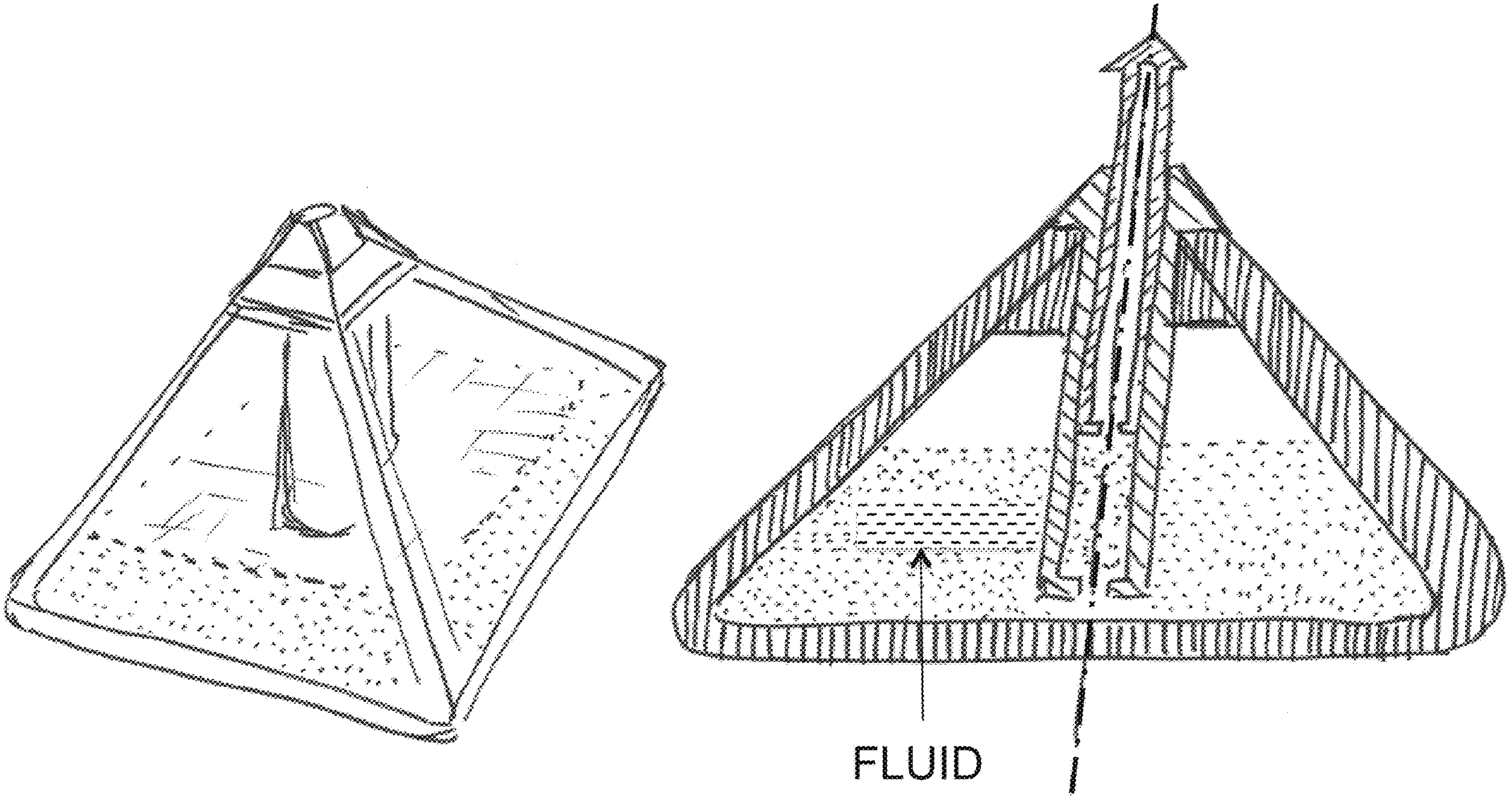

FIG. 115 shows a perspective view of a pyramid geometry reservoir and a cross sectional view of the pyramid geometry reservoir used for fluid transfer.

FIG. 116A shows a cross sectional view of the cartridge and an example of fluid transfer in the bellows.

FIG. 116B shows an exploded view and a cross sectional view of the cartridge.

FIG. 116C shows an example of fluid transfer in the flexible bellows cartridge.

Figure 116D:
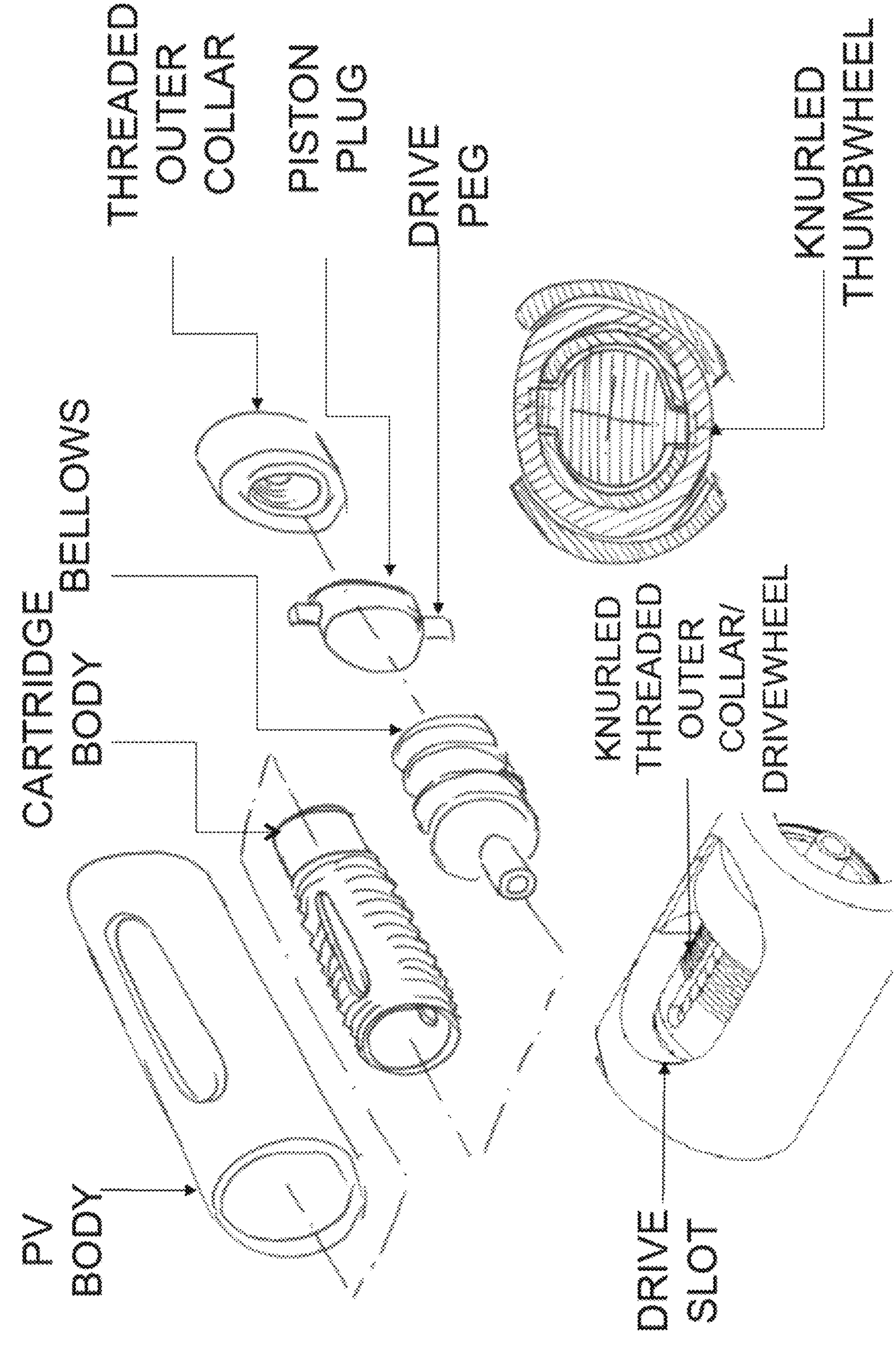

FIG. 116D shows an exploded view of the bellows cartridge.

FIG. 116E shows a cross sectional view of the cartridge and a perspective view of the cartridge slot.

KEY TO NUMERALS IN THE FIGURES

1 Personal Vaporiser—PV

2 PV holder and receptacle chassis

3 Reservoir (a user-replaceable e-liquid cartridge)
4 Pump
5 4 Way Sliding Contact Block
6 Case—L/h
7 Case—R/h
8 Cam Block
9 Guide Plate
10 Pawl/Lever
11 Solenoid Mounting Block
12 Chassis Lid
13 Valve Mounting Cup
14 Valve Mounting Cap
15 Reservoir Gasket
16 PCB—Main Case
17 Leaf Spring
18 Pivot Screw
19 Spring—Pawl/Lever
20 Split Spring Pin—Pawl Spring
21 Split Spring Pin—Pawl Pivot
22 Solenoid
23 Spring—4 Way Sliding Contact Block
24 Contact Finger
25 Ring Contact
26 Insulating Ring
27 Seal Inlet—PV
28 O Ring—PV Chamber
29 Valve—PV Tip
30 Spring—PV Tip Valve
31 Grub Screw—PV Tip
32 PV Tip
33 Screw—Guide Plate
34 Valve—Pump
35 Screw—Leaf Spring
36 End Cap—Ring Connector
37 PCB Mounting Cap/Ring Connector
38 Pin—180°-Ring Connector
39 Pin—135°-Ring Connector
40 Pin—45°-Ring Connector
41 Pin—0°-Ring Connector
42 Ring Contact
43 Insulation Ring
44 Screw—Ring Connector
45 Support Ring—4 Way Sliding Connector
46 Body—4 Way Sliding Connector
47 Wires—4 Way Connector Block
48 Fluid Chamber—PV
49 Ring Connector Assembly
50 Vaporiser End Cap
51 Vaporiser Insulating Sleeve
52 Coil and Wick Assembly
53 Vaporiser Outer Body
54 Bush—Vaporiser Body
55 Vaporiser Inner Body
56 Tube Body—Vaporiser
57 Pressure Sensor Housing
58 Pressure Sensor/Transducer
59 Battery—PV
60 PV PCB
61 Hollow Stem Shaft
62 Moulded Rim/Undercut
63 Moulded Lip Seal
64 RGB LED Indicator
65 Reset Switch
66 Arduino Chip
67 Micro USB Connector
67 Battery—Chassis
68 PCB Standoffs
69 Microswitch
70 Power Connection Insulating Bush
80 Fluid chamber inside the pump
81 Fluid inlet end
82 Fluid outlet end
83 Slotted tube for ball
84 Feed-through hole
85 Piston
86 Piston rod
87 Bias spring
88 Valve stem
89 Piston return spring
90 Valve cap
91 Tapered valve seat
92 Ball valve
93 Return spring
94 Valve seal washer
95 Reservoir cap
96 Spring guide
97 Reservoir body
98 longitudinal heating coil
99 heating coil chassis
100 Re-filling and re-charging case
101 PV front tip
102 annular orifice
103 vapourising chamber
104 mechanical fluid transfer valve
105 face seal
106 bias spring
107 valve
108 valve seat
109 channel
110 small e-fluid aperture
111 child reservoir
112 secondary child reservoir
115 atomising coil unit
116 Coil unit holes
117 sintered metal collar
118 vapourising chamber
120 mounting bush
121 insulating bush
122 Electrical contact
123 complete coil assembly
124 manifold/tip housing
126 fluid pathway channels
127 air escape path
128 tip/manifold/coil assembly
130 electronics module assembly
131 male electrical contact pin
132 female electrical contact port
135 oleophobic washer in air escape path
136 ring collar
137 duckbill valve
138 oleophobic barrier or washer2
139 air path through the oleophobic barrier
140 annular ring of concentric rotary slots
141 coilbody holder
142 annular concentric ring of holes in insulation bush
143 neodynium magnets
144 case PCB
144 mild steel plug on hinged PV chassis
145 PV chassis
146 Reed switch
147 PV circuit board
150 replaceable e-liquid cartridge
151 integral pump in the cartridge
152 pivoting lever

153 pivot or pin for the lever
154 end face of the PV
155 tension spring
160 e-liquid cartridge
161 cartridge micro-pump
162 e-liquid 'parent' reservoir
163 duckbill pressure equalisation valve
164 retention catches
165 ball valve
166 e-liquid return hole
167 absorbent pad in PV front tip
168 cartridge stem
169 cavity behind duckbill valve
170 long cavity into which the e-liquid cartridge is slotted

DETAILED DESCRIPTION

Figure 1:
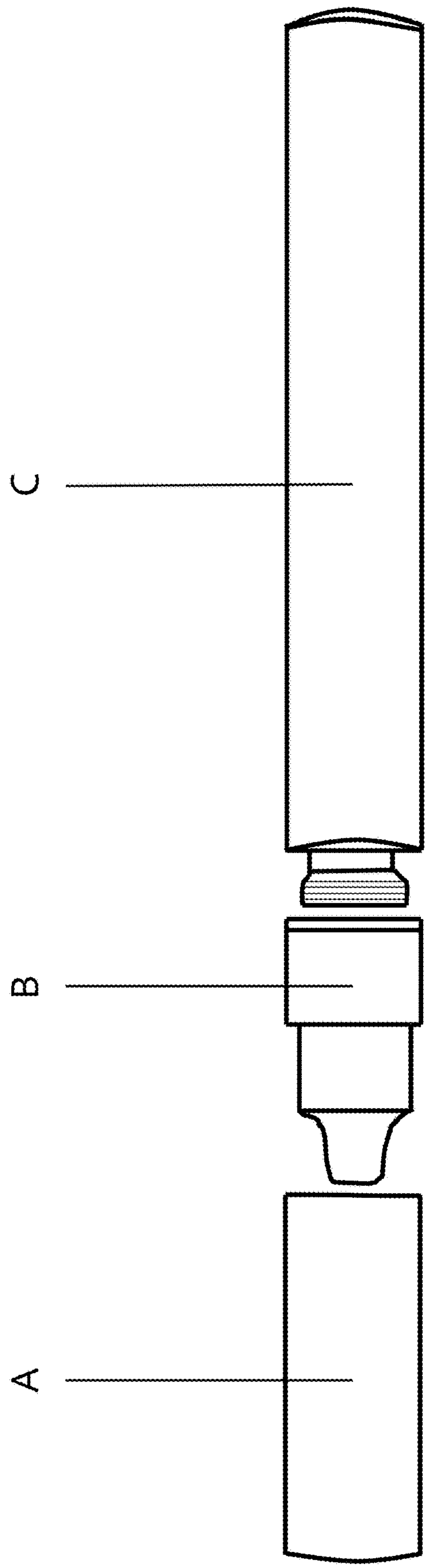
FIGURE 1 Prior art
FIG. 1 is a schematic view of a prior art e-cigarette, showing how the device can be dis-assembled into three pieces.

FIG. 1 shows a conventional personal vapouriser (TV'). The PV includes the following key components: a 'juice' or 'e-liquid' delivery and container system, called a cartridge (A), and an atomizer (B) for vapourising the juice, and a power source (C) to power the atomiser. The cartridge also forms the mouthpiece. A typical design, as shown in FIG. 1, requires the battery (C) to be screwed into the atomiser (B), and the cartridge (A) is then pushed onto the free end of the atomiser B. When the cartridge is fully consumed, the user discards the used cartridge and replaces it with a new one. An alternative design sees the cartridge as user-refillable, typically from a small bottle of e-liquid.

Conventional PV designs suffer a number of drawbacks. This Detailed Description section describes a number of high-level features which address the most significant drawbacks. An implementation of this invention uses one or more of these high level features.

We will organise our description of the features using the following categories:

Section A. E-Liquid Re-Filling and Re-Charging Storing and Carrying Case
- Feature 1. Combined re-charge and re-fill storage and carrying case
- Feature 2. Case with movable PV holder
- Feature 3. Re-Filling the PV
- Feature 4. PV Locking mechanism
- Feature 5. Data connectivity
- Feature 6. E-fulfilment Section B. PV: Simplicity and ease of use
- Feature 7. Re-fillable and re-chargeable PV
- Feature 8. PV with pre-heat
- Feature 9. PV with dosage indication
- Feature 10. PV with drip prevention Section C. User-replaceable e-liquid cartridge
- Feature 11. User-replaceable e-liquid cartridge that fits into the portable storage and carrying case Section D Miscellaneous
- Feature 12 Hygienic PV
- Feature 13 Single capsule dispenser
- Feature 14 Single capsule PV
- Feature 15 Various constructional improvements Section E Section E describes the improvements made over the system described in Sections A—D. A slightly different nomenclature will be used in this Section:

PV Features
- E.1 PV includes an air pressure valve
- E.2 PV includes a mechanical valve that is pushed up from its seat when filling takes place
- E.3 The coil unit or atomiser in the PV is protected from excess e-liquid pressure in the child reservoir that feeds e-liquid into the atomising unit
- E.4 The PV includes an oleophobic barrier separating the vaporising chamber from the portion of the PV containing the electronics and battery
- E.5 PV includes an annular vaporising channel
- E.6 PV has a 'discrete' mode
- E.7 PV includes a 'power mode'
- E.8 The PV includes a piezo-electric pump
- E.9 PV has an IMU
- E.10 PV has replaceable covers
- E.11 PV magnetically latches in the case
- E.12 PV ejection mechanism
- E.13 The PV includes a touch sensor
- E.14 A sensor detects PV release from the case
- E.15 The replaceable tip of the PV includes its own integral atomising heating element and is separable from the e-juice reservoir in the PV.
- E.16 PV has a heated nozzle Cartridge or Other Form of Parent Reservoir Features
- E.17 The cartridge or other form or parent reservoir includes an air pressure valve
- E.18 The cartridge includes a piezo-electric pump to transfer small but accurately and reliably metered quantities of e-liquid
- E.19 Atomiser is integrated into a removable lid or cap to the cartridge
- E.20 The cartridge can be packaged into a container that is the same size as a conventional cigarette pack Case Features
- E.21 The case is the same size as a cigarette pack
- E.22 The case includes a piezo-electric pump
- E.23 The case includes a removable cover Fluid Movement Features
- E.24. PV includes the removable cartridge and a mechanical sealing valve
- E.25 E-liquid is transferred out of the parent reservoir using a piston or other device that decreases the internal volume of the parent reservoir
- E.26 E-liquid is transferred out of a deformable parent reservoir:
- E.27 Archimedes screw
- E.28 Gravity feed Note that each high-level feature listed above, and the related, detailed features listed below for each high-level feature, can be combined with any other high-level feature and any other detailed feature.

INTRODUCTION

The following sections will describe an e-cigarette system that implements aspects of the invention; this system includes:
- an e-cigarette PV; the size and shape can be similar to, or slightly larger than, a conventional cigarette. This is shown in FIG. 2. Mimicking the size and shape of a conventional cigarette is very helpful since it makes the PV much more attractive to smokers trying to quit cigarettes.
- a portable, personal storage and carrying case that both re-charges the battery in the PV and also re-fills the e-liquid chamber in the PV; the size and shape can be similar to, or slightly larger than, a conventional cigarette packet of 20 cigarettes. This is shown in FIG. 3 (PV partly withdrawn from its case) and FIG. 4 (PV fully withdrawn from its case)

a user-replaceable cartridge that is slotted into the case and can be readily swapped out by the user for a fresh cartridge when running low or to try different strengths or flavours of e-liquid. The cartridge capacity can be approximately 10 ml of e-liquid; this might approximate very roughly to five packets of 20 cigarettes. See FIG. 5.

Because the PV can be stored in the case whenever it is not being used, and the case may operate to re-fill the PV from its user-replaceable cartridge and also re-charge the PV, the PV can always be in its fully re-filled and re-charged state whenever it is removed from the case. There is no longer any need for the user to carry around spare batteries for the PV or small re-fill bottles of e-liquid.

One design of this new system, as shown in FIGS. 3 and 4, has the PV being automatically replenished with e-liquid when it is slotted into a holder that hinges outwards from the main body of the case and the user manually pushes the PV up and down, activating a micro-pump that transfers e-liquid from the user-replaceable cartridge in the case to a reservoir in the PV. When the holder is closed into the case, the electrical contacts on the PV engage with charging contacts inside the case, transferring power from the case battery to the rechargeable battery in the PV. This means:

Vaping performance of the PV is always optimal; there is none of the performance degradation associated with a weak PV battery or a nearly empty PV e-liquid reservoir.

The PV can vape at the lower voltages (possibly associated with zero formaldehyde emissions—see Discussion of Related Art above): in a conventional system this can provide a good vaping experience when the resistance of the heating wire in the atomizer is sufficiently low (and hence the overall power is sufficient but not too high, typically in the 6-8 watts band), but leads to the serious disadvantages of high battery drain and high e-liquid consumption. These disadvantages are now rendered wholly irrelevant with the new system because of the ease of both re-filling and re-charging the PV using the storage and carrying case.

Because the storage case is designed to be a portable, personal storage and carrying case (typically similar in size to a pack of 20 cigarettes), the user will generally always carry it with him or her (in their pocket or handbag etc) and hence always store the PV away in it. Because the storage case is considerably larger than a conventional PV, it can store far more e-liquid in its user-replaceable e-liquid cartridge and can include a much larger capacity battery. Hence, the e-liquid cartridge in the carrying case only needs to be replaced relatively infrequently (for a typical 20 cigarette a day smoker switching to this system, then a new cartridge might be needed every five days: very roughly, 10 inhalations consumes 0.1 ml of e-liquid or the equivalent of one cigarette; the PV itself stores typically 2 ml of e-liquid, or the equivalent of twenty cigarettes; and the cartridge in the case typically stores approximately 10 ml of e-liquid for compliance with EU Directive 2014/40/EU (known as the Tobacco Products Directive) or the equivalent of five packets of twenty cigarettes. Further, the case only needs to be re-charged (e.g. using a USB charging cable connected to a laptop or mains power adaptor) infrequently as well (perhaps once a week, depending on use).

This system is designed to re-fill and re-charge a PV many thousands of times without damaging either case or PV. This system gives the user an e-cigarette PV with the form factor of a conventional cigarette, and with the performance and user experience (e.g. vapour intensity) of a large modding kit-type PV, but with none of the inconvenience of dis-assembling the PV to re-fill the PV with e-liquid from a small bottle. This system also replicates the rituals of handling an object similar in size to a packet of twenty cigarettes, of opening that packet and withdrawing a cigarette; and the tactile familiarity of holding a cigarette sized object and inhaling from it. This combination is we believe key to the large-scale consumer adoption of e-cigarettes.

Section A. E-Liquid Re-Filling and Re-Charging Storage and Carrying Case

In this Section A, we will describe the e-liquid re-filling and re-charging storage and carrying case. The case implements a number of useful features:

| | |
|---|---|
| Feature 1. | Combined re-charge and re-fill storage and carrying case |
| Feature 2. | Case with movable PV holder |
| Feature 3. | Re-Filling the PV |
| Feature 4. | PV Locking mechanism |
| Feature 5. | Data connectivity |
| Feature 6. | E-fulfilment |

In this Section A, we will summarise each of these six features in turn, and then describe them in detail. Appendix 1 collects these features into a consolidated summary.

Feature 1. Combined Re-Charge and Re-Fill Storage and Carrying Case

The feature is: A portable, personal storage and carrying case for an e-liquid e-cigarette PV in which the case includes: (a) a power source for re-charging a rechargeable battery in the PV; (b) a reservoir for holding e-liquid; and (c) a fluid transfer system adapted to transfer e-liquid from the reservoir to a chamber in the PV. The reservoir for holding e-liquid is, in one implementation, a user-replaceable e-liquid cartridge.

As noted above, this approach is key to an e-cigarette PV with the form factor of a conventional cigarette, and with the performance and user experience of a large modding kit-type PV: re-filling and re-charging of the PV is fast and convenient, since it can occur readily and easily whenever the user returns the PV to its case. The e-liquid cartridge in the case requires relatively infrequent (e.g. weekly) but fast, and mess-free replacement; it is far easier than re-filling manually by squeezing e-liquid from a small bottle. It may also have a simple relationship with conventional cigarette consumption (e.g. 'one hundred cigarettes in a case').

Note also that the two features of re-charging the PV's battery and re-filling the PV's e-liquid chamber have a working interrelation that produces an overall improved result—we have a synergistic combination of features, entirely lacking for example in the non-analagous field of metered dose inhalers, exemplified by U.S. Pat. No. 6,637,430 Ponwell.

Specifically, an effective e-liquid PV consumes a significant amount of e-liquid and also current. Cigalites have not sold well in the market because they permit neither high e-liquid consumption nor high current. Cases that can merely re-charge a PV are not good enough because the PVs need to be frequently re-filled with e-liquid, which means dis-assembling them, which is messy and inconvenient. But if you add an e-liquid feature to the case, as envisaged in this Feature 1, then that means you can run the heating element in the PV at a sufficiently high current to give much better performance—the fact that you are also now consuming more e-liquid since you are heating it faster and also now depleting the PV battery faster does not matter anymore because you can both conveniently re-fill the PV with e-liquid when you insert the PV back into the carrying case and also re-charge the PV battery. So adding an e-liquid PV re-fill capability has a working interrelationship with the PV battery re-charging function—it enables the PV to run at higher current and also higher juice consumption rates, giving much better vaping performance, but without the inconvenience of having to regularly dis-assemble the PV for re-filling or battery change.

Also, with this Feature 1, we can run the atomiser at the lower voltages (e.g. 3.3V) that likely produce no formaldehyde if we use low resistance wire in the atomiser—this not only produces no formaldehyde but will also produce warmer vapour and more vapour than would be made if the device were running at 5V.

Systems that do not have a combined re-fill and re-charge carry case cannot replicate this experience at lower voltages like 3.3V, because a 3.3V and low resistance wire combination means faster battery drain and faster e-liquid consumption than a higher voltage and higher resistance wire combination. As noted above, faster PV battery drain and faster e-liquid consumption are not disadvantages with the present Feature 1 because re-charging the PV and re-filling it with e-Liquid is fast and convenient and can happen readily whenever the PV is returned to the storage and carrying case.

Feature 2. Case with Movable PV Holder

The feature is: A portable, personal storage and carrying case for an e-liquid e-cigarette PV in which moving a movable holder or chassis, into which the PV has been inserted, brings electrical charging contacts on the PV into direct or indirect engagement with electrical charging contacts in the case that are connected to a power source, such as a rechargeable battery in the case.

By requiring the PV to be inserted into a movable holder or chassis in the case, it becomes much easier to guide the PV into accurate alignment with the electrical charging contacts in the case, as well as (preferably) guide an e-liquid filling aperture in the PV into accurate alignment with an e-liquid nozzle used to transfer e-liquid into the PV. Accurate alignment is highly desirable to ensure good electrical contact, to minimise leakage and to ensure optimum performance of the e-liquid fluid transfer mechanism.

Feature 3. Re-Filling the PV

The feature is: A portable, personal storage and carrying case for an e-liquid e-cigarette PV which re-fills the PV with e-liquid if the PV is inserted, fully or in part, into the case, whilst maintaining the PV whole and intact.

By ensuring that the PV remains entirely intact (in contrast for example to some medicinal inhalation devices which require a needle in the canister that stores medication fluids to puncture a rubber septum in the inhalation device), the design is robust and can be used for thousands of re-filling operations (as opposed to a very small number with a needle that punctures a rubber septum).

Another related high-level feature is: A portable, personal storage and carrying case for an e-liquid e-cigarette PV which re-fills the PV using a fluid transfer system, such as a pump activated by depressing and releasing the entire, complete PV, whilst the PV is held in a holder of the case in accurate alignment with the fluid transfer mechanism.

Using a holder to hold the PV in accurate alignment with a fluid transfer system is highly desirable to minimise leakage and to ensure optimum performance of the e-liquid fluid transfer mechanism, particularly where that mechanism is a pump activated by relative motion of the PV against the pump, since if the PV is not aligned correctly (e.g. along the longitudinal axis of the pump nozzle), the pump may not operate efficiently and there may be leakage.

A related high-level feature is: An e-liquid e-cigarette PV adapted to be re-filled with e-liquid when inserted into a case, in which the PV includes an e-liquid filling aperture positioned centrally along the main axis of the PV to minimise any off-centre forces that could otherwise compromise e-liquid sealing.

Another high-level feature is: A portable, personal storage and carrying case for an e-liquid e-cigarette PV in which the case is adapted to transfer e-liquid to an e-cigarette PV from a user-replaceable e-liquid cartridge in the case.

If the case includes a user-replaceable cartridge, then it becomes fast and mess-free for the user to replace user cartridges and try new flavours or strengths of e-liquid by swapping our the cartridge. Since the cartridge capacity will be much greater than the PV's e-liquid chamber (for example, 10 ml for the user-replaceable cartridge as compared to 1 or 2 ml in the PV chamber), replacement of the cartridge happens relatively infrequently—typically once every 5 days for a user replicating smoking 20 cigarettes a day. That also gives the user an easy to grasp measure of the effectiveness of any nicotine reduction program they are following—moving progressively from replacing a cartridge from every 5 days, to every 6 days, to every 7 days etc. For many ordinary users, this is an easy metric to follow.

Feature 4. PV Locking Mechanism

The feature is: A portable, personal storage and carrying case for an e-liquid e-cigarette PV which is adapted to lock the PV securely in a charging position; and when the PV is locked in the charging position, then electrical charging contacts on the PV are in direct or indirect engagement with electrical charging contacts in the case that are connected to a power source, such as a rechargeable battery, in the case.

By ensuring that the PV is locked in position, effective charging can occur and also the risk of damaging the electrical contacts (on both PV and in the case) by inadvertent movement of the PV is reduced. That is especially important since the case is a portable storage and carrying case.

Feature 5. Case with Data Connectivity

The feature is: A portable, personal storage and carrying case for an e-liquid e-cigarette PV in which the case includes (a) user-replaceable e-liquid cartridge; and (b) a fluid transfer system adapted to transfer e-liquid from the cartridge to a chamber in the PV; in which the case includes a data processor that controls sending a signal requesting a replacement for the user-replaceable e-liquid cartridge in the case.

Enabling the case to send a request for a replacement e-liquid cartridge is very convenient for the user and also ensures that replacement cartridges are supplied in a timely manner—this is especially important when the user is on a tobacco or nicotine reduction programme since if the case runs out of e-liquid, then the user may well be tempted back to using cigarettes. So the efficacy of adopting this system as a cigarette replacement (and health concerns with cigarettes is overwhelmingly the reason given for e-cigarette adoption) benefits greatly from the timely, automatic, background ordering and supply direct to the end-user of replacement cartridges.

Feature 6. E-Fulfilment Method

The high-level feature is: Method used in portable, personal storage and carrying case adapted specifically for a refillable e-cigarette PV and that re-fills and re-charges the PV, the method including the steps of the case (a) transferring e-liquid from a user-replaceable e-liquid cartridge to the PV and (b) automatically sending a signal requesting a replacement for the user-replaceable e-liquid cartridge to an e-fulfilment platform, either directly or via a connected smartphone. The method may include the steps of the case (a) detecting the level of or quantity of e-liquid in a user-replaceable e-liquid cartridge in the case and (b) automatically sending a signal requesting a replacement for the user-replaceable e-liquid cartridge to an e-fulfilment platform, either directly or via a connected smartphone.

This feature is the method that is associated with Feature 5 and the same advantages apply. Note that 'detecting the level of or quantity of e-liquid in a user-replaceable e-liquid cartridge in the case' could be direct, or could be indirect, such as inferred from the number of re-fills of the PV that have been completed with that cartridge, or the total number of inhalations made with that cartridge.

Further optional features (each of which can be combined with any of the others high-level features 1-6 above) include the following:

- the movable chassis also has mounted on it an e-fluid reservoir, a battery, a printed circuit board and a fluid transfer mechanism
- a metered dose or quantity of the e-liquid is delivered by the fluid transfer mechanism in the case to the PV—typically 0.1 ml per individual pumping action where a micro-pump is used.
- the portable re-filling case or unit comprises a holder for housing, securing or engaging with the personal vapouriser.
- the holder comprises a biasing means for receiving the personal vapouriser in a support position, the biasing means being arranged such that a user depressing the personal vapouriser causes the biasing means to allow the personal vapouriser to engage with the refill mechanism, in a refill position.
- the holder can be rotatably connected to the portable re-filling unit such that it can move between an open and closed configuration, the open and closed configurations having corresponding personal vapouriser positions, wherein in the closed configuration the personal vapouriser engages with the refill mechanism to receive a dose of substance and in the open configuration the personal vapouriser is disengaged from the refill mechanism.
- the refill mechanism comprises a pump.
- the refill mechanism comprises a refill valve.
- the refill mechanism is electronically controlled.
- the portable re-filling case further comprises a counter/measuring system for counting or estimating substance consumption-related data, such as the number of times a personal vapouriser has been refilled from the fluid reservoir.
- The counter/measuring system counts the number of times the personal vapouriser has been inserted into the unit for re-filling.
- the counter/measuring system is resettable and the portable re-filling unit stores and/or displays a value provided by the counter/measuring system which corresponds to the number of times the personal vapouriser has been refilled from the fluid reservoir.
- The counter/measuring system directly measures consumption-related data by measuring the change in the amount of substance stored in the unit.
- the portable re-filling case or unit stores the consumption-related data and transmits that data to another device, such as a smartphone, using a wireless or non-wireless connection.
- the fluid reservoir is a liquid cartridge which is removable from the portable re-filling unit such that it can be replaced.
- The portable re-filling case or unit is further adapted to modify the amount of vapour fluid in a delivered dose of vapour fluid.

In the next section of Section A, we will detail the operation of the following features:

| | |
|---|---|
| Feature 1: | Combined re-charge and re-fill storage and carrying case |
| Feature 2: | Case with movable PV holder |
| Feature 3: | Re-Filling the PV |
| Feature 4: | PV Locking mechanism |

Features 1, 2, 3 and 4. Combined re-charge and re-fill storage and carrying case;
Case with movable PV holder;
Re-Filling the PV;
PV Locking mechanism The following section describes the case and the PV in more detail, focusing on these four features. The relevant Figures are FIGS. 6-10.

A portable charging device for replenishing the e-liquid or vapour fluid of an e-cigarette PV comprises: an e-liquid reservoir for storing multiple dosages of e-liquid; and a refill mechanism configured to engage with the e-cigarette PV to deliver a dose of e-liquid from the reservoir to the e-cigarette PV.

Embodiments may provide a re-filling case for refuelling the e-cigarette PV with single dose (or predetermined by end user) multiple doses of e-liquid. The e-liquid may be supplied to the e-cigarette PV from a tank in the charging and re-filling case holding a larger reserve of e-liquid. The tank may be a user-replaceable cartridge.

A single dose of e-liquid delivered to the PV (and subsequently held in the e-liquid chamber within the PV) may be equivalent to a single measure of substance (such as the quantum of nicotine inhaled in one ordinary cigarette). Typically, 0.1 ml is delivered using the micro-pump design described later in this section with each pumping action; this is equivalent to approximately ten puffs of a cigarette. The e-liquid chamber in the PV typically holds between 1 ml and 3 ml of e-liquid, very roughly equivalent to between ten and thirty cigarettes.

The fluid reservoir in the charging and re-filling case may store multiple dosages of e-liquid; the amount of e-liquid stored in the reservoir can be 10 ml and is hence significantly greater than the fluid in a conventional cartridge or vial inserted into a conventional electronic cigarette. This makes re-filling the case with a fresh e-liquid cartridge far less frequent; with a conventional PV, the cartridge in the PV has to be replenished or replaced once that relatively small dose is consumed; with our approach, it is the cartridge slotted into the carrying case that has to be replaced and this is readily done; as this holds far more than a conventional PV cartridge, replacement occurs far less frequently. Re-filling the PV occurs easily and quickly whenever the user inserts the PV back into the carrying case. This is not only more convenient for the end-user, but also significantly reduces waste. The cartridges are ideally fully recyclable.

A high-capacity e-liquid cartridge that is easily user-replaceable is especially important in a relatively low voltage, low resistance (e.g. closer to 3.3V than 5V; resistance closer to 2 ohms than 2.8 ohms or higher—typically 2.4 ohms-1.9 ohms for 3.3V) since e-liquid consumption by the PV can be quite high. This high consumption would, with a conventional PV design be highly inconvenient because of the need to disassemble the PV and manually drip e-liquid into a small reservoir by squeezing a bottle of e-liquid. But it is no longer a problem because of the ease of re-filling the PV with e-liquid whenever it is slotted back into the case.

A user is also now able to monitor use of the PV (and hence nicotine use) in a similar way to conventional cigarette consumption. For example, a single dose may be equivalent to the amount of e-liquid required to simulate nicotine consumption equivalent to a single tobacco cigarette. With the micro-pump system described later in this section, pressing the PV down just once against the micro-pump causes approximately 0.1 ml to be transferred from the case to the PV; this is approximately equivalent to ten puffs of a cigarette. The user could hence pump the PV down just once to transfer e-liquid equivalent to a single cigarette, or say five times for five cigarettes, or ten times for ten cigarettes.

In one design, the volume of e-liquid stored in the PV chamber may be equivalent to the volume of e-liquid required for an electronic cigarette to simulate a pack of twenty tobacco cigarettes. Therefore, the user may be able to conveniently regulate their consumption of nicotine via the PV. The maximum capacity of the e-liquid chamber in the PV could be 2 ml, and hence very approximately equivalent to twenty cigarettes. This easy to understand equivalence to conventional cigarettes is important in enabling users to gauge their useage and hence important for nicotine reduction useage; users find correlating useage of conventional e-cigarettes to their previous tobacco consumption difficult and this lack of transparency inhibits broader adoption of e-cigarettes, despite the significant body of scientific opinion that holds e-cigarettes to be very considerably safer than conventional cigarettes.

A single dose may also be any other quantity set as equivalent to a single dose, for example by the end-user, or automatically by the PV or its case if for example the end-user is following a nicotine reduction program. This generalisation applies throughout this specification and to all of the various innovative features described in it.

Embodiments may provide a rechargeable case battery where the portable charging and re-filling case is adapted to allow the PV to recharge its battery from the rechargeable case battery. The portable charging and re-filling case may offer the advantage that a user is able to simultaneously refill the PV with e-liquid and also recharge the battery of the PV. This ensures that, whenever the PV is withdrawn from the case, it can have sufficient e-liquid and power to provide a good vaping experience.

The portable charging and re-filling case may comprise a PV holder for housing the PV. The holder may support the PV in a specific position, provide storage, and enable refilling and charging of the PV.

The PV holder may comprise a biasing means for receiving a PV in a support position. The biasing means may be arranged such that depressing the PV causes the biasing means to allow the PV to engage with the refill mechanism, in a refill position. To refill the PV with a dose of vapour liquid the PV may be inserted into the holder. The holder may be a drawer such that when the PV is placed in the drawer, pushing the PV down allows the PV to engage with the refill mechanism so that e-liquid is pumped into the PV, filling the e-liquid chamber of the PV with one dose of e-liquid.

Alternatively, the PV holder may be rotatably connected to the portable charging and re-filling case such that the PV holder can move between an open and closed configuration, the open and closed positions having corresponding PV positions, wherein in the closed configuration the PV engages with the refill mechanism to receive a dose of e-liquid and in the open configuration the PV is disengaged from the refill mechanism.

The refill mechanism may comprise a pump. In such an example, interaction between the PV and the refill mechanism may cause the pump to deliver a measured dose of e-liquid to the PV. The refill mechanism may comprise a refill valve. The refill mechanism may be electronically controlled. A more detailed walk-through of the e-liquid transfer mechanism will be given later.

The portable charging device or case may comprise a counter/measuring system for counting the number of times the PV has been refilled from the e-liquid reservoir. The counter may be resettable and the portable charging and re-filling case may display a value provided by the counter corresponding to the number of times the PV has been refilled from the e-liquid reservoir in the case. The value may be the number of times the PV has been refilled from the reservoir since the last time it was reset, or it may be the total number of times a dose of e-liquid has been supplied by the reservoir by the refill mechanism. The data may be displayed or stored on a processor within the portable charging and re-filling case to be transmitted by wire or wirelessly to a secondary device for analysis and display, such as a smartphone, a wearable device, a portable computer or directly to the internet. Further, monitoring of usage may be used to determine when the e-liquid in the reservoir is nearly depleted and thus prompt the replacement of the fluid reservoir (by automatically ordering a replacement (or a week or a month's worth of replacements, or some other quantity, at the user's option) from an e-fulfilment platform that will then deliver direct to the user, or advising the user that a replacement will be needed, for example).

Embodiments may be further adapted to vary the amount of e-liquid in a single dose, and such variation may be based on prior usage of the PV (as monitored by a counter for example). In this way, the amount of e-liquid (or the concentration within the vapour fluid) in a delivered dose may be gradually reduced over time, helping a user to reduce consumption of a substance in the vapour fluid (such as nicotine or caffeine, for example). Such a concept may be extended to enabling a user to indicate a time period over which they wish to reduce consumption and by how much. Based on such an indication, an embodiment may moderate the amount of e-liquid in a single dose such that the desired reduction in consumption is achieved automatically, and over a set period of time or following a specific cessation program.

The e-liquid reservoir may be a liquid cartridge which is removable from the portable charging and re-filling case such that it can be easily and quickly replaced by a user, without mess or risk of spillage. Therefore, when the e-liquid reservoir is depleted a user may insert a new liquid cartridge so that the reservoir is replete.

The PV may comprise a liquid chamber for holding a dose of e-liquid, wherein the PV is adapted to engage with the portable charging and re-filling case in order to receive a dose of e-liquid from the fluid reservoir. The PV may comprise a PV valve.

Engagement of the PV valve and refill valve may allow a dose of e-liquid to be pumped from the reservoir of the portable charging and re-filling case to the fluid chamber of the PV. Therefore, when the PV is in or moved to a refill position, a dose of e-liquid may be delivered to the PV. When the PV is not engaged with the refill mechanism, the PV valve may be closed so that the e-liquid is stored in the PV.

In the following section, we will describe the PV and case, with reference to the Figures.

Referring to FIGS. 6 and 7, there is shown a portable charging and re-filling case 100 according to the invention. The portable charging and re-filling case 100 houses a fluid reservoir 3 and a rechargeable case battery 68 both of which are user-removable and replaceable. The PV holder or receptacle chassis 2 is a holder that is sized to securely hold the PV 1; it is shown in an open configuration and is adapted to store the electronic cigarette 1 or any other PV in a specific position that enables the PV 1 to accurately engage with and align against electrical charging contacts, data transfer contacts and e-liquid re-filling nozzle that are all in the case. The PV holder or receptacle chassis 2 in this embodiment is pivotally attached to the main body of the portable charging and re-filling case 100 such that in a closed configuration the PV 1 is stored securely within the casing of the portable charging and re-filling case 100.

In use, the e-cigarette PV 1 is placed in the electronic PV holder or receptacle chassis 2 and the chassis 2 is then moved to the closed configuration in order to store and/or refill the e-cigarette PV 1. In the closed configuration, the electronic cigarette 1 is in a refill position and can be depressed to engage with a fluid transfer mechanism to receive a dose of e-liquid from the fluid i.e. e-liquid reservoir 3 in the case 100 (typically, 0.1 ml is pumped across, as noted above, for each downwards pumping action). Alternatively, the electronic cigarette 1 may be refuelled upon insertion into the PV holder 2 using some other fluid transfer action, such as a pressurised pump, electrical pump, peristaltic pump etc.

The electronic cigarette 1 may also recharge not only its e-fluid chamber but also its internal battery 59 from the recharge case 100. This offers a user an advantage, in that it is no longer necessary to carry spare cartridges of e-liquid in order to refill the electronic cigarette 1 with e-liquid, or spare batteries to power the PV, as re-filling and re-charging can be achieved directly and without mess from the portable charging and re-filling case 100.

FIG. 7 shows, at a schematic level, an example of the portable charging and re-filling case 100 in cross section, and an electronic cigarette 1 for use with the portable charging and re-filling case 100. The e-liquid chamber of the electronic cigarette 1 is adapted to receive and store a single dose of e-liquid fluid. The reservoir 3 of the portable charging and re-filling case 100 stores multiple doses of e-liquid and is connected to a dosed pump 4. The pump 4 includes a valve 34 and valve seals 13 & 14 and a bias spring 87. When the pump 4 is actuated, a dose of e-liquid is delivered from the portable charging and re-filling case 100 to the e-liquid chamber of the electronic cigarette 1 through hollow shaft 61.

The electronic cigarette 1 is placed into the PV holder 2 in a support position. In the support position, the electronic cigarette is disengaged from the refill mechanism. In an embodiment, a biasing member 87 prevents the electronic cigarette 1 from engaging with the refill mechanism 4 such that the electronic cigarette is maintained in the support position.

To actuate the pump 4, the electronic cigarette 1 is depressed. Depression of the electronic cigarette 1 overcomes the biasing force provided by the biasing member 87 and enables the electronic cigarette 1 to move to a refill position, or to re-fill by virtue of being depressed downwards.

When refilling, the electronic cigarette engages with the refill mechanism 4 to receive a dose of e-liquid. A counter (not shown; part of the electronics in the case) monitors the number of doses dispensed by the refill mechanism 4 and displays the value on a display in the case, and/or transmits by wire (e.g. USB) or wireless (e.g. Bluetooth) the usage data to a secondary device (e.g. a smartphone) with a display, to the user. The counter may display the number of doses dispensed by the refill mechanism 4 since the counter was last reset and/or may display the total number of doses the refill mechanism 4 has dispensed. This offers the user the advantage of having the opportunity to monitor their consumption. The counter may indicate to a user when the fluid reservoir 3 holds a lower volume than a threshold value (e.g. when the vapour fluid in the reservoir is nearly depleted).

Detection that the amount of vapour fluid in the reservoir is below the threshold value may be used to prompt the replacement of the fluid reservoir, by automatically ordering the delivery of a replacement fluid reservoir for example.

In the FIG. 7 schematic, the chassis 2 is just a holder for the PV and the pump 4 mechanism; in the more detailed walk-through of the working device we will provide later in this Section A (e.g. FIGS. 21-26) the chassis also supports the case battery, electronics and e-liquid reservoir; this simplifies the connection between pump and e-liquid reservoir, eliminating the need for a flexible e-liquid pipe.

FIG. 8 illustrates a further example of the portable charging and re-filling case 100 in use. Here, the PV holder 2 is rotatably connected to the portable charging and re-filling case 100 and swivels to an open configuration to accept the electronic cigarette 1. In order to refill the electronic cigarette 1 with e-liquid, the electronic cigarette 1 is placed into the PV holder 2 when the PV holder 2 is in the open configuration. The PV holder 2 is then moved to a closed configuration. The position of the electronic cigarette 1 in the closed configuration is such that the electronic cigarette 1 engages with the refill mechanism 4 to receive a specific or predetermined dose of e-liquid.

FIG. 9 shows the interaction between the electronic cigarette 1 and the refill mechanism 4 in more detail. The refill mechanism 4 includes a hollow stem shaft 61 which engages with the electronic cigarette 1 when the electronic cigarette 1 is in the refill position. Pushing the PV 1 down, into the refill position causes vapour fluid to be pumped from the fluid reservoir 3 to the electronic cigarette 1. In an example, the refill mechanism 4 is electronically controlled. For example, the pump 4 may be actuated or the refill valve 34 may open in response to a received signal.

FIG. 10 shows the electronic cigarette 1 stored in the portable charging and re-filling case 100 in the refill position. When the PV holder 2 is in the closed configuration, e-liquid is pumped from the fluid reservoir 3 to the liquid chamber of the electronic cigarette 1 to refuel the electronic cigarette 1. For example, this can be achieved by the top 32 of the PV being pushed downwards by a camming action as the holder 2 is closed, overcoming bias spring 87. Or an electronic pump might be activated once the PV is in the closed configuration. Also, the electronic cigarette 1 may recharge its battery 59 from the rechargeable case battery 68 of the portable charging and re-filling case 100.

Referring to FIG. 11, there is shown an electronic cigarette 1 for use with the portable charging and re-filling case 100. The electronic cigarette 1 has a liquid chamber 48 for storing a dose of e-liquid. The liquid chamber is connected to a PV valve 29. When the electronic cigarette 1 engages with the refill mechanism 4 of the portable charging and re-filling case 100, the PV valve 29 opens to allow a dose of e-liquid to enter the chamber 48. When the electronic cigarette 1 is not engaged with the refill mechanism 4, the PV valve 29 is closed so that the vapour liquid is stored in the liquid chamber and does not leak out.

It will be appreciated that the portable charging and re-filling case 100 is not limited in shape, and may not be rectangular. The refill mechanism 4 may not comprise a pump but some other kind of fluid transfer mechanism, and refilling of the electronic cigarette 1 with electronic cigarette fluid may be achieved by an alternative means. Further, the charging function may also occur using a charging station that is fixed (e.g. desktop based; plugged into a power socket) rather than using a portable charging and re-filling case.

For example, referring now to FIGS. 12 and 13 there are shown modified embodiments where the PV holder 2 is not rotatably connected to the portable charging and re-filling case 100. More specifically, FIG. 12 shows an embodiment where the PV holder is formed as a recess in the side the portable charging and re-filling case 100. The recess is adapted to receive a PV 1.

FIG. 13 shows an alternative embodiment wherein the PV holder is formed as a cylindrical hollow barrel along the central longitudinal axis of a circular portable charging and re-filling case 100. A PV may be placed into the hollow barrel in a support position (as depicted in FIG. 13, left hand-side). In the support position, the PV is disengaged from the refill mechanism.

In an embodiment, a biasing member not shown prevents the PV from engaging with the refill mechanism such that the PV is in a support position. To actuate the refill mechanism of the portable charging and re-filling case 100, the PV is pushed further in to the hollow barrel. Such further depression of the PV overcomes a biasing force provided by a biasing member and enables the PV to move to a refill position as depicted in FIG. 13, right hand-side.

In the refill position, the PV engages with the refill mechanism to receive a dose of e-liquid from the reservoir of the portable charging and re-filling case 100.

FIG. 14 shows that when the e-cigarette PV is depressed down onto the refill nozzle of the case, then case charge contacts electrically contact e-cigarette PV charge contacts, electrically connecting the electronic cigarette to the case battery so that the electronic cigarette can recharge its internal battery from the rechargeable case battery; hence, both the PV's battery as well as its e-liquid reservoir are replenished when inserted into the case. The electronic contacts can also provide the mechanisms through which the data is transferred from the PV to the portable case.

Non-pressurised pump technology can be used in this design to dispense a dose of a given volume of e-liquid. The device is made up of a single pump with a hollow control tube. The pump has a chamber with a predefined volume of e-liquid held for dispensing. When the PV is depressed, the e-liquid is forced under pressure from the e-liquid pump out through the pump nozzle and via a one way valve into the PV chamber. As the pump is released, it returns to its original state under a spring mechanism and in doing so draws liquid through the hollow control tube into the liquid chamber to replenish the pump so that it is ready to transfer e-liquid into the PV on the next down-stroke of the PV.

The pump is preferably a pump termed a "high delivery" pump, which makes it possible to fill the bottle by actuating the pump only once. For example, a pump is suitably used having a delivery of 0.1 ml per shot in order to feed the PV chamber.

The pump dosage volume can be predefined or variable dependent upon usage requirements. For variable dosage the travel of the pump can be variably limited with a screw type mechanism. e.g. half the normal pump travel=half the liquid intake and therefore expelled.

Pressurised pump technology may also be used: the liquid cartridge would be pressurised like a small aerosol to move predetermined volumes of liquid. The vapouriser would depress a valve that contains a liquid chamber. As the system is pressurised no 'pump' is required, instead fluid moves straight from the cartridge to the PV chamber, which is fixed in volume.

A Working System

In the following section, we will describe a working system. For clarity, we will capitalize defined terms, which are indexed in the Brief Description of the Drawings section. The relevant figures are FIGS. 15-54. We suggest reviewing these Figures using the index of defined terms as a first step in understanding the system.

The system comprises several main components, a Personal Vaporiser 1 and a portable, personal re-filling and re-charging Case 100. FIG. 15 shows a working, test prototype (i.e. not with the industrial design finishing of the final consumer product). The remainder of the engineering drawings will also relate to this test prototype. The case 100 is shown with a left hand side 6 and a right hand side 7. The case includes a Receptacle Chassis 2; the Receptacle Chassis 2 serves as the PV holder, securely holding the PV 1 when it is inserted into the case 6, 7. The Receptacle Chassis also serves as the mount on which are placed the e-liquid reservoir 3, fluid transfer mechanism 4, battery 68 and related components.

The entire Receptacle Chassis 2 rotates 15° about a Pivot Screw 18 inside a Case 6, 7 with the Receptacle Chassis 2 being Positively Biased Closed, 0° position, by a Leaf Spring 17 (first shown in FIG. 21) attached to the Receptacle Chassis 2 via Screws 35 (first shown in FIG. 21).

FIG. 15 shows an isometric view of the case 100 with the Receptacle Chassis 2 fully closed; FIG. 16 shows an isometric view of case 100 with the Receptacle Chassis 2 rotated open 15° and showing the top of a PV 1 fully inserted into the PV holder portion of the Receptacle Chassis 2. FIG. 17 shows an isometric view of the case 100 with PV 1 slightly raised and ready for the user to withdraw from the case 100. The PV 1 has been heated to its operational temperature using the battery in the case and is 'ready to vape'. FIG. 18 shows an isometric view of the Receptacle Chassis 2 on its own.

FIG. 19 shows an isometric view of the PV 1 (again, note that this is the test prototype and not the consumer version). The PV 1 has a Tip 32; at the end of the Tip 32 is a centrally positioned aperture through which e-fluid passes when re-filling the PV 1. A Seal Inlet 27 seals the aperture against the pump nozzle of the fluid transfer mechanism to prevent spillage or leakage of e-liquid. Three radially disposed vents are positioned around this central aperture; these are the vents through which vapour is inhaled. A Ring Connector Assembly 49 at the other end of the PV 1 provides electrical power and data contacts that engage with electrical power and data contacts in the Case 100. Tube body 56 contains all components.

FIG. 20 shows a sectioned view of the PV 1. Starting from the left-hand side, Seal Inlet 27 seals the PV against a fluid transfer nozzle in the case; Valve 29 enables e-liquid to pass up into the PV and prevents it leaking out since it is biased in the closed position by Spring 30. Valve 29 only opens when the force exerted by the fluid, driven by the fluid transfer mechanism, exceeds the force of Spring 30. Grub screws 31 secures the Valve 29 and Spring 30 in position. An O-Ring 28 seals Tip 32 against the body of the PV 1. The atomiser includes a Coil and Wick Assembly 52 with a Vapouriser End Cap 50 and Vapouriser Insulating Sleeve 51. Fluid Chamber 48 stores e-liquid; the lengths of wicking element running parallel to the body of the PV are fully immersed in e-liquid in Fluid Chamber 48; the wicking element running perpendicular to the body of the PV, and around which the electrical heating element is wound, is not however immersed in e-liquid, but draws e-liquid up from the limbs that are fully immersed. Further O-Ring 28 seal the e-liquid Chamber 48 from the rest of the Tube Body 56 of the PV 1. The Outer Body 53 of the PV surrounds the vapouriser.

Vaporiser Outer Body 53 and Vaporiser Inner Body 55 are insulated by Bush Vaporiser Body 54. Current is passed to the Vaporiser Inner Body 55 via a wire connected to PCB 60. One leg of the Coil 52 contacts the Vaporiser Inner Body 55, the other Coil Leg contacts Vaporiser Outer Body 53. This can be seen most clearly from FIG. 48. The Vaporiser Outer Body 53 is connected to Earth.

A Pressure Sensor/Transducer 58 is mounted behind the Vaporiser Unit in the Pressure Sensor Housing 57. This is wired to the PCB 60. An Arduino Chip 66 mounted to the PCB 60 is used to monitor, control, set and feedback information pertaining to the vaping functionality.

A 3.7V 140 mAh LiPo Battery 59 sits on the PCB 60. The far end of the PCB 60 is wired to Ring Connector 49 with 4 connections—1 Power, 1 Earth, 2 Signal. Ring Connector 49 is made up of alternating Ring Contacts 42 and Insulation Rings 43, and is mounted on Screw 44 and terminates with End Cap 36.

When air is drawn through the PV 1, the Pressure Sensor/Transducer 58 activates, causing current to be sent to the Coil/Wick Assembly 52. The Coil heats the vaping fluid soaked wick, giving off vapour which entrains into the air stream.

O rings 28 seal the Vaping Chamber 48 from the air path. A unitary (and hence very strong) stainless steel Tube 56 houses all the parts mentioned above with a cut out to allow the RGB LED 64 to display the Status of the PV 1 for both battery power and vaping fluid level. A further small hole sits above the Reset Switch 65 mounted to the PCB 60.

The PV 1 charges its 140 mAh Battery via the Ring Connector 49. Information is also fed back to the PCB Main Case 16 via 2 of the connections on the Ring Connector 49.

If we look now at FIG. 21, we see a sectioned view of the case 100 with the Receptacle Chassis 2 fully closed into the case 100; the PV 1 is omitted for clarity. FIG. 22 shows a sectioned view of case 100 with the Receptacle Chassis 2 rotated open 15, again with no PV inserted for clarity. To Load/Insert PV 1 into Receptacle Chassis 2 hand pressure is applied to the Lower Section of the exposed Receptacle Chassis 2. Receptacle Chassis 2 rotates 15°, using hand pressure, from its closed position, shown in FIG. 21, to its "Open" position shown in FIG. 22, with Leaf Spring 17 supplying a resistive force, bearing against Case 6 & 7 inner walls.

FIG. 22 shows clearly how all critical components needed in the case 100 are mounted on the Receptacle Chassis 2. Key elements are the e-liquid pump 4, which sits in a void in the e-liquid cartridge 3. A hollow stem shaft 61 protrudes from one end of the pump 4, biased upwards by a spring; when a PV is depressed against this hollow stem shaft 61, it depresses that hollow stem shaft 61 downwards, forcing e-liquid within the pump 4 to travel up the hollow stem shaft 61 into the PV; the e-liquid cannot return back into the reservoir 3 because a ball valve 34 at the base of the pump 4 closes. Also mounted on the Receptacle Chassis 2 is the rechargeable battery 68 and a solenoid 22 that triggers an interlock mechanism, a lever or pawl 10 with a tooth at one end that rests against a sliding contact block 5. When the sliding contact block 5 fully engages with the PV, the pawl rises and locks against an edge of the sliding contact block 5, preventing it from moving back into the case 100 and hence locking the PV into position. Various PCB components are also shown mounted on the Receptacle Chassis 2, such as Microswitches 70, and PCB 16. Leaf Spring 17, mounted against Receptacle Chassis 2 with Screws 35, biases the Receptacle Chassis 2 in a closed position, as shown in FIG. 21; it is shown in its opened position in FIG. 22.

Moving to FIG. 23, we now see the PV 1 fully inserted into Receptacle Chassis 2, which is fully closed within the case 100. The PV 1 is retained in position by a small ridge in the top of the sliding contact block 5 that engages with a channel around the top of the PV 1.

There is no power from Receptacle Chassis 2 to Coil & Wick Assembly 52 or Solenoid 22. The system is in standby mode.

Receptacle Chassis 2 is at closed 0° Position

Pawl/Lever 10 is in its disengaged position, biased 6° to the horizontal by Spring 19

4 Way Sliding Contact Block 5 is pushed into contact with Ring Connector Assy 49 by Cam Block 8—the action of rotating Receptacle Chassis 2 to Closed 0° position advances the 4 Way Sliding Contact Block 5 against Spring 23 (see FIGS. 27-30 for more details on the operation of the 4 Way Sliding Contact Block 5.

FIG. 24 shows the device in activated mode, with solenoid 22 activated and pawl/lever 10 activated, locking sliding contact block 5 in position.

Power is supplied from Receptacle Chassis 2 to Solenoid 22. Power is supplied to Solenoid 22 when a small angular displacement of Receptacle Chassis 2 relative to Case 6 & 7 activates a Micro-switch 70 attached to Case 6 & 7

Receptacle Chassis 2 is at the closed 0° Position.

Pawl/Lever is pushed up into its engaged position, 0° to the horizontal, by Solenoid 22, locking the 4 Way Sliding Contact Block 5 into electrical contact with Ring Connector Assembly 49 (see FIGS. 27-30 for more details on the operation of the 4 Way Sliding Contact Block 5). A mechanical interlock between 4 Way Sliding Connector Block 5 and PV 1 is therefore engaged.

FIG. 25 shows the pre-heat mode: the Receptacle Chassis 2 is now fully opened; the PV 1 is locked in position and the sliding contact block 5 is also locked in position by pawl/lever 10; current is drawn from case battery 68 to heat the coil in the Coil and Wick Assembly 52 in PV 1.

Power is only supplied from Receptacle Chassis 2 to Coil & Wick Assembly 52 when the Receptacle Chassis has rotated fully to its 15° to its Open position.

Pawl/Lever pushed into its engaged position, 0° to the horizontal, by Solenoid 22

The 4 Way Sliding Contact Block 5 is in electrical contact with Ring Connector Assembly 49. (See FIGS. 27-30 for more details on the operation of the 4 Way Sliding Contact Block 5).

The mechanical Interlock between 4 Way Sliding Connector Block 5 and PV 1 continues to be engaged.

Once pre-heating is completed, solenoid 22 releases pawl/lever 10 and sliding contact block 5 withdraws away from the PV 1, which is then biased to rise up slightly out of the case 100 by shaft 61 in pump 4, as shown in FIG. 26. So FIG. 26 shows the activated mode.

No power is supplied from Receptacle Chassis 2 to Coil & Wick Assembly 52 or Solenoid 22.

Receptacle Chassis 2 is at Open 15° Position with PV 1 standing 3 mm proud 4 Way Sliding Contact Block 5 is disconnected from Ring Connector Assembly 49 under pressure from Spring 23. (See FIGS. 27-30 for more details on the operation of the 4 Way Sliding Contact Block 5).

Pawl/Lever 10 is in its disengaged position, biased 6° from the horizontal by Spring 19

Mechanical interlock between 4 Way Sliding Connector Block 5 and PV 1 is now disengaged.

FIGS. 27-30 show the operation of the 4 Way Sliding Contact Block 5.

The 4 Way Sliding Contact Block 5 connects Power, Earth and 2 Signal Input/Outputs from the PCB Main Case 16 to the PV PCB 60. A mechanical Interlock between the 4 Way Sliding Contact Block 5 and the PV 1 is incorporated in the design: the body 46 of the 4 Way Sliding Contact Block has a finger protrusion which engages with an undercut on the PV ring connector 49 providing the interlock facility. This is clearest when comparing FIGS. 27-29, which show the finger protrusion locking into the PV, and FIG. 30, which shows the 4 Way Sliding Contact Block 5 after it has slid back into the case and the PV 1 is now released.

Figure 30:
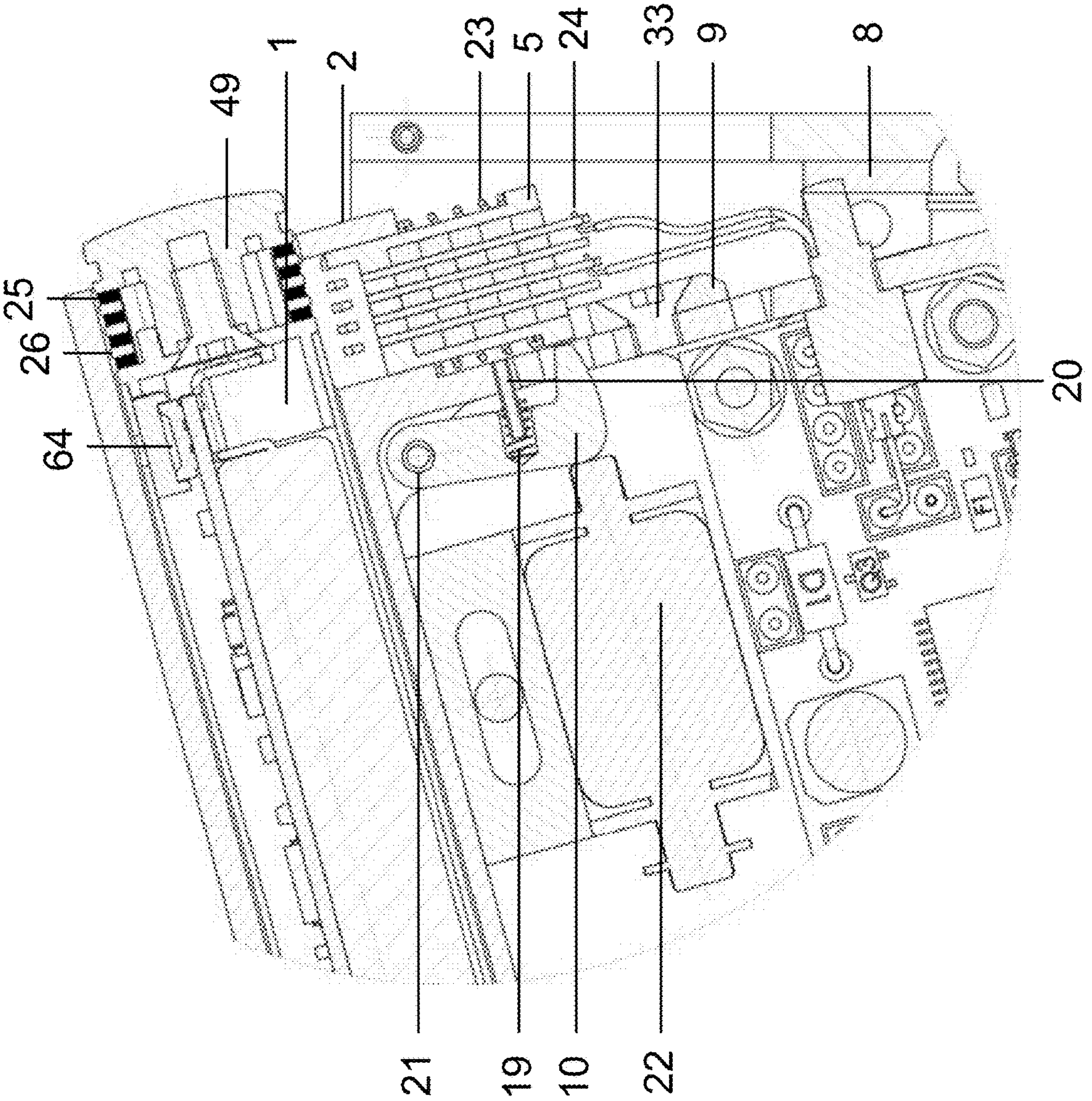

The 4 Way Sliding Contact Block 5 is normally biased away from and out of contact with the Ring Connector 49 on the PV by a helical Spring 23 when mounted in the Receptacle Chassis 2 in the Open 15° position and with the Pawl/Lever in the disengaged 6° position—FIG. 30.

Figure 27:
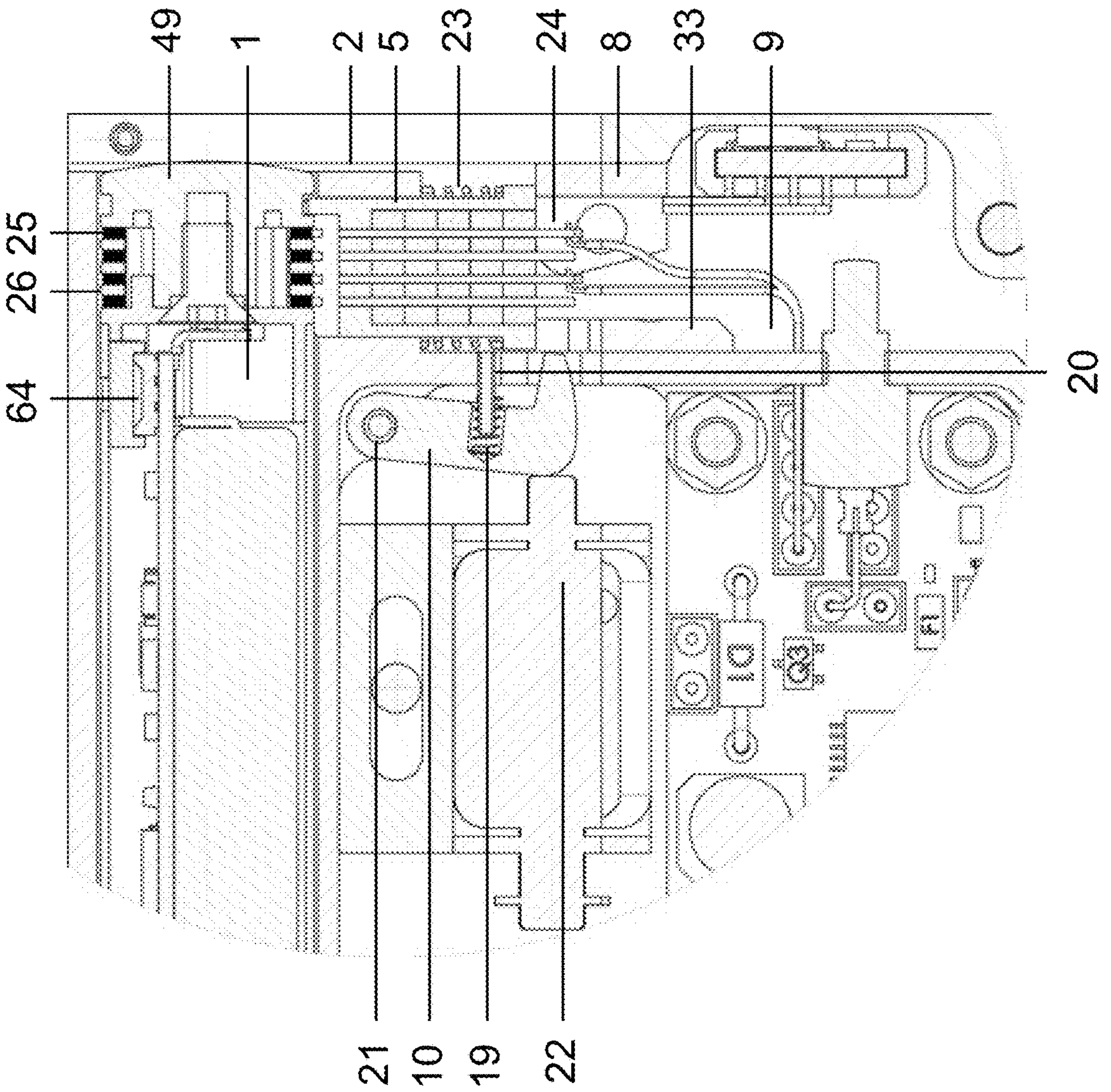
Figure 28:
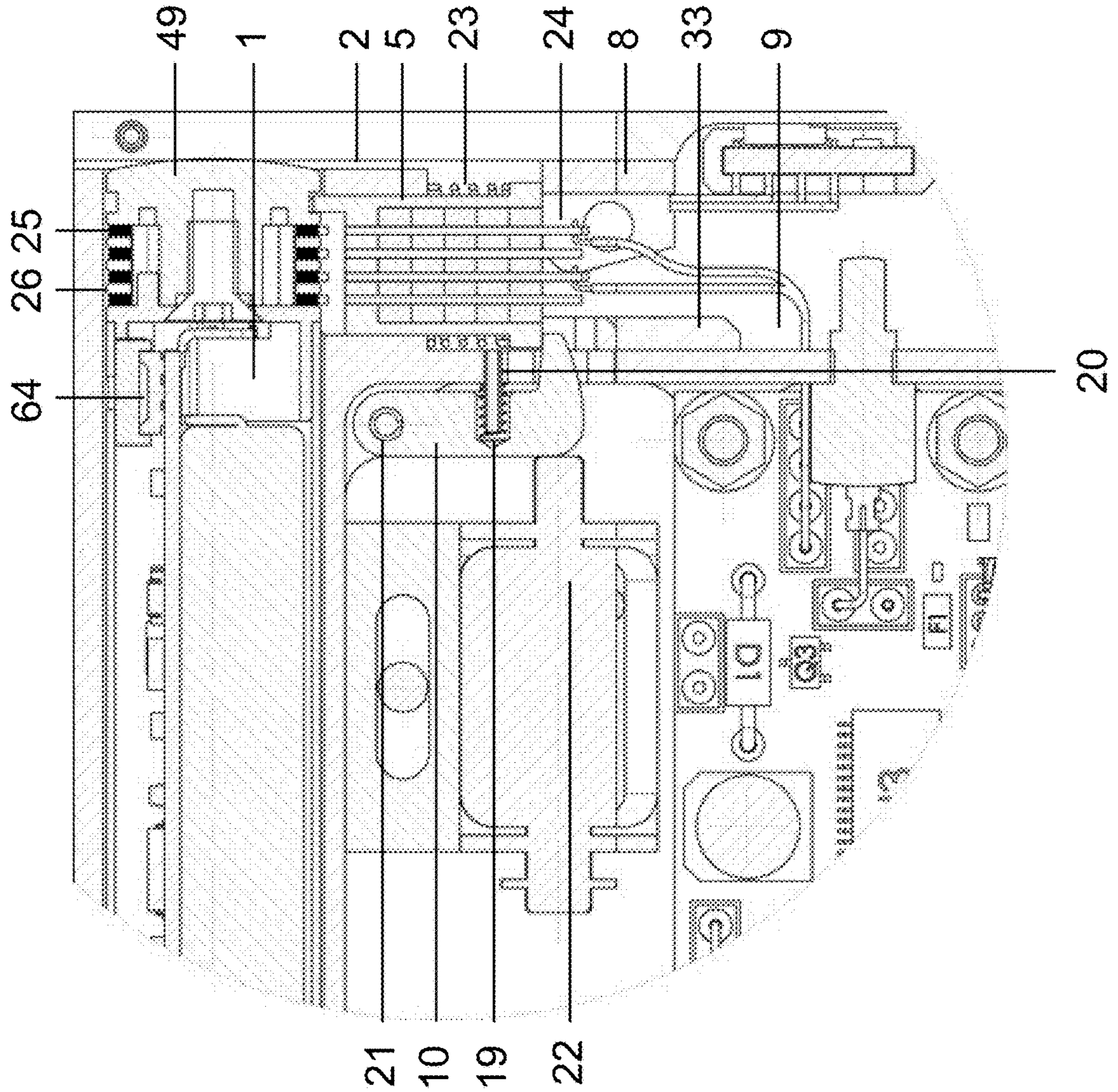
Figure 29:
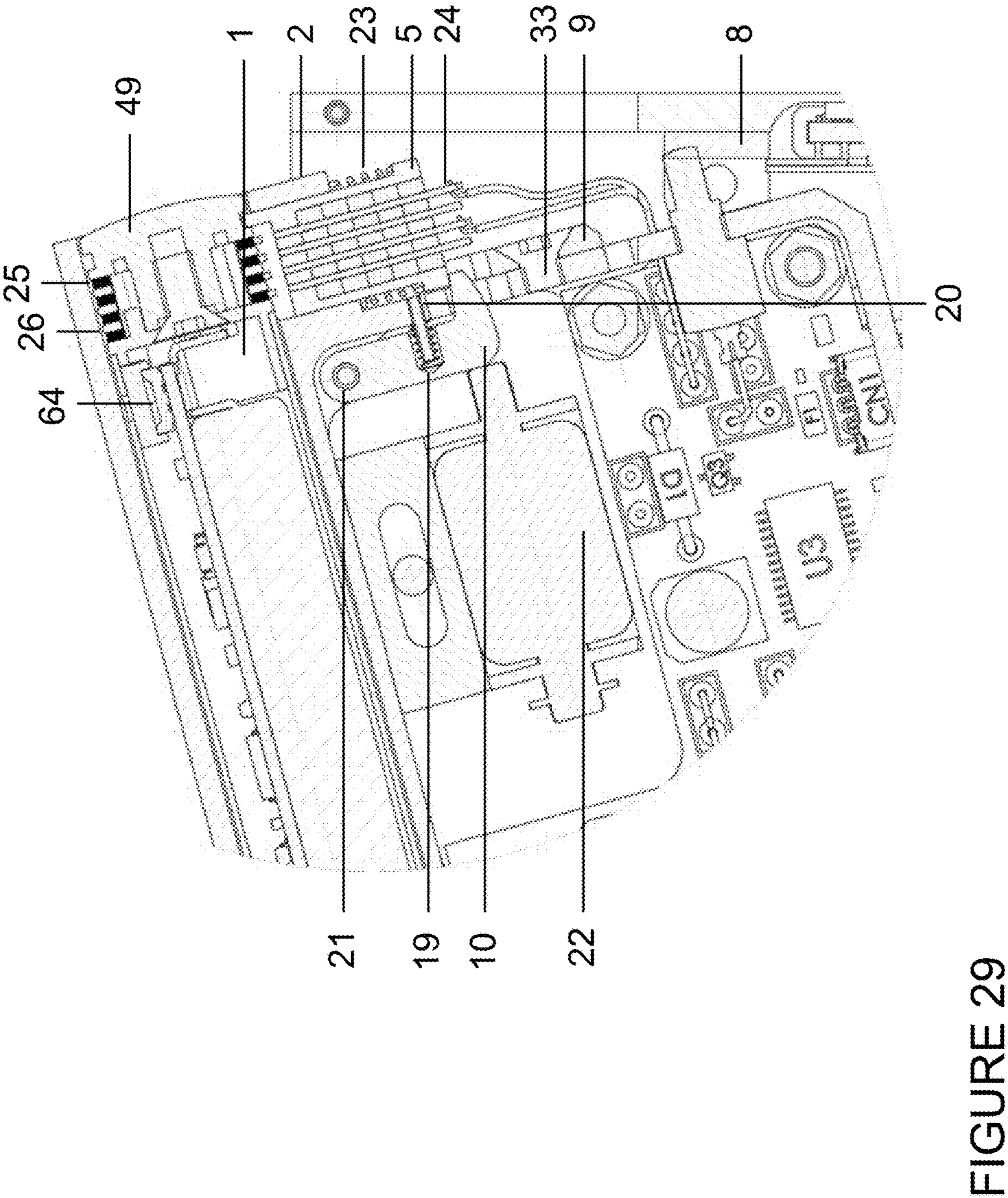

The 4 Way Sliding Contact Block 5 is pushed into contact with the PV Ring Connector 49 when the Receptacle Chassis 2 is rotated back into the Case 6 & 7 to the Closed 0° position—e.g. when storing the PV, as shown in FIGS. 27-28.

A Cam Block 8 is fastened to the Case 6 & 7. When the Receptacle Chassis 2 rotates into the Case 6 & 7 the Spring 23 biasing the 4 Way Sliding Contact Block 5 is compressed as the 4 Way Sliding Contact Block 5 bears against the Cam Block 8.

The 4 Way Sliding Contact Block comprises 4 Contact Fingers 24—FIGS. 31 and 32 show these clearly, housed in Body—4 Way Sliding Contact Block 46 and five Support Rings 45. Four wires are connected to the Contact Fingers 24. These connect back to pads on PCB Main Case 16. The 4 Way Sliding Contact Block 5 is limited to 2 mm in its linear travel by Guide Plate 9.

FIG. 33 is an exploded view of the case 100 and its components, the detailed operation of which has been described above. The Receptacle Chassis 2 forms the main housing for all the major components. When the device is built a Cover 12 is screwed into place. The Receptacle Chassis houses the PCB Main Case 16. This has a 650 mAh battery 68 connected to it and a Micro USB Connector 67 for re-charging the main battery and communications. The PCB Main Case 16 fastens to the Receptacle Chassis 2 by means of PCB Standoffs 69. These also serve as the fixing holes for the Lid 12. Solenoid 22 is attached to the Receptacle Chassis 2 via the Solenoid Mounting Block 11, adjustment is provided via a slotted screw hole in the Solenoid Mounting Block 11. The PCB Main Case 16 has an Arduino Chip mounted to it controlling all electrical functions associated with the device. Consequently, it is possible for the user to alter the power delivered to the atomiser and hence customise the vaping experience to their specific preferences. The Arduino Chip can be controlled from a connected smartphone app., communicating with the Arduino Chip over Bluetooth LE. The following kinds of data could be tracked by the Arduino Chip and relayed to the user's connected smartphone app.:

How many times the PV leaves the case

Duration of PV out of case

Internal clock used by the Arduino Chip stores data relative to first use, i.e. if unconnected for a few days it stores the data On pairing with phone GPS and time data Number of inhalations Duration of each inhalation Frequency of inhalation Depth of inhalation Power provided to the atomizer Current and/or voltage provided to the atomiser Battery power level—case and PV Number of times PV has been inserted and/or withdrawn from the case Number of times the PV has been pumped to re-fill it with e-liquid Vapes remaining (calculation from data)

Cartridge e-liquid volume remaining—(calculation from data).

Whether a fresh cartridge should be ordered

Instruction to order a fresh cartridge

Type of e-liquid used (e.g. strength, flavor, mixtures of different e-liquids)

Unique ID in case and PV, so that the Case will only work with a designated PV

It would be possible also to include power control buttons, dials etc on the Case 100 itself, although this would add to complexity and cost. A Display is provided in the Receptacle Chassis to communicate the Device status to the user.

We will now look at the details of the fluid transfer mechanism. The relevant figures are FIGS. 34, 35 and 36.

Fluid transfer operation is as follows: the PV 1 is dropped into the Receptacle Chassis aperturec2 where it comes to a stop against the top of the Pump 4. Depressing the PV 1 further against the Pump 4 causes a further 3 mm linear travel & the transfer of a metered dose of e-liquid vaping fluid from the Receptacle Chassis 2 to the PV 1. Approximately 0.1 ml of e-liquid is transferred per pumping action. The reservoir in the PV can typically store 1 or 2 ml of e-liquid. The PV 1 Fluid Chamber 48 can be charged by repeatedly pushing the PV 1 down against the Pump 4.

Relaxing hand pressure on the lower section of the Receptacle Chassis 2 allows the Receptacle Chassis 2 to return to its closed 0° position under the Leaf Spring 17 force, closing the PV 1 into Receptacle Chassis 2 for secure storage. The device geometry ensures the top of the PV 1

Cams it in a downward direction against the top inside walls of the Case 6 & 7 when the Receptacle Chassis 2 is returned to its 0° closed position.

The case 100 can accept a custom designed 5 ml Fluid Reservoir 3 which can be fitted and withdrawn from the Receptacle Chassis 2 by pushing in and pulling out. Other sizes of Fluid Reservoir 3 are also possible, typically up to 10 ml. It is retained by means of a Moulded Rim 62 and Sealed to the Pump 4 my means of an integrally Moulded Lip Seal 63. Different types of Vaping Fluid can be easily changed with no disassembly of the Device required.

FIG. 34 shows the loading—discharging position, with the Receptacle Chassis 2 at the Open 15° position. Pump 4 is mounted into Receptacle Chassis 2 and is sandwiched between Valve Mounting Cup 13 & Valve Mounting Cap 14. Reservoir 3 pushes into a slot in Receptacle Chassis 2 from beneath, with Moulded Rim 62 snapping into an undercut section in Receptacle Chassis 2. Reservoir Gasket 15 applies pressure on Moulded Rim 62 to maintain contact with the undercut. Reservoir 3 can be readily inserted and withdrawn by the user. Reservoir 3 has moulded Lip Seal 63 as an integral feature which seals against Pump 4. PV 1 is resting against Hollow Stem Shaft 61 of pump 4, but has not yet started to depress the Hollow Stem Shaft 61.

FIG. 35 shows the re-filling position—with Receptacle Chassis 2 still at the Open 15° position. PV 1 is now shown flush with Valve Mounting Cup 13 & Pump 4. Hollow Stem Shaft 61 has been depressed down 3 mm by the PV 1. Fluid passes up Pump 4 Hollow Stem Shaft 61 and Opens Valve 29 in PV Tip 32. Seal 27 bears against top of Pump 4 Hollow Stem Shaft 61. Valve 29 is moved off its seat by the pressure of the transferring e-liquid fluid. Spring 30 returns Valve 29 to its seat after pressure has equalised with Vaping Fluid entering Fluid Chamber 48.

FIG. 36 shows the standby position—Closed 0° position. Hollow Stem Shaft 61 is fully depressed and PV 1 is in a dormant state. E-liquid previously pumped into the PV 1 is retained with the PV 1, so that it remains ready to use.

The detailed operation of the pump 4 will now be described. The relevant figures are FIGS. 37, 38, 39 and 40.

Figure 37:
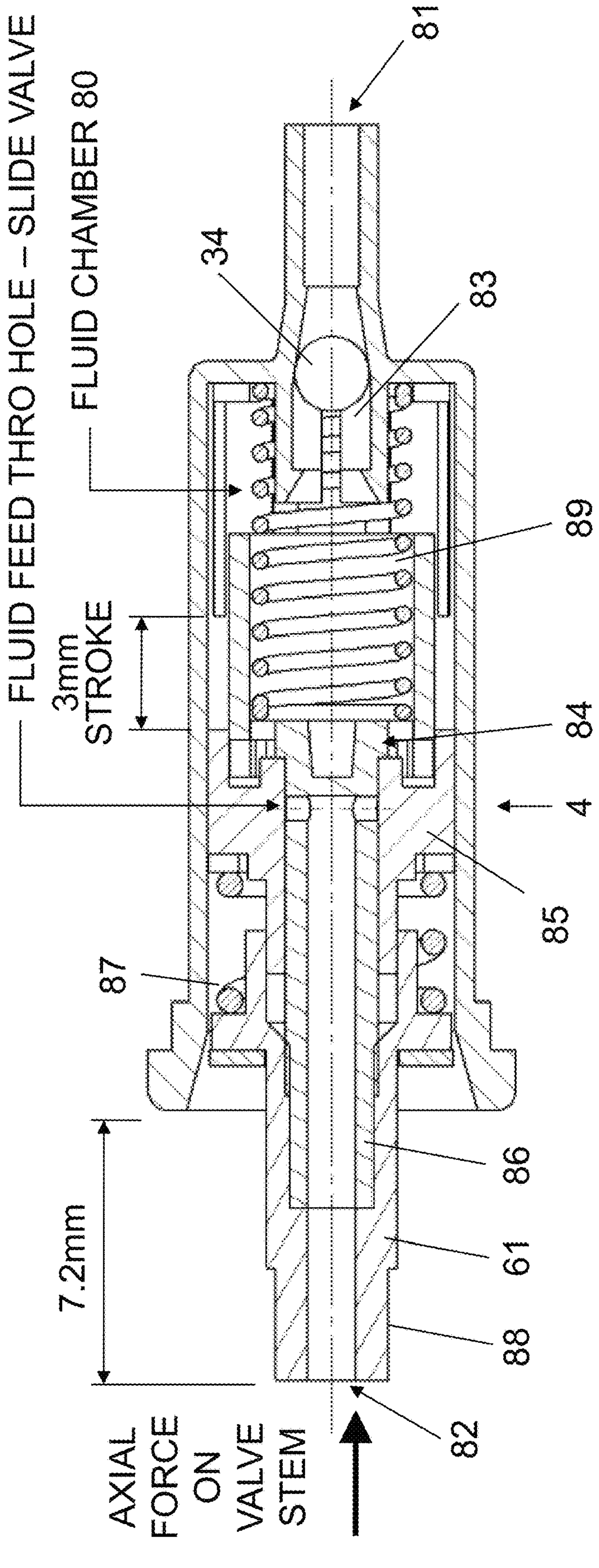

FIG. 37 shows pump 4 at its start position, ready for initial priming.

The pump 4 has a non-return ball valve 34 at fluid inlet end 81 and a slide valve at fluid outlet end 82. The non-return ball valve 34 consists of a steel ball bearing that moves within a short slotted tube 83 with retaining barbs at one end and seats into a shallow taper at the other end, closest to the fluid inlet end 81.

The slide valve consists of a through-hole 84 in the piston rod 86 which is covered and revealed by the action of the piston 85 sliding backwards and forwards over the through-hole 84.

The pump has a piston assembly comprising a valve stem 88, a piston rod 86, a piston 85 and a bias spring 87. The valve stem 88 and piston rod 86 are permanently joined together and move as one. The piston 85 slides on the piston rod 86 and in the valve stem 88. A bias spring 87 keeps the piston 85 positioned forward, at the start position of its 3 mm stroke, and covering the slide valve through-hole 84.

Exerting an axial force on the pump's valve stem 88 (e.g. as occurs when the PV 1 is pressed downwards into the Receptacle Chassis 2), causes the piston assembly to move forward inside the pump body, hence pressurising the fluid ahead of the piston 85 in the fluid chamber 80. Non-return ball valve 34 prevents fluid simply discharging back into the fluid reservoir 3.

As the hydraulic pressure increases, it overcomes the force exerted on the piston 85 by the bias spring 87, hence allowing the piston to move backwards relative to the piston rod 86.

Figure 38:
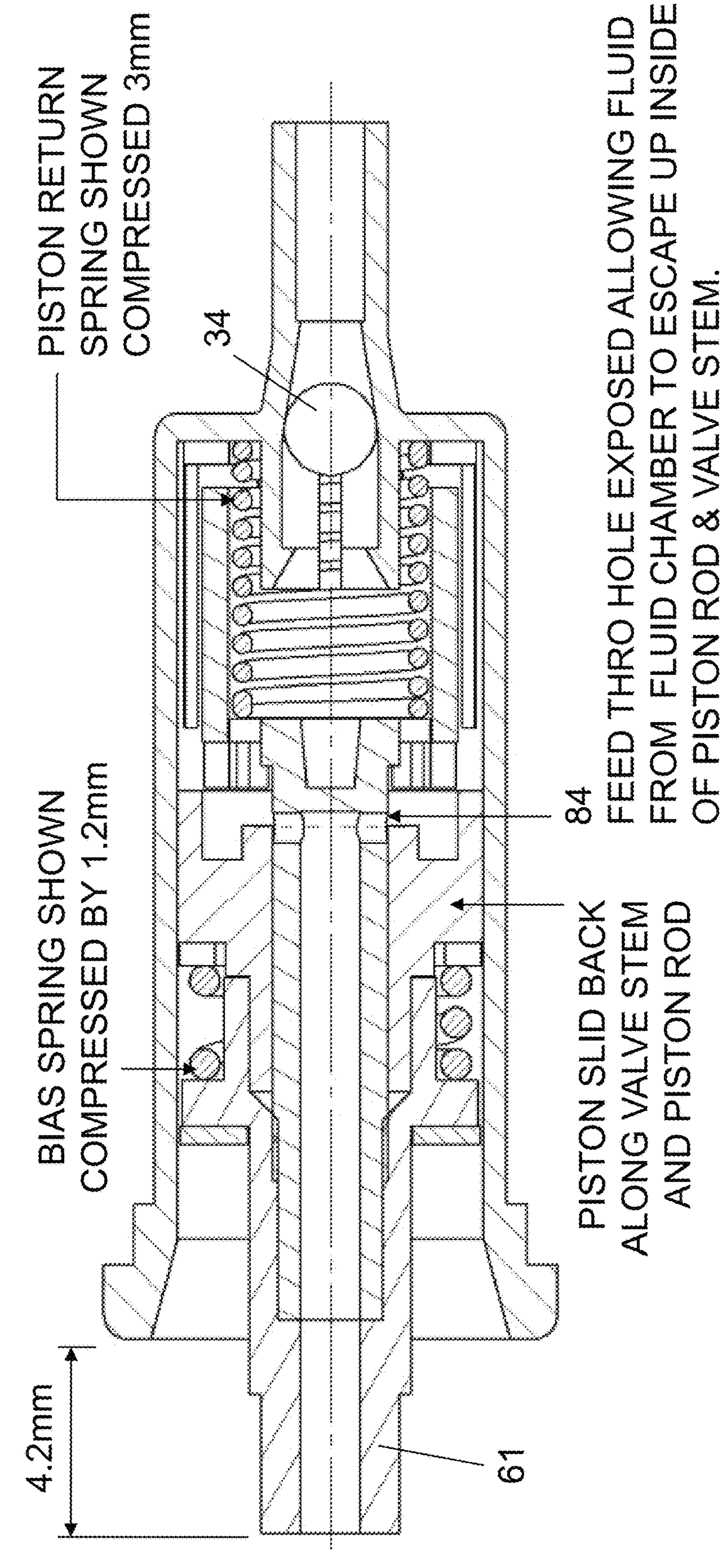

FIG. 38 shows the piston 85 at the end of its 3 mm stroke; the bias spring 87 is now fully compressed, by 1.2 mm. Piston return spring is now also fully compressed, by 3 mm. The feed though-hole 84 in the piston rod 86 is exposed since the piston 85 has been forced backwards relative to the piston rod 86 by the increased hydraulic pressure, which exceeds that of the bias spring 87.

The pressurised fluid in the fluid chamber 80 can now escape through the exposed feed-through hole 84 and up the inside of the piston rod 86 and valve stem 88, as the piston assembly completes it's stroke.

A metered volume (0.1 ml) of e-liquid escapes into the PV 1 as the piston assembly reaches the climax of it's stroke.

Figure 39:
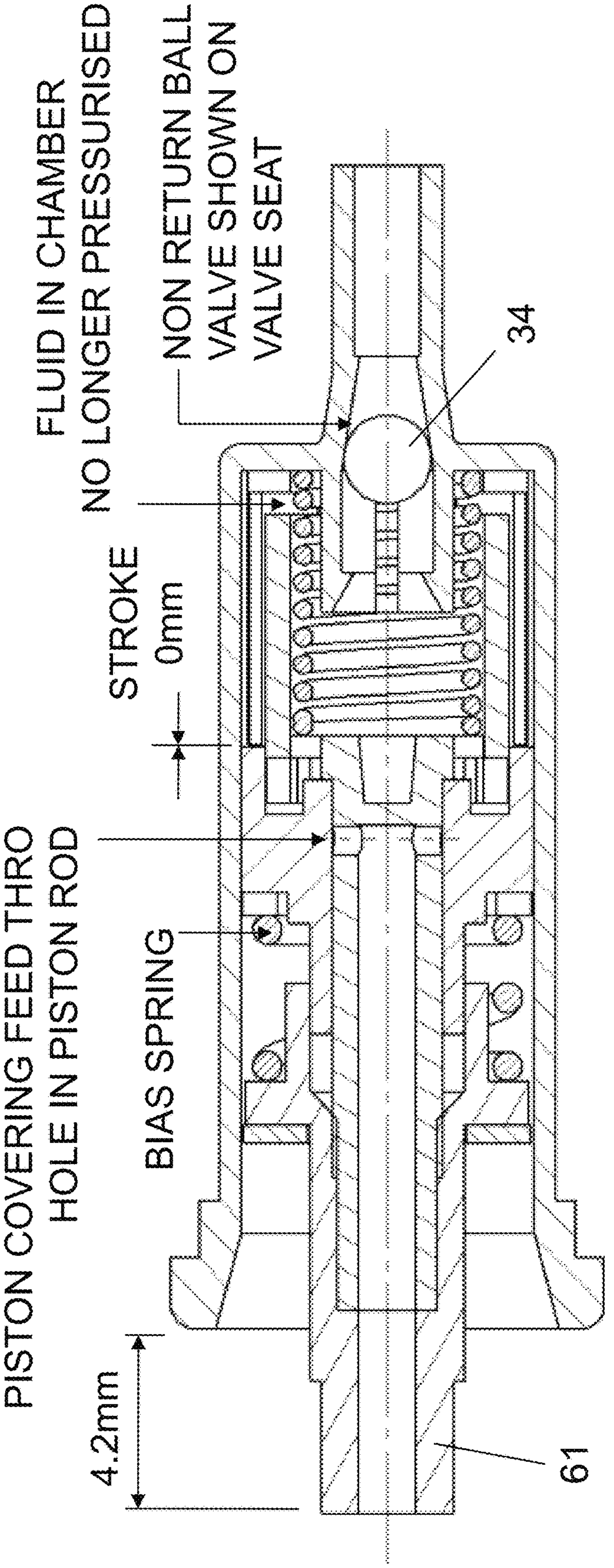

FIG. 39 shows that as the hydraulic pressure drops below the bias spring force, this allows the piston 85 to slide forwards along the piston rod 86 and cover the feed-through hole 84. Fluid chamber 80 is now sealed at both ends.

Figure 40:
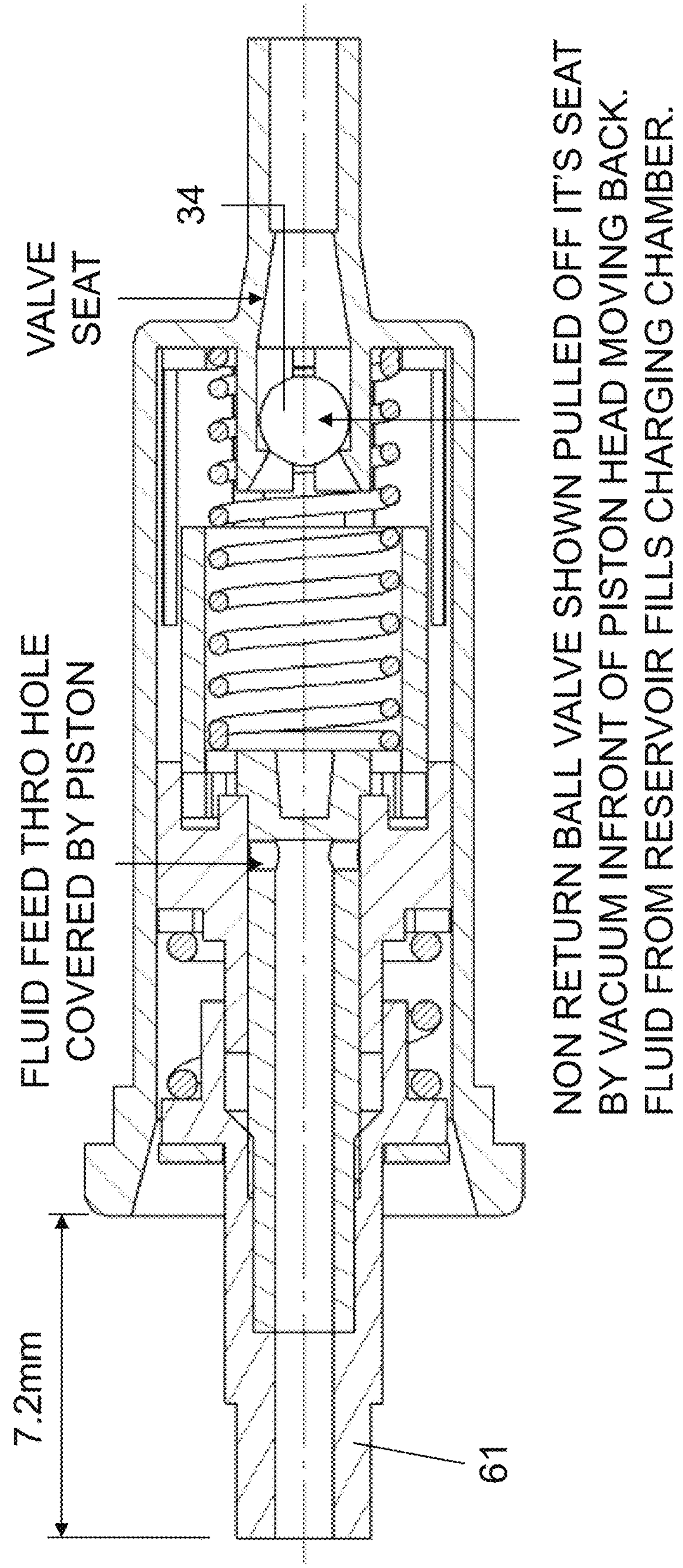

FIG. 40 shows removing the axial force on the valve stem; this allows the piston return spring 89 to send the piston assembly back to it's start point. As the piston assembly moves back to it's start point, a vacuum develops in the pump fluid chamber 80. This pulls the non-return ball valve 34 off it's seat, allowing fluid from the reservoir to fill the void in fluid chamber 80.

The pump cycle is now complete. (As a preliminary step, cycling the piston assembly several times may be needed to dispel air from the fluid chamber 80 and replaces it with fluid. The fluid chamber 80 is now charged).

It is possible also to integrate the pump directly into the user-replaceable cartridge. That has some advantages—specifically, if the pump fails, then it is just the cartridge that needs to be replaced, not the entire case. Also, if the pump is part of the case, and different flavours of e-liquid are desired, that requires different cartridges to be swapped in to the case. There may some residue of the previous flavour in the pump, possibly affecting the vaping experience. Integrating the pump into the cartridge eliminates the problem of flavour tainting through previous e-liquid residue in the pump.

This variant is shown in FIGS. 41-45. The same 0.1 ml pump is used and it operation is fundamentally as described above. The fluid reservoir 3 has a 5 ml capacity and is formed as part of a body moulding. The body cavity is sealed with a valve cap 90 moulding, being ultra sonically welded to the body. Valve cap 90 at the fluid outlet end of the combined pump and cartridge locks the pump in position and also provides guidance for the valve stem 61.

The combined pump and cartridge includes an overflow valve. This is made up of a tapered valve seat 91 in the body moulding, a steel ball bearing 92 and return spring 93. The tapered valve seat 91 is at the end of a bore slightly larger than the bore of the steel ball bearing 92. There are channels cut into the bore to allow for the flow of fluid in the bypass condition. The taper is 180° juxtaposed from the non-return valve taper.

In normal operation, the overflow valve ball 92 remains seated in it's tapered housing kept in place by the return spring 93. If a condition arises where the hydraulic pressure in the pump fluid chamber 80 exceeds the design pressure, the overflow valve ball 92 is forced off it's seat against resistance offered from the return spring 93. Fluid can pass the steel ball 92 and return to the reservoir chamber 3—this is the bypass condition.

Figure 41:
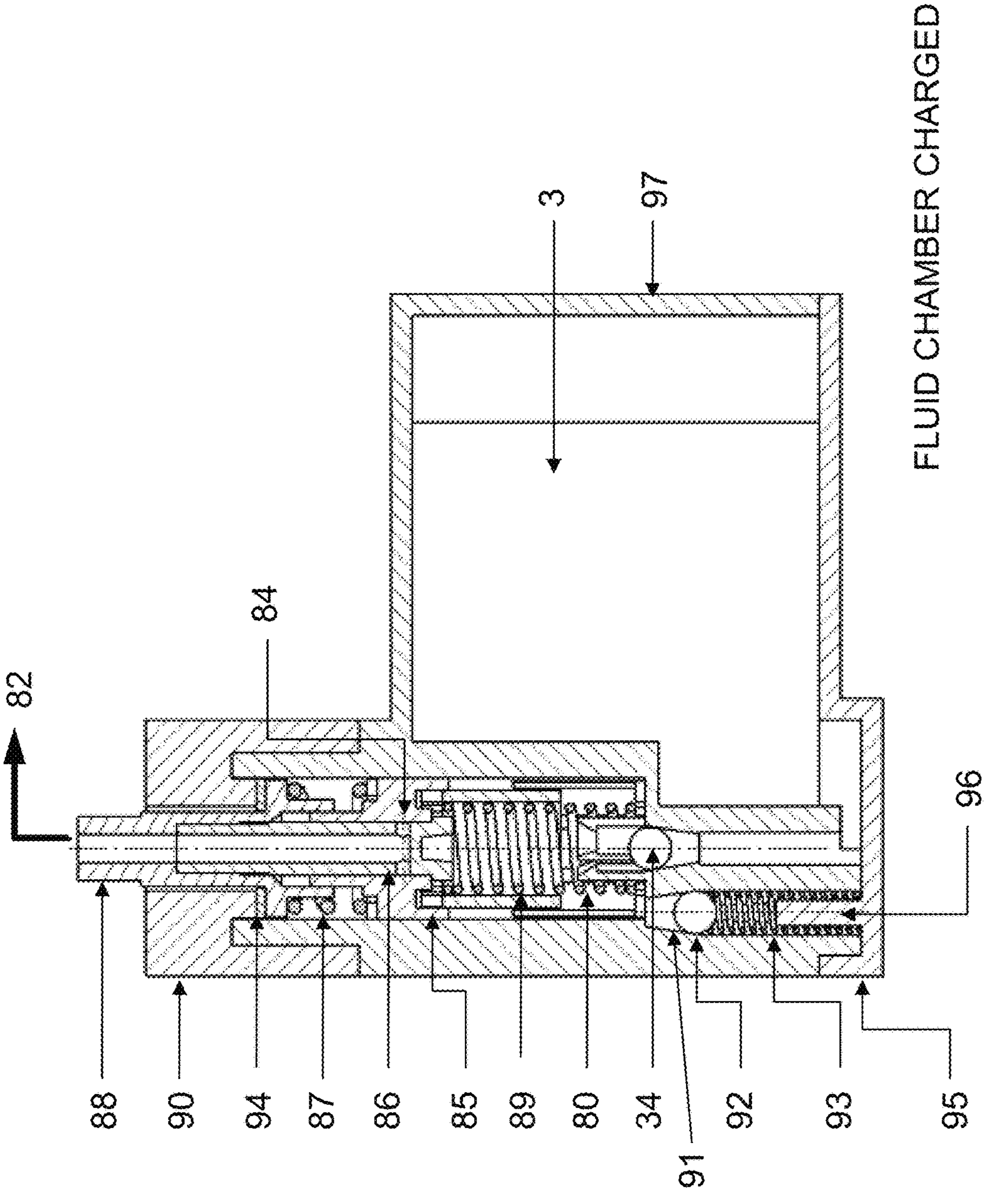

The integrated pump/reservoir/overflow valve can be in one of five different conditions:

Start position—as shown in FIG. 41.

pump fluid chamber 80 is in charged state.

Non-return valve ball 34 is seated in it's tapered housing.

overflow valve ball 92 is seated in it's tapered housing.

pump piston assembly is covering slide valve fluid feed through hole 84.

fluid in pump fluid chamber 80 is in a sealed state.

Figure 42:
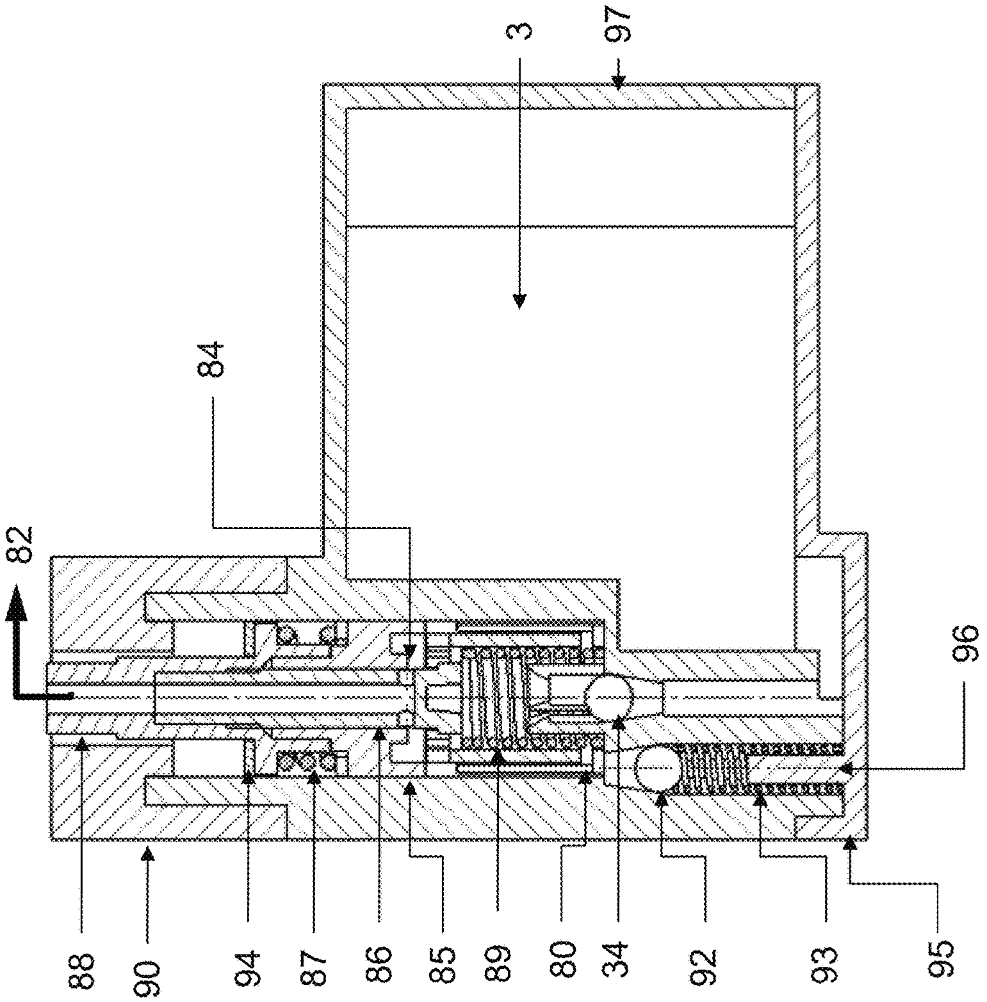

Open position—as shown in FIG. 42 pump piston assembly is travelling through it's 3 mm downstroke.

hydraulic pressure inside pump fluid chamber 80 has overcome the bias spring 87 force allowing upward movement of piston 85.

slide valve has opened, allowing flow of fluid from pump fluid chamber 80 to fluid outlet port 82 via fluid feed through hole 84.

non-return valve 34 remains closed overflow valve 92 remains closed

Figure 43:
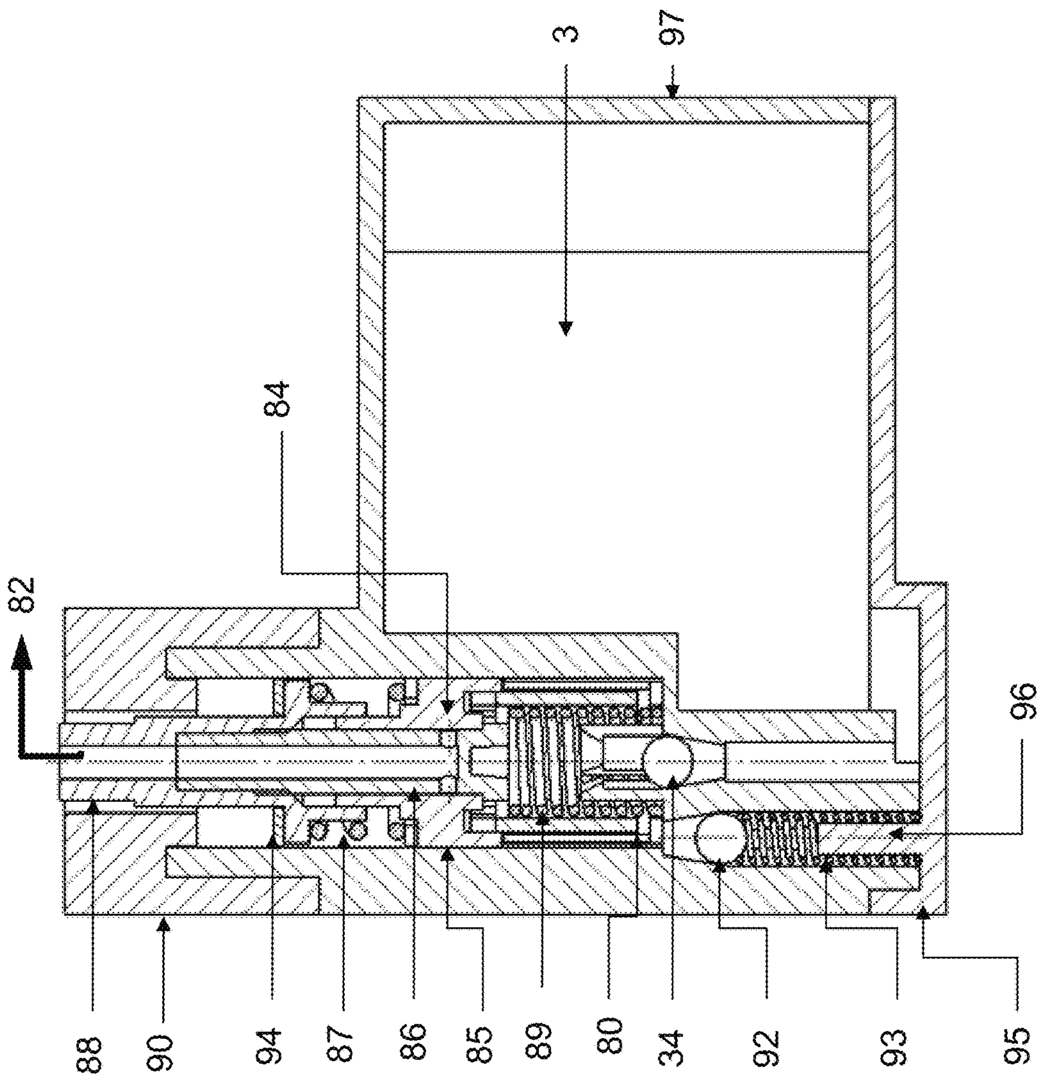

Down position—as shown in FIG. 43 bias spring 87 has closed slide valve with piston 85 covering fluid feed through hole 84.

fluid chamber 80 volume of fluid has been depleted by 0.1 ml.

remaining fluid in fluid chamber 80 no longer pressurised.

piston return spring 87 is compressed and exerting an upward force on piston assembly 85.

Figure 44:
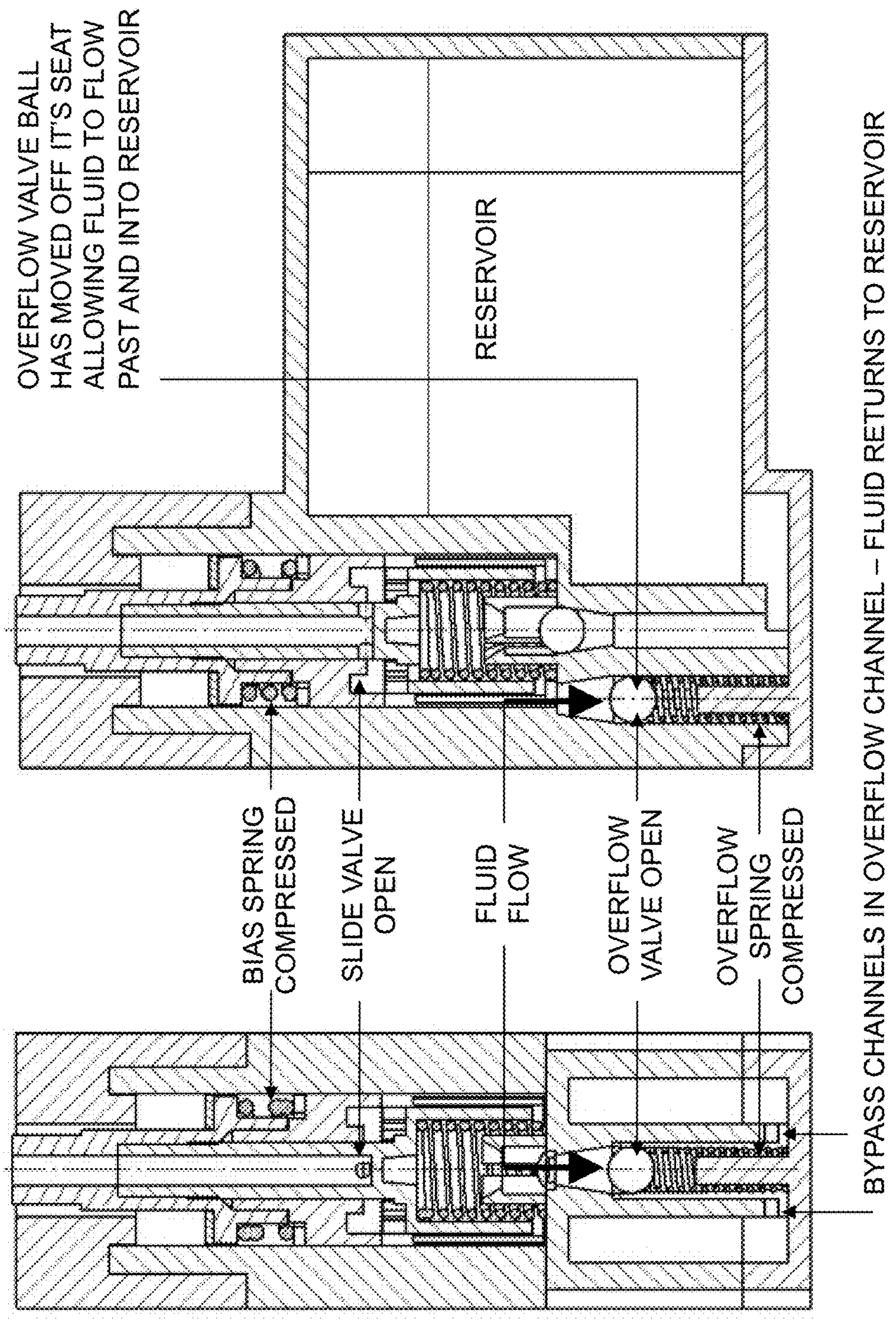

Bypass position (this is conditional on the hydraulic design limit being exceeded and hence protects against damaging the pump 4 and the PV 1)—as shown in FIG. 44 slide valve is in the open position, with piston 85 not covering fluid feed through hole 84.

hydraulic pressure inside pump fluid chamber 80 and valve stem 88 exceeds design pressure.

non-return ball valve 34 is closed.

pressure relief overflow valve 92 opens against pressure from return spring 93.

Ball valve 92 is forced off it's seat by excessive hydraulic pressure in the pump fluid chamber 80. Fluid flows around ball valve 92, through channels and back into reservoir 3.

once sufficient volume of fluid has been expelled from pump fluid chamber 80 into reservoir 3, the hydraulic pressure diminishes in pump fluid chamber 80, allowing pump piston assembly to complete it's stroke. The bias spring 87 pushes the 85 piston over fluid feed-through hole 84, closing the sliding valve.

pump is now in "down" condition.

both "open" and "bypass" positions precede "down" position.

Figure 45:
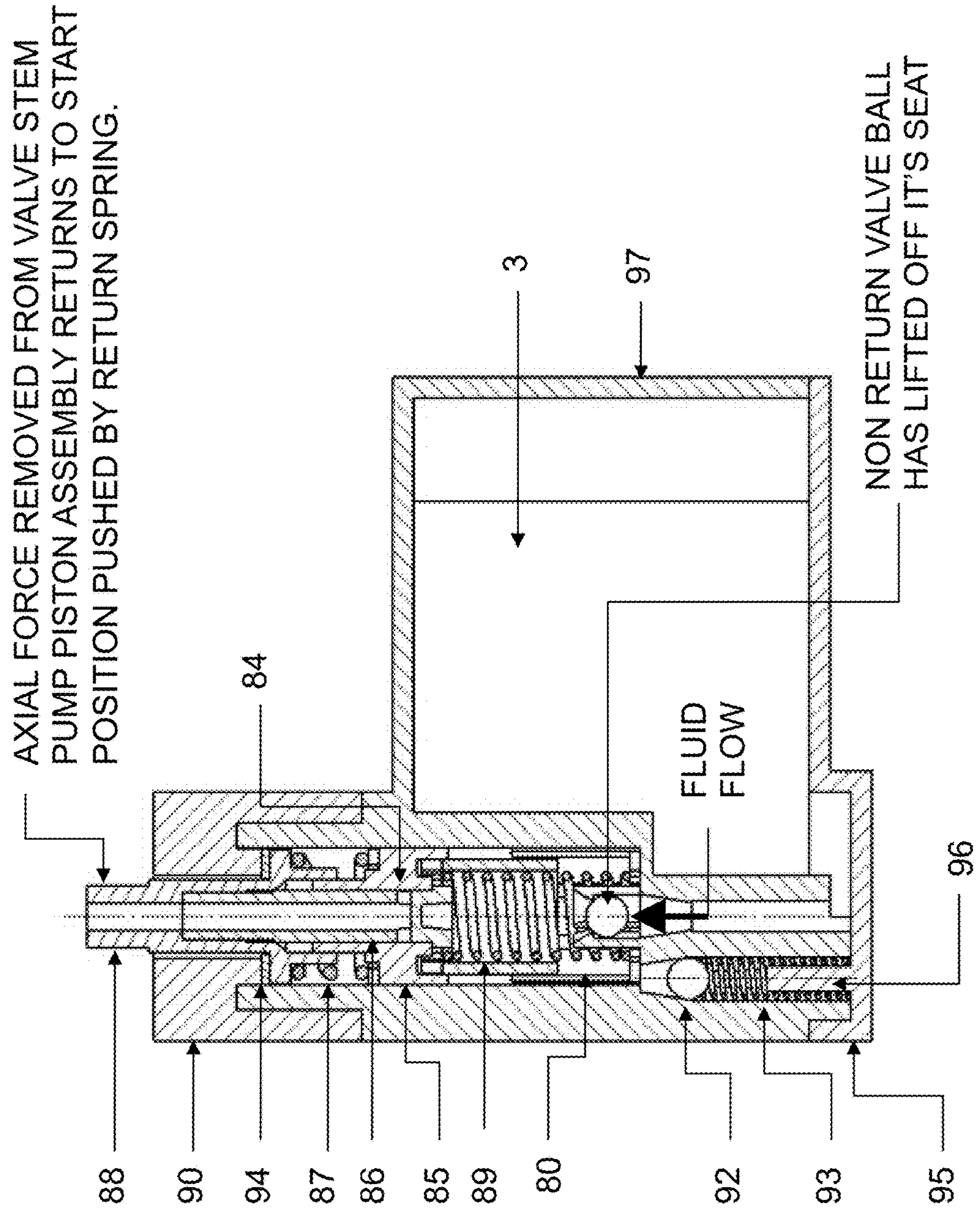

Return position—as shown in FIG. 45 axial force has been removed from valve stem 88.

pump piston assembly returns to it's start position under return spring 89 force.

a vacuum in the pump fluid chamber 80 develops in the wake of the pump piston assembly returning to it's start position.

vacuum causes non-return valve ball 34 to move off it's tapered seat, allowing fluid from the reservoir 3 to fill the void.

pump fluid chamber 80 is now charged and non-return valve ball 34 settles into it's seat.

pump is now in the start position.

We will now look closely at the PV 1 itself.

We earlier looked at a section view of the PV 1 (FIG. 20). FIG. 46 shows an exploded view of PV 1 and FIG. 47 shows an isometric view of PV 1. FIG. 48 shows one design of atomiser assembly. The PV 1 includes a PV Tip 32 containing Valve 29, Valve Spring 30 and Grub Screw 31. PV Tip 32 also has 3 concentric holes, connecting to Air Way, which allow Vaporised Liquid to be inhaled. In this design of atomiser, the heating coil is perpendicular to the long axis of the PV 1. FIG. 49 shows an alternative design in which the wicking material has the same 'U' shape, but also includes a long element running along the long axis of the PV 1. Heating coil 98 is wound around this long element and the Coil & Wick Assembly 52 then retained by chassis 99. The advantage of this alternative design is that a longer heating coil 98 can be used, and airflow over the heated coil 98 should be more uniform and effective since the coil runs parallel to the airflow instead of perpendicular to it.

For both the perpendicular and parallel arrangements, the vaporiser sits behind the Tip 32, and is made up of a Coil & Wick Assembly 52, Vaporiser Outer Body 53 and Vaporiser Inner Body 55. These are insulated by Bush Vaporiser Body 54. Current is passed to the Vaporiser Inner Body 55 via a wire connected to PCB 60. One leg of the Coil 52 contacts the Vaporiser Inner Body 55, the other Coil Leg contacts Vaporiser Outer Body 53. This can be seen most clearly from FIG. 48. The Vaporiser Outer Body 53 is connected to Earth.

A Pressure Sensor/Transducer 58 is mounted behind the Vaporiser Unit in the Pressure Sensor Housing 57. This is wired to the PCB 60. An Arduino Chip 66 mounted to the PCB 60 is used to monitor, control, set and feedback information pertaining to the Vaping Functionality.

A 3.7V 140 mAh LiPo Battery 59 sits on the PCB 60. The far end of the PCB 60 is wired to Ring Connector 49 with 4 connections—1 Power, 1 Earth, 2 Signal.

When air is drawn through the PV 1, the Pressure Sensor/Transducer 58 activates, causing current to be sent to the Coil/Wick Assembly 52. The Coil heats the vaping fluid soaked wick, giving off vapour which entrains into the air stream.

O rings 28 seal the Vaping Chamber 48 from the air path. A unitary (and hence very strong) stainless steel Tube 56 houses all the parts mentioned above with a cut out to allow the RGB LED 64 to display the Status of the PV 1 for both battery power and vaping fluid level. A further small hole sits above the Reset Switch 65 mounted to the PCB 60.

The PV 1 charges its 140 mAh Battery via the Ring Connector 49. Information is also fed back to the PCB Main Case 16 via 2 of the connections on the Ring Connector 49.

We will now look at the Ring Connector 49 in more detail. FIGS. 50 & 51 are the relevant figures.

The Ring Connector Assembly allows the PV 1 to be placed in the Receptacle Chassis 2 in any orientation without it affecting its connectivity. Four Ring Contacts 42 with different length Pins 38, 39, 40, 41 soldered to them are separated by three Insulating Rings 43 which in turn are housed in End Cap-Ring Connector 36. This ensemble is capped with PCB Mounting Cap/Ring Connector 37 fastened with a Screw 44. A wire is soldered to each of the Pins 38, 39, 40, 41 which are then soldered to Pads on PCB 60. The Ring Connector Assembly also has 2 off 1.7 mm Slots which captivate the PV PCB 60. The Ring Connector Assembly is a push fit in the end of the Tube Body—Vaporiser 56.

We will now look at a variable air intake feature. Altering the airflow allows the user to customise the vaping experience to their specific preferences; for example, an experienced vapour looking to produce large quantities of vapour with a variable voltage modding kit type PV might set the voltage used to a much higher power than normal and he would manually fix an air intake that would him to breath in a large volume of vapour. Swapping different air-intakes is generally a matter of screwing out the unwanted air intake and screwing in an air-intake with the required air-hole size(s). One variant of the PV has a variable air intake system in which the casing comprises an inner and an outer tube; the inner tube has a matrix of air-intake holes which can be lined up with air-intake holes in an outer-tube; the user rotates the outer tube until the desired number of holes are lined up. For example, the inner tube could have a regular, square-arrangement or matrix of holes consisting of 6 holes formed radially at 30° intervals repeated over 6 rows. The outer tube then has a square matrix of holes consisting of 6 holes formed radially at 30° intervals repeated over 6 rows. The outer tube slides over inner tube until top rows of holes coincide. The outer tube can be rotated in 30° increments to reveal 0, 1, 2, 3, 4, 5 or 6 columns of holes in inner tube thereby varying cross sectional area of air able to enter the vaporiser body. FIG. 52 shows two rows of holes lined up and FIG. 53 shows 5 rows lined up.

Another variant, shown in FIG. 54, comprises 2 tubes—inner and outer. The inner tube has a square matrix of holes consisting of 6 holes formed radially at 30° intervals repeated over 6 rows. The outer tube has helical matrix of holes consisting of 1 hole per row formed radially at 30° intervals repeated over 6 rows—6 holes in total. The outer tube slides over inner tube until top rows of holes coincide. The outer tube can be rotated in 30° increments to reveal 0, 1, 2, 3, 4, 5 or 6 columns of holes in inner tube thereby varying cross sectional area of air able to enter the vaporiser body.

We will now walk through the electrical functionality of one implementation. Note that some simplification may be used in the consumer product; what we will describe below is the prototype implementation, which has been optimised for testing.

The steps or logic is as follows:

1) The device starts in standby mode and is therefore inactive

2) The user activates the PV 1 by pressing a microswitch 70, protruding from a slot in the outer case 100.

3) A solenoid 22 mounted on the Receptacle Chassis 2 is powered from battery 68, itself also mounted on Receptacle Chassis 2.

4) Solenoid 22 locks 4 Way Sliding Contact Block 5 against the PV Ring Connector 49.

5) Power to solenoid 22 is limited to 10 seconds unless the Receptacle Chassis 2 is rotated 15°.

6) Receptacle Chassis 2 is rotated 15° against resistance of leaf spring 17 (the user squeezes the bottom of the Chassis into the Case 100).

7) Microswitch 70 activates closing contacts at termination of 15° travel.

8) Upon Microswitch activation, power is sent from Battery 68 to the coil and wick assembly 52 in the PV 1, via 4 Way Sliding Connector 5 and the PV Ring Connector 49.

9) The PV coil 52 temperature is monitored by on board electronics (directly or indirectly as a function of power delivered and time).

10) The power supply to the coil 52 is terminated when the coil 52 reaches its operational temperature, or a defied time has elapsed sufficient for the coil to reach operational temperature; generally this is achieved in under 1 s or 2 s.

11) The power supply to Solenoid 22 is then terminated, unlocking 4 Way Sliding Connector 5.

12) 4 Way Sliding Connector 5 then retracts 2 mm under spring 23 force, breaking both electrical connection between PV PCB 60 and the EPV Main Chassis PCB 16 and also terminating the mechanical interlock between the PV 1 and 4 Way Sliding Contact Block 5.

13) The PV 1 then springs upwards and clear of the Receptacle Chassis 2, ready for removal.

14) The PV 1 is then removed from Receptacle Chassis 2 by the user and placed between lips.

15) The user inhales on the mouthpiece of PV 1.

16) Air Pressure Sensor 58 in the air stream inside PV 1 senses air movement and sends power to vaporiser Coil 52.

17) The PV 1 on-board Battery 59 supplies power to vaporiser Coil 52.

18) The PV 1 vaporiser Coil 52 temperature is monitored by on-board electronics whilst there is air flow.

19) The PV 1 vaporiser Coil 52 temperature is controlled by cutting & re-instating power from on-board battery 59.

20) After cessation of vaping, the PV 1 is placed back in the Case 100, i.e. Receptacle Chassis 2.

21) The Receptacle Chassis 2 returns to its Standby Mode Position, 0°, under Spring 17 power.

22) A camming action of the Receptacle Chassis 2 closing against Outer Case 6 & 7 imparts linear travel to EPV.

23) Linear travel causes pump 4 to transfer vaping liquid to replenish the PV 1 on-board reservoir.

24) PV 1 is returned to standby mode—inactive in the case.

One further feature is that the vaping experience is a function of a number of variables, such as e-liquid constituents, power delivered to the atomiser, temperature reached, airflow etc. It is possible for the case to store different profiles, such as 'light', 'smooth', 'intense', 'maximum vapour quantity', 'maximum strength', 'warmer vapour', 'cooler vapour' etc. Each of these could also be a function of a specific brand of e-liquid. The user can then select on their smartphone app the specific profile and/or variables that meet their preferences.

Also, the specific brands of e-liquid could themselves determine specific variables of the case and PV. Hence a user could select on their smartphone app to use say a 'Marlboro' brand of e-liquid, and then the case would automatically configure parameters such as power, temperature etc to give the ideal experience for that specific brand. The parameters could be stored in software or firmware in the case or the PV. It would also be possible to obtain an application from an app store, such as the Apple App Store, or Google Play, specific to a brand of e-liquid; this app would then automatically configure the connected case with the appropriate parameters for optimum performance for that brand of e-liquid.

In the preceding part of Section A, we detailed the operation of the following features:

| | |
|---|---|
| Feature 1: | Combined re-charge and re-fill storage and carrying case |
| Feature 2: | Case with movable PV holder |
| Feature 3: | Re-Filling the PV |
| Feature 4: | PV Locking mechanism |

In the following part of Section A, we will look at:

| | |
|---|---|
| Feature 5. | Data connectivity |
| Feature 6. | E-fulfilment |

Features 5 & 6. Case with Data Connectivity and E-Fulfilment

In this section, we describe in more detail the features of data connectivity and e-fulfillment, first introduced at the start of Section A.

To re-cap on the data connectivity feature: this is a portable, personal storage and carrying case for an e-liquid e-cigarette PV in which the case includes a data processor that controls sending a signal requesting a replacement for a user-replaceable e-liquid cartridge in the case.

The related e-fulfilment method is a method used in portable, personal storage and carrying case adapted specifically for a refillable e-cigarette PV and that re-fills and re-charges the PV, the method including the steps of the case (a) transferring e-liquid from a user-replaceable e-liquid cartridge to the PV and (b) automatically sending a signal requesting a replacement for the user-replaceable e-liquid cartridge to an e-fulfilment platform, either directly or via a connected smartphone.

The method may include the steps of the case (a) detecting the level of or quantity of e-liquid in a user-replaceable e-liquid cartridge in the case and (b) automatically sending a signal requesting a replacement for the user-replaceable e-liquid cartridge to an e-fulfilment platform, either directly or via a connected smartphone. Note that 'detecting the level of or quantity of e-liquid in a user-replaceable e-liquid cartridge in the case' could be direct, or could be indirect, such as inferred from the number of re-fills of the PV that have been completed with that cartridge, or the total number of inhalations made with that cartridge, or any other way of intelligently determining whether a replacement cartridge should be ordered. Machine learning can also be deployed to analyse the user's usage patterns; for example, if the user tends to vape heavily over the weekend but quite lightly during the week, then that can be taken into account when determining when a replacement cartridge should be ordered. Likewise, a degree of direct interaction between e-liquid vendors and end-users is possible; when a user is likely to be ordering replacement cartridge(s), then special offers, or offers for new flavours or new strengths of e-liquid can be sent (e.g. text, instant message etc) to the user, or any other way of cementing brand loyalty.

Enabling the case to send a request for a replacement e-liquid cartridge is very convenient for the user and also ensures that replacement cartridges are supplied in a timely manner—this is especially important when the user is on a tobacco or nicotine reduction programme since if the case runs out of e-liquid, then the user may well be tempted back to using cigarettes. So the efficacy of adopting this system as a cigarette replacement (and health concerns with cigarettes is overwhelmingly the reason given for e-cigarette adoption) benefits greatly from the timely, automatic, background ordering of replacement cartridges.

Optional features (each of which can be combined with others) include the following:

- the data is substance-consumption related data
- the cartridge(s) are in normal use replaceable by a user but are not refillable by a user.
- the processor is programmed to send data over a wire or via a wireless data connectivity interface.
- the processor is programmed to send and/or receive data from the personal vapourising device.
- the processor, or an associated processor, is programmed to determine and store when the case is opened and/or shut.
- the processor, or an associated processor, is programmed to measure or record the charge level of a battery in the portable re-filling unit and also the charge level in a battery in the personal vapouriser.
- the processor, or an associated processor, is programmed to detect cartridge type and volume.
- the portable re-filling unit is adapted to receive substance consumption-related data from the personal vapouriser.
- the processor, or an associated processor, is programmed to measure consumption of the or each substance, including related factors, such as time, location, temperature.
- the processor, or an associated processor, is programmed to output consumption-related data, organized according to any one or more of the following variables: part of the day/night, daily, weekly, seasonal, weather, any other factor.
- the processor, or an associated processor, is programmed to control any one or more of: mixing of e-liquids from different cartridges in the re-filling unit; nicotine or smoking cessation or reduction, period between 'vapes'; re-ordering e-liquid; age/parental controls, social network updates; e-liquid recommendations.
- the processor, or an associated processor, is programmed to use the consumption-related data for the or each substance in an algorithm that calculates when to place an order for one or more replacement cartridges or prompt a user that one or more replacement cartridges should be ordered.
- The processor, or an associated processor, is programmed to order replacement cartridges when running low, either by directly sending a request to a fulfillment server, or sending a message to a connected smartphone or wearable device, for the smartphone or wearable device to send a request to a fulfillment server.
- the processor, or an associated processor, is programmed to control mixing and consumption of the or each substance.
- the processor, or an associated processor, is programmed to use location data, such as location data from a GPS or other satellite or land-based location-finding system.
- the location data is from a location finding system in the portable re-filling unit itself or the personal vapouriser.
- the processor, or an associated processor, is programmed to provide an alert to the user, directly or via a smartphone or wearable device, if close to a retail store where consumables for the personal vapouriser are obtainable.
- the processor is programmed to send and/or receive data with a tablet, smartphone, wearable device or any other secondary computing device, or with a personal vapouriser.
- the tablet, smartphone, wearable device, PC, laptop or other secondary computing device is programmed (e.g. with a downloadable app) to perform any of the functions listed above—i.e. the existing computational power and 3G/4G wireless connectivity and GPS capability of the tablet/smartphone etc. is used instead of having to build that capability into the re-filling unit.
- the processor, or an associated processor, is programmed to provide data to and/or receive data from a downloadable smartphone application.
- the downloadable smartphone application can control the portable re-filling unit.
- the downloadable smartphone application can control any one or more of: mixing of e-liquids from different cartridges in the re-filling unit; nicotine or smoking cessation or reduction, period between 'vapes'; re-ordering e-liquid; age/parental controls, social network updates; e-liquid recommendations; parameters that determine PV performance or the vaping experience (e.g. power, temperature, airflow).

the processor is programmed to integrate with a personal assistant program such as Google Now, Apple Siri, etc.

the portable re-filling unit can be remotely locked and unlocked from the smartphone application, such as by entering a PIN.

the portable re-filling unit can be remotely locked and unlocked from the smartphone application or other remote device, to prevent release of the vapourising device from the re-filling unit, as an aid to cessation or reduction of substance usage, to prevent tampering, to prevent access by children.

the portable re-filling unit can be remotely locked and unlocked automatically depending on whether a smartphone paired with the unit is within a specified range or is able to exchange appropriate data with the unit.

the data is sent over a wireless link, or a direct electrical connection

The following section describes these features with reference to the Figures; the relevant Figures are FIGS. 55 and 57.

FIG. 55 is a high-level schematic showing a portable re-filling case able to communicate wirelessly and also through a wired connection to a smartphone, a laptop and a modem; these devices send data via the internet or other network—this can be any of the consumption data (including how consumption varies according to the various parameters, such as part of the day/night, daily, weekly, seasonal, weather, time, location, temperature and any other factor). This data is especially valuable to PV vendors, especially if it can be associated with a demographic profile of the device user; that demographic profile can be entered by the user when they register their device online (e.g. on first purchase of the PV, or when they wish to buy e-liquids, or set up automatic e-fulfillment of replacement e-liquid), or can be extracted or inferred from social network posted information. The data can also be used by an e-fulfillment company to process the order and to provide replacement consumables (e-liquid, PV, case) to the user.

FIG. 57 shows schematically that the portable re-filling unit includes electronics componentry, such as a memory, wireless/wired connectivity, software, and a controller/processor. Also, the cartridge includes four compartments, each with a different flavor or strength of e-liquid; the case is able to monitor the consumption of e-liquid in each compartment and share that consumption data with the connected smartphone app, as well as the e-fulfillment platform.

The re-filling unit itself can measure how much e-liquid is left in its cartridge(s) or tank(s). There are various ways of doing so:

1. Ultrasonic ranger for depth, some a tilt sensor to detect the angle of the cartridge and whether the e-liquid closes an electrical circuit between different electrical contacts at different levels within the cartridge.

2. Measure the weight of the tank(s)

3. Capacitive sensor. As the e-liquid has a different permittivity with respect to air, if concentric circles of conductors are kept in a vertical position, a height change in e-liquid will result in a proportional change in capacitance between the conductors. This can be fed to a circuit which can detect the change and thereby a change in e-liquid level.

4. Using an air pressure sensor at the top of a flexible tube whose bottom is held just above the bottom of the tank. The pressure in the tube changes as the e-liquid level goes up and down. This would be very safe, inexpensive, rugged and reliable.

Each of these techniques can also be used in the PV itself.

Section B. PV: Simplicity and Ease of Use

Preceding Section A focused on aspects of the re-filling and re-charging case. We will now move on, in this new Section B, to describing various features in the e-cigarette PV itself. The PV implements a number of useful features that contribute to the user experience, defined by simplicity and ease of use.

Following on from the consecutive numbering used in Section A, these features are:

| | |
|---|---|
| Feature 7. | Re-fillable and re-chargeable PV |
| Feature 8. | PV with pre-heat |
| Feature 9. | PV with dosage indication |
| Feature 10. | PV with drip prevention |

We will look at each of these in turn.

Feature 7. Re-Fillable and Re-Chargeable PV

A significant problem with conventional e-cigarette PV designs is that re-filling a cartridge reservoir is slow and can be messy; it typically requires the user to purchase small bottles of e-liquid and to carefully dis-assemble the PV and then re-fill the cartridge by lining up the nozzle of a bottle and squeezing gently. Equally, removing a spent, non-refillable cartridge and replacing it with a new cartridge, whilst not messy, is wasteful, especially as typical cartridges are not recyclable.

The feature is a re-fillable and re-chargeable e-cigarette PV that is not disassembled in normal use for re-filling or replenishing with e-liquid and is also not disassembled in normal use for battery access or replacement or other battery interaction.

A second aspect of this feature is a re-fillable and re-chargeable e-cigarette PV with a casing that includes a rechargeable battery, a re-fillable e-liquid reservoir and an atomiser, none of which are removable from, or separable from, any part of the casing in normal use. The body of the casing may be a one-piece, unitary casing (typically circular or square in profile), with components introduced from either or both ends.

A third aspect of this feature is a re-fillable and re-chargeable e-cigarette PV designed in normal use to only be re-fillable with e-liquid and re-chargeable when inserted into or otherwise engaged with a carrying case for the PV, the carrying case being specifically adapted to re-fill and re-charge the PV.

Ensuring that the PV does not need to be dis-assembled in normal use, for charging or re filling e-liquid, leads to a much simpler user experience. Furthermore, it enables the design to be much more robust, since there need be just a single, strong unitary casing with no screw threads allowing dis-assembly; robustness is very important for a consumer device that will be returned to and withdrawn from its case thousands of times, dropped and generally not treated gently.

A fourth aspect of this feature is a re-fillable and re-chargeable e-cigarette PV with a tip that includes (a) an e-liquid filling aperture that is designed to engage an e-liquid transfer mechanism (b) one or more vapour outlets distributed around the e-liquid filling aperture; and electrical charging contacts spaced apart from the tip.

The relevant Figures are FIGS. 7-11. FIG. 7 shows the PV case 100 which serves also as a e-liquid re-filling unit; it includes a replaceable e-liquid cartridge 3 and a battery 68 that can re-charge the battery in the PV 1. FIG. 7 is a cross-section view of the re-filling unit 100 and the PV 1; FIG. 8 shows the PV 1 being inserted into the re-filling unit 100; FIG. 9 shows the pump action dispenser in the re-filling unit 100 automatically replenishing the e-liquid reservoir in the PV 1 whilst the PV 1 is being pushed down; FIG. 10 shows the PV 1, fully replenished, and stored in case 100 (when the PV 1 is stored in the case, PV 1 is also pushed down to activate the pump dispenser to ensure the PV 1 is fully replenished with e-liquid).

PV 1 is not dis-assembled in normal use for re-filling the reservoir or otherwise replenishing or replacing the substance. The battery 5 in the re-filling unit 1 also charges the battery in the PV 1 whilst PV 1 is stored in the re-filling unit 1.

The detailed design of the working prototype, shown in FIGS. 19 and 20 and fully described in Section A above, also exemplifies the above features.

Feature 8. PV with Pre-heat Conventional e-cigarettes often only start heating the atomiser once an inhalation is detected; as a result, the first inhalation can give quite a poor experience and it is only after two or three inhalations that the atomiser has sufficiently heated the e-liquid that a good vaping experience is provided.

In this section, we describe a number of different 'pre-heat' features. With these 'pre-heat' feature, because the PV can start heating automatically, there is no need for an 'on' switch in the PV, contributing to the simplicity of the user experience, and also reducing cost.

The first pre-heat feature is a portable, personal storage and carrying case for an e-liquid e-cigarette PV that starts providing power to heat an electrical atomising element in a PV automatically when the case in which the PV is stored is opened. By using the battery in the case to provide the power for this pre-heating, this saves depleting the battery in the PV.

The second 'pre-heat' feature is an e-cigarette PV that automatically heats an electrical atomising element when the PV detects that it is no longer in electrical contact with the charging contacts in a portable carry case in which it is stored (e.g. when the case is opened and the PV pops up out of the case).

The first and second pre-heat features can be combined—e.g. the first phase is for the battery in the case to provide power for pre-heating when the case is opened; the second phase is for the battery in the PV to take-over heating when it detects that the PV is no longer in contact with the electrical power contacts in the case and hence can no longer rely on power from the case. Normally, this second phase occurs only once the pressure sensor in the PV detects that the user is inhaling.

A third pre-heat feature is a portable, personal storage and carrying case for an e-liquid e-cigarette PV which includes a locking system to lock the PV securely in a heating position during which time the PV is heating using power from a power source in the case and, after the PV has been sufficiently heated, to release the locking mechanism.

The case automatically may move the PV to a position which allows it to be readily removed from the case by an end-user once the PV has been sufficiently heated. The user can also press the PV back down when it is in the case to initiate heating.

In this section, we also introduce the feature of the PV automatically indicating when it has reached the correct operating temperature: A personal vapourising device storing a substance to be vapourised, the device including a means of indicating by visual cue, audible cue, touch feedback, haptic, vibration, heat or other sensory signal, or prompt, when the device has sufficiently heated the substance to a predetermined temperature or for a predetermined time, so that the device is ready for use. Hence, the PV (or indeed the case) may show when the PV is ready for use because heating to an operational level has been reached or heating for a predefined time has occurred. For example, a simple LED may glow when the PV is ready for inhalation.

This kind of indicator is very useful because if the user tries to inhale before the atomizer is effectively able to create a vapour with the correct characteristics (which happens if the e-liquid is too cool and viscous), then the user experience is very poor.

Optional features of the PV (each of which can be combined with others) include the following:

- heating of the e-liquid begins when a case, such as a portable re-filling case, storing the device is opened to show the device.
- heating of the e-liquid can be done by secondary heating elements in the PV e-liquid chamber; these heating elements are not meant to heat the e-liquid to vapourising temperature, but to simply raise the e-liquids temperature so that the e-liquid transported by the wick to the heating elements that do heat to vapourising temperature is already pre-heated.
- heating of the substance to the temperature at which the device is ready for use can be predicted or inferred with sufficient accuracy because the charge level of the battery used to provide power to heat the substance is known reliably.
- the charge level is known reliably because a sensor directly measures that charge level.
- the charge level is known reliably because it can be assumed to be fully charged because the device is stored in a case that includes a battery that automatically charges the battery in the device.
- heating of the substance begins automatically when the device is removed from its case.
- heating of the substance begins when the device is slotted into or otherwise engaged with the case so as to securely engage, for extraction from the case, a new capsule including the substance to be vapourised.
- the indicator is a visual indication, or a sonic indicator, or a tactile indicator or a vibration indicator.

The following section describes these features with reference to the Figures; the relevant Figure is FIG. 58. Referring to FIG. 58:

A: As the vapouriser leaves the case electrical contact is broken with the case and the vapouriser automatically starts to heat the liquid (pre-heating)

B: Shows how the charge contacts between case and PV are broken as the PV is removed from the case C: A light on the PV flashes or glows when the PV is ready to use, as shown schematically by the small circle with radial lines. The 'ready' indication could instead or in addition be a vibration or sound as well.

Pre-heating can also start when the case is simply opened and before the PV is withdrawn (the user may set (e.g. via a smartphone app) whether pre-heating starts at merely opening the case, or only when the PV is withdrawn from the case). Starting the heating process whilst the PV is still fully in the case enables the battery in the case to be used to provide power (typically by topping up the charge in the PV's internal battery as that internal battery provides the current to the atomizer). The detailed design of the working prototype, and fully described in Section A above (in particular FIGS. 25 and 26 and the related description), also exemplifies the above features.

This document also describes (Feature 13) a single capsule dispenser, in which the PV uses a small capsule with e-liquid and that capsule is extracted from a dispenser by the user inserting the PV into the dispenser; a single capsule is then engaged onto the end of the PV. In this variant, pre-heating of the e-liquid begins when the device is engaged into a case so as to securely engage a capsule including the substance to be vapourised; the PV includes the same kind of indicator to show that the PV is ready for use (e.g. the correct operating temperature has been reached); an alternative is that the PV pops out of the case when it is ready for use.

In each case, the temperature is not typically measured directly (although it may be); instead, that can be inferred from the current drain, resistance of the atomizer heating element, and any other relevant factor(s). Using the elapsed time of heating can be a simple and effective proxy for e-liquid temperature with this system, especially as the local battery in the PV will generally be fully charged or close to fully charged when heating starts, since it is continuously charged whilst the PV is stored in the case. Also, because the PV itself and the case can have knowledge of when the PV was last used and for how long, the remaining charge in the PV battery can be reliably inferred and the predicted time of heating can be automatically altered to compensate for varying levels of charge. In conventional PVs with a small rechargeable battery, time can generally not be used as a proxy because users do not reliably keep the battery close to fully charged.

Feature 9. PV with Dosage Indication

In this section, we describe the feature of an e-cigarette PV that indicates consumption of e-liquid using a visual indicator that extends or moves down the body of the PV away from the mouthpiece. The visual indicator moves or extends fully to indicate that a single dose has been consumed.

Optional features of the PV (each of which can be combined with others) include the following:

- the indication is visual, audible, touch feedback, haptic, vibration, heat or any other sensory signal.
- the indicator can be a visual indicator that extends or moves down towards the end of the device distant from the mouthpiece, and in which extending or moving from a start position to a final position corresponds to consuming or vapourising a single dose of the substance.
- the indicator can also include a visual indicator that extends or moves around the device, and in which extending or moving from a start position to a final position corresponds to consuming or vapourising a single dose of the substance.
- the indicator can provide a visual indication that alters to a specific colour when a single dose of the substance has been consumer or vapourised.
- the indicator can provide a haptic indication.
- the indicator can provide a heat-based indication.
- there is an additional indicator showing the charge level of a battery in the device.
- the or each indicator is implemented in a module that a user can connect in-between a conventional battery and any of: a conventional cartridge, atomizer or cartomiser.
- the module can screw into the conventional battery and the conventional cartridge, atomizer or cartomiser.
- the PV also can include a humidity sensor capable of monitoring humidity changes and is capable of evaluating how much vapour the device is producing.
  - the humidity sensor is positioned at the mouth of a cartomisor.
  - the humidity sensor is implemented in a module that a user can connect in-between a conventional battery and any of the following: conventional cartridge, atomizer or cartomiser.
  - the humidity sensor is implemented in a battery pack component, or a cartomiser, or an atomizer, or a mouthpiece.
  - the PV configured to use humidity data for dosage control.
  - the PV is configured to transmit humidity data to a case, a connected smartphone or directly to a computing device.
- the PV can be designed to engage with a portable re-filling storage and carrying case that includes a reservoir for the e-liquid from which the personal vapouriser can be refilled, and in which the vapouriser can only, in normal use, be refilled when slotted into or otherwise engaged with the portable case and that case is operable to re-fill the personal vapouriser so that the personal vapouriser has a single dose of the substance to be vapourised.
- the PV can be designed to engage with a portable unit for storing the portable vapourising device, in which the unit is programmed to prevent release of the device for predetermined amounts of time as an aid to cessation or reduction of substance usage.
  - time is indicated through colour lights or a countdown timer.

This feature also encompasses a personal vapourising device including a humidity sensor capable of monitoring humidity changes and therefore capable of evaluating how much vapour the device is producing.

Optional features of the PV (each of which can be combined with others) include the following:

- the humidity sensor is implemented in a module that a user can connect in-between a conventional battery and any of the following: a conventional cartridge, atomizer or cartomiser.
- the humidity sensor is implemented in a battery pack component, or a cartomiser, or an atomizer, or a mouthpiece.
- the PV is configured to use humidity data for dosage control.
- the PV is configured to transmit humidity data to a case, a connected smartphone or directly to a computing device.

This feature also encompasses a portable unit for storing a portable vapourising device, in which the unit is programmed to prevent release of a personal vapouriser device for predetermined amounts of time as an aid to cessation or reduction of substance usage. Time may be indicated through coloured lights or a countdown timer on the portable unit, or via data transmitted to a secondary device that could display this information.

The following section describes these features with reference to the Figures; the relevant Figures are FIG. 2, and FIGS. 59-60.

An example of vapouriser including an indication of how much substance has been vapourised is shown in FIG. 59, in which the quantity of vapour inhaled is inferred using a pressure sensor that senses when a user inhales (and optionally the strength of the inhalation or the volume inhaled), plus a time sensor that measure for how long an inhalation lasts.

There are various ways to indicate when a single or end-user set dose of the e-liquid has been consumed or vapourised.

A: A light moves down the vapouriser as if it is 'burning down'. A similar visual indicator is shown in FIG. 2; a series of twelve LEDs progressively light up as the PV consumes nicotine equivalent to a single cigarette—typically one LED lights up per inhalation, where the e-liquid strength used means that twelve inhalations corresponds to smoking a single cigarette. The user can also set the LEDs so that a single LED lights up when nicotine equivalent to an entire cigarette is consumed. Hence, the FIG. 2 device would show when the equivalent of between one and twelve entire cigarettes had been consumed.

B: Single light changes colour to show how much has been inhaled. A traffic light system (green, amber, red) or change in brightness of light (dimming with usage) could be used and when the light shows red or is fully dimmed out it means that the dose has been provided; the PV may at this time stop working for a set period if the user is on a nicotine or smoking cessation or reduction programme.

C: the light, at one end of, or anywhere on the PV, changes colour, as above.

A conventional PV can be adapted to use this feature: FIG. 60 shows a conventional two part PV, with an e-liquid cartridge above the atomizer and the atomiser above the battery, but by adding a third module between the standard cartridge/atomizer/cartomiser and the battery where the additional new module includes an indicator that alters to indicate when a single or end-user set dose of the substance has been consumed or vapourised, as described above. Many conventional PVs use standard sizes, so this approach enables a conventional PV to be upgraded to one that is far more useful in a smoking or nicotine cessation or reduction program.

FIG. 61 is another approach to dosage control: the PV case is programmed to prevent release of the PV for predetermined amounts of time as an aid to cessation or reduction of substance usage, tamper prevention, preventing children accessing the PV etc. The case itself may indicate that a single dose, including an end-user set dose, of the substance has been consumed or vapourised in the PV it is storing. The case can be programmed or controlled (e.g. from the user's smartphone) not to power up for a specified period of time, at certain times, or at a certain frequency or duration; these could all be variable and adjusted by the smartphone app.

FIG. 62 shows the humidity sensor variants as described above.

Feature 10. PV Drip Prevention

In this section, we describe several drip-prevention features in the PV.

The first feature is a PV includes a tip that includes (a) an e-liquid filling aperture that is designed to engage an e-liquid transfer mechanism, the aperture being centrally positioned along the long axis of the PV, the aperture being connected to an e-liquid storage chamber in the PV; (b) one or more vapour outlets distributed around the e-liquid filling aperture; and in which the vapour outlets are connected by passages to a vapour chamber including a vaporising element, and the vapour chamber is sealed from the e-liquid storage chamber.

The second feature is a PV with e-liquid leak suppression where an e-liquid filling aperture in the PV is adapted to align, when inserted into a re-filling unit, with a hollow tube that is part of a fluid transfer system in the re-filling unit, and the aperture includes a flexible seal through which the tube is inserted or passes, the seal ensuring that any drips of e-liquid are retained within the PV when the PV is withdrawn from or removed from the re-filling unit.

The third feature is a PV with e-liquid leak suppression where the vapour passage is not a straight through path from the atomiser but instead includes at least one turn and terminates in one or more vapour outlets distributed around an e-liquid ingestion nozzle positioned centrally along the long axis of the PV.

Optional features of the PV (each of which can be combined with others) include the following:

- the presence of the barriers causes the length of the passage to be substantially longer than if there were no barriers.
- the barriers ensure that the passage is not a straight path.
- the barriers cause the width of the passage to be constricted compared to the width the passage would have if there were no barriers.
- the barriers comprise a double cap.
- the barriers make the passage a serpentine path.
- the passage is lined with an absorbent material to absorb any droplets that escape from the unit, without impeding the flow of vapour through the passage.

These features also encompass a personal vapouriser comprising a unit storing a substance to be vapourised, an atomizer and a passage connecting the atomizer to a mouthpiece through which vapour may be drawn by a user, wherein the passage is lined with an absorbent material to absorb any droplets that escape from the unit, without impeding the flow of vapour through the passage.

The detailed design of the working prototype, fully described in Section A above, also exemplifies the above first and second features.

The following section further describes these features with reference to the Figures; the relevant Figures are FIGS. 63-67.

FIG. 63A shows a second barrier in the mouthpiece that does not significantly impede vapour flow but provides a harder, tortuous path (the dark arrow) for e-liquid droplets to follow. A solid tube around the e-liquid store has been added to stop droplets of e-liquid being squeezed out (conventional PVs may have a flexible tube that can be squeezed). a Soft flexible skin around the solid tube can be provided for better tactility.

FIG. 63B shows a variant in which the vapour path is not tortuous as in FIG. 80A, but instead a double cap is provided in the mouthpiece, making it much less likely that e-liquid droplets will escape.

FIG. 63C shows a further variant in which a series of fins in the mouthpiece makes it much less likely that e-liquid droplets will escape.

Figure 64:
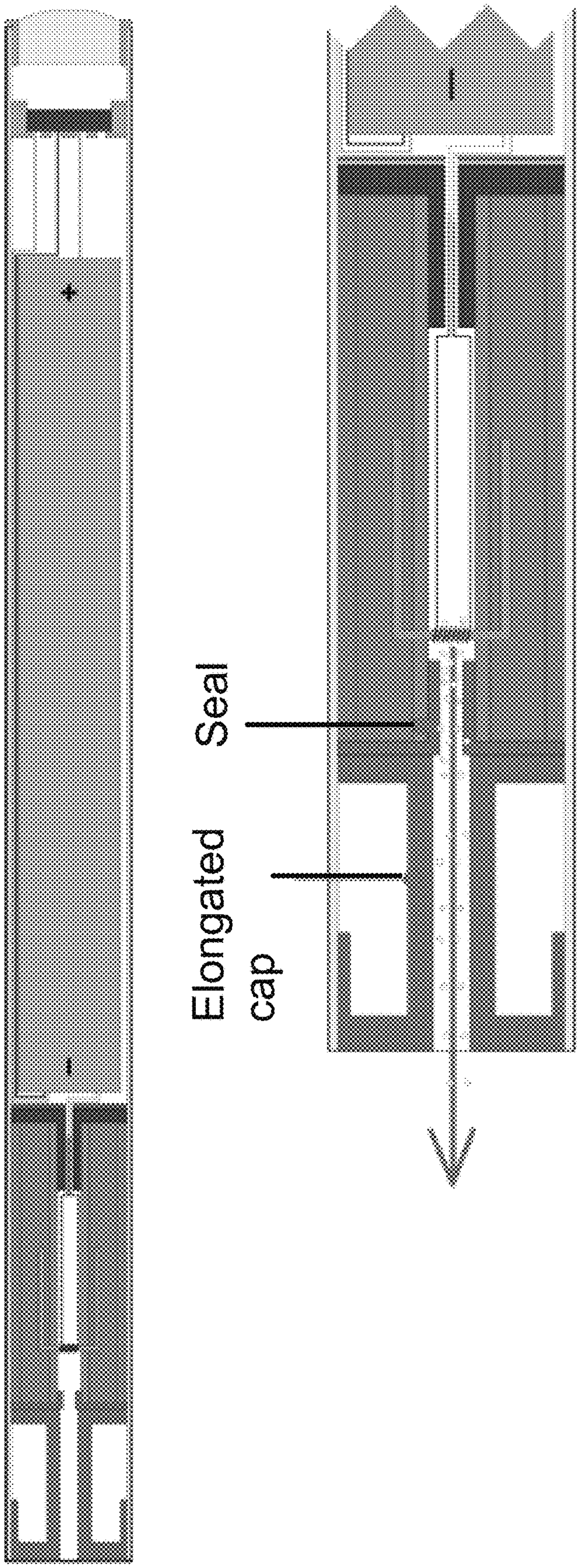

FIG. 64 shows a seal being placed over the end of the e-liquid saturated cloth; by capping the saturated cloth in this way with a consistent and effective seal, it makes it much harder for e-liquid droplets to migrate into the inhalation track. In FIG. 64, this is combined with an elongated cap, again reducing the possibility that any droplets of e-liquid will leak out.

Figure 65:
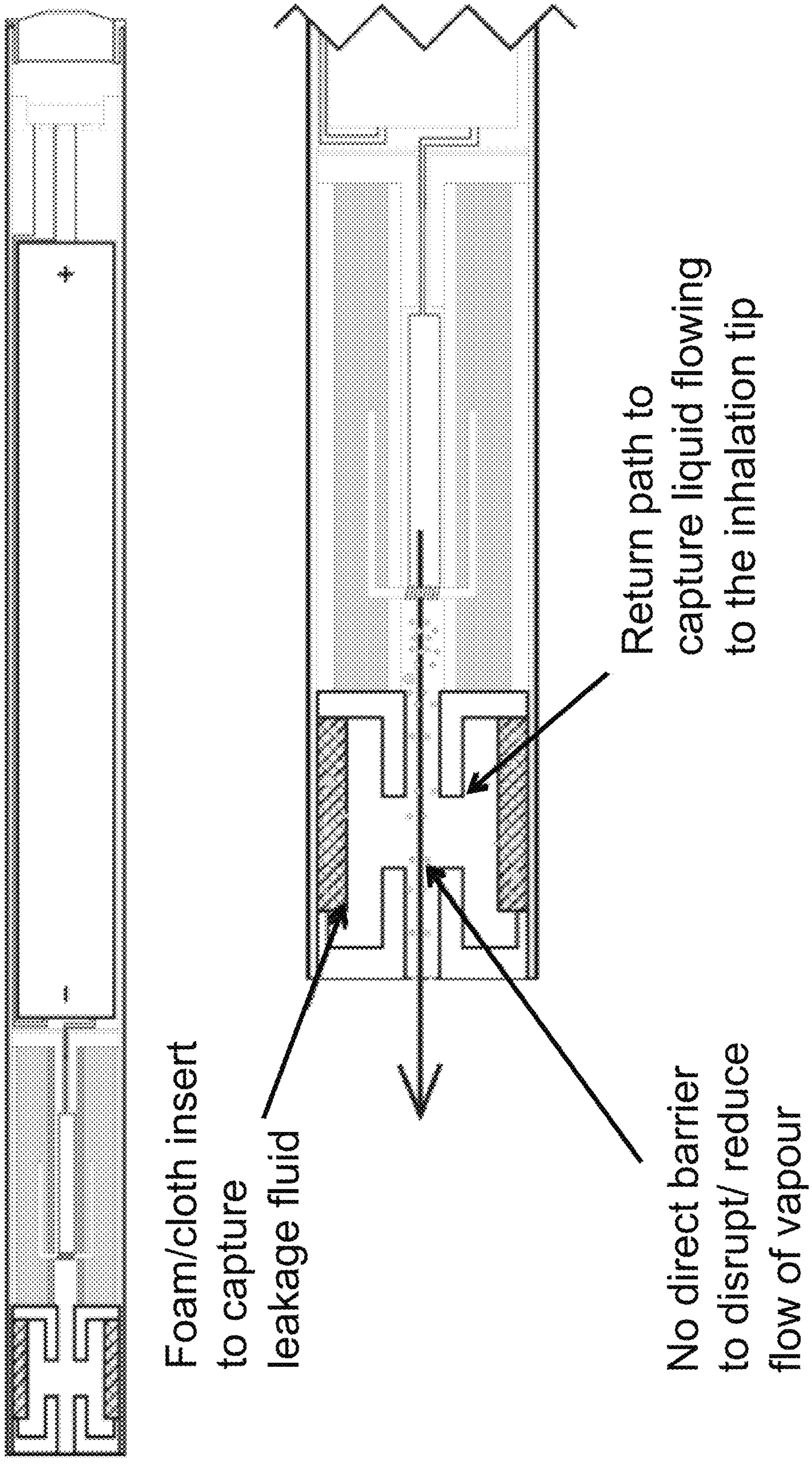

FIG. 65 shows adding a seal to the end of the e-liquid saturated cloth, but also adding a dry cloth or foam insert to absorb any droplets that do escape, and to prevent vapour build up. If any small droplets do adhere to the side of the internal cap, then the return shape of the internal cap leads them away from the inhalation tip.

The choice of absorbent material is important: Hydrophilic absorbent material that absorbs water and water based liquids is effective. The material is in a compact tube form to fit into the small space in an inhalator end, and it swells by absorbing rapidly a liquid such as water or liquidised nicotine based gel. Types of material include but are not limited to:

- Synthetic sponge
- Synthetic Chamois
- Microfiber synthetic cloth
- Hydrogel (Hydrogels are highly absorbent (they can contain over 90% water) natural or synthetic polymeric networks)

Absorption materials should not absorb moisture in vapour suspension as this would harm inhalation, only liquids that are free moving in the vapouriser case are absorbed. The hydrophilic material could also be changed periodically to ensure the vapouriser performance is not reduced.

Figure 66:
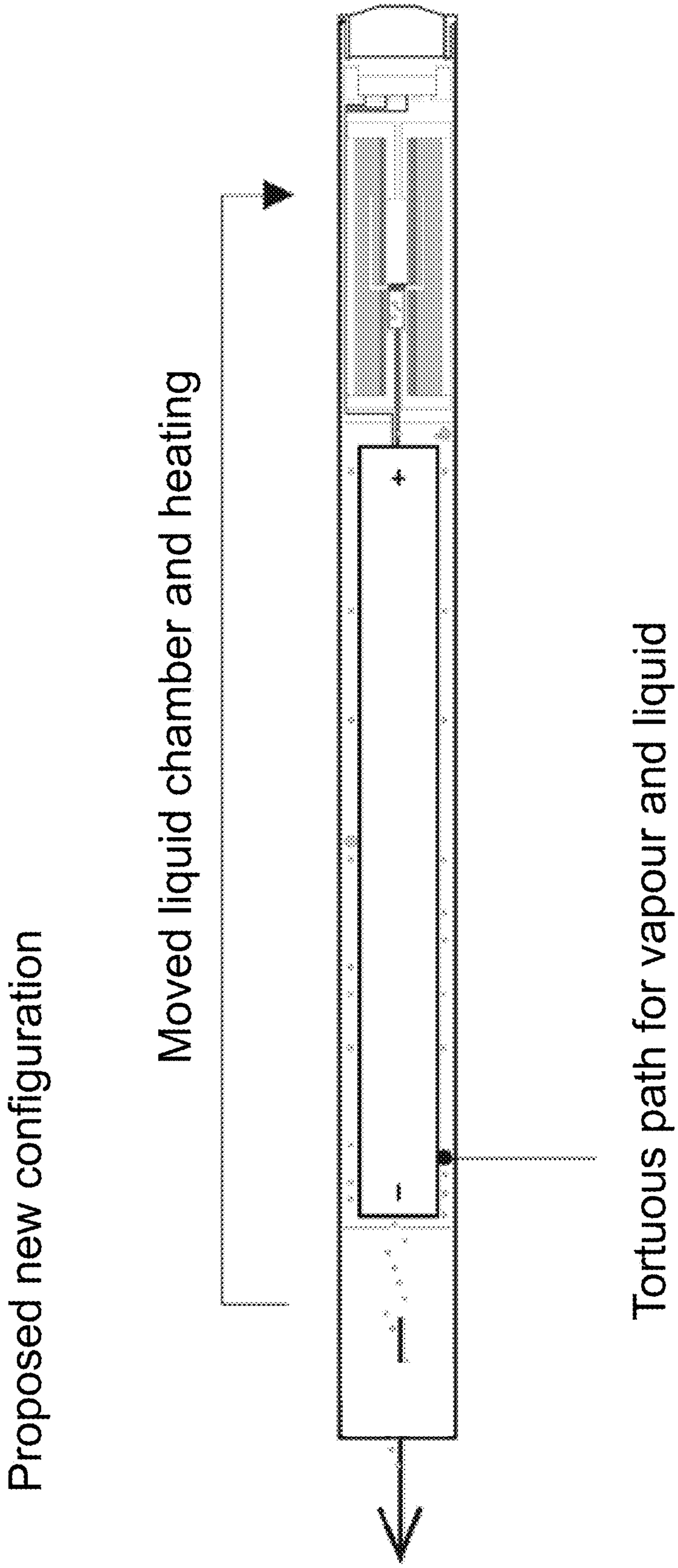

FIG. 66 shows the approach of moving the e-liquid reservoir to the end furthest from the mouthpiece—this provides a much longer path for any e-liquid droplets to flow before reaching the mouthpiece. It also balances the cigarette more naturally and provides a better vaping/vapour experience.

Figure 67:
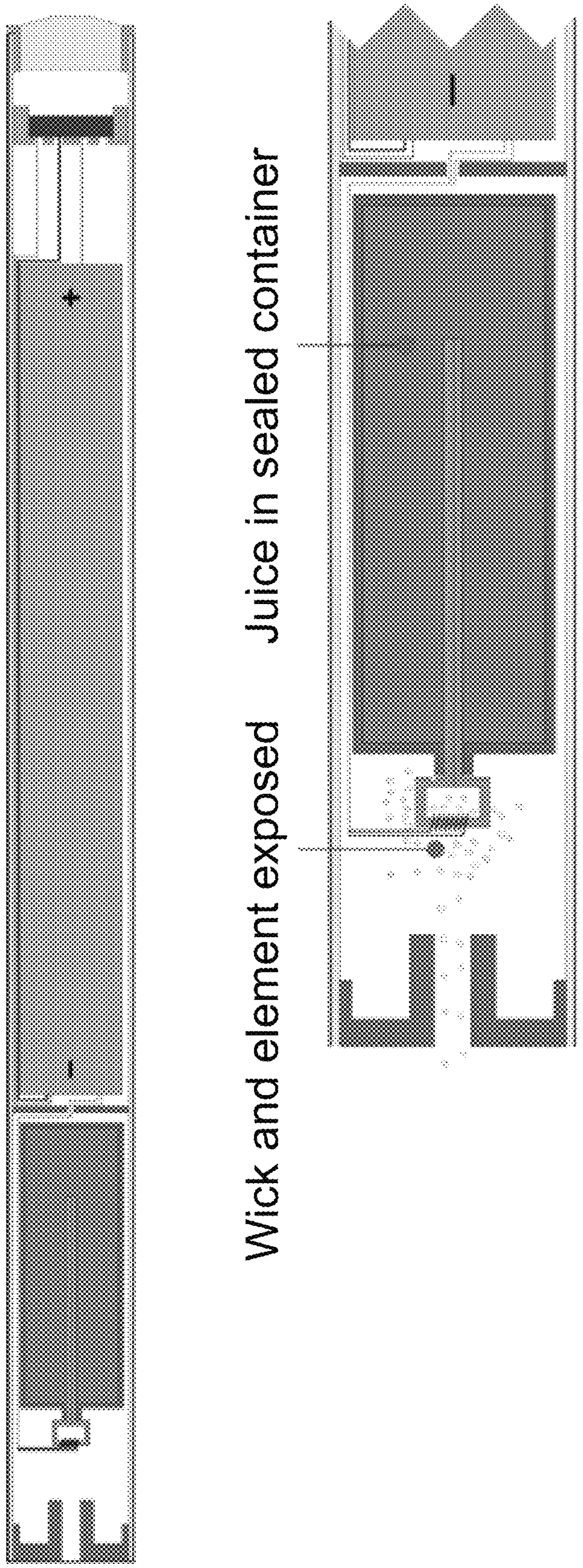

FIG. 67 shows containing the e-liquid in a sealed container to stop droplet migration. The wick will leave the container via a tight hole and use capillary action to retain a wet coating. It is highly unlikely that the wick will itself permit the migration of droplets of e-liquid that could then leak out from the mouthpiece.

Section C: User-replaceable e-liquid cartridge Whereas Section A focused on the storing and carry case, and Section B focused on the PV, in this Section C we describe the features of the user-replaceable e-liquid cartridge.

Following the consecutive numbering in earlier sections:

Feature 11. User-Replaceable e-Liquid Cartridge

A first feature is a user-replaceable e-liquid cartridge adapted to be inserted into or attached to portable, personal storage and carrying case for an e-liquid e-cigarette PV. FIG. 5 shows the cartridge 3 and the Section A description of the working prototype that uses this cartridge. FIG. 6 shows a different design of cartridge 3 withdrawn from case 100. FIG. 7 shows cartridge 3 fully inserted into case 100.

A complimentary feature a portable, personal storage and carrying case for an e-liquid e-cigarette PV in which the case includes a user-removable e-liquid cartridge.

Key subsidiary features:

- e-liquid cartridge has a casing that is adapted to be fitted by a user into a chamber in a portable, personal storage and carrying case for an e-liquid e-cigarette PV.
- cartridge has an outer surface that forms part of the casing of the case (with this variant, the cartridge is still 'in the case', and the case still 'includes the cartridge' as those phrases are used in this specification)
- cartridge attaches to the case—e.g. the cartridge forms an extension to the case; with case and cartridge when combined forming a unitary object (with this variant, the cartridge is still 'in the case', and the case still 'includes the cartridge' as those phrases are used in this specification)
- e-liquid cartridge is not substantially deformable in normal use in order to displace fluid from the cartridge
- e-liquid cartridge is made using PET
- e-liquid cartridge is designed to slot inside a portable, personal storage and carrying case for an e-liquid e-cigarette PV with a press fit against a seal and in which the cartridge is formed with a void designed to receive and engage with a micro-pump that is positioned in the case, the micro-pump sealing against a nozzle in the cartridge.
- e-liquid cartridge is designed to slot inside a portable, personal storage and carrying case for an e-liquid e-cigarette PV with a press fit against a seal and in which the cartridge includes an integral micro-pump
- case includes a user-replaceable cartridge with several compartments and can fill the PV by combining e-liquid from several compartments
- case includes several user-removable e-liquid cartridges and can fill the PV by combining e-liquid from several cartridges
- case and/or cartridge includes an overflow channel that enables excess e-liquid that is pumped up from the cartridge but is not stored in the PV to be captured and returned to the cartridge
- cartridge screws into the case
- cartridge includes electronic identifier, such as RFID chip.
- Cartridge includes physical features on its surface, such as raised or lowered portions, that physically engage with complimentary features in the wall of the case aperture into which the cartridge is inserted.
- The physical features form the shape of a word or logo, such as a trademarked word or logo In this section, we describe in more detail the feature of the re-filling unit including multiple user-replaceable cartridges/chambers: A portable unit for re-filling a reservoir in a portable vapourising device, the unit including multiple user-replaceable cartridges or chambers, each containing a substance to be vapourised, in which the unit enables the portable vapourising device to be filled with one specific substance, or a predetermined mixture of two or more substances.

Optional features (each of which can be combined with others) include the following:

- a user may specify which substance is used to refill the PV.
- a user may specify refilling the substance(s) to create a custom mixture.
- a customised mixture may be in accordance with a smoking or nicotine cessation or reduction program.

Combining the multi cartridge/chamber approach with the features of the Feature 5 'Intelligent case' leads to many useful and novel features: for example, the case can learn which flavours/strengths of e-liquid the user prefers, possibly as a function of time of day, location, day of the week, time of the day. Like a good personal assistant, the case can then prepare in advance the right flavour/strength given these factors or even suggest that it does so to the user (e.g. a message could appear on the user's smartphone app that exchanges data with the PV and/or case). The case and/or related smartphone app (or any other kind of connected electronic device, such as wearable glasses, a smartwatch etc) also recommend new flavour(s) or other things that the user may like, in much the same way as an online music service.

The following section describes these features with reference to the Figures; the relevant Figures are FIGS. 56 and 57.

An example of a portable charging and re-filling case equipped with four separate cartridges (numbered 1, 2, 3 and 4) is shown in FIG. 56A. Four cartridges have been used for illustrative purposes, but this could be more or less.

FIG. 56B shows the four cartridges loaded into a carriage; each cartridge will typically have a different strength or type of e-liquid. For example, if the user following a smoking or nicotine cessation or reduction program, each cartridge could have a different strength of nicotine; one cartridge could be a placebo or a vitamin/mineral e-liquid or just the standard propylene glycol base. Another approach could be to have e-liquids of similar nicotine strength, but with different flavours. It would also be possible to have different flavours of totally nicotine-free e-liquid—this might be especially useful to someone who has successfully completed a nicotine cessation program. Each cartridge is individually user replaceable (but not in normal use refillable, although this is one possible variant).

The carriage has small valves (not shown) used to permit or prevent e-liquid flowing from each cartridge through to the refilling mechanism, under the control of the software and processor in the unit (which may in turn be under the control of the user's smartphone or other device—typically, the user would enter the desired mix into an app running on a smartphone, and the smartphone would then send the appropriate control data to the processor in the unit; the smartphone can be replaced by any other suitable type of computing device, including wearable computing devices receiving touch based and/or spoken commands). The unit may also include a touch screen that enables the user to enter the desired mix directly into the unit. Mixing of the e-liquids can occur in the carriage itself, or in a separate chamber on leaving the cartridge.

FIG. 56C shows a single cartridge with four chambers; the cartridge includes the valves (each shown schematically as circle with a line) that enable different chambers to be opened or closed as appropriate under the control of the software and the processor (again, usually, implementing instruction received from the user's smartphone). Mixing of the e-liquids can occur in the cartridge itself, or in a separate chamber on leaving the cartridge. The whole cartridge is user replaceable (but not in normal use refillable, although this is one possible variant).

FIG. 57 shows how the user's smartphone can display the current levels of e-liquid in each cartridge:

In Step A, the electronics in the case record the level of the cartridges.

In Step B, when the vapouriser is inserted into the case it transfers its usage data to the electronics in the case.

In Step C, the case gives a visual indication when at least one cartridge level is low. This can take into account current levels in the cartridge(s), and also predicted future levels taking into account the rate of consumption by the user and how much e-liquid is left in the PV itself.

In Step D, the case sends data to a connected smartphone device to inform of the low cartridge level. The case may take into account how much e-liquid is left in or has been consumed by the vapouriser, and the rate at which it has been consumed in the past, when determining whether to alert the user or order replacement cartridges.

The smartphone can display a message such as 'Order replacement Cartridge 2, which is nicotine strength xx?', or "We predict that you will run out of e-liquid nicotine strength xx at your current consumption rate in 4 days, shall we re-order?' together with a 'Buy Now' option. If the user selects the 'Buy Now' option, then a message is sent over the internet to an e-fulfillment provider, who then sends out the replacement cartridge to the user, who then installs it into the case.

The above 'Multi-liquid' cartridge can be controlled by an electro-mechanical valve system that regulates the volume of liquid flowing through the valve, whereby moving a pin controls the flow and quantity of liquid into an anti-chamber, in turn creating a defined mixture which is then injected into the vapouriser by either a non-pressurised or pressurised pump system. This could be electronically controlled to mix a predefined volume and mixture of liquids. Examples being

- Predefined smoking cessation program to reduce down the nicotine levels over a period of time.
- To mix several liquids to make unique flavours.
- Move from Menthol inhaling to straight nicotine based inhaling liquid.
- Cartridge Lock-out for child protection Miscellaneous Features Feature 12. Hygienic PV In this section, we introduce the feature of the PV including a hygienic mouthpiece: A personal vapourising device including a housing and a mouthpiece, in which the mouthpiece is extendable from and retractable within a body of the device.

Optional features of the PV (each of which can be combined with others) include the following:

- the mouthpiece is made of a soft touch material.
- the mouthpiece is extended from the housing when the tip of the device at the end opposite to the mouthpiece is depressed by the user.
- extending the mouthpiece causes the device to automatically start heating the substance to be vapourised.
- a second depression by the user causes the mouthpiece to retract within the body of the device.

The following section describes these features with reference to the Figures; the relevant Figures are FIGS. 68 and 69. FIG. 68 shows a PV with an outer sleeve through which the mouthpiece/atomizer and battery parts of the PV can slide. FIG. 68A shows a schematic external view, with the mouthpiece or inhalation tip fully extended; FIG. 68B is a cross sectional view of FIG. 68A, showing the mouthpiece/atomizer and battery parts. In FIG. 68C, the inhalation tip is fully retracted within the sleeve; as a consequence, the battery end of the PV is now protruding out of the sleeve. FIG. 68D shows the internal parts of the FIG. 68C view. When the inhalation tip is fully retracted, the user can click on the other end to cause the inhalation tip to pop out; clicking it again can cause the tip to retract, in much the same was a clicking the top of a ballpoint pen. Clicking the end to cause the inhalation tip to pop out can also be used to turn the PV on to start heating.

FIG. 69 shows the same four views, but this time with a different design of PV (described more fully as Feature 14). In this different design, a single dose capsule is secured at the end of the PV furthest from the inhalation tip; pushing the soft-tip inhalation into the sleeve/housing causes the capsule to be ejected.

Feature 13. Single Capsule Dispenser

In this section, we introduce the feature of a dispenser storing multiple capsules, each containing a substance to be vapourised, wherein the dispenser enables a personal vapourising device to be inserted into the dispenser to securely engage a capsule.

Optional features of the capsule dispenser (each of which can be combined with others) include the following:

- a stack of capsules is inserted into the dispenser and a spring urges the stack up inside the dispenser.
- the spring may be any other type of device for applying a force.
- a capsule is designed to securely engage with the vapourising device when the device is pressed against the capsule.
- a single capsule includes substance equivalent to a single [combustible] cigarette.

- a single capsule includes an amount of substance designed for a nicotine or smoking cessation or reduction program.
- a single capsule can be any of the following: nicotine, caffeine, vitamin, mineral, flavoured substance, or any mixture of any of these.
- different capsules can be selected by the user to be different strengths of nicotine.
- different capsules can be selected by the user to be different flavours of nicotine.
- different capsules can be selected by the user to be different types of vapourisable substance.

The following section describes these features with reference to the Figures; the relevant Figure is FIG. 70.

FIG. 70A: A stack of capsules is inserted into the dispenser and a spring (or any other type of device for applying a force) urges the stack up inside the dispenser.

FIGS. 70B and 70C: A capsule is designed to securely engage (e.g. a press fit) with the PV device when the PV device is inserted down into the case and pressed against the capsule. The capsule engages with the end furthest from the inhalation tip/mouthpiece. The PV can be withdrawn from the case, with the capsule securely attached. A single capsule typically includes e-liquid equivalent to a single cigarette. A single capsule may also include an amount of substance designed for a cigarette or nicotine cessation or reduction program—hence the stack of capsules shown in FIG. 70A may have progressively less nicotine.

Feature 14. Single Capsule PV

In this section, we introduce the feature of a PV with an ejectable single-dose capsule: A personal vapouriser device including a capsule containing substance to be vapourised at one end of a housing furthest from the mouthpiece and where the capsule is ejected by the user pressing a component in the device.

Optional features of the PV (each of which can be combined with others) include the following:

- the component pressed by the user is a button.
- the component pressed by the user is a mouthpiece and in which the mouthpiece is slid out from and retracted back into the housing, the mouthpiece retracting causing the capsule to eject.
- a single capsule includes an amount of substance equivalent to a single cigarette.
- a single capsule includes an amount of substance of a predetermined amount as decided or selected by the user.
- a single capsule includes an amount of substance designed for a cigarette or nicotine cessation program.
- the PV is designed to engage with a dispenser storing multiple capsules, each containing a substance to be vapourised, wherein the vapourising device is inserted in normal use into the dispenser to securely engage a capsule.

This feature encompasses also a personal vapouriser comprising a unit storing a substance to be vapourised, and a mouthpiece at one end, in which the reservoir storing the substance to be vapourised is placed towards the end furthest from the mouthpiece.

Optional features of the PV (each of which can be combined with others) include the following:

- the unit is a capsule that encapsulates the substance.
- the unit is a conventional e-cigarette cartridge.
- unit is pressed on to the end of the vapouriser and securely engages with the vapouriser.

The following section describes these features with reference to the Figures; the relevant Figures are FIGS. 66 and 69.

FIG. 66 shows moving the e-liquid chamber to the end furthest from the mouthpiece; in this case, the entire cartomiser is moved to the end furthest from the mouthpiece. This balances the PV more naturally and so provides a better experience.

FIG. 69 shows a single dose capsule is secured at the end of the PV furthest from the inhalation tip; pushing the soft-tip inhalation into the sleeve/housing causes the capsule to be ejected.

Feature 15. Various Constructional Improvements

This section describes a broad range of constructional improvements; the relevant Figures are FIGS. 71 to 76.

Figure 71:
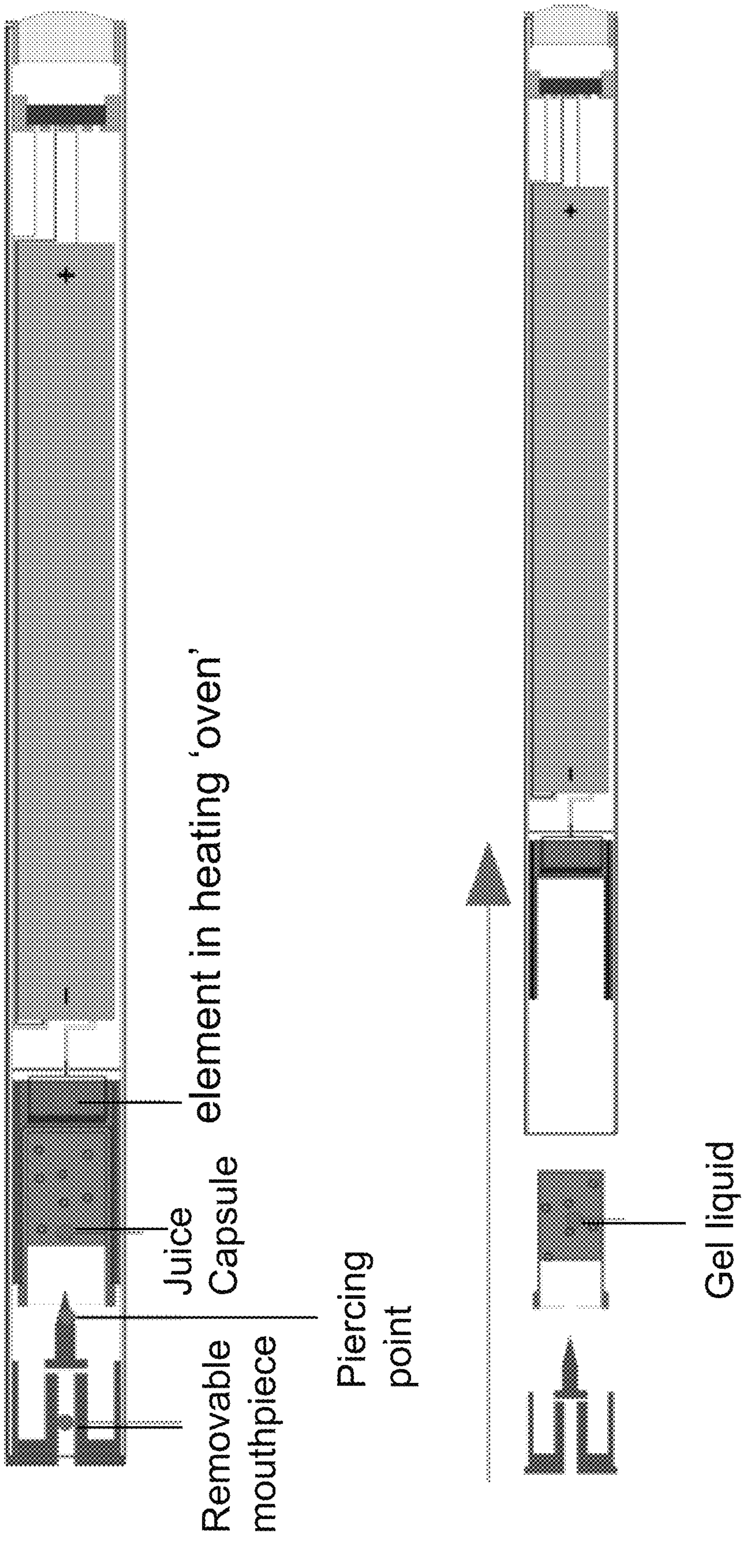

FIG. 71 shows an e-liquid capsule (typically with a single dose of nicotine, e.g. equivalent to a single cigarette, or a pack of 5 cigarettes). The capsule is inserted by the user into the heating atomizer and then places the mouthpiece over the capsule; a piercing point forms a small puncture in the top of the capsule, enabling heated vapour to be drawn through the mouthpiece. This design allows user to know how much they are 'vaping' and is also a much cheaper and easier to use refill approach, compared with conventional approaches.

Figure 72:
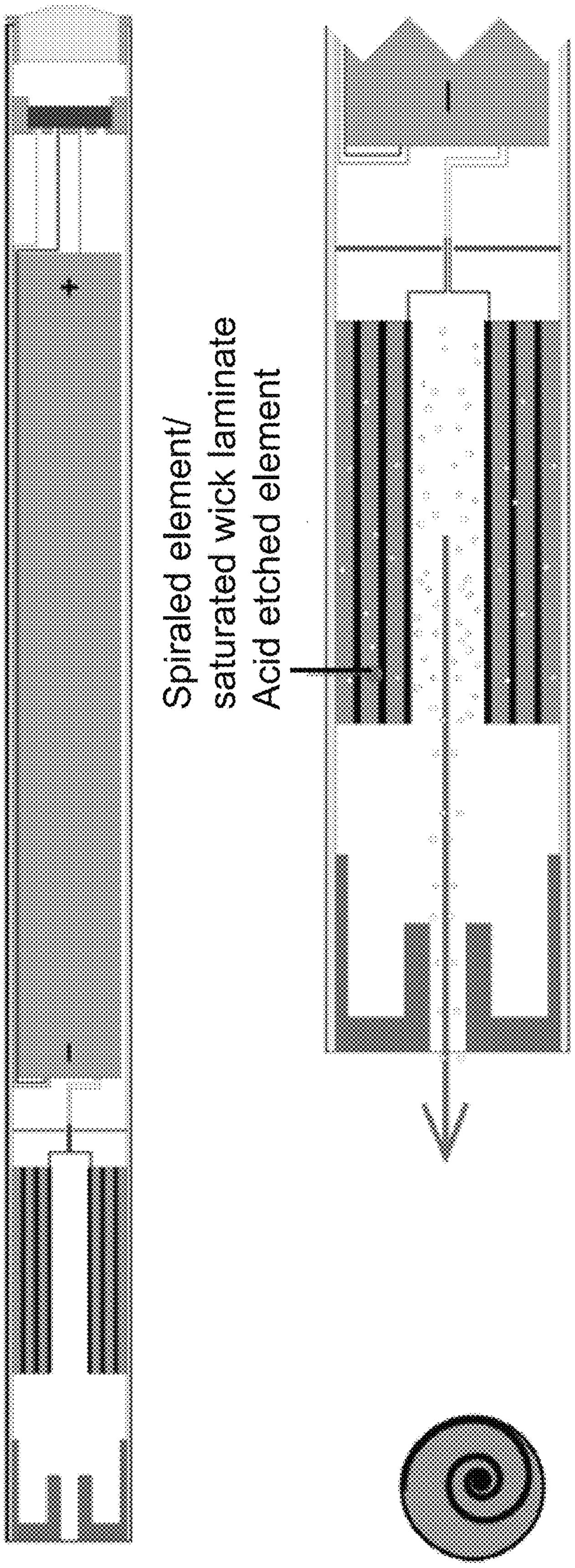

FIG. 72 shows a spiraled, acid etched element being used as the heating element; the acid etching increases the effective surface area of the heating element; rolling the element up in a spiral around a saturated mat allows a much larger element than is normal, again giving faster and more efficient vapour production and also inhibits the saturated mat from releasing droplets of e-liquid.

Figure 73:
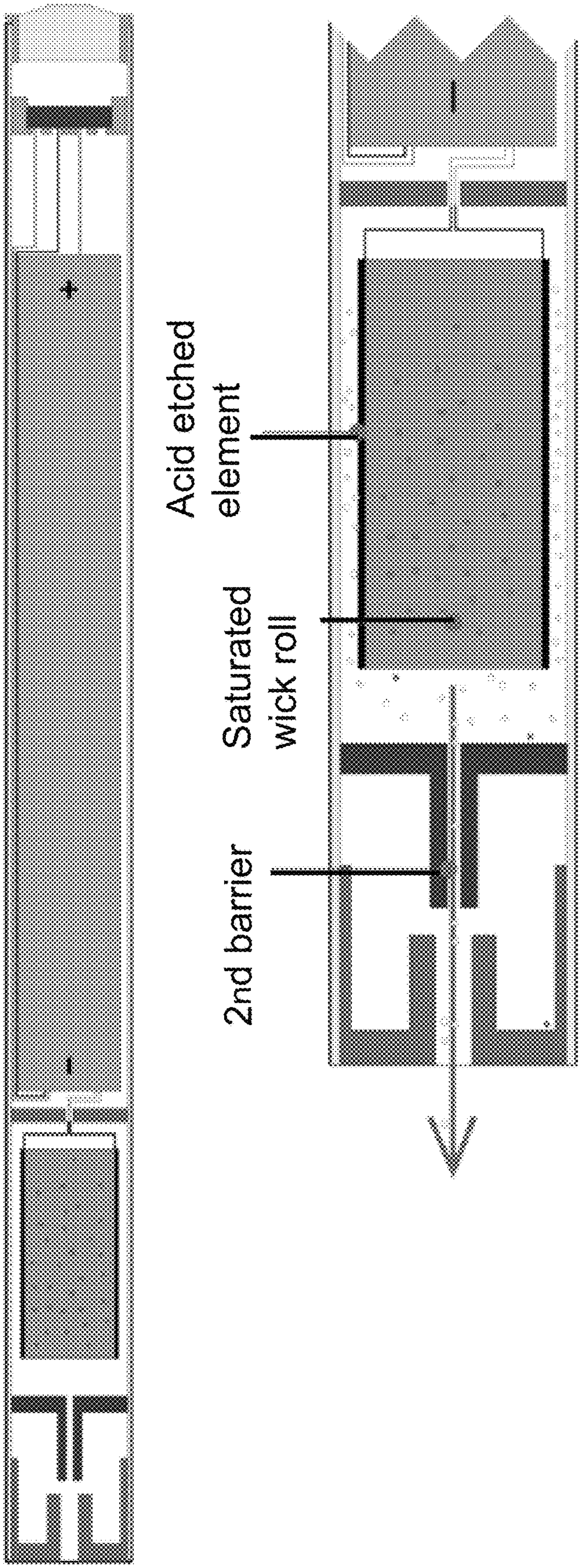

FIG. 73 shows wrapping an acid etched heating element around the outside of an e-liquid saturated core; this approach provides a large heating area, but is simpler than the spiral arrangement of FIG. 111. A second barrier prevents droplet leakage.

Figure 74:
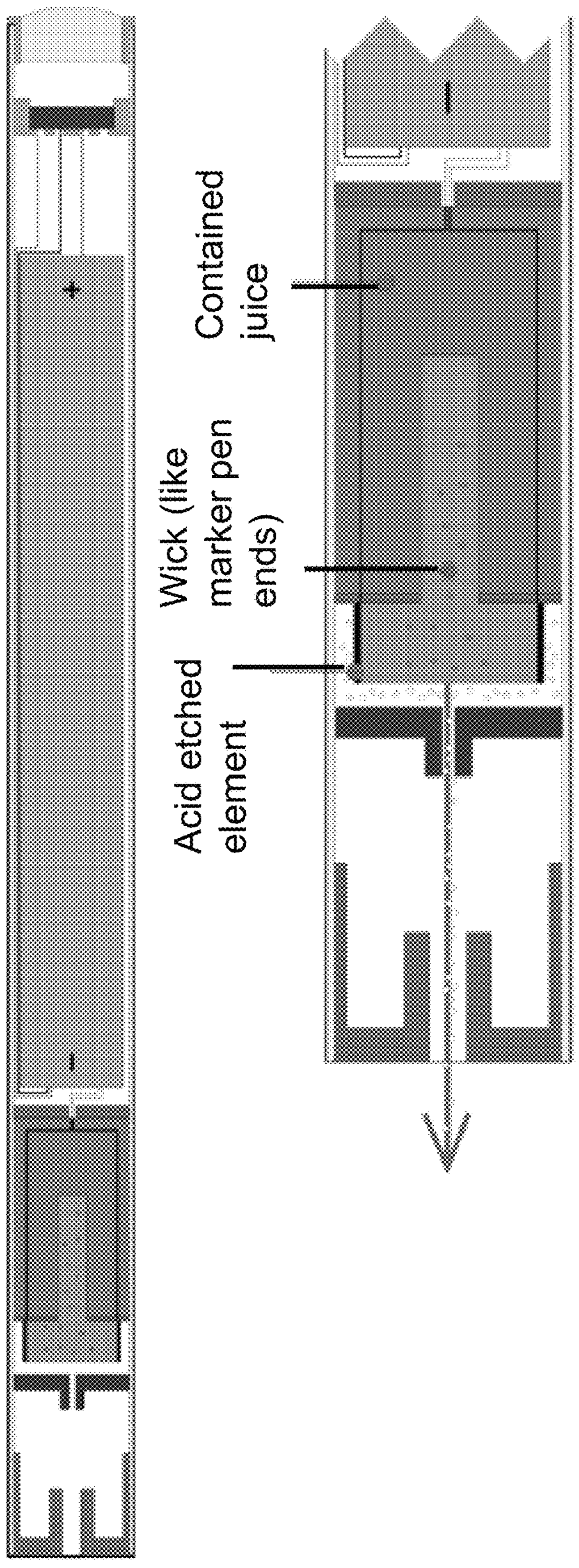

FIG. 74 shows a large wick, made of compressed fibres like a marker pen's nib, inserted into and drawing e-liquid from a container; the sides of the wick that are external to the e-liquid container are in contact with an acid-etched heating element; the effectiveness of the wick in drawing up e-liquid provide a consistent vapour.

Figure 75:
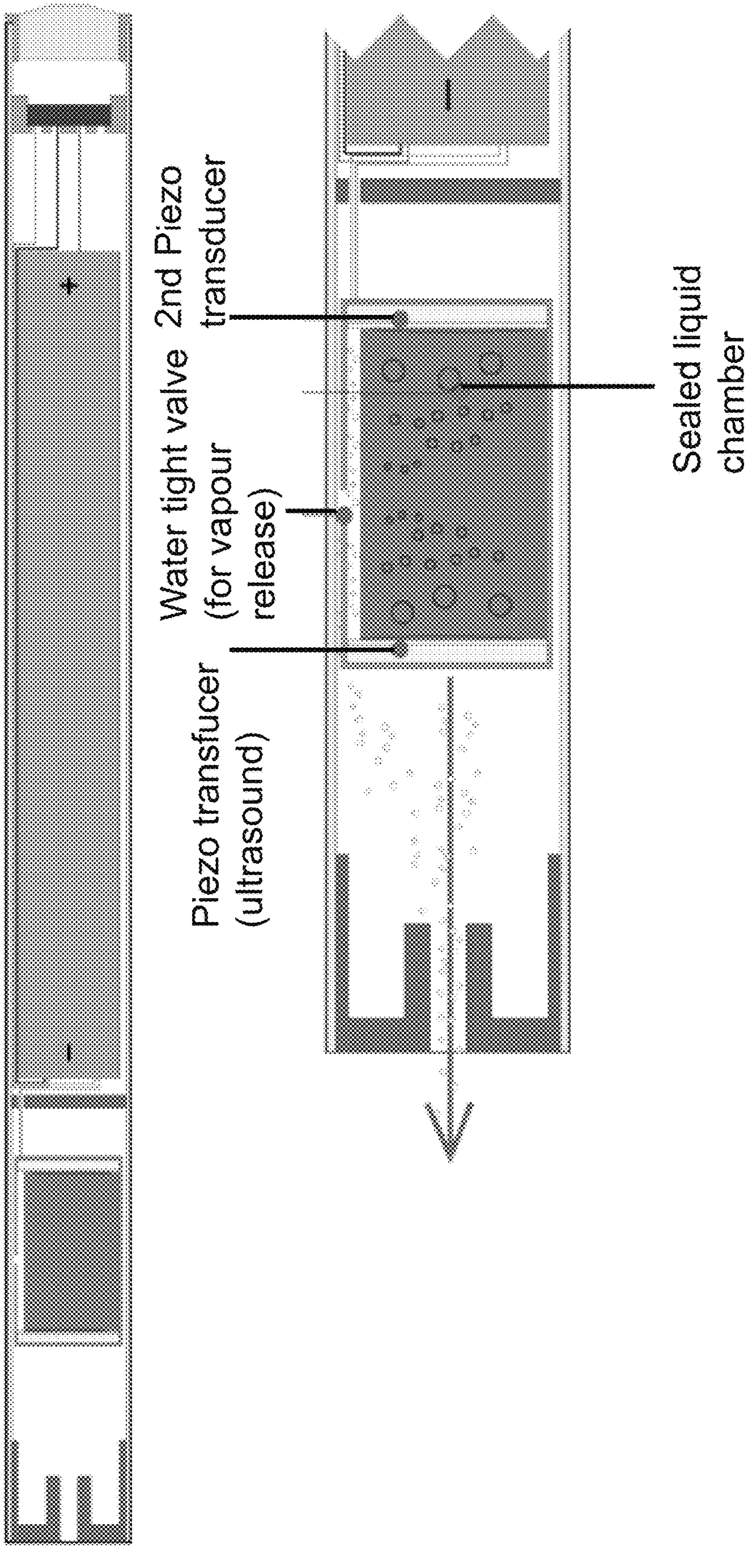

FIG. 75 shows using a pair of piezo transducers that generate ultrasonic waves to produce the e-liquid vapour; the e-liquid is in a sealed chamber with a water tight valve that can release vapour but not droplets.

Figure 76:
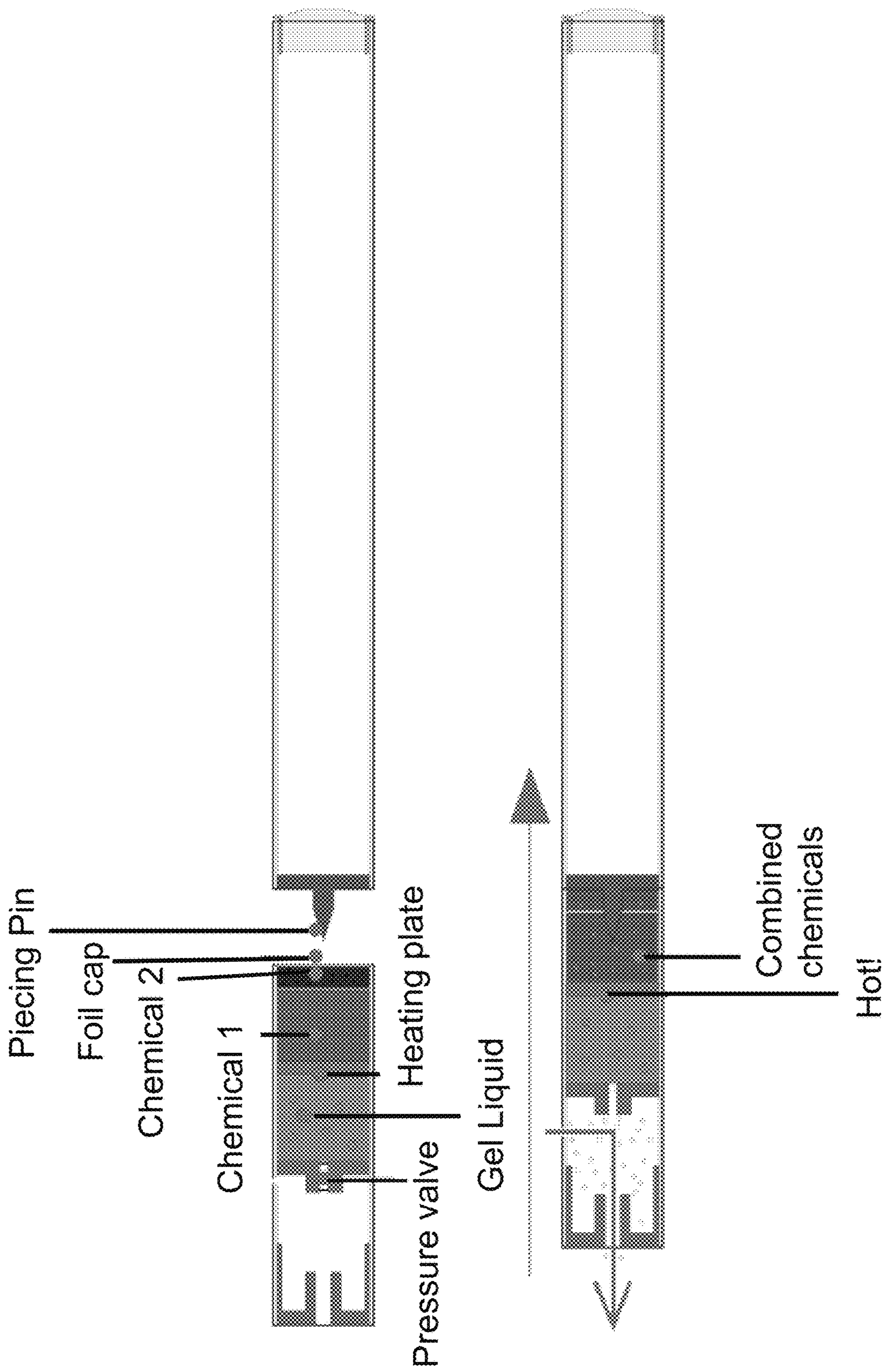

FIG. 76 shows using a chemical heat source to heat the e-liquid; a combination of chemicals are encapsulated together with an e-liquid container; when the capsule is pushed against a piercing pin at one end of a sleeve, mixing of the chemicals generates enough heat to create a vapour, which the user sucks through the mouthpiece. Enough heat could be provided to vapourise a single dose. This design eliminates the need for batteries or control electronics. It would be cheap to manufacture.

Section E In this Section E, we describe a number of improvements made over the system described in previous Section A—D. Each improvement can be combined with any one or more other improvements, or other features described earlier in this specification. As usual in this specification, when we cite an example (for instance, by stating "e.g." or "such as") then that example is a non-limiting, non-exclusive example; the skilled implementer will understand the broad range of equivalents and variants that are covered.

PV Features

E.1 PV includes an air pressure valve: the PV includes an air pressure valve or device so that excess air can escape from the e-liquid 'child' reservoir in the PV. The 'child' reservoir is the reservoir in the PV that is directly filled by a 'parent' reservoir; the 'parent' reservoir can be the e-liquid cartridge that is removable from the PV or case. This child reservoir is designed to enable the atomizing coil unit to draw in controlled amounts of e-liquid for vaping; e-liquid in the secondary child reservoir is typically wicked into the atomising coil unit. So, to re-cap, the parent reservoir, typically a user-removable and replaceable, sealed or closed e-liquid capsule or cartridge, perhaps of capacity 5 mL or 10 mL, is slotted into the PV or the re-fill/re-charge case, and a fluid transfer mechanism operates to transfer e-liquid from the capsule or cartridge into the 'child' reservoir in the PV, typically 2 mL or less. The heating coil unit is arranged to gradually wick some of the e-liquid up from the child reservoir in normal vaping operation.

Air needs to escape from the child reservoir in the PV when that reservoir is being filled up with e-liquid, otherwise excessively high pressures can build up in the e-liquid in the child reservoir, which can lead to leakage as the e-liquid finds a way to escape via the atomising coil unit and hence out through the vapour inhalation apertures that are connected to the coil unit. Also, air needs to enter into the child reservoir as e-liquid is consumed in normal use, since otherwise a partial vacuum would be created, which would tend to prevent or retard e-liquid in the child reservoir wicking/entering the atomising coil unit.

Also, if the ambient air pressure changes, for example in an aircraft where the ambient pressure can fall to significantly lower than sea-level atmospheric pressure, then the valve will operate to ensure that the air pressure in the reservoir can rapidly and reliably equalise to ambient air pressure in the aircraft cabin, again preventing leakages of e-liquid from the PV.

Hence, the PV includes a valve that, for example, equalises the air pressure in the PV to ambient air pressure, or alters it to bring it closer to ambient air pressure ('normalising') in order to prevent leakage when filling the PV with e-liquid and to ensure correct operation whilst the PV is consuming e-liquid.

The air-pressure valve or device could have no moving parts, but instead be a barrier made of an air-porous material, such as a sintered polymer or metal, coated with or otherwise including a barrier or layer of an air-porous substance that is not porous to e-liquid, such as an oleophobic material or a hydrophobic or super-hydrophobic material. The air-pressure valve or device could be positioned to allow air to flow out from the 'child' reservoir. Equally, it will allow air to flow into the child reservoir as e-liquid is consumed and also as ambient pressure rises (e.g. as an aircraft descends from high altitude). Examples of suitable oleophobic materials are sintered phosphor bronze, sintered stainless steel and sintered PU plastic.

E.2 PV includes a mechanical valve that is pushed up from its seat when filling takes place: The PV includes a mechanical valve that opens when the PV is being filled—for example, a nozzle or stem from the device/cartridge with the parent reservoir etc. is inserted into the PV (or as the PV is inserted into the device/cartridge) for filling the PV with e-liquid and this causes the valve to be pushed open or rise up from its seat, moving against the bias force of a small coil spring, so that e-liquid can freely flow through the nozzle or stem into a child reservoir in the PV. When the nozzle or stem is withdrawn (e.g. the PV is withdrawn from the re-fill case or the filling cartridge or capsule withdrawn from its filling position in the PV where that capsule fits directly into the PV and not a re-fill and re-charge case) then the valve automatically closes by resting back on its seat. Hence, when the PV is not being actively filled with e-liquid, for example, it is being held for vaping, or is stored in a bag, the valve is fully closed and this prevents any e-liquid in the 'child reservoir' in the PV from leaking out into the user's mouth. The child reservoir is connected to one or more small channels that lead into a second child reservoir which surrounds the atomising unit and from which e-liquid is drawn (e.g. by a wick or other porous member) into the atomising chamber (e.g. a heating coil inside an air chamber).

Once the PV is withdrawn from the case, or the stem from the filling 'parent' reservoir is withdrawn from the PV, then the valve sits back down under the biasing force of a small spring and the valve then re-seals against its seat, preventing leakage of any e-fluid out from the child reservoir in the PV. Ensuring that there is no leakage from the e-liquid filling process is especially important if the filling nozzle or aperture in the PV is at the same end as the inhalation nozzles, but this solution applies irrespective of where the filling nozzle or aperture is located.

The stem or nozzle that protrudes from the cartridge or other form of parent reservoir and that engages with the valve in the PV to push it off its seat passes through a duckbill valve or a series of two or more duckbill valves; when the stem or nozzle is withdrawn then the duckbill wipes any droplets of e-juice from the stem, ensuring that those droplets are not deposited on any surface from where they could be ingested by the user, but are instead retained in a cavity in the PV behind the duckbill valve.

E.3 The coil unit or atomiser in the PV is protected from excess e-liquid pressure in the child reservoir that feeds e-liquid into the atomising unit: High fluid pressures can build up when e-liquid is being pumped into the child reservoir in the PV; since the child reservoir feeds e-liquid into the atomising chamber or coil unit, high fluid pressures can lead to e-liquid not being gradually released into the wicking system in the coil unit but instead flooding in at a rate that the wicking system cannot cope with. The result is that e-liquid can leak through the atomising chamber and out through the inhalation nozzles or apertures that are connected to the atomising chamber. Since it is critical to eliminate e-liquid leakage, we have several different approaches to solving this problem. Note however that if the PV (e.g. the child reservoir outside of the coil unit) includes some form or pressure equalisation valve, then air can escape through that valve when the PV is being pumped full of e-liquid, and hence excess pressures should not build up. But we nevertheless still employ one or more of the following solutions in any case for added protection against leakage. Note that the atomising unit does not have to be a coil based atomiser, but any other sort of atomiser (e.g. piezo, thermal bubble jet, heating element that is not coil based etc).

E.3A The coil unit in the PV sits inside a 'child' e-liquid reservoir that can be filled with e-liquid. A cover, made of a material that is porous to e-liquid, such as a sintered metal or polymer, covers at least the holes in the wall of the coil unit through which e-liquid has to pass to reach the atomising coil inside the coil unit. The porous material enables e-liquid to pass gradually into the wick inside the coil unit, even when the e-liquid is at an excessively high pressure. The small holes in the wall of the coil unit permit e-liquid which has passed through the sintered metal collar to contact a wick inside the coil unit; a heating coil is wound around the wick. Using a cover that is porous to e-liquid not only ensures a gradual release of e-liquid into the coil unit, even when the e-liquid is at an excessively high pressure, but also acts as a porous store of e-liquid, reducing the chance that the coil will ever heat up without there being sufficient e-liquid to atomise (if a coil heats up without there being sufficient e-liquid to atomise, then the vapour inhaled can be very unpleasant and the coil can be damaged). The porous cover can be shaped as a long dovetail shape unit that slides into a matching channel in the wall of the coil unit; as the coil unit typically is cylindrical in shape and has a pair of holes facing each other, 180 degrees apart, there are then two porous covers, 180 degrees apart. Alternatively, each porous cover could be a small plug with an interference fit into the hole in the coil unit. It is not necessary to substantially surround the coil unit with the porous cover, since that is wasteful of material.

E.3B The cover need not be made of a porous material; instead, it could be a non-porous material, such as metal or plastic, that fits closely over the holes in the coil unit, but that includes features on its inner surface (i.e. the surface contacting the coil unit) or that interacts with features on the outer surface of the coil unit, to allow some e-liquid to reach the holes in the coil unit, but that prevent high pressure e-liquid from reaching those holes. For example, the coil unit and/or the cover could include a scored ring or channel that leads to each hole; this ring or channel could be perpendicular to the long axis of the coil or could be a different pattern or shape at some other orientation. Where the cover is a ring or collar that surrounds and fits closely around the coil unit, with a pair of opposing e-fluid inlet apertures, then the outer surface of the coil unit could include a scored ring that connects opposing holes in the coil unit; the cover is then fitted over the coil unit, with the holes in the cover not aligned with the holes in the coil unit, forcing the e-liquid to seep or pass through the holes in the cover and then pass along the scored ring until it reaches the holes in the coil unit—this will prevent the entry of high-pressure fluid into the coil unit. In an alternative design, irrespective of whether there is a scored ring or channel linking the holes in the coil unit, the inside surface of the collar that contacts the outer surface of the coil unit is now roughened, again permitting only e-liquid at low pressure to reach the coil unit. In an alternative design, irrespective of whether there is a scored ring or channel linking the holes in the coil unit, the inside surface of the collar includes a spiral, scored groove or channel through which e-liquid can pass.

E.4 The PV includes an oleophobic barrier separating the vaporising chamber from the portion of the PV containing the electronics and battery: The PV includes a washer or other form of barrier that permits air to pass but not e-liquid; the barrier separates the portion of the PV including the battery and the electronics from the portion of the PV which e-liquid or vapour comes into contact with. The washer/barrier could have no moving parts, but instead be made of an air-porous material, such as a sintered polymer or metal, coated with or otherwise including a layer or barrier of a substance that is air-porous but not porous to e-liquid, such as an oleophobic material or a hydrophobic or super-hydrophobic material. Examples of suitable oleophobic materials are sintered phosphor bronze, sintered stainless steel, sintered PU plastic.

E.5 PV includes an annular vaporising channel: The PV inhalation tip includes an annular aperture through which vapour can be drawn by a user; the annular aperture offers greater airflow than discrete holes. The annular aperture may surround an e-liquid filling nozzle. The annular aperture leads to an annular airflow channel extending along the body of the PV and leading back, at a tapering section, to the atomisation chamber. The annular airflow channel surrounds the filling nozzle; an child e-liquid reservoir immediately adjacent to the filling nozzle is also inside the annular airflow channel. This design gives significantly greater airflow than small inhalation holes.

E.6 PV has a 'discrete' mode: PV includes a 'discrete mode'—e.g. to reduce the amount of vapour produced, the user can activate a button or sensor on the PV (or case, or connected app) and that alters the operation of the operation of the atomising device in such a way as to decrease the vapour produced—for example, it could reduce the power used, or increase the VG proportion compared to PG, if that is possible—e.g. the case or PV can mix differing proportions of PG and VG, or alter the frequency or other operational parameters (e.g. duty cycle) of a piezo-electric, thermal bubble jet or ultrasonic atomiser. Consequently, the density or thickness of the vapour produced by the PV can be significantly reduced; this is particularly useful indoors, when the user might wish to vape very discretely. The strength of the 'hit' can also be decreased too, because the amount of nicotine inhaled will be reduced; this can be useful where the user wishes to reduce their nicotine consumption.

E.7 PV includes a 'power mode'—e.g. to increase the amount of vapour produced, the user can activate a button or sensor on the PV (or case, or connected app) and that alters the operation of the operation of the atomising device in such a way as to increase the vapour produced—for example, it may increase the power used, or increase the VG proportion compared to PG, if that is possible—e.g. the case or PV can mix differing proportions of PG and VG, or increase the frequency or duty cycle of a piezo-electric, thermal bubble jet or ultrasonic atomiser. Consequently, the density or thickness of the vapour produced by the PV can be significantly increased; the strength of the 'hit' can also be increased too, because the amount of nicotine inhaled will be greater.

E.8 The PV includes a piezo-electric pump: The PV includes a piezo-electric pump to transfer small, but accurately and reliably metered, quantities of e-liquid from a cartridge or other form of parent reservoir into a child reservoir in the PV; the piezo-electric pump may also be used in reverse to expel out any residual e-liquid in the PV back into the cartridge/parent reservoir. Because the amounts delivered can be accurately metered, this means that the PV (or case or associated application running on a smartphone) can accurately determine the total consumption of e-liquid and/or the amount of e-liquid remaining in a cartridge and also in the PV itself. This in turn can be used in the automatic re-ordering function—for example, when the system knows that the cartridge is down to its last 20% by volume of e-liquid, then the app running on the user's smartphone can prompt the user with a message asking if the user would like to order a replacement cartridge or cartridges. Low-cost piezo-electric pumps used ordinarily for delivering ink in an inkjet printer may be used.

E.9 PV has an IMU: The PV includes an IMU (inertial measurement unit) to detect when it is being lifted up and out of the case so it can start heating (e.g. the atomising coil); it can also tell if it is left on a table and so can power down. Movement-related data can be stored and uploaded to a server (for example, sent over Bluetooth to the user's connected smartphone, which in turn sends it to the server).

This data can be useful since it shows how the PV is being used, the duration of a vaping session etc.

E.10 PV has replaceable covers: The PV includes a user replaceable cover to enable customizing of the appearance of the PV. The cover may be a clip on cover.

E.11 PV magnetically latches in the case. The PV, or the chassis that holds the PV in the case, is magnetically latched into the case (e.g. one or more magnets are placed somewhere on the PV or the chassis so that the charging and/or data contacts on the PV latch reliably to their corresponding contacts in the case). For example, a small neodymium magnet in the case and a matching magnet or metal item in the PV (or vice versa) ensure that, when the PV is nearly fully inserted into the case, the PV is drawn in the rest of the way to a secure, final position, which is also the position needed for fluid transfer from a parent e-liquid reservoir (e.g. the e-liquid cartridge that slots into the case) to a child reservoir in the PV.

The charging and data transfer contacts in the PV and the case are optimally and securely positioned in contact with one another. The magnets stop the PV from falling out of the case if the case is tipped upside down and also eliminate contact bounce—i.e. when the PV is dropped into the case. Furthermore, they ensure that the fluid transfer mechanism is correctly positioned (e.g. the filling aperture or nozzle in the PV is correctly lined up with the filling stem or nozzle from the cartridge or other form of parent reservoir). In one implementation, one or more small magnets near to the battery and data contacts ensure that the corresponding battery and the data contacts in the PV and case magnetically latch to one another when the PV is fully inserted into the case or the chassis part of the case that holds the PV; the magnets do not need to be placed near to the contacts but can be positioned anywhere suitable, for example, either at one end of the PV, or alternatively are positioned somewhere along the main body of the PV.

Whilst magnetically securing the charging contacts in a PV against the power electrodes in a charging case is known, it is not known to use magnetic latching to ensure that not only are the power contacts correctly and reliably positioned in relation to each other, but so also are the data contacts and the fluid transfer mechanism. Magnetic latching can be applied to any one or more of the following: the power contacts, the data contacts, the fluid transfer mechanism. When applied directly to say just the power contacts (e.g. only the power electrodes have adjacent magnets), then the data contacts and the fluid transfer mechanism can be taken into correct alignment anyway, so it is not necessary to have multiple magnets in the PV or case.

Equally, a small neodymium magnet in the case and a matching magnet or metal item in the hinged chassis described earlier (or vice versa) ensure that, when the chassis is nearly fully closed, the chassis is drawn in the rest of the way to a secure, final position, which is also the position needed for fluid transfer from a parent e-liquid reservoir (e.g. the e-liquid cartridge that slots into the case) to a child reservoir in the PV. This again eliminates contact bounce, gives a good tactile feel to closing the chassis into the case, and ensures that the power and data connections are properly aligned.

E.12 PV ejection mechanism: An automatic lifting mechanism (e.g. magnetic or spring-based) that gently lifts the PV up a few mm from the case to enable a user to easily grasp it and may also prevent it from falling out if tipped upside down. A mechanical lifting system could be a simple pivoting lever that contacts a part of the PV (e.g. its front face); a damped spring is placed under tension if the PV is inserted fully into the case; when the PV is released from the case (e.g. by pushing a release button), then the lever cause the PV to gently rise up by about, for example, 12 mm. A magnetic lifting mechanism could involve a permanent magnet at one part of the PV and an adjacent electro-magnet placed in the case and powered by the main battery in the case; slowly energising the electro-magnet when the PV needs to be released causes the PV to gracefully rise up out of the case.

E.13 The PV includes a touch sensor: The PV can sense when you are touching it—e.g. with a capacitive sensor. It can be programmed to detect specific touch inputs and control the PV accordingly. For example, the touch inputs are not merely to either activate or de-activate the PV, but more sophisticated actions as well. For example, tap twice on the body of the PV to bring it up to heat; tap three times to put it to sleep. Or the PV could detect when it is held by at least two fingers, and then automatically turn on and start heating. The sensor could detect a touch control input anywhere on the PV, or at a specific region. Using a capacitive sensor removes the need for a discrete button. All touch data can be stored and uploaded to a server (for example, sent over Bluetooth to user's the connected smartphone, which in turn sends it to the server). This data can be useful since it shows how the PV is being used, the duration of a vaping session etc.

E.14 A sensor detects PV release from the case: A sensor (e.g. a non-contact magnetic sensor, such as a reed switch, Hall effect sensor) detects when the PV enters and leaves the charge/re-fill case by sensing the presence, proximity or movement of a small magnet or strip of metal in the PV (or some other mechanism for disrupting the local magnetic field around the sensor); a non-contact switch like a magnetic sensor has the advantage of being robust and reliable and does not affect the smooth, tactile quality of inserting and withdrawing the PV from the case. Similarly, a light sensor could be used; for example, a light sensor in the PV could detect when light was incident on the PV, inferring that the PV is now in an open case or no longer in the case at all; alternatively, the case could include a small light sensor facing a LED light source in the case; withdrawal of the PV triggers the light sensor since light from the LED is no longer incident. Many variants of sensor are possible. When withdrawal of the PV is detected by the PV, it can automatically start heating the atomising coil so that the PV is at its optimal operational temperature when the user takes his first vape.

E.15 The replaceable tip of the PV includes its own integral atomising heating element and is separable from the e-juice reservoir in the PV. (Cartomizers could be said to include a replaceable tip with a heating element, but they include the e-juice reservoir).

E.16 PV has a heated nozzle: Those parts of the PV (especially the nozzle) on which e-liquid vapour might otherwise condense if those parts of the nozzle were cold, are heated using e.g. an electrical heating element. Condensation of the e-liquid vapour on internal components of the PV is a problem if those condensed droplets can trickle into the user's mouth. If those components are heated (e.g. using an electrical heating coil in thermal connection with the component(s)), then the possibility of condensation forming can be reduced. Heating the components can also be used to warm the e-liquid vapour to a desired temperature; this is especially useful if atomisation of the e-liquid arises using a non-heating system, such as ultrasonic atomisation using piezo-electric or other form of droplet-on-demand system.

Cartridge or Other Form of Parent Reservoir Features

E.17 The cartridge or other form or parent reservoir includes an air pressure valve. As the fluid level inside the cartridge/reservoir falls (e.g. because fluid is being transferred into the child reservoir in the PV), atmospheric pressure forces open the air pressure valve, such as a duckbill valve, to allow air to flow in and ensure equalisation of the air pressure. If no air pressure valve is provided, then, as the cartridge empties, a partial vacuum forms, retarding fluid transfer out of the cartridge. The valve also prevents air or contaminants from entering the cartridge/reservoir, which hence preserves the condition and stability of the e-liquid (e-liquid can deteriorate when exposed to free flowing air for long periods). The cartridge is non-refillable, tamper evident and with an airtight seal to preserve e-liquid stability. Air pressure equalisation or normalisation is also important whenever the ambient air pressure alters (e.g. when in an aircraft) since it prevents the e-fluid leakage that might otherwise occur.

E.18 The cartridge includes a piezo-electric pump to transfer small but accurately and reliably metered quantities of e-liquid: the piezo-electric pump can be used as the fluid transfer mechanism to transfer e-liquid from the cartridge or parent reservoir into the child reservoir in the PV. It can also be used in reverse to suck back out any residual e-liquid in the PV. Because the amounts delivered can be accurately metered, this means that the PV (or case or associated application running on a Smartphone) can accurately determine the total consumption of e-liquid and/or the amount of e-liquid remaining in a cartridge and also in the PV itself. This in turn can be used in the automatic re-ordering function—for example, when the system knows that the cartridge is down to its last 20% by volume of e-liquid, then the app running on the user's smartphone can prompt the user with a message asking if the user would like to order a replacement cartridge or cartridges. Low-cost piezo-electric pumps used ordinarily for delivering ink in an inkjet printer may be used.

E.19 Atomiser is integrated into a removable lid or cap to the cartridge—when the PV engages with the lid/cap, the lid/cap is filled with a small quantity of e-liquid and locks onto the PV; so when the PV is lifted up, the lid is locked into to one end. Hence, every cartridge comes with its own atomizer.

E.20 The cartridge can be packaged into a container that is the same size as a conventional cigarette pack: this enables distribution through existing cigarette vending machines and point of sale systems.

Case Features

E.21 The case is the same size as a cigarette pack: the case, or its packaging, is the same size as a conventional cigarette pack (e.g. a pack of twenty cigarettes)—e.g. this enables distribution through existing cigarette vending machines and point of sale systems.

E.22 The case includes a piezo-electric pump—the case includes a piezo-electric pump to transfer small but accurate quantities of e-liquid in from the cartridge or parent reservoir to a child reservoir in the PV. This enables mixing from multiple cartridges too. As with D.18 above, the piezo-electric pump can be used as the fluid transfer mechanism to transfer e-liquid from the cartridge or parent reservoir into the child reservoir in the PV. It can also be used in reverse to suck back out any residual e-liquid in the PV. Because the amounts delivered can be accurately metered, this means that the PV (or case or associated application running on a smartphone) can accurately determine the total consumption of e-liquid and/or the amount of e-liquid remaining in a cartridge and also in the PV itself. This in turn can be used in the automatic re-ordering function—for example, when the system knows that the cartridge is down to its last 20% by volume of e-liquid, then the app running on the user's Smartphone can prompt the user with a message asking if the user would like to order a replacement cartridge or cartridges. Low-cost piezo-electric pumps used ordinarily for delivering ink in an inkjet printer may be used.

E.23 Case includes a removable cover: Case includes a removable, e.g. a clip-on, cover or decorative panel(s) to enable a user to customize appearance; the main side faces of the case can be removed and a new face press-fitted into position.

PV with Removable Cartridge and No Filling or Re-Charge Case

E.24. PV includes the removable cartridge and a mechanical sealing valve: The PV includes a removable e-liquid cartridge that slots into or attaches directly to the PV, without the need for a separate re-fill and re-charge case; a fluid transfer mechanism transfers e-liquid from the cartridge to a child reservoir in the PV; that child reservoir feeds e-liquid to a separate atomising unit (i.e. the child reservoir is separate from the atomising unit but feeds e-liquid to it via, for example, channels or some other mechanism). The cartridge is similar in structure to the cartridge described elsewhere in this specification but is not meant for insertion into a re-fill/re-charge case. The e-liquid cartridge is an air-tight, closed unit that cannot be re-filled by a user. The filling or fluid transfer mechanism is similar too: a micro-pump in the cartridge is activated by moving the cartridge relative to the rest of the PV to transfer e-liquid from the cartridge to a child reservoir in the PV. The PV includes the mechanical valve described above as feature E.2 that is lifted off its seat by when the stem or nozzle of the filling device or cartridge is introduced; this valve prevents leakage of any e-liquid during or after filling the PV child reservoir. The cartridge can remain inside or attached to the PV whilst the PV is being vaped. The PV can include any of the other features listed above (E1 to E16). The cartridge includes some form of air pressure equalisation as otherwise, when the fluid volume diminishes, a partial vacuum will develop behind the fluid retarding it's transfer. However if a bellows type of cartridge is employed the lost volume is automatically compensated for. The cartridge can include any of the other features listed above (E17 to E20).

Fluid Movement Features

E.25 E-liquid is transferred out of the parent reservoir using a piston or other device that decreases the internal volume of the parent reservoir: A cartridge or other form of parent reservoir stores e-liquid; a plunger, piston or other means of reducing the internal volume of the parent reservoir is activated and as the internal volume decreases, e-liquid is forced out of a nozzle into a child reservoir in the PV. A foil cap seals the nozzle prior to use and is penetrated by a hollow spigot or tube when the cartridge is inserted into the device for filling a PV (the device could be a case or the PV itself).

The plunger, or piston etc could be forced forwards using a screw being turned within a thread inside the reservoir and directly pushing the plunger or piston forward, or a rack and pinion system in which the user turns a thumbwheel as the pinion, which causes the plunger, connected to the rack that is forced forwards as the thumbwheel is turned.

Similarly, there could be a rotary end cap, mounted on a thread external to the reservoir; when the end cap is turned, it drives the plunger or piston forwards.

The plunger, or piston etc could also be forced forwards using a rotary cam; rotating an end-cap causes a cam follower to push linearly forward against the plunger/piston, forcing that forward.

The plunger, or piston etc could also move forward inside a tube or other device and be connected to an outer collar or other device that sits outside of the tube and can be moved forward along a slot in the tube; as the user drags the collar forward along the slot, the plunger is also forced forwards. The outer collar could also be mounted on a thread so that rotating the collar causes it to move forward along the thread, moving the plunger forward as it does so.

Alternatively, the plunger, or piston could include a magnet (e.g. formed as a collar or other device) and then another magnet (e.g. formed as an outer collar that sits outside the magnetic collar on the plunger) could move forward, forcing the magnetic collar on the plunger forward. The outer magnetic collar could be mounted on a thread, so that turning the outer magnetic collar takes it forward along the thread and hence also takes the internal magnetic collar and the plunger forward too, decreasing the volume of the chamber and forcing e-liquid out.

In all of the above cases, the piston or plunger moves forward. But equally, the plunger could remain fixed, with the body of the parent reservoir moving in a direction to reduce the internal volume of the parent reservoir. This approach is especially relevant where the parent reservoir is inserted directly into the PV, and not a separate re-fill/re-charge case.

Also, the plunger or piston can force the e-liquid out of an aperture in the parent reservoir at the end of the cartridge facing the plunger, or anywhere else as well—for example, the aperture could be in a stem or nozzle that passes through the plunger.

E.26 E-liquid is transferred out of a deformable parent reservoir: A cartridge or other form of parent reservoir stores e-liquid; it is connected to a chamber, such as a bellows, whose internal volume can be increased, sucking in e-liquid from the parent reservoir, and then decreased, expelling e-liquid into a child reservoir in the PV. There is a one-way valve at each end of the chamber; one valve opens when the other closes. So for example, the valve at the cartridge/parent end of the chamber opens to fill the chamber, whilst the valve at the other end remains closed. If the chamber is compressed, then the valve at the cartridge/parent end of the chamber shuts, and the valve at the other end opens, enabling fluid to be transferred to a child reservoir in the PV.

The chamber could be formed for example as a bellows (e.g. made of silicone), with folds or ridges that move apart when the chamber is expanding and move closer together when the chamber is contracting.

The chamber could be a simple deformable tube, e.g. a rubber tube; squeezing the tube squirts e-liquid out from the chamber; allowing the tube to regain its shape causes e-liquid to be sucked into the tube from the parent. Again, there is a one-way valve at each end of the chamber; one valve opens when the other closes. Another variant, which removes the need for one-way valves at each end, is a rotating pump with lobes or vanes that, as they rotate, force e-liquid through the tube.

E.27 Archimedes screw: A cartridge or other form of parent reservoir stores e-liquid; an Archimedes screw inside the reservoir, when turned, transfers e-liquid through the reservoir & out of a nozzle at one end to the child reservoir in the PV.

E.28 Gravity feed: A cartridge or other form of parent reservoir stores e-liquid; a gravity-based fluid transfer mechanism could be used to transfer e-liquid from the parent to a child reservoir in the PV. Air pressure equalisation can be achieved by using an air vent that allows air to enter the reservoir as fluid leaves it, but to prevent leakage or passage of any e-liquid. For example, the vent could have no moving parts, but instead be an air-porous material, such as a sintered polymer or metal, coated with a layer or barrier of a substance that is air-porous but not porous to e-liquid, such as an oleophobic material or a hydrophobic material. Various form factors for the cartridge/reservoir are possible, such as a concentric ring shaped to fit around the PV; a spiral tube that wraps around the PV; a serpentine or matrix tube that wraps around the PV.

We will now look at some specific implementations.

Key to reference numerals used in this section:

101 PV front tip
102 annular orifice
103 vapourising chamber
104 mechanical fluid transfer valve
105 face seal
106 bias spring
107 valve
108 valve seat
109 channel
110 small e-fluid aperture
111 child reservoir
112 secondary child reservoir
115 atomising coil unit
116 Coil unit holes
117 sintered metal collar
118 vapourising chamber
120 mounting bush
121 insulating bush
122 Electrical contact
123 complete coil assembly
124 manifold/tip housing
126 fluid pathway channels
127 air escape path
128 tip/manifold/coil assembly
130 electronics module assembly
131 male electrical contact pin
132 female electrical contact port
135 oleophobic washer in air escape path
136 ring collar
137 duckbill valve
138 oleophobic barrier or washer2
139 air path through the oleophobic barrier
140 annular ring of concentric rotary slots
141 coilbody holder
142 annular concentric ring of holes in insulation bush
143 neodynium magnets
144 case PCB
144 mild steel plug on hinged PV chassis
145 PV chassis
146 Reed switch
147 PV circuit board
150 replaceable e-liquid cartridge
151 integral pump in the cartridge
152 pivoting lever
153 pivot or pin for the lever
154 end face of the PV
155 tension spring
160 e-liquid cartridge
161 cartridge micro-pump
162 e-liquid ‘parent’ reservoir
163 duckbill pressure equalisation valve
164 retention catches

165 ball valve
166 e-liquid return hole
167 absorbent pad in PV front tip
168 cartridge stem
169 cavity behind duckbill valve
170 long cavity into which the e-liquid cartridge is slotted In FIG. 77, we have a cross section through the front portion of a PV, showing the integrated manifold, tip and coil assembly. Working from the left side, the front tip 101 includes an annular orifice 102 that is the vapour inhalation channel. This annular orifice 102 is a cylindrical channel that continues along the front section of the PV; it tapers to meet the outlet of the vapourising chamber 103. A mechanical fluid transfer valve assembly 104 sits within the cylindrical section of the annular orifice; the purpose of the valve is to ensure that e-liquid can be transferred into the PV from a parent reservoir (e.g. the user-replaceable closed or sealed cartridge) without leakage, as explained in section D.2 above. The mechanical fluid transfer valve assembly 104 includes a face seal 105 that seals against the nozzle of the pump in the cartridge (not shown). The mechanical fluid transfer valve 104 includes a bias return spring 106; when the nozzle of the pump is pressed against the face seal 105, then the transfer valve assembly 104 is pushed forwards against the bias force of the return spring 106, and this causes the valve 107 to be lifted away from its valve seat 108 by approximately 2 mm. E-fluid passes under pressure from the pump and through channel 109, emerging from a small e-fluid aperture 110 into child reservoir 111. The e-fluid then flows under pressure through the fluid path way channels 126 to the secondary child reservoir 112 that surrounds the coil unit; the exact route it takes will be explained using FIG. 78. But, to complete the walk-through of FIG. 77, the secondary child reservoir 112 surrounds the atomising coil unit 115. Coil unit holes permit e-fluid in the secondary child reservoir 112 to reach a wicking substance in the coil unit 115; a resistance wire is wound around the wick in the conventional manner. (Other non-wick-based atomising approaches, as described in this specification, may also be used). A sintered metal collar 117 occludes the coil unit holes 116 and is porous to e-liquid, but prevents e-liquid at excessively high pressure entering the coil unit 115 and flooding the coil unit 115; if high pressure e-liquid were to enter the coil unit 115, then it would dribble out through the vaporising chamber 103 and trickle along the annular orifice 102 and out through the tip 101. But in normal operation, with the sintered metal collar or plugs 117 in place, then only sufficient e-liquid enters the wicking system in coil unit 115 to enable effective vapour production; the e-liquid is heated in the coil unit 115 in the normal manner to produce vapour, and that vapour is drawn by the user's inhalation of air from the vapourising chamber 118, through the annular orifice 102 and out through the tip 101.

The coil unit 115 is fitted onto mounting bush 120, compressing an '0' ring seal. An insulating bush 121 is fitted onto the rear of the mounting bush 120. Electrical contact 122 fits into the insulating bush 121. An earth connection is made through the body of the mounting bush 120 to the manifold/tip housing 124. The power connection is made by the electrical contact 122 contacting the back (power) point on the coil unit 115. The complete coil assembly 123 includes the coil unit 115, the mounting bush 120, the insulating bush 121 and the electrical contact 122.

If we look now at FIG. 78, we can see how the e-liquid moves from the child reservoir 111 to the secondary child reservoir 112 that sits around and directly feeds the coil unit 115. FIG. 78 is a cross-sectional view of the PV shown in FIG. 77, but at a slightly different orientation that slices through fluid pathway channels 126 that lead from child reservoir 111 to the secondary child reservoir 112. A tortuous air escape path 127 is shown leading from the secondary child reservoir 112 to the outside of the PV: this enables air to escape from the secondary child reservoir 112 when the PV is being filled with e-liquid; and to allow air to flow back into the secondary child reservoir as the e-liquid is depleted through normal vaping use. A valve is provided to prevent e-liquid escaping, but to permit air to pass through, as described in section E.1 above.

FIG. 79A shows a cross-section of the complete PV, so that the portion shown in FIGS. 77 and 78, the tip/manifold/coil assembly 128 can be understood in context. FIG. 79B shows the tip/manifold/coil assembly 128 joined to the electronics module assembly 130, which includes all electronics and the battery. Electrical contact 122 has a male electrical contact pin 131 that engages with a female electrical contact port 132.

FIG. 80A shows another cross section through the tip/manifold/coil assembly 128; this differs from FIGS. 77 and 78 because the mechanical fluid transfer valve 104 is shown back on its seat, so that there is no longer any fluid path linking the child reservoir 111 and the front tip; hence, leakage of e-liquid from child reservoir 111 out past the mechanical fluid transfer valve 104 is not possible. The air escape path 127 that leads from the secondary child reservoir 112 to the outside of the PV housing could provide a leakage path for high pressure e-liquid, but the end of the air escape path terminates at an an oleophobic washer 135, which permits air to pass, but not e-liquid, as described at D.1 above. A ring collar 136 traps and seals the oleophobic washer 135. Hence, as e-liquid enters the secondary child reservoir 112 under pressure from the fluid transfer system, the air in front of the e-liquid is forced into the air escape path 127 and into a small chamber below the oleophobic washer 135. The air percolates through the sintered metal oleophobic washer 135, but the e-liquid remains behind and does not leak out. As the e-liquid level falls in the secondary child reservoir 112, air can make the return journey from the outside of the PV and through the oleophobic washer 135, equalising the air pressure between the secondary child reservoir 112 and the external atmosphere. FIG. 80 also shows a duckbill valve 137 that wipes any residual e-liquid off the nozzle inserted against the face seal 105 of the mechanical fluid transfer valve 104, retaining that e-liquid inside the PV.

FIG. 80B shows how the region that contains e-liquid is separated from the portion of the PV containing the electronics and battery using another oleophobic barrier, as described in section D.4 above. Oleophobic barrier 138 is formed as a ring washer, as more clearly shown in FIG. 81 and FIG. 82. The oleophobic barrier 138 is a sintered polymer material with an oleophobic coating on both sides. FIG. 81 shows the air path 139 through the oleophobic barrier 138. Air ahead of fluid transferred from the parent reservoir in the cartridge to the secondary child reservoir 112 escapes through an annular ring of concentric rotary slots 140 in the coil body holder 141. Air then percolates through the oleophobic washer 138. Once through oleophobic washer 138, air escapes through annular concentric ring of holes 142 in the insulation bush 121. The oleophobic washer 138 fits on to a spigot on coil body holder 141. An insulation nut screws onto coil body holder 141 on a thread, hence clamping and sealing oleophobic washer 138 to the coil body holder 141. Atomising coil unit 115 screws into the front of the coil body holder 141. Male electrical contact pin 131 screws into the back of insulating bush 121 until it makes contact with the power point on the atomising coil unit 115.

When the PV is being filled with pressurised e-liquid, air percolates through the oleophobic washer 138 and then through the concentric ring of holes 140 in insulating bush 121, venting to the atmosphere. The e-liquid displaces the air but cannot go through the oleophobic washer 138. As fluid is consumed, the fluid level falls in the child reservoir 112, and air can make the return journey through the holes 140 and the oleophobic washer 138, equalising the air pressure within the secondary child reservoir 112 and also the child reservoir 111 and the atmosphere.

FIG. 83 shows a cross section view of the re-fill and re-charge case with a PV securely held within it. A pair of neodymium magnets 143 are mounted into a magnet holder, which is then itself mounted on the case PCB (printed circuit board) 144. A mild steel plug screws 144 into the PV chassis 145; the chassis 145 is the holder into which the PV is slid; it is hinged in the case so that, when opened, the PV can be inserted into it, and it can be hinged closed to securely contain the PV. When the hinged chassis is shut, the mild steel plug 144 aligns with the neodymium magnets 143 and this ensures that the data and power contacts between PV and case are firmly aligned and it also eliminates contact bounce.

FIG. 84 is a close-up cross-sectional view of a portion of the re-fill and re-charge case with a PV securely held within it. The neodymium magnets 143 are shown, as is a Reed switch 146, mounted on the PV circuit board 147. When the Reed switch 146 is in proximity to the neodymium magnets 143, then its contacts close, sending a signal to the processor on the PV circuit board 147 indicating that the PV is in the case and hence data transfer and charging can commence. Conversely, when the Reed switch 146 is not in proximity to the neodymium magnets 143, then its contacts remain open, and the PV circuit board 147 does not initiate or permit data transfer or charging.

FIGS. 85A and B show a cross-sectional view of a portion of the re-fill and re-charge case with a PV securely held within it, this time showing the automatic PV lifting mechanism. FIG. 85A, shows the user-replaceable e-liquid cartridge 150, with integral pump 151. The stem 168 of the integral pump 151 is shown pushing against the face seal 105 of the PV, lifting up the mechanical fluid transfer valve 104 from its seat. A pivoting lever 152, hinged at pivot or pin 153, bears on the end face 154 of the PV; spring 155 is under tension when assembled and hence biases lever 152 to pushing the PV up and out of the case, as shown in FIG. 85B. In FIG. 85B, the PV is lifted approximately 12 mm up by the lever 152 when the lever 152 is in its fully forward position. When no PV is in position in the case, lever 152 remains in the fully forward position. When the PV is inserted back into the chassis and pressed downwards (e.g. by the camming action of the chassis being closed in the case) then lever 152 is moved to its back position, with the spring 155 now under maximum tension. The PV then latches in position.

FIG. 86 shows a cross-sectional view through the user-replaceable, e-liquid cartridge 160. The cartridge include a micro-pump 161 and a reservoir 162 (the ‘parent’ reservoir), typically 5 mL or 10 mL in capacity. The cartridge 160 includes a duckbill pressure equalisation valve 163; as fluid level inside the parent reservoir 162 diminishes, the external air pressure opens, allowing air pressure equalisation; without this valve, fluid transfer out from the cartridge would be inhibited. A duckbill valve is a valve manufactured from e.g. rubber or synthetic elastomer, and shaped like the beak of a duck, with a flattened shape. The flattened end opens to permit air to pass through if the external air pressure is sufficiently higher than the pressure in the parent reservoir. Although we specifically reference a duckbill valve in this specification, that term should include any other design of valve that achieves the same result. When the external air pressure is no longer sufficiently high, then the flattened end closes and seals. The duckbill valve ensures that, whilst the reservoir 162 is full (e.g. whilst the cartridge is in transport or storage, prior to use) no air can enter the cartridge; this airtight seal preserves the stability of the e-liquid. Two small retention catches 164 can be provided to allow the cartridge to lock into the case and to facilitate withdrawal. The cartridge can also magnetically latch into the case, using a magnet in the case and a strip of steel in the cartridge.

FIG. 87 shows a cross-sectional view through a different design of user-replaceable, e-liquid cartridge 150. The PV is engaged with the integral pump in the cartridge 151 and fluid flows from the parent reservoir 162 in the cartridge 151 to the child reservoir 111 in the PV through the mechanical fluid transfer valve 104. Transferring fluid from the parent reservoir 162 in the cartridge 151 to the child reservoir 111 in the PV causes the air ahead of the fluid to be pressurised and purged. When the air volume has been purged and the child reservoir 111 is completely full of fluid, further mechanical force applied to the pump 151 in the cartridge will raise the fluid’s hydraulic pressure. This is detrimental to the functioning of the PV and can cause leakage. To eliminate this problem, a spring-biased ball valve 165 is incorporated into the cartridge 160 and set to open at a pre-determined pressure. When the ball valve 165 lifts off it’s seat, fluid flows past the ball seat and into a return hole 166 connected to the reservoir 162 in the cartridge. Once the fluid’s hydraulic pressure has dropped below the maximum working pressure, the spring in the ball valve 165 returns the ball onto it’s seat, hence sealing the pump area from the reservoir 162.

FIG. 88 shows a cross-sectional view of the PV front tip 101 showing the one-way duckbill valve 137 and an absorbent pad 167. The duckbill valve 137 is a valve manufactured from rubber or synthetic elastomer, and shaped like the beak of a duck, with a flattened shape. The flattened end opens to permit the valve stem 168 to pass through it; when valve stem is withdrawn, the flattened end closes and seals. As the stem of the cartridge (not shown) is withdrawn relative to the duckbill valve 137, any residual e-liquid on the stem is wiped off by the duckbill valve 137 and retained in cavity 169.

FIG. 89 shows how this operates in practice: cartridge valve stem 168 penetrates duckbill valve 137 and seals against face seal 105 of the PV. The valve stem 168 pushes the mechanical fluid transfer valve 104 open and so fluid transfers from the parent reservoir 162 in the cartridge 160 to the child reservoir 111 in the PV. When valve stem 168 is withdrawn, the duckbill valve 137 closes, wiping the valve stem 168 and retaining fluid in the cavity 169 behind the duckbill valve. An absorbent pad 167 in the valve chamber soaks up any spilled fluid. The duckbill valve 137 is a robust and low cost solution to the potential problem of fluid leaking or leaving a moist residue at the junction of the cartridge valve stem 168 with the inlet valve face seal 105.

FIG. 90 shows a variant for a user-replaceable e-liquid cartridge that can be inserted directly into a PV and not a re-fill/re-charge case. The e-liquid cartridge 160 includes a liquid ‘parent’ reservoir 162 (volume e.g. 1.3 cc) and an integral micro-pump 151 with a stem 168. The cartridge 160 and micro-pump 151 operates as described above, although not all features are shown for simplicity (hence any one or more of the D1-D28 features could be implemented in this variant).

FIG. 91 shows the front portion of the PV that includes the mechanical fluid transfer valve 104, the coil assembly and the annular inhalation orifice or channel 102. The PV differs from that described earlier in having a long cavity 170 into which the e-liquid cartridge 160 (not shown in FIG. 114) is inserted.

FIG. 92 shows the cartridge 160 of FIG. 113 positioned in the cavity 170 of the PV shown in FIG. 114; the cartridge 160 is not fully inserted and the mechanical fluid transfer valve 104 can be seen to be closed, with cartridge stem 168 not having reached the mechanical fluid transfer valve 104. Pushing the cartridge 160 in further will both open the mechanical fluid transfer valve 104 and also activate the micro pump 151 in the cartridge 160, leading to e-fluid being transferred from the reservoir 162 in the cartridge to the child reservoir 111 in the PV. The cartridge 160 can be pumped manually in and out several times to transfer a metered quantity of e-liquid.

FIGS. 93-99 are sketches showing various approaches to preventing high pressure e-liquid from entering the coil unit, as described earlier at E.3.

FIGS. 100-116 are sketches showing various approaches for fluid transfer, as described earlier at D25-D28 above.

Section E Key Concepts

This section summarises the main innovative features described above.

E.1 A e-cigarette PV that includes an air pressure valve or device so that excess air can escape from an e-liquid reservoir in the PV when that reservoir is being filled under pressure with e-liquid from a parent reservoir.

Other optional features:

- the reservoir is a child reservoir and is filled by a parent reservoir, being an e-liquid cartridge that is removable from the PV or a case that stores, re-fills with e-liquid and re-charges the PV with power.
- the child reservoir is designed to enable the atomizing unit to draw in controlled amounts of e-liquid for vaping.
- the parent reservoir is a user-removable and replaceable, sealed or closed e-liquid capsule or cartridge, of capacity 10 mL or less, and is slotted into or otherwise used by the PV or a portable re-fill/re-charge case for the PV, and a fluid transfer mechanism operates to transfer e-liquid from the capsule or cartridge into the child reservoir in the PV, of capacity 3 mL or less.
- the child reservoir is connected to one or more small channels that lead into a second child reservoir which surrounds the atomising unit and from which e-liquid is drawn (e.g. by a wick or other porous member) into the atomising chamber (e.g. a heating coil inside an air chamber).
- the valve or device permits air to enter into the child reservoir in the PV as e-liquid is consumed in normal use.
- the valve or device permits air to enter into the child reservoir if the ambient air pressure changes, for example in an aircraft.
- the valve or device is a barrier made of an air-porous material, such as a sintered polymer or metal, coated with or otherwise including a barrier or layer of an air-porous substance that is not porous to e-liquid.
- the barrier or layer of the air-porous substance that is not porous to e-liquid as an oleophobic material or a hydrophobic or super-hydrophobic material.
- the valve or device in which the oleophobic material is one of: sintered phosphor bronze, sintered stainless steel and sintered PU plastic.

E.2 A e-cigarette PV that includes a mechanical valve that is pushed up from its seat when filling the PV with e-liquid takes place and returns to seal against its seat at other times.

Other optional features:

- a nozzle or stem from an e-liquid filling device, such as a removable cartridge, is inserted into the PV for filling the PV with e-liquid and this causes the valve to be pushed open or rise up from its seat, moving against the bias force of a small coil spring or other biasing device, so that e-liquid can freely flow from the e-liquid filling device through the nozzle or stem into a child reservoir in the PV.
- when the nozzle or stem is withdrawn then the valve automatically closes by resting back on its seat.
- the child reservoir is connected to one or more small channels that lead into a second child reservoir which surrounds the atomising unit and from which e-liquid is drawn (e.g. by a wick or other porous member) into the atomising chamber (e.g. a heating coil inside an air chamber).
- the stem or nozzle that protrudes from the cartridge or other form of parent reservoir and that engages with the valve in the PV to push it off its seat passes through a duckbill valve or a series of two or more duckbill valves; when the stem or nozzle is withdrawn then the duckbill wipes any droplets of e-juice from the stem, ensuring that those droplets are not deposited on any surface from where they could be ingested by the user, but are instead retained in a cavity in the PV behind the duckbill valve.

E.3A A PV including an atomising with at least one cover or barrier made of material that is porous to e-liquid and that prevents e-liquid at excess pressure from passing into the atomising unit.

Other optional features:

- one or more covers or other form of barrier, made of a material that is porous to e-liquid, cover at least the holes or other apertures in the wall of the atomising unit through which e-liquid has to pass to reach the atomising device in the unit, or form part or all of that wall.
- the porous material enables e-liquid to pass gradually into the atomising device at a rate suitable for effective vaping, even when the e-liquid is at an excessively high pressure in the reservoir that feeds e-liquid into the atomising unit.
- the porous material is a sintered metal or polymer
- the or each porous cover is shaped as a long dovetail shape unit that slides into a matching channel in the wall of the atomising unit;
- the or each porous cover is a small plug with an interference fit into the hole or aperture in the atomising unit through which e-liquid has to pass.

E.3B An e-cigarette PV including an atomising unit with at least one cover or barrier made of material that is shaped or formed to prevent e-liquid at excess pressure from passing into the atomising unit and is not porous to e-liquid.

Other optional features:

- the cover or barrier is made of an e-liquid non-porous material, such as metal or plastic, that fits closely over the holes or apertures in the atomising unit through which e-liquid needs to pass to reach the atomising device, but that includes features on its inner surface or that interacts with features on the outer surface of the atomising unit, to allow some e-liquid to reach the holes or other apertures in the atomising unit, but that prevent high pressure e-liquid from passing through those holes or apertures.

the atomising unit and/or the cover or barrier include a scored ring or channel that leads to each hole or aperture in the atomising unit through which e-liquid needs to pass to reach the atomising device the ring or channel is circular and perpendicular to the long axis of the coil the ring or channel is a different pattern or shape at some other orientation.

where the cover is a ring or collar that surrounds and fits closely around the atomising unit, with one or more-fluid inlet apertures in the atomising unit, then the outer surface of the atomising unit includes a scored ring or feature that connects the apertures in the atomising unit; the cover is then fitted over the atomising unit, with one or more apertures in the cover not aligned with the apertures in the atomising unit, forcing the e-liquid to seep or pass through the apertures in the cover and then pass, in-between the outer wall of the atomising unit and the inner wall of the cover, along the scored ring or feature until it reaches the apertures in the coil unit and can then enter the atomising unit.

the inside surface of the cover or collar that contacts the outer surface of the atomising unit is roughened, permitting only e-liquid at a sufficiently low pressure to reach the atomising unit.

the inside surface of the collar or cover includes a spiral, scored groove or channel through which e-liquid can pass, permitting only e-liquid at a sufficiently low pressure to reach the atomising unit.

E.4 An e-cigarette PV including a barrier separating the vaporising chamber in the PV from the portion of the PV containing the electronics and battery, the barrier permitting air to pass but not e-liquid.

Other optional features:

The barrier is made of an air-porous material, such as a sintered polymer or metal, coated with or otherwise including a layer or barrier of a substance that is air-porous but not porous to e-liquid, The air-porous material is an oleophobic material or a hydrophobic or super-hydrophobic material.

The oleophobic materials is one of: sintered phosphor bronze, sintered stainless steel, sintered PU plastic.

E.5 An e-cigarette PV including an annular vaporising channel through which vapour can be drawn by a user.

Other optional features:

The annular aperture surrounds an e-liquid filling nozzle.

The annular aperture leads to an annular airflow channel extending along the body of the PV and leading back, at a tapering section, to an atomisation chamber.

E.6 An e-cigarette PV that can be set by the user to a 'discrete' mode to reduce the amount of vapour produced.

Other optional features:

the user can activate a button or sensor on the PV, or case, or connected application running on a connected smartphone or other device, that alters the operation of the atomising device in such a way as to decrease the vapour produced.

The 'discrete' mode involves reducing the power used by the atomising unit

The 'discrete' mode involves increasing the VG (vegetable glycerin) proportion compared to PG (propylene glycol)

The 'discrete' mode involves altering the frequency or other operational parameters (e.g. duty cycle) of a piezo-electric, thermal bubble jet or ultrasonic atomiser.

E.7 An e-cigarette PV that can be set by the user to a 'power' mode to increase the amount of vapour produced.

Other optional features:

the user can activate a button or sensor on the PV, or case, or connected application running on a connected smartphone or other device, that alters the operation of the atomising device in such a way as to increase the vapour produced.

The 'power' mode involves increasing the PG proportion compared to VG

The 'power' mode involves altering the frequency or other operational parameters (e.g. duty cycle) of a piezo-electric, thermal bubble jet or ultrasonic atomiser.

E.8 An e-cigarette PV that includes a piezo-electric pump to transfer e-liquid from a cartridge or other form of parent reservoir into a child reservoir in the PV.

Other optional features:

the piezo-electric pump is used in reverse to expel out any residual e-liquid in the PV back into the cartridge/parent reservoir.

the amounts of e-liquid delivered are accurately metered, enabling the PV (or case or associated application running on a smartphone) to accurately determine the total consumption of e-liquid and/or the amount of e-liquid remaining in a cartridge and also in the PV itself.

the metered data is used in an automatic re-ordering function for new cartridges.

the piezo-electric pump is a low-cost piezo-electric pump of the kind used ordinarily for delivering ink in an inkjet printer.

E.9 An e-cigarette PV that includes an IMU (inertial measurement unit) to detect when it is being lifted up and out of the case so it can start heating (e.g. the atomising coil.

Other optional features:

data from the IMO enables the PV to tell if it is not being used and so can power down.

movement-related data can be stored and uploaded to a server

E.10 An e-cigarette PV that includes or enables replaceable covers to be fitted to it to enable customizing the appearance of the PV.

E.11 An e-cigarette PV that magnetically latches into a portable case.

Other optional features:

the PV is directly magnetically latched into the case a chassis that mechanically holds the PV in the case is directly magnetically latched into the case one or more magnets are placed somewhere on the PV or the chassis so that the charging and/or data contacts on the PV latch reliably to their corresponding contacts in the case.

a small neodymium magnet in the case and a matching magnet or metal item in the PV (or vice versa) ensure that, when the PV is nearly fully inserted into the case, the PV is drawn in the rest of the way to a secure, final position, which is also the position needed for fluid transfer from a parent e-liquid reservoir (e.g. the e-liquid cartridge that slots into the case) to a child reservoir in the PV.

the magnetic latching ensures that the charging and data transfer contacts in the PV and the case are optimally and securely positioned in contact with one another.

the magnetic latching stops the PV from falling out of the case if the case is tipped upside down and also eliminates contact bounce and also ensures that the fluid transfer mechanism is correctly positioned (e.g. the filling aperture or nozzle in the PV is correctly lined up with the filling stem or nozzle from the cartridge or other form of parent reservoir).

a small neodymium magnet in the case and a matching magnet or metal item in the hinged chassis ensure that, when the chassis is nearly fully closed, the chassis is drawn in the rest of the way to a secure, final position, which is also the position needed for fluid transfer from a parent e-liquid reservoir (e.g. the e-liquid cartridge that slots into the case) to a child reservoir in the PV.

E.12 A case for an e-cigarette PV, the case including an automatic lifting mechanism (e.g. magnetic or spring-based) that gently lifts the PV up a few mm from the case to enable a user to easily grasp it.

Other optional features:

the lifting mechanism is a pivoting lever that contacts a part of the PV (e.g. its front face) and a damped spring that is placed under tension if the PV is inserted fully into the case so that when the PV is released from the case, then the lever cause the PV to gently rise up by about, for example, 12 mm.

the lifting mechanism is a permanent magnet at one part of the PV and an adjacent electro-magnet placed in the case and powered by the main battery in the case; so that slowly energising the electro-magnet when the PV needs to be released causes the PV to gracefully rise up out of the case.

E.13 An e-cigarette PV that includes a touch sensor and is programmed to detect specific multiple different kinds of touch inputs and to control the PV accordingly.

Other optional features:

the touch inputs are not merely to either activate or de-activate the PV, but more sophisticated actions.

the touch inputs include tapping a defined number of times, e.g. twice on the body of the PV, to bring it up to heat; tapping a defined number of times to put it to sleep.

The PV detects when it is held by at least two fingers, and then automatically turns on and starts heating.

All touch data is stored and uploaded to a server

The touch data is sent over Bluetooth to the user's the connected smartphone, which in turn sends it to the server.

E.14 An e-cigarette PV that includes or receives data from a sensor that detects PV release from a case in which the PV is stored.

Other optional features:

the sensor is a non-contact magnetic sensor, such as a reed switch, or Hall effect sensor that detects when the PV enters and leaves a charge/re-fill case by sensing the presence, proximity or movement of a small magnet or strip of metal in the PV or some other mechanism for disrupting the local magnetic field around the sensor.

a light sensor in the PV detects when light is incident on the PV, inferring that the PV is now in an open case or no longer in the case at all;

the case includes a small light sensor facing a LED light source in the case;

withdrawal of the PV triggers the light sensor since light from the LED is no longer incident.

when withdrawal of the PV from the case is detected by the PV or the PV receives data indicating that the PV has been withdrawn from the case, it automatically starts heating the atomising coil so that the PV is at its optimal operational temperature when the user takes his first vape.

the case is a re-fill and re-charge case

E.15 An e-cigarette PV with a replaceable tip of the PV includes its own integral atomising heating element and is separable from the e-juice reservoir in the PV.

E.16 An e-cigarette PV that includes a heated nozzle designed to prevent condensation of e-liquid on the nozzle.

Other optional features:

The heated nozzle is designed so that those parts of the PV on which e-liquid vapour might otherwise condense if those parts of the nozzle were cold, are heated using e.g. an electrical heating element.

heating the components is also used to warm the e-liquid vapour to a desired temperature the PV uses a non-heating atomisation system, such as ultrasonic atomisation using piezo-electric or other form of droplet-on-demand system.

Cartridge or Other Form of Parent Reservoir Features

E.17 An e-liquid cartridge or other form or parent reservoir designed to supply e-liquid to an e-cigarette, in which the cartridge includes an air pressure valve.

Other optional features:

the air pressure valve is designed so that as the fluid level inside the cartridge/reservoir falls (e.g. because fluid is being transferred into the child reservoir in the PV), atmospheric pressure forces open the air pressure valve to allow air to flow in and ensure equalisation of the air pressure.

the valve is a duckbill valve the cartridge is non-refillable, tamper evident and with an airtight seal to preserve e-liquid stability during storage and transportation.

E.18 An e-liquid cartridge or other form or parent reservoir designed to supply e-liquid to an e-cigarette, in which the cartridge includes a piezo-electric pump to transfer small but accurately and reliably metered quantities of e-liquid.

Other optional features:

the piezo-electric pump is used as the fluid transfer mechanism to transfer e-liquid from the cartridge or parent reservoir into the child reservoir in the PV.

the piezo-electric pump is used in reverse to suck back out any residual e-liquid in the PV.

the amount of e-liquid transferred by the piezo-electric pump is metered.

the metered data enables the total consumption of e-liquid and/or the amount of e-liquid remaining in a cartridge and also in the PV itself to be measured or assessed.

The metered data is used in an automatic re-ordering function for new cartridges.

the piezo-electric pump is a low-cost piezo-electric pump of the kind used ordinarily for delivering ink in an inkjet printer.

E.19 An e-cigarette PV including an atomiser that is integrated into a removable lid or cap for an e-liquid cartridge so that when the PV engages with the lid/cap, the lid/cap is filled with a small quantity of e-liquid and locks onto the PV; and when the PV is lifted up, the lid is locked into to one end.

E.20 A package for a user-replaceable e-liquid cartridge designed to fit into or be otherwise used by an e-cigarette PV or a case for that e-cigarette PV, in which the package is the same size and shape as a conventional cigarette pack to enable distribution through existing cigarette vending machines and point of sale systems.

Other optional features:

The package is made of cardboard or paper and is designed so that the cartridge slides out of the package.

Case Features

E.21 A case for storing, re-filling with e-liquid and re-charging an e-cigarette PV, in which the case is the same size as, or presented in a package that is the same size as, a cigarette pack, to enable distribution through existing cigarette vending machines and point of sale systems.

E.22 A case for storing, re-filling with e-liquid and re-charging an e-cigarette PV, in which the case includes a piezo-electric pump to transfer quantities of e-liquid to a child reservoir in the PV.

Other optional features:

the piezo-electric pump is used in reverse to suck back out any residual e-liquid in the PV.

the amount of e-liquid transferred by the piezo-electric pump is metered.

the metered data enables the total consumption of e-liquid and/or the amount of e-liquid remaining in a cartridge and also in the PV itself to be measured or assessed.

The metered data is used in an automatic re-ordering function for new cartridges.

the piezo-electric pump is a low-cost piezo-electric pump of the kind used ordinarily for delivering ink in an inkjet printer.

E.23 A case for storing, re-filling with e-liquid and re-charging an e-cigarette PV in which the case includes a removable cover to enable a user to customize the appearance of the case.

We claim:

1. A vaping system that includes a vaporiser body that comprises (i) a heating or atomizing element and a child liquid reservoir; and (ii) a rechargeable battery configured to supply power to the heating or atomizing element, and a user-replaceable, but non user-refillable, liquid cartridge configured to attach to, or be inserted in the vaporiser body, the system further comprising:

a fluid transfer system configured to transfer vaporizable liquid from the user-replaceable liquid cartridge to the child liquid reservoir in the vaporiser body;

and the fluid transfer system includes a gravity-based fluid transfer mechanism, and in which the gravity-based fluid transfer system includes an air vent or a nozzle that allows air to enter the user-replaceable liquid cartridge when the vaporizable liquid is delivered; the fluid transfer system is also configured to allow any residual liquid in the vaporiser to flow back to the user-replaceable liquid cartridge.

2. The vaping system of claim 1 in which the liquid cartridge is a cylinder.

3. The vaping system of claim 1 in which the liquid cartridge includes a nozzle that is sealed by a foil cap.

4. The vaping system of claim 1 in which the liquid cartridge includes an internal piston, plunger or other mechanical device that is movable by a motor and is operable to advance a screw thread and the internal piston or plunger is advanced as the screw thread turns.

5. The vaping system of claim 1 in which the liquid cartridge is configured to attach to, or be inserted in, a portable case device.

6. The vaping system of claim 1 in which the liquid cartridge has a liquid capacity that is at least three times greater than the liquid capacity of the child liquid reservoir.

7. The vaping system of claim 1 in which the liquid cartridge includes an electronic identifier.

8. The vaping system of claim 7 in which the electronic identifier includes a RFID chip.

9. The vaping system of claim 1 in which the liquid cartridge forms one of a set of multiple user-replaceable liquid cartridges that are each configured (i) to attach to, or be inserted in, the vaporiser body at the same time.

10. The vaping system of claim 1 in which, when the liquid cartridge is fully inserted into the vaporiser body, a foil cap which seals a nozzle of the liquid cartridge prior to use is penetrated or pierced by a hollow spigot or tube for liquid filling.

11. The vaping system of claim 1 in which the fluid transfer system includes a micro-pump.

12. The vaping system of claim 1 in which the system is not disassembled for re-filling with liquid.

13. The vaping system of claim 1 in which the user-replaceable liquid cartridge includes an internal piston, plunger or other mechanical device that is movable to decrease the internal liquid volume of the user-replaceable liquid cartridge, to thereby expel vaporizable liquid from the user-replaceable liquid cartridge into the child liquid reservoir.

14. The vaping system of claim 1 in which the liquid cartridge stores vaporizable liquid and is connected to a chamber in the vaporiser body, the fluid transfer system is configured to transfer vaporizable liquid from the liquid cartridge to the connected chamber, then to the child reservoir.

15. The vaping system of claim 1 in which the liquid cartridge stores vaporizable liquid and is connected to a chamber, the vaporiser body includes at least a one-way valve at one end of the chamber, when filling the child reservoir, the valve at the end of the chamber opens, enabling fluid to be transferred from the chamber to the child reservoir.

16. The vaping system of claim 1 in which the heating or atomising element is a wick and coil assembly.

17. The vaping system of claim 1 in which the vaping system is a case, generally rectangular in shape, with opposing short sides and opposing long sides, and the user replaceable liquid cartridge forms, when attached to or inserted into the vaporiser body, a corner of the case, including part of adjacent short and long sides of the vaping system.

18. The vaping system of claim 1 in which the user-replaceable liquid cartridge includes a nozzle or filling stem that is insertable into a liquid filling aperture in the vaporiser body.

19. The vaping system of claim 1 in which the liquid includes any one or more of: (i) nicotine; (ii) vitamins; (iii) a legally permissible recreational drug.

* * * * *